US007709670B2

(12) United States Patent
Voskoboynikov et al.

(10) Patent No.: US 7,709,670 B2
(45) Date of Patent: May 4, 2010

(54) PROCESS FOR PRODUCING SUBSTITUTED METALLOCENE COMPOUNDS FOR OLEFIN POLYMERIZATION

(75) Inventors: Alexander Z. Voskoboynikov, Moscow (RU); Alexey N. Ryabov, Moscow (RU); Catalina L. Coker, Baytown, TX (US); Jo Ann M. Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1041 days.

(21) Appl. No.: 11/302,997

(22) Filed: Dec. 14, 2005

(65) Prior Publication Data
US 2006/0160968 A1 Jul. 20, 2006

Related U.S. Application Data

(60) Provisional application No. 60/636,662, filed on Dec. 16, 2004.

(51) Int. Cl.
C07F 17/00 (2006.01)
C07F 7/00 (2006.01)
(52) U.S. Cl. ............................................. 556/53; 556/1
(58) Field of Classification Search ................... 556/1, 556/53
See application file for complete search history.

(56) References Cited

U.S. PATENT DOCUMENTS

| | | | |
|---|---|---|---|
| 4,794,096 | A | 12/1988 | Ewen |
| 5,594,081 | A | 1/1997 | Uchino et al. |
| 5,763,542 | A | 6/1998 | Winter et al. |
| 5,840,644 | A | 11/1998 | Küber et al. |
| 5,936,053 | A | 8/1999 | Fukuoka et al. |
| 6,075,171 | A | 6/2000 | Sullivan et al. |
| 6,087,292 | A | 7/2000 | Winter et al. |
| 6,291,699 | B1 | 9/2001 | Birmingham et al. |
| 6,369,254 | B1 | 4/2002 | Resconi et al. |
| 6,399,723 | B1 | 6/2002 | Burkhardt et al. |
| 6,414,095 | B1 | 7/2002 | Burkhardt et al. |
| 6,465,700 | B1 | 10/2002 | Sullivan et al. |
| 6,492,539 | B1 | 12/2002 | Bingel et al. |
| 2004/0260107 | A1 | 12/2004 | Oberhoff et al. |

FOREIGN PATENT DOCUMENTS

| | | |
|---|---|---|
| DE | 3 443 087 | 5/1986 |
| EP | 0 416 815 | 3/1991 |
| EP | 0 582 195 | 2/1994 |
| EP | 0 693 502 | 1/1996 |
| EP | 0 846 122 | 6/1998 |
| EP | 1 034 190 | 9/2000 |
| JP | 07216011 | 8/1995 |
| JP | 08301914 | 11/1996 |
| JP | 11001508 | 1/1999 |
| JP | 11060588 | 3/1999 |
| JP | 11080183 | 3/1999 |
| JP | 11171925 | 6/1999 |
| WO | WO 9104257 | 4/1991 |
| WO | WO 96/04317 | 2/1996 |
| WO | WO 9604317 | 2/1996 |
| WO | WO 9638458 | 12/1996 |
| WO | WO 9926985 | 6/1999 |
| WO | WO 02092647 | 11/2002 |
| WO | WO 03000744 | 1/2003 |
| WO | WO 03050131 | 6/2003 |

OTHER PUBLICATIONS

Bandy et al., "Polymerisation of Ethylene and Propene using New Chiral Zirconium Derivatives, Crystal Structure of [ZrL$^1$Cl$_2$]-[H$_2$L$^1$=(4S,5S)-trans-4,5-bis(1H-inden-1-ylmethyl)-2,2-dimethyl-1,3-dioxolane]," J. Chem. Soc., Dalton Trans. 1991, 2207.

Conway et al., "Formation and Reactivity of Halogen Derivatives of (η5-Cyclopentadienyl) thallium," Organometallics 1985, 4, 688-693.

Erker et al., "Hydroboration of Bis(alkenylcyclopentadienyl)zirconium Dichlorides1)," Chemische Berichte Apr. 1991, vol. 124, No. 4, 1301.

Erker et al., "Cp-Substituent Additivity Effects Controlling the Stereochemistry of the Propene Polymerization Reaction at Conformationally Unrestricted (Cp-CHR1R2)2ZrCl2 / Methylalumoxane Catalysts," J. Am. Chem.. Soc. 1991, 113, 7594-7602.

Erker et al., "Synthesis of ansa-Metallocenes by Intramolecular Photochemical [2+2] Cycloaddition of Bis(alkenylcyclopentadienyl)zirconium Complexes," Organometallics 1993, 12, 2140-2151.

Finch et al., "Substituent Effects on the Cleavage Rates of Titanocene Metallacyclobutanes," J. Am. Chem. Soc. 1988, 110, 2406-2413.

Halterman et al., "Synthesis of C7,C7'-Ethylene- and C7,C7'-Methylene-Bridged C2-Symmetric Bis(indenyl)zirconium and -titanium Dichlorides," Organometallics 1998, 17, 3900-3907.

Halterman et al., "Synthesis, Characterization, and Polymerization Properties of Bis(2-menthylindenyl)zirconium Dichloride and Bis(2-menthyl-4,7-dimethylindenyl)zirconium Dichloride," Organometallics 2000, 19, 5464-5470.

Hassan et al., "Aryl-Aryl Bond Formation One Century after the Discovery of the Ullmann Reaction," Chem. Rev. 2002, 102, 1359-1469.

Hollis et al., "Preparation and Properties of (S,S)-[Ti((R,R)-cyclacene)Cl$_2$], a Chiral Strapped Bent Metallocene," Organometallics 1992, 11, 2812-2816.

Johnston et al., "Investigation of the Electrochemical Properties of Substituted Titanocene Dichlorides," Electrochimica Acta, 1995, vol. 40, No. 4, pp. 473-477.

(Continued)

Primary Examiner—Caixia Lu

(57) ABSTRACT

A process for producing a substituted metallocene compound comprises reacting a first compound with a transfer-agent, wherein the first compound comprises a complex of a transition metal atom selected from Group 3, 4, 5 or 6 of the Periodic Table of Elements, or a lanthanide metal atom, or actinide metal atom and at least one monocyclic or polycyclic ligand that is pi-bonded to M and is substituted with at least one halogen or sulfonate substituent and the transfer-agent comprises a hydrocarbyl, substituted hydrocarbyl, halocarbyl, substituted halocarbyl, silylcarbyl, or germylcarbyl radical capable of replacing said at least one halogen or sulfonate substituent of said first compound under reaction conditions.

36 Claims, No Drawings

OTHER PUBLICATIONS

Kato et al., "Synthesis of Novel ansa-Metallocene Complex with Bridged Bis(indenyl) Ligand and Its Application for Olefin Polymerization," Studies in Surface Science and Catalysis 1999, vol. 121 (Science and Technology in Catalysis 1998), 473-476.

Larsonneur et al., "Synthesis, Characterization, and Chemical Reactivity of Zirconium Dihydride [($C_5$ $H_4$R)$_2$Zr(μ-H)H]$_2$ (R = SiMe$_3$, CMe$_3$). H/D Exchange Reactions of Anionic Species [($C_5H_4$R)$_2$ZrH$_2$]-. X-ray Crystal Structure of [($C_5H_4$SiMe$_3$)$_2$Zr(μ-H)H]$_2$," Organometallics 1993, 12, 3216-3224.

MacDowell et al., "Keto-Enol Tautomerism in the Thiophene Analogues of Naphthacen-5-one," J. Org. Chem. 1982, 47, 705-709.

McEwen et al., "Hydrogen Bonding of Hydroxy Groups to Carbanions in Indenide and Fluorenide Derivatized Alcohols Directly Observed by UV, IR, and NMR Spectroscopy," J. Am. Chem. Soc. 1993, 115, 3989-3996.

Ogasawara et al., "Metathesis Route to Bridged Metallocenes," J. Am. Chem. Soc. 2002, 124, 9068-9069.

Panarello et al., "Use of Oxirane Ring-Opening Reactions for Synthesis of Ethylene-bis(indenyl) Ligands Containing Alkene Tethers," Synlett, No. 5, 2005, pp. 797-800.

Piccolrovazzi et al., "Electronic Effects In Homogeneous Indenylzirconium Ziegler-Natta Catalysts," Organometallics 1990, 9, 3098-3105.

Rausch et al., "The formation of ring-substituted titanocene derivatives containing chloro and carbomethoxy substituents," Journal of Organometallic Chemistry, 1988, 358, 161-168.

Rheingold et al., "Preparation and Properties of Chiral Titanocene and Zirconocene Dichloride Complexes of a Chiral Ligand," Organometallics 1992, 11, 1869-1876.

Ryabov et al., "Zirconium Complexes with Cyclopentadienyl Ligands Involving Fused a Thiophene Fragment," Organometallics 2002, 21, 2842-2855.

Schäfer et al., "XII. Diastereomeric Derivatisation and Enantiomer Separation of Ethylenebis(Tetrahydroindenyl)-Titanium and—Zirconium Dichlorides," Journal of Organometallic Chemistry 1987, 328, 87-99.

Schaverien et al., "A New Class of Chiral Bridged Metallocene: Synthesis, Structure, and Olefin (Co)polymerization Behavior of rac- and meso-1,2-CH$_2$CH$_2$[4-(7-Me-indenyl)]$_2$ZrCl$_2$," J. Am. Chem. Soc. 1998, 120(38), 9945-9946.

Schmid et al., "Unverbrückte (pentamethylcyclopentadienyl) (fluorenyl)-Komplexe des Zirconiums und HAfniums. Die Molekülstruckturen von (C5Me5)(2,7-Me2-C13h7)mcl2 (M=Zr, Hf)," J. Organometallic Chem. vol. 525, 1996, pp. 9-14.

Schmid et al., "Unbridged cyclopentadienyl-fluorenyl complexes of zirconium as catalysts for homogeneous olefin polymerization," Journal of Organometallic Chemistry 1995, vol. 501, 101-106.

Siedle et al., "Synthesis of unsymmetrical ansa-fluorenyl metallocenes," Journal of Molecular Catalysis A: Chemical, vol. 214, 2004, 187-198.

Wild et al., "IV. Synthesis and Molecular Structures of Chiral ansa-Titanocene Derivatives with Bridged Tetrahydroindenyl Ligands," Journal of Organometallic Chemistry 1982, 232, 233-247.

Zhang et al., "General Synthesis of Racemic Me2Si-Bridged Bis(indenyl) Zirconocene Complexes," J. Am. Chem. Soc. 2000, 122, 8093-8094.

PROCESS FOR PRODUCING SUBSTITUTED METALLOCENE COMPOUNDS FOR OLEFIN POLYMERIZATION

CROSS REFERENCE TO RELATED APPLICATIONS

This application claims priority from U.S. Provisional Patent Application No. 60/636,662, filed on Dec. 16, 2004.

FIELD

This invention relates to a process for producing substituted metallocene compounds for use in olefin polymerization and to a process to polymerize olefins using such substituted metallocene compounds.

BACKGROUND

Various processes and catalysts exist for the homopolymerization or copolymerization of olefins. For many applications, it is desirable for a polyolefin to have a high weight average molecular weight while having a relatively narrow molecular weight distribution. A high weight average molecular weight, when accompanied by a narrow molecular weight distribution, typically provides a polyolefin with high strength properties.

Traditional Ziegler-Natta catalysts systems comprise a transition metal compound co-catalyzed by an aluminum alkyl and are typically capable of producing polyolefins having a high molecular weight, but with a broad molecular weight distribution.

More recently metallocene catalyst systems have been developed wherein the transition metal compound has one or more cyclopentadienyl, indenyl or fluorenyl ring ligands (typically two). Metallocene catalyst systems, when activated with cocatalysts, such as alumoxane, are effective to polymerize monomers to polyolefins having not only a high weight average molecular weight but also a narrow molecular weight distribution.

Certain metallocenes containing substituted, bridged indenyl derivatives are noted for their ability to produce isotactic propylene polymers having high isotacticity and narrow molecular weight distribution. Considerable effort has been made towards obtaining metallocene-produced propylene polymers having ever-higher molecular weight and melting point, while maintaining suitable catalyst activity. Researchers currently theorize that there is a direct relationship between the way in which a metallocene is substituted, and the molecular structure of the resulting polymer. For the substituted, bridged indenyl type metallocenes, it is believed that the type and arrangement of substituents on the indenyl groups, as well as the type of bridge connecting the indenyl groups, determines such polymer attributes as molecular weight and melting point.

There is, therefore, significant interest in producing metallocene compounds with a variety of substituents on the arenyl ligands. However, current methods for producing substituted metallocene compounds, and especially Group 4 metallocene compounds, involve synthesis of each individual ligand family and then reaction with a simple metal derivative, such as $MCl_4$ and $M(N(CH_3)_2)_4$, where M=Ti, Zr, or Hf, using transmetallation and amine elimination reactions, respectively. This methodology requires preliminary ligand synthesis or modification, and, then, metallocene preparation starting from each ligand synthesized.

For example, U.S. Pat. No. 5,840,644 describes certain metallocenes containing aryl-substituted indenyl derivatives as ligands, which are said to provide propylene polymers having high isotacticity, narrow molecular weight distribution and very high molecular weight. However, synthesis of these compounds involves initial assembly of each aryl-substituted indene ligand from a substituted diphenyl compound and then reaction of the ligand with $MCl_4$. Thus Example A discloses synthesis of rac-dimethylsilylbis(2-methyl-4-phenyl-indenyl)zirconium dichloride by reaction of 2-phenylbenzyl bromide with diethylmethyl malonate and then KOH to produce 2-(2-phenylbenzyl)propionic acid, followed by cyclization of the 2-(2-phenylbenzyl)propionic acid to produce 2-methyl-4-phenylindan-1-one and reduction of the 2-methyl-4-phenylindan-1-one to produce 2-methyl-7-phenylindene. The 2-methyl-7-phenylindene is then reacted with dimethyldichlorosilane to produce dimethylbis(2-methyl-4-phenylindenyl)silane, which is then reacted with butyllithium and zirconium tetrachloride to produce the desired bridged metallocene.

According to the present invention, a novel method of producing substituted metallocene complexes of early transition metals has been developed in which halogen substituents on existing metallocene compounds are directly replaced with other groups, such as hydrocarbyl groups. In this way, a single base synthesis of a given halogen-substituted metallocene compound can be used to generate a large number of final metallocene products with varying ligand substituents.

Modification of the coordinated ligands of late transition complexes, particularly, ferrocene derivatives, has been described (see Hassan, J.; Sevignon, M.; Gozzi, C.; Schulz, E.; Lemaire, M. Chem. Rev. 2002, 102, 1359, and references therein). However, no similar transformations of early transition metal complexes, which include highly polarized and reactive metal-ligand bonds, have been described so far.

Scarce examples of transformations of the coordinated cyclopentadienyl ligands of Group 4 metal complexes resulting in no modification of the nearest coordination polyhedron have been described, e.g. H/D exchange in $\eta^5$-cyclopentadienyls (Larsonneur, A.-M.; Choukroun, R.; Jaud, J. Organometallics 1993, 12, 3216); Pd/C or $PtO_2$ catalyzed hydrogenation of $\eta^5$-indenyls giving $\eta^5$-tetrahydroindenyls (Wild, F. R. W. P.; Zsolnai, L.; Huttner, G.; Brintzinger, H. H. *J. Organomet. Chem.* 1982, 232, 233. Schäfer, A.; Karl, E.; Zsolani, L.; Huttner, G.; Brintzinger, H. H. *J. Organomet. Chem.* 1987, 328, 87. Bandy, J. A.; Green, M. L. H.; Gardiner, I. M.; Prout, K. *J. Chem. Soc., Dalton Trans.* 1991, 2207. Rheingold, A. L.; Robinson, N. P.; Whelan, J.; Bosnich, B. *Organometallics* 1992, 11, 1869. Hollis, T. K.; Rheingold, A. L.; Robinson, N. P.; Whelan, J.; Bosnich, B. *Organometallics* 1992, 11, 2812); hydroboration of allyl- and vinyl-$\eta^5$-cyclopentadienyl complexes (Erker, G.; Nolfe, R.; Aul, R.; Wilker, S.; Kriiger, C.; Noe, R. *J. Am. Chem. Soc.* 1991, 113, 7594. Erker, G.; Aul, R. *Chem. Ber.* 1991, 124, 1301); intramolecular photochemical [2+2] cycloaddition of vinyl-$\eta^5$-cyclopentadienyl complexes (Erker, G.; Wilker, S.; Krüger, C.; Nolte, M. *Organometallics* 1993, 12, 2140); Ru-catalyzed metathesis of bis(allyl-$\eta^5$-cyclopentadienyl)zirconium and -hafnium dichlorides (Ogasawara, M.; Nagano, T.; Hayashi, T. *J. Am. Chem. Soc.* 2002, 124, 9068).

SUMMARY

In one aspect, the invention resides in a process producing a substituted transition metal compound, the process comprising contacting: (a) a transition metal compound comprising at least one ligand having a halogen or sulfonate substituent directly bonded to any sp² carbon atom at a bondable ring position of said ligand, with (b), a transfer-agent capable of replacing the halogen or sulfonate substituent of the ligand with a hydrocarbyl, substituted hydrocarbyl, halocarbyl, substituted halocarbyl, silylcarbyl, or germylcarbyl substituent, and (c) a coupling-catalyst.

In a further aspect, the invention resides in a process producing a substituted metallocene compound, the process comprising:

(a) providing a first compound represented by the formula (1):

$AMX_{n-1}$ wherein:

M is a transition metal atom having a coordination number of n (typically 2, 3, 4, 5, or 6) selected from Group 3, 4, 5 or 6 of the Periodic Table of Elements, or a lanthanide metal atom, or actinide metal atom, preferably a Group 4 transition metal atom selected from titanium, zirconium or hafnium;

A is a monocyclic or polycyclic ligand that is pi-bonded to M and is substituted with at least one halogen or sulfonate substituent directly bonded to any sp² carbon atom at a bondable ring position of the ligand; and each X is, independently, a univalent anionic ligand, or two X are joined and bound to the metal atom to form a metallocycle ring, or two X are joined to form a chelating ligand, a diene ligand, or an alkylidene ligand; and (b) reacting said first compound with a transfer-agent which comprises a hydrocarbyl, substituted hydrocarbyl, halocarbyl, substituted halocarbyl, silylcarbyl, or germylcarbyl radical capable of replacing said at least one halogen or sulfonate substituent of said first compound under reaction conditions, and in the presence of a coupling-catalyst.

In a further aspect, the invention resides in a process for producing a substituted metallocene compound, the process comprising:

(a) providing a first compound represented by the formula (3):

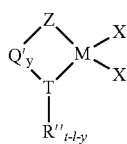

wherein

M is a Group 3, 4, 5 or 6 transition metal atom, or a lanthanide metal atom, or actinide metal atom, preferably a Group 4 transition metal atom selected from titanium, zirconium or hafnium;

Z is a substituted or unsubstituted, monocyclic or polycyclic ligand that is pi-bonded to M;

Q' is an optional bridging group that is bonded to Z and T, and is present when y is one and absent when y is zero;

y is zero or one; and

T is a heteroatom with a coordination number of three from Group 15 or with a coordination number of two from Group 16 of the Periodic Table of Elements, and preferably is nitrogen;

R" is selected from a $C_3$-$C_{100}$ substituted or unsubstituted monocyclic or polycyclic ring structure substituent that is partially unsaturated, unsaturated or aromatic; or a $C_2$-$C_{100}$ substituted or unsubstituted, unsaturated or partially unsaturated, linear or branched alicyclic hydrocarbyl substituent; or a $C_1$-$C_{100}$ substituted or unsubstituted saturated hydrocarbyl radical;

t is the coordination number of the heteroatom T where "t-1-y" indicates the number of R" substituents bonded to T; and each X is, independently, a univalent anionic ligand, or two X are joined and bound to the metal atom to form a metallocycle ring, or two X are joined to form a chelating ligand, a diene ligand, or an alkylidene ligand;

provided that Z is substituted with at least one halogen or sulfonate substituent directly bonded to any sp² carbon atom at a bondable ring position of the ligand Z, or that R" is substituted with at least one halogen or sulfonate substituent bonded to an sp² carbon atom, or both.

(b) reacting said first compound with a transfer-agent which comprises a hydrocarbyl, substituted hydrocarbyl, halocarbyl, substituted halocarbyl, silylcarbyl, germylcarbyl radical capable of replacing said at least one halogen or sulfonate substituent of said first compound under reaction conditions, and in the presence of a coupling-catalyst.

In a preferred embodiment, Z is a substituted monocyclic or polycyclic arenyl ligand. In other embodiments, Z may include one or more ring heteroatoms selected from boron, a Group 14 atom that is not carbon, a Group 15 atom, and a Group 16 atom. For example, Z can be a substituted cyclopentadienyl or heterocyclopentadienyl ligand, a substituted indenyl or heteroindenyl ligand, or a substituted fluorenyl or heterofluorenyl ligand, or a substituted cyclopentanaphthyl or heterocyclopentanaphthyl ligand.

In yet a further aspect, the invention resides in a process for producing a substituted metallocene compound, the process comprising:

(a) providing a first compound represented by the formula (2):

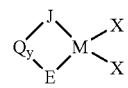

wherein

M is a group 3, 4, 5 or 6 transition metal atom, or a lanthanide metal atom, or actinide metal atom, preferably a Group 4 transition metal atom selected from titanium, zirconium or hafnium;

each of J and E is independently a substituted or unsubstituted, monocyclic or polycyclic ligand pi-bonded to M, wherein at least one of J and E includes at least one halogen or sulfonate substituent directly bonded to an sp² carbon atom at a bondable ring position of the ligand;

Q is an optional bridging group that is bonded to E and J, and is present when y is one and absent when y is zero;

y is zero or one; and each X is, independently, a univalent anionic ligand, or two X are joined and bound to the metal atom to form a metallocycle ring, or two X are joined to form a chelating ligand, a diene ligand, or an alkylidene ligand; and (b) reacting said first compound with a transfer-agent which comprises a hydrocarbyl, substituted hydrocarbyl, halocarbyl, substituted halocarbyl, silylcarbyl, germylcarbyl radical capable of replacing said at least one halogen or sulfonate substituent of said first compound under reaction conditions, and in the presence of a coupling-catalyst.

In a preferred embodiment, each of J and E may be independently selected from a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, or a substituted or unsubstituted fluorenyl ligand, a substituted or unsubstituted heterofluorenyl ligand, and a substituted or unsubstituted cyclopentanaphthyl or a substituted or unsubstituted heterocyclopentanaphthyl ligand. In another embodiment, at least one of J and E includes one or more ring heteroatoms selected from boron, a Group 14 atom that is not carbon, a Group 15 atom, and a Group 16 atom. For example, Preferably, the halogen or sulfonate substituent bonded to J or E is a chloro, bromo, iodo, tosylate or triflate substituent, and preferably is a chloro or bromo substituent.

In a preferred embodiment, M is a Group 4 transition metal atom selected from titanium, zirconium and hafnium. In a preferred embodiment the transfer agent is an organometallic compound, for example an organozinc compound or an organic compound of an alkali metal. In still a further aspect, the invention relates to a substituted metallocene compound produced by the process described herein and the use of the substituted metallocene compound in olefin polymerization catalyst systems and methods.

DEFINITIONS

As used herein, the numbering scheme for the Periodic Table Groups is the new notation as set out in CHEMICAL AND ENGINEERING NEWS, 63(5), 27 (1985).

As used herein, is methyl, Et is ethyl, t-Bu and $^t$Bu are tertiary butyl, iPr and $^i$Pr are isopropyl, Cy is cyclohexyl, THF (also thf) is tetrahydrofuran, Ph is phenyl, Tf is triflate, and Ts is tosylate.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be a radical, which contains hydrogen atoms and up to 100 carbon atoms and which may be linear, branched, or cyclic, and when cyclic, may be aromatic or non-aromatic.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N($R^*$)—, =N—, —P($R^*$)—, =P—, —As($R^*$)—, =As—, —Sb($R^*$)—, =Sb—, —B($R^*$)—, =B—, —Si($R^*$)$_2$—, —Ge($R^*$)$_2$—, —Sn($R^*$)$_2$—, —Pb($R^*$)$_2$— and the like, where $R^*$ is independently a hydrocarbyl or halocarbyl radical, and two or more $R^*$ may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N($R^*$)—, =N—, —P($R^*$)—, =P—, —As($R^*$)—, =As—, —Sb($R^*$)—, =Sb—, —B($R^*$)—, =B—, —Si($R^*$)$_2$—, —Ge($R^*$)$_2$—, —Sn($R^*$)$_2$—, —Pb($R^*$)$_2$— and the like, where $R^*$ is independently a hydrocarbyl or halocarbyl radical provided that at least one halogen atom remains on the original halocarbyl radical. Additionally, two or more $R^*$ may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where $R^*$ is independently a hydrocarbyl or halocarbyl radical and two or more $R^*$ may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^*_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, and the like where $R^*$ is independently a hydrocarbyl or halocarbyl radical and two or more $R^*$ may join together to form a substituted or unsubstituted saturated, partially unsaturated or aromatic cyclic or polycyclic ring structure.

Polar radicals, fiuctional groups or polar groups are groups in which a heteroatom functionality is bonded directly to the indicated atom or atoms. They include heteroatoms of Groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, sulfonates, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR^*_2$, $OR^*$, $SeR^*$, $TeR^*$, $PR^*_2$, $AsR^*_2$, $SbR^*_2$, $SR^*$, $BR^*_2$, $SnR^*_3$, $PbR^*_3$ and the like where $R^*$ is independently a hydrocarbyl, substituted hydrocarbyl, halocarbyl or substituted halocarbyl radical as defined above and two $R^*$ may join together to form a substituted or unsubstituted saturated, partially unsaturated or aromatic cyclic or polycyclic ring structure. Also preferred are sulfonate radicals, $S(=O)_2OR^*$, where $R^*$ is independently a hydrocarbyl, substituted hydrocarbyl, halocarbyl or substituted halocarbyl radical as defined above and two $R^*$ may join together to form a substituted or unsubstituted saturated, partially unsaturated or aromatic cyclic or polycyclic ring structure. Examples include $SO_3Me$ (mesylate), $SO_3(4$-tosyl) (tosylate), $SO_3CF_3$ (triflate), $SO_3(n$-$C_4F_9)$ (nonaflate) and the like.

In using the terms "substituted or unsubstituted cyclopentadienyl ligand", "substituted or unsubstituted heterocyclopentadienyl ligand", "substituted or unsubstituted indenyl ligand", "substituted or unsubstituted heteroindenyl ligand", "substituted or unsubstituted fluorenyl ligand", "substituted or unsubstituted heterofluorenyl ligand", "substituted or unsubstituted cyclopentanaphthyl ligand", "substituted or unsubstituted heterocyclopentanaphthyl ligand", "substituted or unsubstituted heterocyclopenta-pentayl ligand", "substituted or unsubstituted heterophenyl ligand", "substituted or unsubstituted heteropentalenyl ligand", "substituted or unsubstituted heterocyclopentapentalenyl ligand", "substituted or unsubstituted heterocyclopentaindenyl ligand", "substituted or unsubstituted heterobenzocyclopentaindenyl ligand", "substituted or unsubstituted pentalenyl ligand", "substituted or unsubstituted monocyclic ligand", "substituted or unsubstituted monocyclic arenyl ligand", "substituted or unsubstituted polycyclic ligand", or "substituted or unsubstituted polycyclic arenyl ligand", the substitution to the aforementioned ligand is on a bondable ring position, and each occurrence is selected from hydrocarbyl, substituted hydrocarbyl, halocarbyl, substituted halocarbyl, silylcarbyl, germylcarbyl, a halogen radical, or a polar group.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For nomenclature purposes, the following numbering schemes are used for cyclopentadienyl, indenyl, fluorenyl and cyclopentanaphthyl (also termed benzindenyl). It should be noted that indenyl can be considered as cyclopentadienyl with a fused benzene ring. Analogously, fluorenyl can be considered as indenyl with a benzene ring fused to the five-membered ring on the indenyl. Each structure below is drawn and named as an anion.

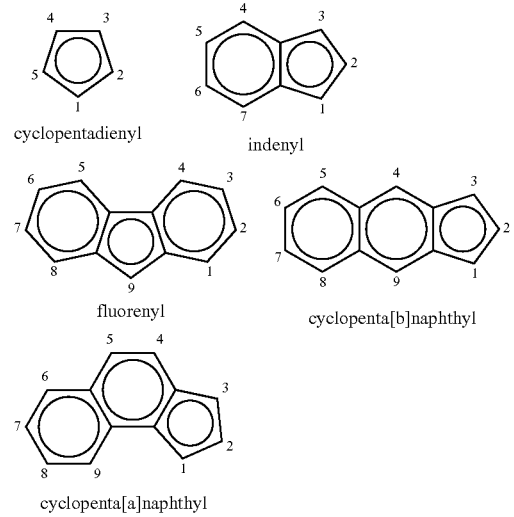

A similar numbering and nomenclature scheme is used for heterocyclopentadienyls, heterophenyls, heteropentalenyls, heterocyclopentapentalenyls, heteroindenyls, heterofluorenyls, heterocyclopentanaphthyls, heterocyclopentaindenyls, heterobenzocyclopentaindenyls, and the like, as illustrated below. Each structure is drawn and named as an anion.

Non-limiting examples of heterocyclopentadienyls include:

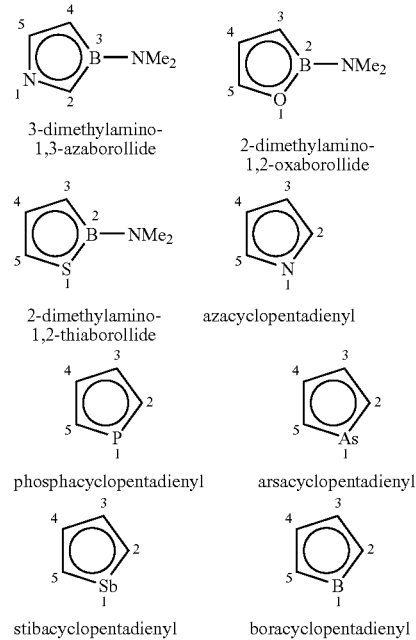

Further non-limiting examples of heterocyclopentadienyls include 1,3-diazacyclopentadienyl, 1,3-diphosphacyclopentadienyl, 1,3-diarsacyclopentadienyl, 1,3-distibacyclopentadienyl, 1,3-diboracyclopentadienyl, 1,3-azaphosphacyclopentadienyl, 1,3-azaarsacylcopentadienyl, 1,3-azastibacyclopentadienyl, 1,3-azaboracyclopentadienyl, 1,3-arsaphosphacyclopentadienyl, 1,3-arsastibacyclopentadienyl, 1,3-arsaboracyclopentadienyl, 1,3-boraphosphacyclopentadienyl, 1,3-borastibacylcopentadienyl, 1,3-phosphastibacyclopentadienyl, 1,2-diazacyclopentadienyl, 1,2-diphosphacyclopentadienyl, 1,2-diarsacyclopentadienyl, 1,2-distibacyclopentadienyl, 1,2-diboracyclopentadienyl, 1,2-azaphosphacyclopentadienyl, 1,2-azaarsacylcopentadienyl, 1,2-azastibacyclopentadienyl, 1,2-azaboracyclopentadienyl, 1,2-arsaphosphacyclopentadienyl, 1,2-arsastibacyclopentadienyl, 1,2-arsaboracyclopentadienyl, 1,2-boraphosphacyclopentadienyl, 1,2-borastibacylcopentadienyl, 1,2-phosphastibacyclopentadienyl, 3-dihydrocarbylamino-1,3-azaborollide, 2-dihydrocarbylamino-1,2-oxaborollide, 2-dihydrocarbylamino-1,2-thiaborollide, 3-hydrocarbyloxy-1,3-azaborollide, 2-hydrocarbyloxy-1,2-oxaborollide, 2-hydrocarbyloxy-1,2-thiaborollide, 3-hydrocarbyl-1,3-azaborollide, 2-hydrocarbyl-1,2-oxaborollide, and 2-hydrocarbyl-1,2-thiaborollide, where hydrocarbyl is a "hydrocarbyl radical" as previously defined.

Non-limiting examples of heterophenyls include:

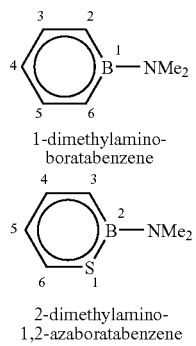
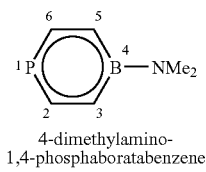
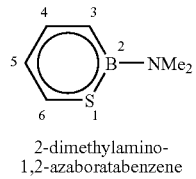

Further non-limiting examples of heterophenyls include 1-dihydrocarbylaminoboratabenzene, 4-dihydrocarbylamino-1,4-phosphaboratabenzene, 2-dihydrocarbylamino-1,2-azaboratabenzene, 1-hydrocarbyloxyboratabenzene, 4-hydrocarbyloxy-1,4-phosphaboratabenzene, 2-hydrocarbyloxy-1,2-azaboratabenzene, 1-hydrocarbylboratabenzene, 4-hydrocarbyl-1,4-phosphaboratabenzene, and 2-hydrocarbyl-1,2-azaboratabenzene, where hydrocarbyl is a "hydrocarbyl radical" as previously defined.

Non-limiting examples of heteropentalenyls include:

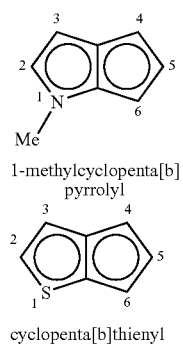
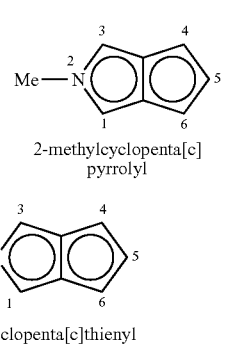
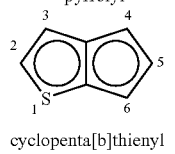
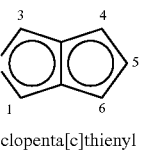

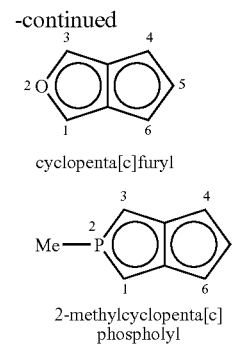

Further non-limiting examples of heteropentalenyls include cyclopenta[b]selenophenyl, cyclopenta[c]selenophenyl, cyclopenta[b]tellurophenyl, cyclopenta[c]tellurophenyl, 1-hydrocarbylcyclopenta[b]arsolyl, 2-hydrocarbylcyclopenta[c]arsolyl, 1-hydrocarbylcyclopenta[b]stibolyl, 2-hydrocarbylcyclopenta[c]stibolyl, 1-hydrocarbylcyclopenta[b]pyrrolyl, 2-hydrocarbylcyclopenta[c]pyrrolyl, 1-hydrocarbylcyclopenta[b]phospholyl, and 2-hydrocarbylcyclopenta[c]phospholyl, where hydrocarbyl is a "hydrocarbyl radical" as previously defined.

Non-limiting examples of heterocylopentapentalenyls include the following, where Z″ and Q″ independently represent the heteroatoms O, S, Se, or Te, or heteroatom groups, NR, PR, AsR, or SbR where R** is hydrogen, or a hydrocarbyl, substituted hydrocarbyl, halocarbyl, substituted halocarbyl, silylcarbyl, or germylcarbyl substituent.

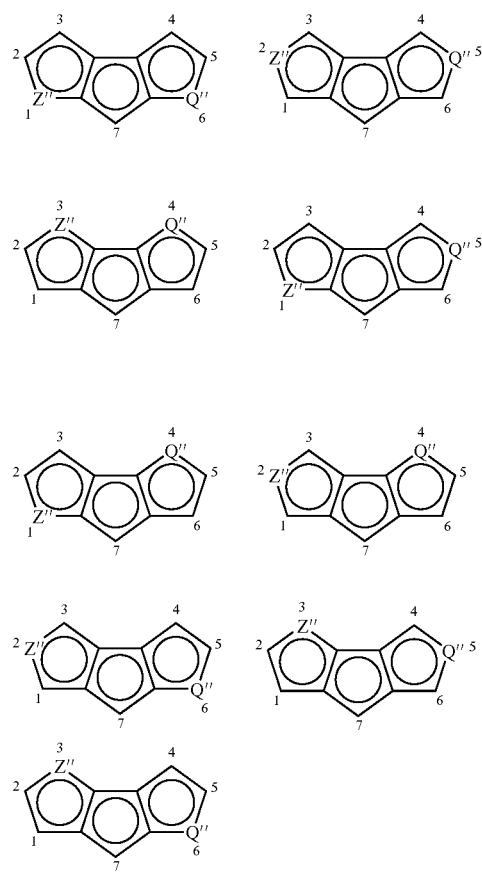

Non-limiting examples of heteroindenyls include:

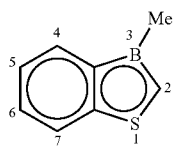
3-dimethylamino-1,3-benzothiaborollide

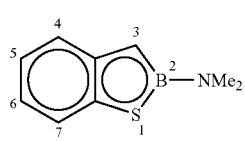
2-dimethylamino-1,2-benzothiaborollide

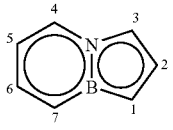
3a, 7a-azaborindenyl

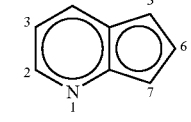
cyclopenta[b]pyridyl

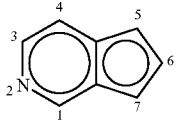
cyclopenta[c]pyridyl

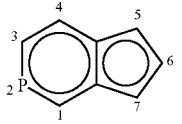
cyclopenta[c]phosphinyl

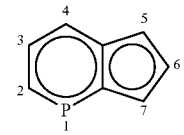
cyclopenta[b]phosphinyl

Further non-limiting examples of heteroindenyls include cyclopenta[b]arsinyl, cyclopenta[c]arsinyl, cyclopenta[b]stibinyl, cyclopenta[c]stibinyl, 3-dihydrocarbylamino-1,3-benzothiaborollide, 2-dihydrocarbylamino-1,2-benzothiaborollide, 3-hydrocarbyloxy-1,3-benzothiaborollide, 2-hydrocarbyloxy-1,2-benzothiaborollide, 3-hydrocarbyl-1,3-benzothiaborollide, and 2-hydrocarbyl-1,2-benzothiaborollide, where hydrocarbyl is a "hydrocarbyl radical" as previously defined.

Non-limiting examples of heterofluorenyls include:

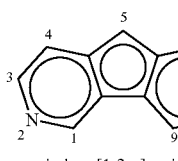
indeno[1,2-c]pyridyl

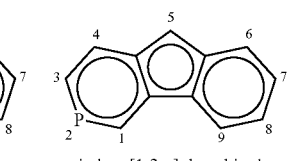
indeno[1,2-c]phosphinyl

Non-limiting examples of heterocyclopentanaphthyls include:

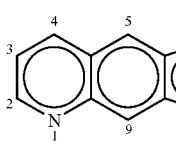
cyclopenta[g]quinolyl

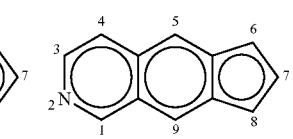
cyclopenta[g]isoquinolyl

Further non-limiting examples of heterocyclopentanaphthyls include cyclopenta[g]phosphinolyl, cyclopenta[g]isophosphinolyl, cyclopenta[g]arsinolyl, and cyclopenta[g]isoarsinolyl.

Non-limiting examples of heterocyclopentaindenyls include:

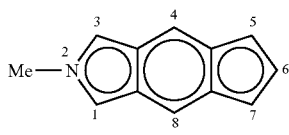
2-methylcyclopenta[f]isoindolyl

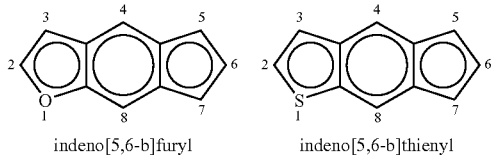
indeno[5,6-b]furyl

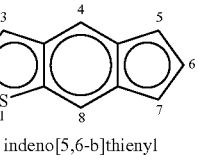
indeno[5,6-b]thienyl

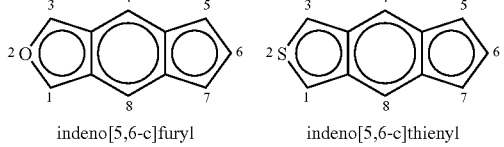
indeno[5,6-c]furyl

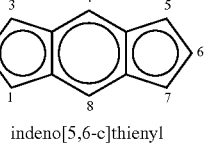
indeno[5,6-c]thienyl

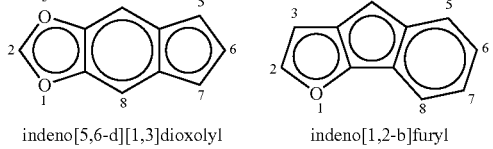
indeno[5,6-d][1,3]dioxolyl

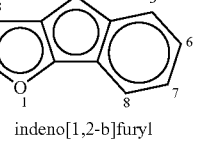
indeno[1,2-b]furyl

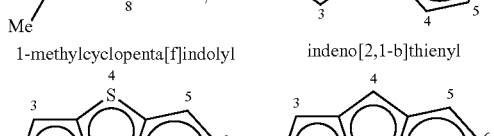
1-methylcyclopenta[f]indolyl

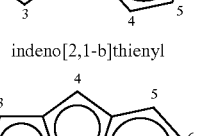
indeno[2,1-b]thienyl

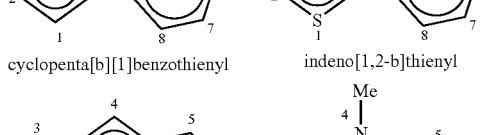
cyclopenta[b][1]benzothienyl

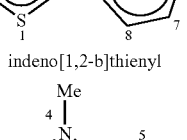
indeno[1,2-b]thienyl

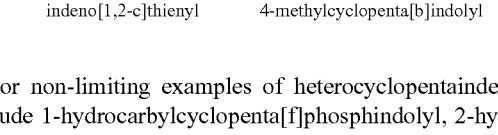
indeno[1,2-c]thienyl

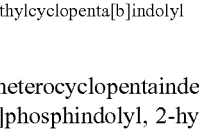
4-methylcyclopenta[b]indolyl

For non-limiting examples of heterocyclopentaindenyls include 1-hydrocarbylcyclopenta[f]phosphindolyl, 2-hydrocarbylcyclopenta[f]isophosphindolyl, 1-hydrocarbylcyclopenta[f]arsindolyl, 2-hydrocarbylcyclopenta[f]isoarsindolyl, indeno[5,6-b]selenophenyl, indeno[5,6-b]tellurophenyl, indeno[5,6-c]selenophenyl, indeno[5,6-c]tellurophenyl, 2-hydrocarbylcyclopenta[f]isoindolyl, and 1-hydrocarbylcyclopenta[f]indolyl, where hydrocarbyl is a "hydrocarbyl radical" as previously defined.

Non-limiting examples of heterobenzocyclopentaindenyls include:

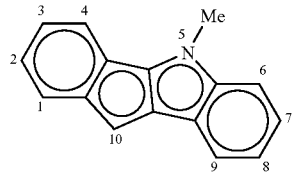

5-methylindeno[1,2-b]indolyl

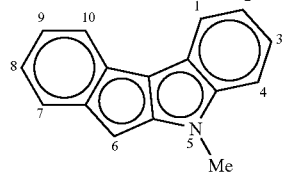

5-methylindeno[2,1-b]indolyl

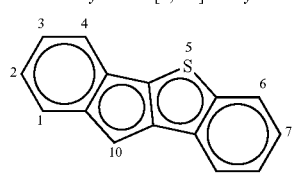

indeno[1,2-b][1]benzothienyl

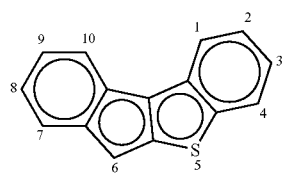

indeno[2,1-b][1]benzothienyl

Further non-limiting examples of heterobenzocyclopentaindenyls include 5-hydrocarbylindeno[1,2-b]indolyl and 5-hydrocarbylindeno[2,1-b]indolyl, where hydrocarbyl is a "hydrocarbyl radical" as previously defined.

A "ring heteroatom" is a heteroatom that is within a cyclic ring structure. A "heteroatom substituent" is a heteroatom containing group that is directly bonded to a ring structure through the heteroatom. The terms "ring heteroatom" and "heteroatom substituent" are illustrated below where Z" is a heteroatom group preferably S, O, Se, Te, N—R#, P—R#, As—R#, Sb—R# or B—R# and each R# is independently hydrogen or a hydrocarbyl, substituted hydrocarbyl, halocarbyl or substituted halocarbyl radical as defined above, and two R# may join together to form a substituted or unsubstituted saturated, partially unsaturated or aromatic cyclic or polycyclic ring structure. If R# is bonded to boron, R# can additionally be a Group 15 or Group 16 group where the heteroatom is directly bonded to boron and R# is then preferably an O—R## group or an N—R##$_2$ group, where each R## is independently hydrogen or a hydrocarbyl, substituted hydrocarbyl, halocarbyl or substituted halocarbyl radical as defined above and two R## may join together to form a substituted or unsubstituted saturated, partially unsaturated or aromatic cyclic or polycyclic ring structure.

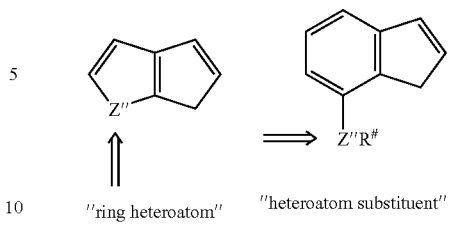

"ring heteroatom"  "heteroatom substituent"

A "ring carbon atom" is a carbon atom that is part of a cyclic ring structure. By this definition, an indenyl fragment has nine ring carbon atoms.

A "bondable ring position" is a ring position that is capable of bearing a substituent or bridging substituent. For example, cyclopenta[b]thienyl has five bondable ring positions (at the carbon atoms) and one non-bondable ring position (the sulfur atom); cyclopenta[b]pyrrolyl has six bondable ring positions (at the carbon atoms and at the nitrogen atom).

The term "arenyl" ligand is used herein to mean an unsaturated cyclic hydrocarbyl ligand that can consist of one ring, or two or more fused or catenated rings. Cyclopentadienyl ligands, indenyl ligands, and fluorenyl ligands are all examples of arenyl ligands.

As used herein, the term "monocyclic ligand" is intended to mean any substituted or unsubstituted $C_5$ to $C_{100}$ monoanionic aromatic five-membered or six-membered single ring structure composed of ring carbon atoms, either alone or in combination with one or more ring heteroatoms. Further, the term "monocyclic arenyl ligand" is used herein to mean a substituted or unsubstituted monoanionic $C_5$ to $C_{100}$ hydrocarbyl ligand that contains an aromatic five-membered single hydrocarbyl ring structure (also referred to as a cyclopentadienyl ring).

As used herein, the term "polycyclic ligand" is intended to mean any substituted or unsubstituted C5 to C103 monoanionic partially unsaturated or aromatic multiple fused ring structure containing at least one aromatic five-membered ring structure, said ligand composed of ring carbon atoms, either alone or in combination with one or more ring heteroatoms. Further, the term "polycyclic arenyl ligand" is used herein to mean a substituted or unsubstituted monoanionic C8 to C103 hydrocarbyl ligand that contains an aromatic five-membered hydrocarbyl ring (also referred to as a cyclopentadienyl ring) that is fused to one or two partially unsaturated, or aromatic hydrocarbyl ring structures which may be fused to additional saturated, partially unsaturated, or aromatic hydrocarbyl rings.

Monocyclic ligands include, but are not limited to, substituted or unsubstituted heterocyclopentadienyls, heterophenyls, and cyclopentadienyls. Monocyclic arenyl ligands, include substituted or unsubstituted cyclopentadienyls. Polycyclic ligands include, but are not limited to, substituted or unsubstituted, partially unsaturated or aromatic heteroindenyls, heteropentalenyls, heterocyclopentapentalenyls, heterofluorenyls, heterocyclopentanaphthyls, heterocyclopentaindenyls, heterobenzocyclopentaindenyls, indenyls, pentalenyls, fluorenyls, and cyclopentanaphthyls. Polycyclic arenyl ligands include, but are not limited to, substituted or unsubstituted, partially unsaturated or aromatic indenyls, pentalenyls, fluorenyls, and cyclopentanaphthyls.

Non-limiting examples of polycyclic arenyl ligands, named as monoanionic ligands, include indenyl, 4,5-dihydroindenyl, 4,7-dihydroindenyl, 4,5,6,7-tetrahydroindenyl, fluorenyl, 1,2-dihydrotetrahydrofluorenyl, 1,4-dihydrotetrahydrofluorenyl, 3,4-dihydrotetrahydrofluorenyl, 1,2,3,4-tetrahydrofluorenyl, 1,2,5,6-tetrahydrofluorenyl, 1,2,7,8-tetrahydrofluorenyl, 3,4,5,6-tetrahydrofluorenyl, 1,4,5,8-tetrahydrofluorenyl, 1,2,3,4,5,6,7,8-octahydrofluorenyl, cyclopenta[b]naphthyl, 4,4a-dihydrocyclopenta[b]naphthyl, 5,6-dihydrocyclopenta[b]naphthyl, 5,8-dihydrocyclopenta[b]naphthyl, 4,9-dihydrocyclopenta[b]naphthyl, 4,4a,5,6-tetrahydrocyclopenta[b]naphthyl, 4,5,8,9-tetrahydrocyclopenta[b]naphthyl, 4,4a,7,8-tetrahydrocyclopenta[b]naphthyl, 4,4a,8a,9-tetrahydrocyclopenta[b]naphthyl, 5,6,7,8-tetrahydrocyclopenta[b]naphthyl, 4,4a,5,8-tetrahydrocyclopenta[b]naphthyl, 4,5,6,9-tetrahydrocyclopenta[b]naphthyl, 4,6,7,8-tetrahydrocyclopenta[b]naphthyl, 4,6,7,9-tetrahydrocyclopenta[b]naphthyl, 4,4a,5,9-tetrahydrocyclopenta[b]naphthyl, 4,4a,5,6,7,8-hexahydrocyclopenta[b]naphthyl, 4,4a,5,6,8a,9-hexahydrocyclopenta[b]naphthyl, 4,4a,5,8,8a,9-hexahydrocyclopenta[b]naphthyl, 4,5,6,7,8,9-hexahydrocyclopenta[b]naphthyl, 4,4a,5,6,7,9-hexahydrocyclopenta[b]naphthyl, 4,4a,5,6,7,8,8a,9-octahydrocyclopenta[b]naphthyl, cyclopenta[a]naphthyl, 4,5-dihydrocyclopenta[a]naphthyl, 6,7-dihydrocyclopenta[a]naphthyl, 8,9-dihydrocyclopenta[a]naphthyl, 5a,9a-dihydrocyclopenta[a]naphthyl, 6,9-dihydrocyclopenta[a]naphthyl, 7,9a-dihydrocyclopenta[a]naphthyl, 4,9a-dihydrocyclopenta[a]naphthyl, 5a,8-dihydrocyclopenta[a]naphthyl, 4,5,5a,9a-tetrahydrocyclopenta[a]naphthyl, 4,5,6,7-tetrahydrocyclopenta[a]naphthyl, 4,5,8,9-tetrahydrocyclopenta[a]naphthyl, 5a,6,7,9a-tetrahydrocyclopenta[a]naphthyl, 6,7,8,9-tetrahydrocyclopenta[a]naphthyl, 5a,8,9,9a-tetrahydrocyclopenta[a]naphthyl, 4,5,7,9a-tetrahydrocyclopenta[a]naphthyl, 5a,6,7,9a-tetrahydrocyclopenta[a]naphthyl, 7,8,9,9a-tetrahydrocyclopenta[a]naphthyl, 4,6,7,9a-tetrahydrocyclopenta[a]naphthyl, 4,8,9,9a-tetrahydrocyclopenta[a]naphthyl, 4,5,6,9-tetrahydrocyclopenta[a]naphthyl, 4,5,5a,8-tetrahydrocyclopenta[a]naphthyl, 5a,6,7,8-tetrahydrocyclopenta[a]naphthyl, 5a,6,9,9a-tetrahydrocyclopenta[a]naphthyl, 5a,6,7,8,9,9a-hexahydrocyclopenta[a]naphthyl, 4,6,7,8,9,9a-hexahydrocyclopenta[a]naphthyl, 4,5,7,8,9,9a-hexahydrocyclopenta[a]naphthyl, 4,5,5a,8,9,9a-hexahydrocyclopenta[a]naphthyl, 4,5,5a,6,9,9a-hexahydrocyclopenta[a]naphthyl, 4,5,5a,6,7,9a-hexahydrocyclopenta[a]naphthyl, 4,5,5a,6,7,8-hexahydrocyclopenta[a]naphthyl, 4,5,6,7,8,9-hexahydrocyclopenta[a]naphthyl, 4,5,5a,6,7,8,9a-hexahydrocyclopenta[a]naphthyl, 4,5,5a,6,7,8,9,9a-octahydrocyclopenta[a]naphthyl, 5,6-trimethyleneindenyl, 4,5-trimethyleneindenyl, 5,6-pentamethyleneindenyl, 4,5-pentamnethyleneindenyl, 5,6-hexamethyleneindenyl, 4,5-hexamethyleneindenyl, 5,6-heptamethyleneindenyl, 4,5-heptamethyleneindenyl, 5,6-octamethyleneindenyl, 4,5-octamethyleneindenyl, 5,6-nonamethyleneindenyl, 4,5-nonamethyleneindenyl, 5,6-decamethyleneindenyl, 4,5-decamethyleneindenyl, 5,6-undecamethyleneindenyl, 4,5-undecamethyleneindenyl, 5,6-dodecamethyleneindenyl, 4,5-dodecamethyleneindenyl, 5,6-tridecamethyleneindenyl, 4,5-tridecamethyleneindenyl, 5,6-tetradecarnethyleneindenyl, 4,5-tetradecamethyleneindenyl, 5,6-pentadecamethyleneindenyl, 4,5-pentadecamethyleneindenyl, 5,6-hexadecamethyleneindenyl, 4,5-hexadecamethyleneindenyl, 5,6-heptadecamethyleneindenyl, 4,5-heptadecamethyleneindenyl, 5,6-octadecamethyleneindenyl, 4,5-octadecamethyleneindenyl, 5,6-nonadecamethyleneindenyl, 4,5-nonadecanethyleneindenyl, 5,6-eicosamethyleneindenyl, 4,5-eicosamethyleneindenyl, (6Z, 8Z, 10Z)-cycloocta[e]indenyl, (5Z 7Z, 9Z)-cycloocta[f]indenyl, (5E, 7Z, 9E, 11Z 13E)-cyclododeca[f]indenyl, (6E,8Z, 10E, 12Z, 14E)-cyclododeca[e]indenyl, benz[a]fluorenyl, benz[b]fluorenyl, benz[c]fluorenyl, naphth[2,3-a]fluorenyl, naphth[2,3-b]fluorenyl, naphth[2,3-c]fluorenyl, naphth[1,2-a]fluorenyl, naphth[1,2-b]fluorenyl, naphth[1,2-c]fluorenyl, 2,3-tetramethylenefluorenyl, 1,2-tetramethylenefluorenyl, 3,4-tetrarnethylenefluorenyl, 2,3-trimethylenefluorenyl, 1,2-trimethylenefluorenyl, 3,4-trimethylenefluorenyl, 2,3-pentamethylenefluorenyl, 1,2-pentamethylenefluorenyl, 3,4-pentamethylenefluorenyl, 2,3-hexamethylenefluorenyl, 1,2-hexarnethylenefluorenyl, 3,4-hexamethylenefluorenyl, 2,3-heptamethylenefluorenyl, 1,2-heptamethylenefluorenyl, 3,4-heptamethylenefluorenyl, 2,3-octamethylenefluorenyl, 1,2-octamethylenefluorenyl, 3,4-octamethylenefluorenyl, 2,3-nonamethylenefluorenyl, 1,2-nonamethylenefluorenyl, 3,4-nonamethylenefluorenyl, 2,3-decamethylenefluorenyl, 1,2-decamethylenefluorenyl, 3,4-decamethylenefluorenyl, 2,3-undecamethylenefluorenyl, 1,2-undecamethylenefluorenyl, 3,4-undecamethylenefluorenyl, 2,3-dodecamethylenefluorenyl, 1,2-dodecamethylenefluorenyl, 3,4-dodecamethylenefluorenyl, 2,3-tetramethylene-6,7-tetramethylenefluorenyl, 1,2-tetramethylene-7,8-tetramethylenefluorenyl, 3,4-tetramethylene-5,6-tetramethylenefluorenyl, bis-benz[2,3;6,7]fluorenyl, bis-benz[2,3 ;5,6]fluorenyl, bis-benz[1,2;7,8]fluorenyl, bis-benz[1,2;5,6]fluorenyl, bis-benz[1,2;6,7]fluorenyl, bis-benz[1,2;7,8]fluorenyl, and bis-benz[3,4;5,6]fluorenyl, Partially hydrogenated polycyclic arene ligands retain the numbering scheme of the parent polycyclic arene ligand, namely the numbering schemes defined for indenyl, fluorenyl, cyclopenta[b]naphthyl, cyclopenta[a]naphthyl ligands.

In the context of this document, "homopolymerization" would produce a polymer made from one monomer. For example, homopolymerization of propylene would produce homopolypropylene. Homopolymerization of ethylene would produce homopolyethylene. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers.

Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane.

Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

Non-limiting examples of vinylaromatic olefins include styrene, para-methylstyrene, para-t-butylstyrene, vinylnaphthylene, vinyltoluene, and divinylbenzene.

Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and non-silicon atoms such as for example B, O, S, Se, Te, N, P, Ge, Sn, Pb, As, F, Cl, Br, or I, are contemplated, where such non-carbon or non-silicon moieties are sufficiently far removed from the double bond so as not to interfere with the coordination polymerization reaction with the catalyst and so to retain the generally hydrocarbyl characteristic. By sufficiently far removed from the double bond we intend that the number of carbon atoms, or the number of carbon and silicon atoms, separating the double bond and the non-carbon or non-silicon moiety is preferably 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or non-silicon moiety. Examples include 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the monomer(s) used in the oligomerization or polymerization reaction. For example, the mer of polyethylene would be ethylene.

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The transition metal compound may be neutral as in a precatalyst, or a charged species with a counter ion as in an activated catalyst system.

Catalyst precursor is also often referred to as precatalyst, catalyst, catalyst compound, catalyst precursor, transition metal compound or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

DETAILED DESCRIPTION OF THE EMBODIMENTS

The present invention is directed to a process for producing substituted transition metal compounds, preferably substituted metallocene compounds, from precursors containing halogen and/or sulfonate substituted monocyclic or polyclic ligands, and to the use of the resulting transition metal compounds in combination with suitable activators as catalysts for the the polymerization of olefins, such as ethylene and propylene.

In one embodiment, the invention relates to a process for producing a substituted transition metal compound, the process comprising contacting: (a) a transition metal compound comprising at least one ligand having a halogen or sulfonate substituent directly bonded to any sp² carbon atom at a bondable ring position of said ligand, with (b) a transfer-agent capable of replacing the halogen or sulfonate substituent of the ligand with a hydrocarbyl, substituted hydrocarbyl, halocarbyl, substituted halocarbyl, silylcarbyl, or germylcarbyl substituent, and (c) a coupling-catalyst.

Preferably, the transition metal is a Group 3-10 element, preferably a Group 4 element.

Generally, the halogen or sulfonate substituent on the ligand is a chloro, bromo, iodo, tosylate or triflate substituent, and preferably is a chloro or bromo substituent.

In another embodiment, the present invention provides a process for producing a substituted metallocene compound, the process comprising:

(a) providing a first compound represented by the formula (1):

wherein:

M is a transition metal atom having a coordination number of n (preferably 2, 3, 4, 5, or 6) selected from Group 3, 4, 5 or 6 of the Periodic Table of Elements, or a lanthanide metal atom, or actinide metal atom, preferably a Group 4 transition metal atom selected from titanium, zirconium or hafnium;

A is a monocyclic or polycyclic ligand that is pi-bonded to M and is substituted with at least one halogen or sulfonate substituent directly bonded to any sp² carbon atom at a bondable ring position of the ligand; and each X is, independently, a univalent anionic ligand, or two X are joined and bound to the metal atom to form a metallocycle ring, or two X are joined to form a chelating ligand, a diene ligand, or an alkylidene ligand; and (b) reacting said first compound with a transfer-agent which comprises a hydrocarbyl, substituted hydrocarbyl, halocarbyl, substituted halocarbyl, silylcarbyl, or germylcarbyl radical capable of replacing said at least one halogen or sulfonate substituent of said first compound under reaction conditions, and in the presence of a coupling-catalyst In a preferred embodiment, the ligand A may be a substituted monocyclic or substituted polycyclic ligand, preferably a substituted monocyclic arenyl or substituted polycyclic arenyl ligand. In another embodiment, the ligand A may include one or more ring heteroatoms selected from boron, a Group 14 atom that is not carbon, a Group 15 atom, and a Group 16 atom. Alternately, the ligand A may be selected from substituted cyclopentadienyl, substituted heterocyclopentadienyl, substituted indenyl, substituted heteroindenyl, substituted fluorenyl, substituted heterofluorenyl, substituted cyclopentanaphthyl, substituted heterocyclopentanaphthyl, substituted heterophenyl, substituted heterocyclopentapentalenyl, substituted heterocyclopentaindenyl, and substituted heterobenzocyclopentaindenyl ligands.

In a particularly preferred embodiment ligand A is a halogenated cylopentadienyl, halogenated indenyl, or halogenated fluorenyl group, preferably a brominated cylopentadienyl, brominated indenyl, or brominated fluorenyl group.

Generally, the halogen or sulfonate substituent of ligand A is a chloro, bromo, iodo, tosylate or triflate substituent, and preferably is a chloro or bromo substituent. The transfer-agent will normally be an organometallic transfer-agent comprising a R*M' unit, where the metal M' is selected from boron, tin, magnesium, lithium, aluminum, silicon, copper, and zinc, and R* is selected from hydrocarbyl, substituted hydrocarbyl, halocarbyl, substituted halocarbyl, silylcarbyl, or a germylcarbyl radical. Alternatively, the transfer-agent can be an organic molecule R*H where R* is selected from hydrocarbyl, substituted hydrocarbyl, halocarbyl, substituted halocarbyl, silylcarbyl, or a germylcarbyl radical. Preferred examples of R*** include methyl, ethyl, n-propyl, isopropyl, n-butyl, sec-butyl, isobutyl, tert-butyl, cyclopentyl, cyclohexyl, benzyl, 4-methylbenzyl, 4-methoxybenzyl, 4-trifluoromethyl, diphenylmethyl, adamantyl, cyclohexenyl, isopropenyl, 2-phenylethenyl, trimethylsilylmethyl, neopentyl, methoxymethyl, 3-methoxypropyl, dimethylaminomethyl, diphenylphosphinomethyl, 2-pyridyl, 4-pyridyl, 2-thienyl, 2-benzothienyl, 2-benzofuryl, 3-(N-methylindolyl), phenyl, 2-methylphenyl, 3-methylphenyl, 4-methylphenyl, 4-tert-butylphenyl, 2,6-dimethylphenyl, 2,6-diisopropylphenyl, 3,5-dimethylphenyl, 2,5-dimethylphenyl, 3,5-diisopropylphenyl, 3,5-di-tert-butylphenyl, 2-isopropylphenyl, 3-trifluoromethylphenyl, 4-fluorophenyl, 4-methoxyphenyl, 2-methoxyphenyl, 4-dimethylaminophenyl, 1-naphthyl, 2-naphthyl, and pentafluorophenyl.

In a further embodiment, the present invention provides a process for producing a substituted metallocene compound, the process comprising:

(a) providing a first compound represented by the formula (2):

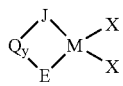

wherein

M is a group 3, 4, 5 or 6 transition metal atom, or a lanthanide metal atom, or actinide metal atom, preferably a Group 4 transition metal atom selected from titanium, zirconium or hafnium;

each of J and E is independently a substituted or unsubstituted, monocyclic or polycyclic ligand pi-bonded to M, wherein at least one of J and E includes at least one halogen or sulfonate substituent directly bonded to an $sp^2$ carbon atom at a bondable ring position of the ligand;

Q is an optional bridging group that is bonded to E and J, and is present when y is one and absent when y is zero;

y is zero or one; and each X is, independently, a univalent anionic ligand, or two X are joined and bound to the metal atom to form a metallocycle ring, or two X are joined to form a chelating ligand, a diene ligand, or an alkylidene ligand; and (b) reacting said first compound with a transfer-agent which comprises a hydrocarbyl, substituted hydrocarbyl, halocarbyl, substituted halocarbyl, silylcarbyl, germylcarbyl radical capable of replacing said at least one halogen or sulfonate substituent of said first compound under reaction conditions, and in the presence of a coupling-catalyst.

Each of the ligands J and E may be a substituted or unsubstituted monocyclic or polycyclic ligand, provided that at least J or E is a substituted moncylclic or polycyclic ligand. For example, the ligands J and E may each be selected from substituted or unsubstituted cyclopentadienyl, heterocyclopentadienyl, indenyl, heteroindenyl, fluorenyl, heterofluorenyl, cyclopentanaphthyl, heterocyclopentanaphthyl, heterophenyl, heterocyclopentapentalenyl, heterocyclopentaindenyl, and heterobenzocyclopentaindenyl ligands. In some embodiments, the ligand J and or E may include one or more ring heteroatoms selected from boron, a Group 14 atom that is not carbon, a Group 15 atom, and a Group 16 atom. In a preferred embodiment, each of J and E is independently a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, or a substituted or unsubstituted fluorenyl ligand, a substituted or unsubstituted heterofluorenyl ligand, and a substituted or unsubstituted cyclopentanaphthyl, or a substituted or unsubstituted heterocyclopentanaphthyl ligand, or a substituted or unsubstituted heterophenyl ligand, or a substituted or unsubstituted heterocyclopentapentalenyl ligand, or a substituted or unsubstituted heterocyclopentaindenyl ligand, or a substituted or unsubstituted heterobenzocyclopentaindenyl ligand.

Generally, the halogen or sulfonate substituent is a chloro, bromo, iodo, tosylate or triflate substituent, and preferably is a chloro or bromo substituent.

Preferably, Q is present and is a bridging group containing at least one Group 13, 14, 15, or 16 element, in particular boron or a Group 14, 15 or 16 element, and Q can be bonded to any bondable ring position of J and E. Examples of suitable bridging groups include P(=S)R', P(=Se)R', P(=O)R', R'2C, R'2Si, R'2Ge, R'2CCR'2, R'2CCR'2CR'2, R'2CCR'2CR'2CR'2, R'C=CR', R'C=CR'CR'2, R'2CCR'=CR'CR'2, R'C=CR'CR'=CR', R'C=CR'CR'2CR'2, R'2CSiR'2, R'2SiSiR'2, R'2CSiR'2CR'2, R'2SiCR'2SiR'2, R'C=CR'SiR'2, R'2CGeR'2, R'2GeGeR'2, R'2CGeR'2CR'2, R'2GeCR'2GeR'2, R'2SiGeR'2, R'C=CR'GeR'2, R'B, R'2C—BR', R'2C—BR'—CR'2, R'2C—O—CR'2, R'2CR'2C—O—CR'2CR'2, R'2C—O—CR'2CR'2, R'2C—O—CR'=CR', R'2C—S—CR'2, R'2CR'2C—S—CR'2CR'2, R'2C—S—CR'2CR'2, R'2C—S—CR'=CR', R'2C—Se—

CR'2, R'2CR'2C—Se—CR'2CR'2, R'2C—Se—CR'2CR'2, R'2C—Se—CR'=CR', R'2C—N=CR', R'2C—NR'—CR'2, R'2C—NR'—CR'2, R'2C—NR'—CR'=CR', R'2CR'2C—NR'—CR'2CR'2, R'2C—P=CR', R'2C—PR'—CR'2, O, S, Se, Te, NR', PR', AsR', SbR', O—O, S—S, R'N—NR', R'P—PR', O—S, O—NR', O—PR', S—NR', S—PR', and R'N—PR' where R' is hydrogen or a C1-C20 containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferred examples for the bridging group Q include CH2, CH2CH2, CH(CH3)2, SiMe2, SiPh2, SiMePh, Si(CH2)3, Si(CH2)4, O, S, NPh, PPh, NMe, PMe, NEt, NPr, NBu, PEt, PPr, and PBu.

The transfer-agent will normally be an organometallic transfer-agent comprising an R*M' unit, where the metal M' is selected from boron, tin, magnesium, lithium, aluminum, silicon, copper, and zinc, and R* is selected from hydrocarbyl, substituted hydrocarbyl, halocarbyl, substituted halocarbyl, silylcarbyl, or a germylcarbyl radical. Alternatively, the transfer-agent can be an organic molecule R*H where R* is selected from hydrocarbyl, substituted hydrocarbyl, halocarbyl, substituted halocarbyl, silylcarbyl, or a germylcarbyl radical. Preferred examples of R*** include methyl, ethyl, n-propyl, isopropyl, n-butyl, sec-butyl, isobutyl, tert-butyl, cyclopentyl, cyclohexyl, benzyl, 4-methylbenzyl, 4-methoxybenzyl, 4-trifluoromethyl, diphenylmethyl, adamantyl, cyclohexenyl, isopropenyl, 2-phenylethenyl, trimethylsilylmethyl, neopentyl, methoxymethyl, 3-methoxypropyl, dimethylaminomethyl, diphenylphosphinomethyl, 2-pyridyl, 4-pyridyl, 2-thienyl, 2-benzothienyl, 2-benzofuryl, 3-(N-methylindolyl), phenyl, 2-methylphenyl, 3-methylphenyl, 4-methylphenyl, 4-tert-butylphenyl, 2,6-dimethylphenyl, 2,6-diisopropylphenyl, 3,5-dimethylphenyl, 2,5-dimethylphenyl, 3,5-diisopropylphenyl, 3,5-di-tert-butylphenyl, 2-isopropylphenyl, 3-trifluoromethylphenyl, 4-fluorophenyl, 4-methoxyphenyl, 2-methoxyphenyl, 4-dimethylaminophenyl, 1-naphthyl, 2-naphthyl, and pentafluorophenyl.

In yet a further embodiment, the present invention provides a process for producing a substituted metallocene compound, the process comprising:

(a) providing a first compound represented by the formula (3):

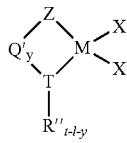

wherein

M is a Group 3, 4, 5 or 6 transition metal atom, or a lanthanide metal atom, or actinide metal atom, preferably a Group 4 transition metal atom selected from titanium, zirconium or hafnium;

Z is a substituted or unsubstituted, monocyclic or polycyclic ligand that is pi-bonded to M;

Q' is an optional bridging group that is bonded to Z and T, and is present when y is one and absent when y is zero;

y is zero or one; and

T is a heteroatom with a coordination number of three from Group 15 or with a coordination number of two from Group 16 of the Periodic Table of Elements, and preferably is nitrogen;

R" is selected from a $C_3$-$C_{100}$ substituted or unsubstituted monocyclic or polycyclic ring structure substituent that is partially unsaturated, unsaturated or aromatic; or a $C_2$-$C_{100}$ substituted or unsubstituted, unsaturated or partially unsaturated, linear or branched alicyclic hydrocarbyl substituent; or a $C_1$-$C_{100}$ substituted or unsubstituted saturated hydrocarbyl radical;

t is the coordination number of the heteroatom T where "t-1-y" indicates the number of R" substituents bonded to T; and each X is, independently, a univalent anionic ligand, or two X are joined and bound to the metal atom to form a metallocycle ring, or two X are joined to form a chelating ligand, a diene ligand, or an alkylidene ligand;

provided that Z is substituted with at least one halogen or sulfonate substituent directly bonded to any $sp^2$ carbon atom at a bondable ring position of the ligand Z, or that R" is substituted with at least one halogen or sulfonate substituent bonded to an $sp^2$ carbon atom, or both; and (b) reacting said first compound with a transfer-agent which comprises a hydrocarbyl, substituted hydrocarbyl, halocarbyl, substituted halocarbyl, silylcarbyl, germylcarbyl radical capable of replacing said at least one halogen or sulfonate substituent of said first compound under reaction conditions, and in the presence of a coupling-catalyst.

The ligand Z may be a substituted or unsubstituted monocyclic or polycyclic ligand. For example, the ligand Z may be selected from substituted or unsubstituted cyclopentadienyl, heterocyclopentadienyl, indenyl, heteroindenyl, fluorenyl, heterofluorenyl, cyclopentanaphthyl, heterocyclopentanaphthyl, heterophenyl, heterocyclopentapentalenyl, heterocyclopentaindenyl, and heterobenzocyclopentaindenyl ligands. In some embodiments, Z may include one or more ring heteroatoms selected from boron, a Group 14 atom that is not carbon, a Group 15 atom, and a Group 16 atom. Generally, the halogen or sulfonate substituent on the Z ligand is a chloro, bromo, iodo, tosylate or triflate substituent, and preferably is a chloro or bromo substituent.

When R" is a C3-C100 substituted or unsubstituted monocyclic or polycyclic ring structure substituent that is partially unsaturated, unsaturated or aromatic, and is optionally substituted with a halogen or sulfonate directly bonded to any sp2 carbon atom at a bondable position of the substituent, non-limiting examples of R" include all isomers of cycloalkenes, and all isomers of hydrocarbyl, substituted hydrocarbyl, halocarbyl, substituted halocarbyl, silylcarbyl, germylcarbyl, halogen, or polar group (including sulfonate) substituted cycloalkanes including: cyclopropenyl, cyclobutenyl, cyclopentenyl, cyclohexenyl, cycloheptenyl, cyclooctenyl, cyclononenyl, cyclodecenyl, cycloundecenyl, cyclododecenyl, cyclotridecenyl, cyclotetradecenyl, cyclopentadecenyl, cyclohexadecenyl, cycloheptadecenyl, cyclooctadecenyl, cyclononadecenyl, cycloeicosenyl, cycloheneicosenyl, cyclodocosenyl, cyclotricosenyl, cyclotetracosenyl, cyclopentacosenyl, cyclohexacosenyl, cycloheptacosenyl, cyclooctacosenyl, cyclononacosenyl, cyclotriacontenyl, cyclobutadienyl, cyclopentadienyl, cyclohexadienyl, cycloheptadienyl, cyclooctadienyl, cyclononadienyl, cyclodecadienyl, cycloundecadienyl, cyclododecadienyl, cyclotridecadienyl, cyclotetradecadienyl, cyclopentadecadienyl, cyclohexadecadienyl, cycloheptadecadienyl, cyclooctadecadienyl, cyclononadecadienyl, cycloeicosadienyl, cycloheneicosadienyl, cyclodocosadienyl, cyclotricosadienyl, cyclotetracosadienyl, cyclopentacosadienyl, cyclohexacosadienyl, cycloheptacosadienyl, cyclooctacosadienyl, cyclononacosadienyl, cyclotriacontadienyl, cyclohexatrienyl, cycloheptatrienyl, cyclooctatrienyl, cyclononatrienyl, cyclodecatrienyl, cycloundecatrienyl, cyclododecatrienyl, cyclotridecatrienyl, cyclotetradecatrienyl, cyclopentadecatrienyl, cyclohexadecatrienyl, cycloheptadecatrienyl, cyclooctadecatrienyl, cyclononadecatrienyl, cycloeicosatrienyl, cycloheneicosatrienyl, cyclodocosatrienyl, cyclotricosatrienyl, cyclotetracosatrienyl, cyclopentacosatrienyl, cyclohexacosatrienyl, cycloheptacosatrienyl, cyclooctacosatrienyl, cyclononacosatrienyl, cyclotriacontatrienyl, cyclooctatetrenyl, cyclononatetrenyl, cyclodecatetrenyl, cycloundecatetrenyl, cyclododecatetrenyl, cyclotridecatetrenyl, cyclotetradecatetrenyl, cyclopentadecatetrenyl, cyclohexadecatetrenyl, cycloheptadecatetrenyl, cyclooctadecatetrenyl, cyclononadecatetrenyl, cycloeicosatetrenyl, cycloheneicosatetrenyl, cyclodocosatetrenyl, cyclotricosatetrenyl, cyclotetracosatetrenyl, cyclopentacosatetrenyl, cyclohexacosatetrenyl, cycloheptacosatetrenyl, cyclooctacosatetrenyl, cyclononacosatetrenyl, cyclotriacontatetrenyl, cyclodecapentaenyl, cycloundecapentaenyl, cyclododecapentaenyl, cyclotridecapentaenyl, cyclotetradecapentaenyl, cyclopentadecapentaenyl, cyclohexadecapentaenyl, cycloheptadecapentaenyl, cyclooctadecapentaenyl, cyclononadecapentaenyl, cycloeicosapentaenyl, cycloheneicosapentaenyl, cyclodocosapentaenyl, cyclotricosapentaenyl, cyclotetracosapentaenyl, cyclopentacosapentaenyl, cyclohexacosapentaenyl, cycloheptacosapentaenyl, cyclooctacosapentaenyl, cyclononacosapentaenyl, cyclotriacontapentaenyl, cyclododecahexaenyl, cyclotridecahexaenyl, cyclotetradecahexaenyl, cyclopentadecahexaenyl, cyclohexadecahexaenyl, cycloheptadecahexaenyl, cyclooctadecahexaenyl, cyclononadecahexaenyl, cycloeicosahexaenyl, cycloheneicosahexaenyl, cyclodocosahexaenyl, cyclotricosahexaenyl, cyclotetracosahexaenyl, cyclopentacosahexaenyl, cyclohexacosahexaenyl, cycloheptacosahexaenyl, cyclooctacosahexaenyl, cyclononacosahexaenyl, cyclotriacontahexaenyl, cyclotetradecaheptaenyl, cyclopentadecaheptaenyl, cyclohexadecaheptaenyl, cycloheptadecaheptaenyl, cyclooctadecaheptaenyl, cyclononadecaheptaenyl, cycloeicosaheptaenyl, cycloheneicosaheptaenyl, cyclodocosaheptaenyl, cyclotricosaheptaenyl, cyclotetracosaheptaenyl, cyclopentacosaheptaenyl, cyclohexacosaheptaenyl, cycloheptacosaheptaenyl, cyclooctacosaheptaenyl, cyclononacosaheptaenyl, cyclotriacontaheptaenyl, cyclohexadecaoctaenyl, cycloheptadecaoctaenyl, cyclooctadecaoctaenyl, cyclononadecaoctaenyl, cycloeicosaoctaenyl, cycloheneicosaoctaenyl, cyclodocosaoctaenyl, cyclotricosaoctaenyl, cyclotetracosaoctaenyl, cyclopentacosaoctaenyl, cyclohexacosaoctaenyl, cycloheptacosaoctaenyl, cyclooctacosaoctaenyl, cyclononacosaoctaenyl, cyclotriacontaoctaenyl, cyclooctadecanonaenyl, cyclononadecanonaenyl, cycloeicosanonaenyl, cycloheneicosanonaenyl, cyclodocosanonaenyl, cyclotricosanonaenyl, cyclotetracosanonaenyl, cyclopentacosanonaenyl, cyclohexacosanonaenyl, cycloheptacosanonaenyl, cyclooctacosanonaenyl, cyclononacosanonaenyl, cyclotriacontanonaenyl, cycloeicosadecaenyl, cycloheneicosadecaenyl, cyclodocosadecaenyl, cyclotricosadecaenyl, cyclotetracosadecaenyl, cyclopentacosadecaenyl, cyclohexacosadecaenyl, cycloheptacosadecaenyl, cyclooctacosadecaenyl, cyclononacosadecaenyl, cyclotriacontadecaenyl, cyclodocosaundecaenyl, cyclotricosaundecaenyl, cyclotetracosaundecaenyl, cyclopentacosaundecaenyl, cyclohexacosaundecaenyl, cycloheptacosaundecaenyl, cyclooctacosaundecaenyl, cyclononacosaundecaenyl, cyclotriacontaundecaenyl, cyclotetracosadodecaenyl, cyclopentacosadodecaenyl, cyclohexacosadodecaenyl, cycloheptacosadodecaenyl, cyclooctacosadodecaenyl, cyclononacosadodecaenyl, cyclotriacontadodecaenyl, cyclohexacosatridecaenyl, cycloheptacosatridecaenyl, cyclooctacosatridecaenyl, cyclononacosatridecaenyl, cyclotriacontatridecaenyl, cyclooctacosatetradecaenyl, cyclononacosatetradecaenyl, cyclotriacontatetradecaenyl, cyclotriacontapentadecaenyl, and the like; all isomers of polycyclic alkenes, and all isomers of hydrocarbyl, substituted hydrocarbyl, halocarbyl, substituted halocarbyl, silylcarbyl, germylcarbyl, halogen, or polar group (including sulfonate) substituted polycyclic alkenes including: norbornyl, norbornadienyl spiro[4.5]decenyl, spiro[5.7]tridecenyl, and the like; phenyl, and all isomers of hydrocarbyl, substituted hydrocarbyl, halocarbyl, substituted halocarbyl, silylcarbyl, germylcarbyl, halogen, or polar group (including sulfonate) substituted phenyl including: methylphenyl, dimethylphenyl, trimethylphenyl, tetramethylphenyl, ethylphenyl, diethylphenyl, triethylphenyl, tetraethylphenyl, propylphenyl, dipropylphenyl, tripropylphenyl, tetrapropylphenyl, butylphenyl, dibutylphenyl, tributylphenyl, tetrabutylphenyl, hexylphenyl, dihexylphenyl, trihexylphenyl, tetrahexylphenyl, dimethylethylphenyl, dimethylpropylphenyl, dimethylbutylphenyl, dimethylpentylphenyl, dimethylhexylphenyl, diethylmethylphenyl, diethylpropylphenyl, diethylbutylphenyl, diethylpentylphenyl, diethylhexylphenyl, dipropylmethylphenyl, dipropylethylphenyl, dipropylbutylphenyl, dipropylpentylphenyl, dipropylhexylphenyl, dibutylmethylphenyl, dibutylethylphenyl, dibutylpropylphenyl, dibutylpentylphenyl, dibutylhexylphenyl, methylethylphenyl, methylpropylphenyl, methylbutylphenyl, methylpentylphenyl, methylhexylphenyl, ethylpropylphenyl, ethylbutylphenyl, ethylpentylphenyl, ethylhexylphenyl, propylbutylphenyl, propylpentylphenyl, propylhexylphenyl, butylpentylphenyl, butylhexylphenyl, methoxyphenyl, ethoxyphenyl, propoxyphenyl, butoxyphenyl, pentoxyphenyl, hexoxyphenyl, dimethoxyphenyl, phenoxyphenyl, methylmethoxyphenyl, dimethylaminophenyl, dipropylaminophenyl, bis(dimethylamino)phenyl, methyl(dimethylamino)phenyl, trimethylsilylphenyl, trimethylgermylphenyl, trifluoromethylphenyl, bis(trifluoromethyl)phenyl, trifluoromethoxyphenyl and the like; benzyl, and all isomers of hydrocarbyl, substituted hydrocarbyl, halocarbyl, substituted halocarbyl, silylcarbyl, germylcarbyl, halogen, or polar group (including sulfonate) substituted benzyl including: methylbenzyl, dimethylbenzyl, trimethylbenzyl, tetramethylbenzyl, ethylbenzyl, diethylbenzyl, triethylbenzyl, tetraethylbenzyl, propylbenzyl, dipropylbenzyl, tripropylbenzyl, tetrapropylbenzyl, butylbenzyl, dibutylbenzyl, tributylbenzyl, tetrabutylbenzyl, hexylbenzyl, dihexylbenzyl, trihexylbenzyl, tetrahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, methoxybenzyl, ethoxybenzyl, propoxybenzyl, butoxybenzyl, pentoxybenzyl, hexoxybenzyl, dimethoxybenzyl, phenoxybenzyl, methylmethoxybenzyl, dimethylaminobenzyl, dipropylaminobenzyl, bis(dimethylamino)benzyl, methyl(dimethylamino)benzyl, trifluoromethylbenzyl, bis(trifluoromethylbenzyl), trifluoromethyoxybenzyl, trimethylsilylbenzyl, bis(trimethylsilyl)benzyl, trimethylgermylbenzyl and the like; all isomers of polycyclic areneyls, and all isomers of hydrocarbyl, substituted hydrocarbyl, halocarbyl, substituted halocarbyl, silylcarbyl, gennylcarbyl, halogen, or polar group (including sulfonate) substituted polycyclic areneyls including: aceanthrylenyl, acenaphthylene, acephenanthrylenyl, anthracenyl, azulenyl, biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, naphthalenyl, ovalenyl, pentacenyl, pentalenyl, pentaphenyl, perylenyl, phenalenyl, phenanthrenyl, picenyl, pleiadenyl, pyranthrenyl, pyrenyl, rubicenyl, naphthacenyl, tetraphenylenyl, trinaphthylenyl, triphenylenyl, hexahelicenyl, dibenza[a,h]anthracenyl, indanyl, cholanthrenyl, aceanthrenyl, acephenanthrenyl, 1,2,3,4-tetrahydronaphthalenyl, 5,6-didehydroazulenyl, 1,4-dihydronaphthalenyl, 5H-cyclobut[e]indenyl, cycloheptabk[jk]phenanthrenyl, benz[e]acephenanthrylenyl, octalenyl, pentalene[1,6-cd]pentalenyl, cyclobut[c]indenyl, cyclopenta[1]phenanthrene, naphtha[2,1,8-cde]azulene, fullerenyl and the like; all isomers of substituted ring assemblies, and all isomers of hydrocarbyl, substituted hydrocarbyl, halocarbyl, substituted halocarbyl, silylcarbyl, germylcarbyl, halogen, or polar group (including sulfonate) substituted ring assemblies including: biphenyl, terphenyl, binaphthyl, binorbornenyl, phenyl-terphenyl, phenyl-naphthyl, phenyl-anthracenyl, phenyl-phenanthrenyl, bianthracenyl, biphenanthrenyl, and the like; all isomers of bridged monocyclic and polycyclic arenyls, and all isomers of hydrocarbyl, substituted hydrocarbyl, halocarbyl, substituted halocarbyl, silylcarbyl, germylcarbyl, halogen, or polar group (including sulfonate) substituted bridged monocyclic and polycyclic arenyls including: 1,1-diphenylmethano, 1,2-diphenylethano, 1,2-diphenyletheno, 1,2-dinaphthylethano, 1,2-dinaphthyletheno, 1,1-dinaphthylmethano, 1,1-dianthracenylmethano, 1,2-dianthracenylethano, 1,2-dianthracenyletheno and the like; all isomers of heterocycles, and all isomers of hydrocarbyl, substituted hydrocarbyl, halocarbyl, substituted halocarbyl, silylcarbyl, germylcarbyl, halogen, or polar group (including sulfonate) substituted heterocycles including: acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, □-carbolinyl, chromenyl, thiochromenyl, cinnolinyl, furanyl, imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl, triphenodioxazinyl, triphenodithiazinyl, xanthenyl, chromanyl, thiochromanyl, indolinyl, isochromanyl, isothiochromanyl, isoindolinyl, bipyridyl, pyrido[2,1,6-de]quinolizinyl and the like.

When R" a $C_2$-$C_{100}$ substituted or unsubstitued, unsaturated or partially unsaturated, linear or branched alicyclic hydrocarbyl substituent, and is optionally substituted with a halogen or sulfonate directly bonded to any $sp^2$ carbon atom at a bondable position of the substituent, non-limiting examples of R" include all isomers of alkenes and all isomers of hydrocarbyl, substituted hydrocarbyl, halocarbyl, substituted halocarbyl, silylcarbyl, germylcarbyl, halogen, or polar group (including sulfonate) substituted alkenes including: ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, nonadecadienyl, eicosadienyl, heneicosadienyl, docosadienyl, tricosadienyl, tetracosadienyl, pentacosadienyl, hexacosadienyl, heptacosadienyl, octacosadienyl, nonacosadienyl, triacontadienyl, hexatrienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, octadecatrienyl, nonadecatrienyl, eicosatrienyl, heneicosatrienyl, docosatrienyl, tricosatrienyl, tetracosatrienyl, pentacosatrienyl, hexacosatrienyl, heptacosatrienyl, octacosatrienyl, nonacosatrienyl, triacontatrienyl, octatetrenyl, nonatetrenyl, decatetrenyl, undecatetrenyl, dodecatetrenyl, tridecatetrenyl, tetradecatetrenyl, pentadecatetrenyl, hexadecatetrenyl, heptadecatetrenyl, octadecatetrenyl, nonadecatetrenyl, eicosatetrenyl, heneicosatetrenyl, docosatetrenyl, tricosatetrenyl, tetracosatetrenyl, pentacosatetrenyl, hexacosatetrenyl, heptacosatetrenyl, octacosatetrenyl, nonacosatetrenyl, triacontatetrenyl, decapentaenyl, undecapentaenyl, dodecapentaenyl, tridecapentaenyl, tetradecapentaenyl, pentadecapentaenyl, hexadecapentaenyl, heptadecapentaenyl, octadecapentaenyl, nonadecapentaenyl, eicosapentaenyl, heneicosapentaenyl, docosapentaenyl, tricosapentaenyl, tetracosapentaenyl, pentacosapentaenyl, hexacosapentaenyl, heptacosapentaenyl, octacosapentaenyl, nonacosapentaenyl, triacontapentaenyl, dodecahexaenyl, tridecahexaenyl, tetradecahexaenyl, pentadecahexaenyl, hexadecahexaenyl, heptadecahexaenyl, octadecahexaenyl, nonadecahexaenyl, eicosahexaenyl, heneicosahexaenyl, docosahexaenyl, tricosahexaenyl, tetracosahexaenyl, pentacosahexaenyl, hexacosahexaenyl, heptacosahexaenyl, octacosahexaenyl, nonacosahexaenyl, triacontahexaenyl, tetradecaheptaenyl, pentadecaheptaenyl, hexadecaheptaenyl, heptadecaheptaenyl, octadecaheptaenyl, nonadecaheptaenyl, eicosaheptaenyl, heneicosaheptaenyl, docosaheptaenyl, tricosaheptaenyl, tetracosaheptaenyl, pentacosaheptaenyl, hexacosaheptaenyl, heptacosaheptaenyl, octacosaheptaenyl, nonacosaheptaenyl, triacontaheptaenyl, hexadecaoctaenyl, heptadecaoctaenyl, octadecaoctaenyl, nonadecaoctaenyl, eicosaoctaenyl, heneicosaoctaenyl, docosaoctaenyl, tricosaoctaenyl, tetracosaoctaenyl, pentacosaoctaenyl, hexacosaoctaenyl, heptacosaoctaenyl, octacosaoctaenyl, nonacosaoctaenyl, triacontaoctaenyl, octadecanonaenyl, nonadecanonaenyl, eicosanonaenyl, heneicosanonaenyl, docosanonaenyl, tricosanonaenyl, tetracosanonaenyl, pentacosanonaenyl, hexacosanonaenyl, heptacosanonaenyl, octacosanonaenyl, nonacosanonaenyl, triacontanonaenyl, eicosadecaenyl, heneicosadecaenyl, docosadecaenyl, tricosadecaenyl, tetracosadecaenyl, pentacosadecaenyl, hexacosadecaenyl, heptacosadecaenyl, octacosadecaenyl, nonacosadecaenyl, triacontadecaenyl, docosaundecaenyl, tricosaundecaenyl, tetracosaundecaenyl, pentacosaundecaenyl, hexacosaundecaenyl, heptacosaundecaenyl, octacosaundecaenyl, nonacosaundecaenyl, triacontaundecaenyl, tetracosadodecaenyl, pentacosadodecaenyl, hexacosadodecaenyl, heptacosadodecaenyl, octacosadodecaenyl, nonacosadodecaenyl, triacontadodecaenyl, hexacosatridecaenyl, heptacosatridecaenyl, octacosatridecaenyl, nonacosatridecaenyl, triacontatridecaenyl, octacosatetradecaenyl, nonacosatetradecaenyl, triacontatetradecaenyl, triacontapentadecaenyl, cyclopentylidene, cyclohexylidene, cycloheptylidene, cyclooctylidene, cyclononylidene, cyclodecylidene, cycloundecylidene, cyclododecylidene, and the like.

When R" is a $C_1$-$C_{100}$ substituted or unsubstituted saturated hydrocarbyl radical, non-limiting examples of R" include methyl, ethyl, and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, and triacontyl; cyclopropyl, and all isomers of cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl, cycloeicosyl, cycloheneicosyl, cyclodocosyl, cyclotricosyl, cyclotetracosyl, cyclopentacosyl, cyclohexacosyl, cycloheptacosyl, cyclooctacosyl, cyclononacosyl, and cyclotriacontyl; all isomers of norbornyl, adamantyl, cubanyl, prismanyl, and spiro[4,5]decanyl; pefluoromethyl, perfluoroethyl, and all isomers of perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, and perfluorotriacontyl; fluoromethyl, and all isomers of fluoroethyl, fluoropropyl, fluorobutyl, fluoropentyl, fluorohexyl, fluoroheptyl, fluorooctyl, fluorononyl, fluorodecyl, perfluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, and fluorotriacontyl; methoxymethyl, ethoxymethyl, and all isomers of methoxyethyl, methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, ethoxyethyl, ethoxypropyl, ethoxybutyl, ethoxypentyl, ethoxyhexyl, ethoxyheptyl, ethoxyoctyl, ethoxynonyl, ethoxydecyl, ethoxyundecyl, ethoxydodecyl, ethoxytridecyl, ethoxytetradecyl, ethoxypentadecyl, ethoxyhexadecyl, ethoxyheptadecyl, ethoxyoctadecyl, ethoxynonadecyl, ethoxyeicosyl, ethoxyheneicosyl, ethoxydocosyl, ethoxytricosyl, ethoxytetracosyl, ethoxypentacosyl, ethoxyhexacosyl, ethoxyheptacosyl, ethoxyoctacosyl, ethoxynonacosyl, ethoxytriacontyl, propoxymethyl, propoxyethyl, propoxypropyl, propoxybutyl, propoxypentyl, propoxyhexyl, propoxyheptyl, propoxyoctyl, propoxynonyl, propoxydecyl, propoxyundecyl, propoxydodecyl, propoxytridecyl, propoxytetradecyl, propoxypentadecyl, propoxyhexadecyl, propoxyheptadecyl, propoxyoctadecyl, propoxynonadecyl, propoxyeicosyl, propoxyheneicosyl, propoxydocosyl, propoxytricosyl, propoxytetracosyl, propoxypentacosyl, propoxyhexacosyl, propoxyheptacosyl, propoxyoctacosyl, propoxynonacosyl, propoxytriacontyl, butoxymethyl, butoxyethyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, and butoxytriacontyl; dimethylaminomethyl, and all isomers of dimethylaminoethyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, and dimethylaminotriacontyl; trimethylsilylmethyl, and all isomers of trimethylsilylethyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, and trimethylsilyltriacontyl; trimethylgermylmethyl, and all isomers of trimethylgermylethyl, trimethylgermylpropyl, trimethylgermylbutyl, trimethylgermylpentyl, trimethylgermylhexyl, trimethylgermiylheptyl, trimethylgermyloctyl, trimethylgermylnonyl, trimethylgermyldecyl, trimethylgermylundecyl, trimethylgermyldodecyl, trimethylgermyltridecyl, trimethylgermyltetradecyl, trimethylgermylpentadecyl, trimethylgermylhexadecyl, trimethylgermylheptadecyl, trimethylgermyloctadecyl, trimethylgermylnonadecyl, trimethylgermyleicosyl, trimethylgermylheneicosyl, trimethylgermyldocosyl, trimethylgermyltricosyl, trimethylgermyltetracosyl, trimethylgermylpentacosyl, trimethylgermylhexacosyl, trimethylgermylheptacosyl, trimethylgermyloctacosyl, trimethylgermylnonacosyl, and trimethylgermyltriacontyl.

When the halogen or sulfonate substituent is not on R", preferably, R" is selected from methyl, ethyl, all propyl isomers, all butyl isomers, phenyl, benzyl, phenethyl, 1-adamantyl, cyclododecyl, cyclohexyl and norbornyl.

When the halogen or sulfonate substituent is on R", preferably, R" is selected from 2-bromophenyl, 3-bromophenyl, 4-bromophenyl, 2,6-diisopropyl-4-bromophenyl, 2,6-dimethyl-4-bromophenyl, 2,4,6-trimethyl-3-bromophenyl, 2-bromo-4,6-dimethylphenyl, 2-bromo-4-methylphenyl, 2-bromo-3,4,6-trimethylphenyl, 2-bromo-4-fluorophenyl, 2-bromo-4,6-difluorophenyl, 2,6-dibromophenyl, 2,6-dibromo-4-methylphenyl, 2,6-dibromo-4-fluorophenyl, 2,5-dibromophenyl, and 2,4-dibromophenyl.

Conveniently, in formula (3), t-1-y is equal to 1 and preferably T is a nitrogen atom.

Conveniently, Q' in formula (3) is present and is a bridging group containing at least one Group 13, 14, 15, or 16 element, in particular boron or a Group 14, 15 or 16 element, and Q' in formula (3) can be bonded to any propoxyheneicosyl, propoxydocosyl, propoxytricosyl, propoxytetracosyl, propoxypentacosyl, propoxyhexacosyl, propoxyheptacosyl, propoxyoctacosyl, propoxynonacosyl, propoxytriacontyl, butoxymethyl, butoxyethyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, and butoxytriacontyl; dimethylaminomethyl, and all isomers of dimethylaminoethyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, and dimethylaminotriacontyl; trimethylsilylmethyl, and all isomers of trimethylsilylethyl, trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, and trimethylsilyltriacontyl; trimethylgermylmethyl, and all isomers of trimethylgermylethyl, trimethylgermylpropyl, trimethylgermylbutyl, trimethylgermylpentyl, trimethylgermylhexyl, trimethylgermylheptyl, trimethylgermyloctyl, trimethylgermylnonyl, trimethylgermyldecyl, trimethylgermylundecyl, trimethylgermyldodecyl, trimethylgermyltridecyl, trimethylgermyltetradecyl, trimethylgermylpentadecyl, trimethylgermylhexadecyl, trimethylgermylheptadecyl, trimethylgermyloctadecyl, trimethylgermylnonadecyl, trimethylgermyleicosyl, trimethylgermylheneicosyl, trimethylgermyldocosyl, trimethylgermyltricosyl, trimethylgermyltetracosyl, trimethylgermylpentacosyl, trimethylgermylhexacosyl, trimethylgermylheptacosyl, trimethylgermyloctacosyl, trimethylgermylnonacosyl, and trimethylgermyltriacontyl.

When the halogen or sulfonate substituent is not on R", preferably, R" is selected from methyl, ethyl, all propyl isomers, all butyl isomers, phenyl, benzyl, phenethyl, 1-adamantyl, cyclododecyl, cyclohexyl and norbornyl.

When the halogen or sulfonate substituent is on R", preferably, R" is selected from 2-bromophenyl, 3-bromophenyl, 4-bromophenyl, 2,6-diisopropyl-4-bromophenyl, 2,6-dimethyl-4-bromophenyl, 2,4,6-trimethyl-3-bromophenyl, 2-bromo-4,6-dimethylphenyl, 2-bromo-4-methylphenyl, 2-bromo-3,4,6-trimethylphenyl, 2-bromo-4-fluorophenyl, 2-bromo-4,6-difluorophenyl, 2,6-dibromophenyl, 2,6-dibromo-4-methylphenyl, 2,6-dibromo-4-fluorophenyl, 2,5-dibromophenyl, and 2,4-dibromophenyl.

Conveniently, in formula (3), t-1-y is equal to 1 and preferably T is a nitrogen atom.

Conveniently, Q' in formula (3) is present and is a bridging group containing at least one Group 13, 14, 15, or 16 element, in particular boron or a Group 14, 15 or 16 element, and Q' in formula (3) can be bonded to any bondable ring position of Z. Examples of suitable bridging groups include P(=S)R', P(=Se)R', P(=O)R', R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'—, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', and R'$_2$C—PR'—CR'$_2$ where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferred examples for the bridging group Q' include $CH_2$, $CH_2CH_2$, $CH(CH_3)_2$, $SiMe_2$, $SiPh_2$, SiMePh, $Si(CH_2)_3$, and $Si(CH_2)_4$.

The transfer-agent will normally be an organometallic transfer-agent comprising a R*M' fragment, where the metal M' is selected from boron, tin, magnesium, lithium, aluminum, silicon, copper, and zinc, and R* is selected from hydrocarbyl, substituted hydrocarbyl, halocarbyl, substituted halocarbyl, silylcarbyl, or a germylcarbyl radical. Alternatively, the transfer-agent can be an organic molecule R*H where R* is selected from hydrocarbyl, substituted hydrocarbyl, halocarbyl, substituted halocarbyl, silylcarbyl, or a germylcarbyl radical. Preferred examples of R*** include methyl, ethyl, n-propyl, isopropyl, n-butyl, sec-butyl, isobutyl, tert-butyl, cyclopentyl, cyclohexyl, benzyl, 4-methylbenzyl, 4-methoxybenzyl, 4-trifluoromethyl, diphenylmethyl, adamantyl, cyclohexenyl, isopropenyl, 2-phenylethenyl, trimethylsilylmethyl, neopentyl, methoxymethyl, 3-methoxypropyl, dimethylaminomethyl, diphenylphosphinomethyl, 2-pyridyl, 4-pyridyl, 2-thienyl, 2-benzothienyl, 2-benzofuryl, 3-(N-methylindolyl), phenyl, 2-methylphenyl, 3-methylphenyl, 4-methylphenyl, 4-tert-butylphenyl, 2,6-dimethylphenyl, 2,6-diisopropylphenyl, 3,5-dimethylphenyl, 2,5-dimethylphenyl, 3,5-diisopropylphenyl, 3,5-di-tert-butylphenyl, 2-isopropylphenyl, 3-trifluoromethylphenyl, 4-fluorophenyl, 4-methoxyphenyl, 2-methoxyphenyl, 4-dimethylaminophenyl, 1-naphthyl, 2-naphthyl, and pentafluorophenyl.

Different cross-coupling reactions can be used to produce substituted metallocene compounds according to the process described herein. Generic reaction schemes for coupling reactions are illustrated below where M, X, y, and R*** are as previously defined, Y is Q or Q' as previously defined (in the following formulae, Y is not yttrium) and X* is X* is chloro, bromo, iodo or sulfonate (sulfonate=$OSO_2G$ where G is a hydrocarbyl or halocarbyl):

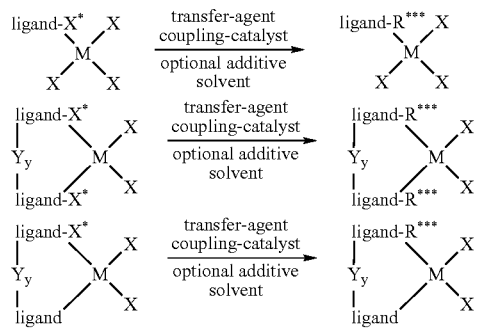

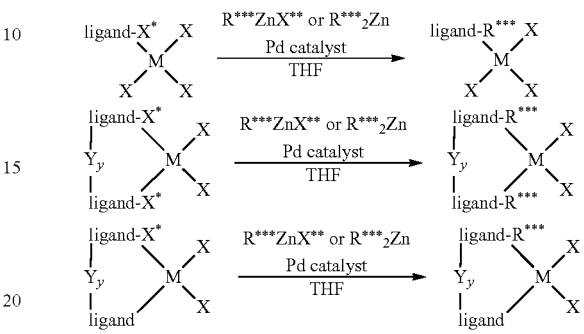

Essentially, the processes described above for producing the substituted transition metal compounds, particularly substituted metallocene compounds, involve a coupling reaction or cross-coupling reaction in which a transfer-agent comprising a R*M' unit, or an organic molecule R*H, is reacted with an a transition metal compound comprising at least one ligand having a halogen or sulfonate substituent directly bonded to any $sp^2$ carbon atom at a bondable ring position of said ligand, where said substituted ligand is represented by ligand-X* where X* is chloro, bromo, iodo or sulfonate (sulfonate=$OSO_2G$ where G is a hydrocarbyl or halocarbyl), usually in the presence of a coupling-catalyst or combination of coupling-catalysts and, when required, in the presence of additives, to produce a substituted transition metal compound wherein the ligand(s) of said substituted transition metal compound is represented by ligand-R*. The transfer-agent, comprising a R*M' unit, contains the nucleophile R*** to be transferred to ligand-X*, as well as a metal-containing fragment M'. Typical metals "M'" useful herein include Al, Zr, Si, B, Li, Mg, Sn, Cu, Zn, and mixtures thereof. R*** is substituted or unsubstituted hydrocarbyl, substituted or unsubstituted halocarbyl, substituted or unsubstituted silylcarbyl, or substituted or unsubstituted germylcarbyl radical. Ligand-X* includes, but is not limited to substituted or unsubstituted cyclopentadienyl, heterocyclopentadienyl, indenyl, heteroindenyl, fluorenyl, heterofluorenyl, cyclopentanaphthyl, heterocyclopentanaphthyl, heterophenyl, heterocyclopentapentalenyl, heterocyclopentaindenyl, and heterobenzocyclopentaindenyl ligands. Additionally, ligand-X* may comprise substituted or unsubstituted monocyclic or polycyclic ring structure substituents that are partially unsaturated, unsaturated or aromatic; or may comprise substituted or unsubstituted, unsaturated or partially unsaturated, linear or branched alicyclic hydrocarbyl substituents. Coupling-catalsyts are catalytic reagents that promote the reaction and are typically selected from nickel, palladium, copper, silver and cobalt compounds. The additives are compounds that enhance the coupling reaction by, for example, increasing regioselectivity, increasing enantioselectivity, suppressing undesired side reactions, activating the coupling-catalyst or other reagents, regenerating the coupling-catalyst, stabilizing the coupling-catalyst or intermediates, coordinating counterions, or accelerating the coupling reaction.

Different cross-coupling reactions can be used to produce substituted metallocene compounds according to the process described herein. For example, the Negishi coupling reaction uses a substituted or unsubstituted hydrocarbyl zinc transfer-agent (R*ZnX or R*$_2$Zn where X is chloride, bromide or iodide, and R*** is substituted or unsubstituted hydrocarbyl, substituted or unsubstituted halocarbyl, substituted or unsubstituted silylcarbyl, or substituted or unsubstituted germylcarbyl radical) with a palladium coupling-catalyst such as bis(tri-tert-butylphosphine)palladium to react with bromine substituent(s) on the metallocene according to the following reactions (where X*, M, X, R*, X, and y are as defined above and Y is as defined for Q and Q' (in the following formulae, Y is not yttrium)):

After reaction, trimethylsilyl chloride is added to react with excess organozinc transfer-agent present. The entire reaction mixture is then evaporated to dryness and tetrahydrofuran (THF) contamination of the metallocene product is eliminated by refluxing the metallocene in toluene. When the bridge, Y, is P(R*), where R* is as defined above, it is first oxidized to P(=O)R* using air or another soft oxidizing agent. After the Negishi coupling reaction, the bridge, P(=O)R*, is reduced back to P(R*) using trichlorosilane. Alternatively, the bridge, P(R*), can be reacted with elemental sulfur or selenium to form the respective P(=S)R* and P(=Se)R* bridges. After the Negishi coupling reaction, the P(=S)R* and P(=Se)R* bridges can be reduced back to P(R***) using trichlorosilane.

Palladium coupling-catalysts that may be used in the Negishi coupling reaction on a metallocene include bis(tri-tert-butyl)phosphine palladium, bis(tricyclohexylphosphine) palladium, trans-dichlorbis(tricyclohexylphosphine) palladium(II), trans-dichlorbis(triphenylphosphine) palladium (II), trans-dichlorbis(tri-o-tolylphosphine) palladium(II), tetrakis(triphenylphosphine) palladium (0), dichloro[1,1'-bis(diphenylphosphino)ferrocene] palladium (II), or palladium compounds such as palladium(II) acetate, palladium(0) dibenzylideneacetone, palladium (II) chloride, palladium (II) bromide, palladium (II) iodide, allyl palladium chloride dimer, palladium (II) trifluoroacetate, bis(tri-o-tolylphoshine) palladium (II) chloride, dichloro(1,5-cyclooctadiene) palladium (II), dichlorobis(benzonitrile) palladium (II), dichlorobis(acetonitrile) palladium (II), bis(2-methylallyl) palladium chloride dimer, crotyl palladium chloride dimer, tris(dibenzylideneacetone) dipalladium (0), or dichlorobis(benzonitrile)palladium (II) used in combination with any of the phosphine and phosphine like reagents (A through N) listed below. When the metallocene is substituted with an iodo ligand, any of the palladium compounds listed above will work to catalyze the coupling reaction even in the absence of phosphine and phosphine like reagents.

Preferred palladium coupling-catalysts that may be used in the Negishi coupling reaction on a metallocene include bis(tri-tert-butyl)phosphine palladium, or palladium(II) acetate, palladium(0) dibenzylideneacetone used in combination with any of the phosphine and phosphine like reagents (A through N) listed below.

Organozinc reagents, R\*\*\*ZnX\*\* or R\*\*\*$_2$Zn, that may be used in the Negishi coupling reaction are those where X\*\* selected from chloride, bromide or iodide, and where R\*\*\* is, independently, selected from (a) hydrocarbyls and all isomers of hydrocarbyls including methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl;

(b) halocarbyls and all isomers of halocarbyls including perfluoropropyl, perfluorobutyl, perfluoropentyl, perfluorohexyl, perfluoroheptyl, perfluorooctyl, perfluorononyl, perfluorodecyl, perfluoroundecyl, perfluorododecyl, perfluorotridecyl, perfluorotetradecyl, perfluoropentadecyl, perfluorohexadecyl, perfluoroheptadecyl, perfluorooctadecyl, perfluorononadecyl, perfluoroeicosyl, perfluoroheneicosyl, perfluorodocosyl, perfluorotricosyl, perfluorotetracosyl, perfluoropentacosyl, perfluorohexacosyl, perfluoroheptacosyl, perfluorooctacosyl, perfluorononacosyl, perfluorotriacontyl, perfluorobutenyl, perfluorobutynyl, fluoropropyl, fluorobutyl, fluoropentyl, fluorohexyl, fluoroheptyl, fluorooctyl, fluorononyl, fluorodecyl, fluoroundecyl, fluorododecyl, fluorotridecyl, fluorotetradecyl, fluoropentadecyl, fluorohexadecyl, fluoroheptadecyl, fluorooctadecyl, fluorononadecyl, fluoroeicosyl, fluoroheneicosyl, fluorodocosyl, fluorotricosyl, fluorotetracosyl, fluoropentacosyl, fluorohexacosyl, fluoroheptacosyl, fluorooctacosyl, fluorononacosyl, fluorotriacontyl, difluorobutyl, trifluorobutyl, tetrafluorobutyl, pentafluorobutyl, hexafluorobutyl, heptafluorobutyl, octafluorobutyl;

(c) substituted hydrocarbyl radicals and all isomers of substituted hydrocarbyl radicals including methoxymethyl, methoxyethyl, methoxypropyl, methoxybutyl, methoxypentyl, methoxyhexyl, methoxyheptyl, methoxyoctyl, methoxynonyl, methoxydecyl, methoxyundecyl, methoxydodecyl, methoxytridecyl, methoxytetradecyl, methoxypentadecyl, methoxyhexadecyl, methoxyheptadecyl, methoxyoctadecyl, methoxynonadecyl, methoxyeicosyl, methoxyheneicosyl, methoxydocosyl, methoxytricosyl, methoxytetracosyl, methoxypentacosyl, methoxyhexacosyl, methoxyheptacosyl, methoxyoctacosyl, methoxynonacosyl, methoxytriacontyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, ethoxyundecyl, ethoxydodecyl, ethoxytridecyl, ethoxytetradecyl, ethoxypentadecyl, ethoxyhexadecyl, ethoxyheptadecyl, methoxyoctadecyl, ethoxynonadecyl, ethoxyeicosyl, ethoxyheneicosyl, ethoxydocosyl, ethoxytricosyl, ethoxytetracosyl, ethoxypentacosyl, ethoxyhexacosyl, ethoxyheptacosyl, methoxyoctacosyl, ethoxynonacosyl, ethoxytriacontyl, propoxymethyl, propoxyethyl, propoxypropyl, propoxybutyl, propoxypentyl, propoxyhexyl, propoxyheptyl, propoxyoctyl, propoxynonyl, propoxydecyl, propoxyundecyl, propoxydodecyl, propoxytridecyl, propoxytetradecyl, propoxypentadecyl, propoxyhexadecyl, propoxyheptadecyl, mpropoxyoctadecyl, propoxynonadecyl, propoxyeicosyl, propoxyheneicosyl, propoxydocosyl, propoxytricosyl, propoxytetracosyl, propoxypentacosyl, propoxyhexacosyl, propoxyheptacosyl, mpropoxyoctacosyl, propoxynonacosyl, propoxytriacontyl, butoxymethyl, butoxyethyl, butoxypropyl, butoxybutyl, butoxypentyl, butoxyhexyl, butoxyheptyl, butoxyoctyl, butoxynonyl, butoxydecyl, butoxyundecyl, butoxydodecyl, butoxytridecyl, butoxytetradecyl, butoxypentadecyl, butoxyhexadecyl, butoxyheptadecyl, butoxyoctadecyl, butoxynonadecyl, butoxyeicosyl, butoxyheneicosyl, butoxydocosyl, butoxytricosyl, butoxytetracosyl, butoxypentacosyl, butoxyhexacosyl, butoxyheptacosyl, butoxyoctacosyl, butoxynonacosyl, butoxytriacontyl, dimethylaminopropyl, dimethylaminobutyl, dimethylaminopentyl, dimethylaminohexyl, dimethylaminoheptyl, dimethylaminooctyl, dimethylaminononyl, dimethylaminodecyl, dimethylaminoundecyl, dimethylaminododecyl, dimethylaminotridecyl, dimethylaaminotetradecyl, dimethylaminopentadecyl, dimethylaminohexadecyl, dimethylaminoheptadecyl, dimethylaminooctadecyl, dimethylaminononadecyl, dimethylaminoeicosyl, dimethylaminoheneicosyl, dimethylaminodocosyl, dimethylaminotricosyl, dimethylaminotetracosyl, dimethylaminopentacosyl, dimethylaminohexacosyl, dimethylaminoheptacosyl, dimethylaminooctacosyl, dimethylaminononacosyl, dimethylaminotriacontyl, methoxybenzyl, ethoxybenzyl, propoxybenzyl, butoxybenzyl, methoxyphenyl, ethoxyphenyl, propoxyphenyl, butoxyphenyl, dimethylaminobenzyl, diethylaminobenzyl, dipropylaminobenzyl, dibutylaminobenzyl, dimethylaminophenyl, diethylaminophenyl, dipropylaminophenyl, dibutylaminophenyl, methylthiobenzyl, ethylthiobenzyl, propylthiobenzyl, butylthiobenzyl, methylthiophenyl, ethylthiophenyl, propylthiophenyl, butylthiophenyl, dimethylphosphinobenzyl, diethylphosphinobenzyl, dipropylphosphinobenzyl, dibutylphosphinobenzyl, methoxychlorophenyl, methoxybromophenyl, methoxyiodophenyl, methoxyfluorophenyl, ethoxychlorophenyl, ethoxybromophenyl, ethoxyiodophenyl, ethoxyfluorophenyl, propoxychlorophenyl, propoxybromophenyl, propoxyiodophenyl, propoxyfluorophenyl, butoxychlorophenyl, butoxybromophenyl, butoxyiodophenyl, butoxyfluorophenyl, dimethylchloroaminophenyl, diethylchloroaminophenyl, dipropoxychlorophenyl, dibutoxychlorophenyl, dimethylbromoaminophenyl, diethylbromoaminophenyl, dipropoxybromophenyl, dibutoxybromophenyl, dimethyliodoaminophenyl, diethyliodoaminophenyl, dipropoxyiodophenyl, dibutoxyiodophenyl, dimethylfluoroaminophenyl, diethylfluoroaminophenyl, dipropoxyfluorophenyl, dibutoxyfluorophenyl, dimethylaminochlorophenyl, diethylaminochlorophenyl, dipropylaminochlorophenyl, dibutylaminochlorophenyl, dimethylaminobromophenyl, diethylaminobromophenyl, dipropylaminobromophenyl, dibutylaminobromophenyl, dimethylaminoiodophenyl, diethylaminoiodophenyl, dipropylaminoiodophenyl, dibutylaminoiodophenyl, dimethylaminofluorophenyl, diethylaminofluorophenyl, dipropylaminofluorophenyl, dibutylaminofluorophenyl, methylthiochlorophenyl, ethylthiochlorophenyl, propylthiochlorophenyl, butylthiochlorophenyl, methylthiobromophenyl, ethylthiobromophenyl, propylthiobromophenyl, butylthiobromophenyl, methylthioiodophenyl, ethylthioiodophenyl, propylthioiodophenyl, butylthioiodophenyl, methylthiofluorophenyl, ethylthiofluorophenyl, propylthiofluorophenyl, butylthiofluorophenyl, benzoyl acid methyl ester, benzoyl acid ethyl ester, benzoyl acid propyl ester, benzoyl acid butyl ester, and the like;

(d) all isomers of silylcarbyl radicals including trimethylsilylpropyl, trimethylsilylbutyl, trimethylsilylpentyl, trimethylsilylhexyl, trimethylsilylheptyl, trimethylsilyloctyl, trimethylsilylnonyl, trimethylsilyldecyl, trimethylsilylundecyl, trimethylsilyldodecyl, trimethylsilyltridecyl, trimethylsilyltetradecyl, trimethylsilylpentadecyl, trimethylsilylhexadecyl, trimethylsilylheptadecyl, trimethylsilyloctadecyl, trimethylsilylnonadecyl, trimethylsilyleicosyl, trimethylsilylheneicosyl, trimethylsilyldocosyl, trimethylsilyltricosyl, trimethylsilyltetracosyl, trimethylsilylpentacosyl, trimethylsilylhexacosyl, trimethylsilylheptacosyl, trimethylsilyloctacosyl, trimethylsilylnonacosyl, trimethylsilyltriacontyl, dimethylphenylsilylpropyl, dimethylphenylsilylbutyl, dimethylphenylsilylpentyl, dimethylphenylsilylhexyl, dimethylphenylsilylheptyl, dimethylphenylsilyloctyl, dimethylphenylsilylnonyl, dimethylphenylsilyldecyl, dimethylphenylsilylundecyl, dimethylphenylsilyldodecyl, dimethylphenylsilyltridecyl, dimethylphenylsilyltetradecyl, dimethylphenylsilylpentadecyl, dimethylphenylsilylhexadecyl, dimethylphenylsilylheptadecyl, dimethylphenylsilyloctadecyl, dimethylphenylsilylnonadecyl, dimethylphenylsilyleicosyl, dimethylphenylsilylheneicosyl, dimethylphenylsilyldocosyl, dimethylphenylsilyltricosyl, dimethylphenylsilyltetracosyl, dimethylphenylsilylpentacosyl, dimethylphenylsilylhexacosyl, dimethylphenylsilylheptacosyl, dimethylphenylsilyloctacosyl, dimethylphenylsilylnonacosyl, dimethylphenylsilyltriacontyl, triethylsilylpropyl, triethylsilylbutyl, triethylsilylpentyl, triethylsilylhexyl, triethylsilylheptyl, triethylsilyloctyl, triethylsilylnonyl, triethylsilyldecyl, triethylsilylundecyl, triethylsilyldodecyl, triethylsilyltridecyl, triethylsilyltetradecyl, triethylsilylpentadecyl, triethylsilylhexadecyl, triethylsilylheptadecyl, triethylsilyloctadecyl, triethylsilylnonadecyl, triethylsilyleicosyl, triethylsilylheneicosyl, triethylsilyldocosyl, triethylsilyltricosyl, triethylsilyltetracosyl, triethylsilylpentacosyl, triethylsilylhexacosyl, triethylsilylheptacosyl, triethylsilyloctacosyl, triethylsilylnonacosyl, triethylsilyltriacontyl, 1,1-dimethyl-silolanyl, 1,1-dimethyl-silinanyl, 1,1-dimethyl-silepanyl, 1,1-diethyl-silolanyl, 1,1-diethyl-silinanyl, 1,1-diethyl-silepanyl and the like;

(e) phenyl and isomers of methylphenyl, ethylphenyl, propylphenyl, butylphenyl, pentylphenyl, hexylphenyl, heptylphenyl, octylphenyl, nonylphenyl, decylphenyl, undecylphenyl, dodecylphenyl, tridecylphenyl, tetradecylphenyl, pentadecylphenyl, hexadecylphenyl, heptadecylphenyl, octadecylphenyl, nonadecylphenyl, eicosylphenyl, heneicosylphenyl, docosylphenyl, tricosylphenyl, tetracosylphenyl, pentacosylphenyl, hexacosylphenyl, heptacosylphenyl, octacosylphenyl, nonacosylphenyl, triacontylphenyl, dimethylphenyl, diethylphenyl, dipropylphenyl, dibutylphenyl, dipentylphenyl, dihexylphenyl, diheptylphenyl, dioctylphenyl, dinonylphenyl, didecylphenyl, diundecylphenyl, didodecylphenyl, trimethylphenyl, triethylphenyl, tripropylphenyl, tributylphenyl, tripentylphenyl, trihexylphenyl, triheptylphenyl, trioctylphenyl, trinonylphenyl, tridecylphenyl, triundecylphenyl, tridodecylphenyl, tetramethylphenyl, tetraethylphenyl, tetrapropylphenyl, tetrabutylphenyl, tetrapentylphenyl, tetrahexylphenyl, pentamethylphenyl, pentaethylphenyl, pentapropylphenyl, pentabutylphenyl, ethylmethylphenyl, methylpropylphenyl, butylmethylphenyl, methylpentylphenyl, hexylmethylphenyl, heptylmethylphenyl, methyloctylphenyl, nonylmethylphenyl, decylmethylphenyl, methylundecylphenyl, dodecylmethylphenyl, dimethylethylphenyl, dimethylpropylphenyl, butyldimethylphenyl, dimethylpentylphenyl, dimethylhexylphenyl, dimethylheptylphenyl, dimethyloctylphenyl, dimethylnonylphenyl, decyldimethylphenyl, dimethylundecylphenyl, dimethyldodecylphenyl, diethylmethylphenyl, diethylpropylphenyl, butyldiethylphenyl, diethylpentylphenyl, diethylhexylphenyl, diethylheptylphenyl, diethyloctylphenyl, diethylnonylphenyl, decyldiethylphenyl, diethylundecylphenyl, diethyldodecylphenyl, dipropylmethylphenyl, dipropylethylphenyl, butyldipropylphenyl, dipropylpentylphenyl, dipropylhexylphenyl, dipropylheptylphenyl, dipropyloctylphenyl, dipropylnonylphenyl, decyldipropylphenyl, dipropylundecylphenyl, dipropyldodecylphenyl, dibutylmethylphenyl, dibutylethylphenyl, dibutylpropylphenyl, dibutylpentylphenyl, dibutylhexylphenyl, dibutylheptylphenyl, dibutyloctylphenyl, dibutylnonylphenyl, decyldibutylphenyl, dibutylundecylphenyl, dibutyldodecylphenyl, vinylphenyl, propenylphenyl, butenylphenyl, methylvinylphenyl, trimethylsilylphenyl, trimethylgermylphenyl, trifluoromethylphenyl, bis(triflouromethyl)phenyl and the like;

(f) halo substituted phenyl and all isomers of halo substituted phenyl (where halo is, independently, fluoro, chloro, and iodo) including halophenyl, dihalophenyl, trihalophenyl, tetrahalophenyl, and pentahalophenyl; from all isomers of halo substituted hydrocarbyl substituted phenyl (where halo is, independently, fluoro, chloro, and iodo) including halomethylphenyl, dihalomethylphenyl, trihalomethylphenyl, tetrahalomethylphenyl, haloethlyphenyl, dihaloethylphenyl, trihaloethylphenyl, tetrahaloethylphenyl, halopropylphenyl, dihalopropylphenyl, trihalopropylphenyl, tetrahalopropylphenyl, halobutylphenyl, dihalobutylphenyl, trihalobutylphenyl, tetrahalobutylphenyl, dihalodimethylphenyl, dihalo(trifluoromethyl)phenyl and the like;

(g) all isomers of benzyl, and all isomers of hydrocarbyl substituted benzyl including methylbenzyl, dimethylbenzyl, trimethylbenzyl, tetramethylbenzyl, pentamethylbenzyl ethylbenzyl, diethylbenzyl, triethylbenzyl, tetraethylbenzyl, pentaethylbenzyl, propylbenzyl, dipropylbenzyl, tripropylbenzyl, tetrapropylbenzyl, pentapropylbenzyl butylbenzyl, dibutylbenzyl, tributylbenzyl, tetrabutylbenzyl, pentabutylbenzyl, hexylbenzyl, dihexylbenzyl, trihexylbenzyl, tetrahexylbenzyl, pentahexylbenzyl, dimethylethylbenzyl, dimethylpropylbenzyl, dimethylbutylbenzyl, dimethylpentylbenzyl, dimethylhexylbenzyl, diethylmethylbenzyl, diethylpropylbenzyl, diethylbutylbenzyl, diethylpentylbenzyl, diethylhexylbenzyl, dipropylmethylbenzyl, dipropylethylbenzyl, dipropylbutylbenzyl, dipropylpentylbenzyl, dipropylhexylbenzyl, dibutylmethylbenzyl, dibutylethylbenzyl, dibutylpropylbenzyl, dibutylpentylbenzyl, dibutylhexylbenzyl, methylethylbenzyl, methylpropylbenzyl, methylbutylbenzyl, methylpentylbenzyl, methylhexylbenzyl, ethylpropylbenzyl, ethylbutylbenzyl, ethylpentylbenzyl, ethylhexylbenzyl, propylbutylbenzyl, propylpentylbenzyl, propylhexylbenzyl, butylpentylbenzyl, butylhexylbenzyl, trimethylsilylbenzyl, bis(trimethylsilyl)benzyl, trimethylgermylbenzyl, diphenylmethyl and the like;

(h) trihydrocarbyl-silyl, -germyls, -stannyls and -plumbyls including trimethylsilyl, trimethylgermyl, trimethylstannyl, trimethylplumbyl, triethylsilyl, triethylgermyl, dimethylethylsilyl, dimethylethylgermyl, diethylmethylsilyl, diethylmethylgermyl, triphenylsilyl, triphenylgermyl, and all isomers of tripropylsilyl, tripropylgermyl, tributylsilyl, tributylgermyl, tris(trifluormethyl)silyl, bis(perfluoromethyl)methylsilyl, and the like;

(i) all isomers of hydrocarbyl substituted isomers of polycyclic areneyls including pyrenyl, aceanthrylenyl, acenaphthylene, acephenanthrylenyl, azulenyl biphenylenyl, chrysenyl, coronenyl, fluoranthenyl, fluorenyl, heptacenyl, heptalenyl, heptaphenyl, hexacenyl, hexaphenyl, as-indacenyl, s-indecenyl, indenyl, ovalenyl, pentacenyl, pentalenyl, pentaphenyl, perylenyl, phenalenyl, phenanthrenyl, picenyl, pleiadenyl, pyranhrenyl, rubicenyl, naphthacenyl, tetraphenylenyl, trinaphthylenyl, triphenylenyl, hexahelicenyl, naphthyl, anthracenyl, dibenza[a,b]anthracenyl, indanyl, acenaphthenyl, cholanthrenyl, aceanthrenyl, acephenanthrenyl, 1,2,3,4-tetrahydronapthalene, fullerenyl, and the like;

(j) all isomers of hydrocarbyl substituted alicyclic, monocyclic and polycyclic hydrocarbon rings including cyclopropyl, cyclobutyl, cyclopentyl, cyclohexyl, cyclohexenyl, cycloheptyl, cyclooctyl, cyclononyl, cyclodecyl, cycloundecyl, and cyclododecyl, dimethylcyclohexyl, norbornyl, norbornenyl, adamantyl, cubanyl, prismanyl, spiro[4,5]decanyl, and the like;

(k) all isomers of heterocycles and hydrocarbyl substituted heterocycles including acridarsinyl, acridinyl, acridophosphinyl, 1H-acrindolinyl, anthrazinyl, anthyridinyl, arsanthridinyl, arsindolyl, arsindolizinyl, arsinolinyl, arsinolizinyl, benzofuranyl, carbazolyl, β-carbolinyl, chromenyl, thiochromenyl, cinnolinyl, furanyl (also called furyl), imidazolyl, indazolyl, indolyl, indolizinyl, isoarsindolyl, isoarsinolinyl, isobenzofuranyl, isochromenyl, isothiochromenyl, isoindolyl, isophosphindolyl, isophosphinolinyl, isoquinolinyl, isothiazolyl, isoxazolyl, naphthyridinyl, oxazolyl, perimidinyl, phenanthrazinyl, phenanthridinyl, phenanthrolinyl, phenazinyl, phosphanthridinyl, phosphindolyl, phosphindolizinyl, phosphinolizinyl, phthalazinyl, pteridinyl, phthaloperinyl, purinyl, pyranyl, thiopyranal, pyrazinyl, pyrazolyl, pyridazinyl, pyridinyl, pyrindinyl, pyrimidinyl, pyrrolyl, pyrrolizinyl, quinazolinyl, quindolinyl, 1H-quinindolinyl, quinolinyl, quinolizinyl, quinoxalinyl, selenophenyl, thebenidinyl, thiazolyl, thiophenyl (also called thienyl), triphenodioxazinyl, triphenodithiazinyl, xanthenyl, chromanyl, thiochromanyl, imidazolidinyl, indolinyl, isochromanyl, isothiochromanyl, isoindolinyl, morpholinyl, piperazinyl, piperidinyl, pyrozolidinyl, pyrrolidinyl, quinuclidinyl, methylthiopehnyl, methylfuranyl, ethylthiopehnyl, ethylfuranyl, propylthiopehnyl, propylfuranyl, butylthiopehnyl, butylfuranyl, pentylthiopehnyl, pentylfuranyl, hexylthiopehnyl, hexylfuranyl, dimethylacridarsinyl, dimethylacridinyl, dimethylacridophosphinyl, dimethyl-1H-acrindolinyl, dimethylanthrazinyl, dimethylanthyridinyl, dimethylarsanthridinyl, dimethylarsindolyl, dimethylarsindolizinyl, dimethylarsinolinyl, dimethylarsinolizinyl, dibutylbenzofuranyl, dibutylcarbazolyl, dibutyl-β-carbolinyl, dibutylchromenyl, dibutylthiochromenyl, butylcinnolinyl, dibutylfuranyl, dimethylimidazolyl, dimethylindazolyl, dipropylindolyl, dipropylindolizinyl, dimethylisoarsindolyl, methylisoarsinolinyl, dimethylisobenzofuranyl, diphenylisochromenyl, dibutylisothiochromenyl, phenylisoindolyl, butylisophosphindolyl, dibutylisophosphinolinyl, dimethylisoquinolinyl, methylisothiazolyl, butylisoxazolyl, butylnaphthyridinyl, dimethyloxazolyl, methylphenylperimidinyl, tetrabutylphenanthrazinyl, propylphenanthridinyl, dibutylphenanthrolinyl, tetramethylphenazinyl, butylphosphanthridinyl, phenylphosphindolyl, dimethylphosphindolizinyl, methylphosphinolizinyl, dibutylphthalazinyl, trimethylpteridinyl, methylphthaloperinyl, dimethylpurinyl, dibutylpyranyl, dibutylthiopyranal, trimethylpyrazinyl, phenylpyrazolyl, dipropylpyridazinyl, dimethylpyridinyl, methylpropylpyrindinyl, triethylpyrimidinyl, dibutylpyrrolyl, diethylpyrrolizinyl, dibutylquinazolinyl, dibutylquindolinyl, dibutyl-1H-quinindolinyl, dimethylquinolinyl, propylquinolizinyl, methylquinoxalinyl, methylbutylselenophenyl, methylthebenidinyl, dimethylthiazolyl, trimethylthiophenyl, dibutyltriphenodioxazinyl, dibutyltriphenodithiazinyl, dibutylxanthenyl, trimethylchromanyl, dimethylthiochromanyl, dimethylimidazolidinyl, dimethylindolinyl, dibutylisochromanyl, dibutylisothiochromanyl, phenylisoindolinyl, dibutylmorpholinyl, dimethylpiperazinyl, dimethylpiperidinyl, dimethylpyrozolidinyl, dimethylpyrrolidinyl, bipyridyl, pyrido[2,1,6-de]quinolizinyl, hexamethylquinuclidinyl, 5,7-dioxa-6-phosphadibenzo[a,c]cycloheptene-6-oxide, 9-oxa-10-phosphaphenanthrene-10-oxide and the like.

Preferred zinc transfer-agents include: methyl zinc chloride, phenyl zinc chloride, para-tolyl zinc chloride, para-tert-butylphenyl zinc chloride, biphenyl zinc chloride, meta-tolyl zinc chloride, ortho-tolyl zinc chloride, ortho-methoxyphenyl zinc chloride, para-fluorophenyl zinc chloride, meta-trifluoromethylphenyl zinc chloride, mesityl zinc chloride, 1-naphthyl zinc chloride, 2-thienyl zinc chloride, 2-ftiryl zinc chloride, 1-benzothien-2-yl zinc chloride, 1-benzofur-2-yl zinc chloride, 5-methyl-2-thienyl zinc chloride, and 5-methyl-2-fuiryl zinc chloride.

While the Negishi coupling reactions are preferred, other palladium catalyzed coupling reactions such as the Kumada reaction (using R*MgX, Ni catalyzed), the Suzuki-Miyaura reaction (using $NaBPh_4/LiBR*_3Ar$), the Stille reaction (using $R*_3SnAr$), the Heck reaction (using $H_2C=CHR*$), and the Sonogashira reaction (using $HC\equiv CR*$) may be used, where Ar is an arene, R* is as defined above, X is chlorine, bromine and iodine.

The general protocols for the Negishi reaction using organozinc transfer-agents, the Kumada reaction using Grignard transfer-agents, the Suzuki-Miyaura reaction using organoboron transfer-reagents (particularly $NaBPh_4$, boronic acids and their ethers), the Stille reaction using organotin based transfer-agents, and other cross-coupling reactions are described in *Metal-Catalyzed Cross-Coupling Reactions*, Ed. by F. Diederich, P. J. Stang, Wiley, 1998 and the references cited therein.

In addition to the organozinc transfer-agents described above, other transfer-agents that can be used in the coupling reactions described herein include but are not limited to:

A) boron transfer-agents such as $R^1B(OR*\#)_2$, $R^1_2B(OR*\#)$, $R^1_3B$, $R^1B(OR*\#O)$, $R^1B(R*\#)_2$, or $NaBR^1_4$, where R*# is, independently, hydrogen or hydrocarbyl, and two or more R*# may join together to form a substituted or unsubstituted saturated, partially saturated or aromatic cyclic or polycyclic ring structure and R' is a substituted or unsubstituted hydrocarbyl, or substituted or unsubstituted fluorocarbyl;

B) tin transfer-agents such as $R^1SnR*\#\#_3$, where R*## is a halide, an alkoxide, a carboxylate, or an alkyl, preferably methyl or butyl, and $R^1$ is substituted or unsubstituted hydrocarbyl, or substituted or unsubstituted fluorocarbyl;

C) copper transfer-agents such as $R^1Cu$, where and $R^1$ is a substituted or unsubstituted hydrocarbyl, or substituted or unsubstituted fluorocarbyl;

D) magnesium transfer-agents such as $R^1MgX^{*}$, where $R^1$ is substituted or unsubstituted hydrocarbyl, or substituted or unsubstituted fluorocarbyl, and $X^{*}$ is chloride, bromide, an alkoxide, or a carboxylate;
E) aluminum alkyls;
F) lithium transfer-agents such as $LiR^1$, where $R^1$ is substituted or unsubstituted hydrocarbyl, or substituted or unsubstituted fluorocarbyl;
G) zirconium transfer-agents such as $R^1ZrCp_2X$ or $R^1{}_2ZrCp_2$, where $R^1$ is substituted or unsubstituted hydrocarbyl, or substituted or unsubstituted fluorocarbyl, Cp is a cyclopentadienyl group (including an indenyl or fluorenyl group), and X is a halide, an alkoxide or any other monoanionic polar group; and
H) organosilanes such as $R^1SiX^2{}_nR^{*'}{}_{3-n}$ or $R^1{}_{n+1}SiX^2{}_nR^{*'}{}_{3-n}$ where $R^{*'}$ is an alkyl or aryl group, $R^1$ is a substituted or unsubstituted hydrocarbyl, or substituted or unsubstituted fluorocarbyl, and $X^2$ is a halide, an alkoxide or any other monoanionic polar group, preferably F, and n=0, 1, 2, or 3.

Specific examples of suitable boron transfer-agents include but are not limited to methylboronic acid, ethylboronic acid, n-propylboronic acid, isopropylboronic acid, n-butylboronic acid, sec-butylboronic acid, isobutylboronic acid, tert-butylboronic acid, cyclopentylboronic acid, cyclohexylboronic acid, benzylboronic acid, 4-methylbenzylboronic acid, 4-methoxybenzylboronic acid, 4-trifluoromethylboronic acid, diphenylmethylboronic acid, adamantylboronic acid, cyclohexenylboronic acid, isopropenylboronic acid, 2-phenylethenylboronic acid, trimethylsilylmethylboronic acid, neopentylboronic acid, methoxymethylboronic acid, 3-methoxypropylboronic acid, dimethylaminomethylboronic acid, diphenylphosphinomethylboronic acid, 2-pyridylboronic acid, 4-pyridylboronic acid, 2-thienylboronic acid, 2-benzothienylboronic acid, 2-benzofurylboronic acid, 3-(N-methylindolyl) boronic acid, phenylboronic acid, sodium tetraphenylborate, 4,4,5,5-tetramethyl-2-phenyl-1,3,2-dioxaborolane, 2-phenyl-1,3,2-benzodioxaborole, triphenylboron, 2-methylphenylboronic acid, 3-methylphenylboronic acid, 4-methylphenylboronic acid, 4-tert-butylphenylboronic acid, 2,6-dimethylphenylboronic acid, 2,6-diisopropylphenylboronic acid, 3,5-dimethylphenylboronic acid, 2,5-dimethylphenylboronic acid, 3,5-diisopropylphenylboronic acid, 3,5-di-tert-butylphenylboronic acid, 2-isopropylphenylboronic acid, 3-trifluoromethylphenylboronic acid, 4-fluorophenylboronic acid, 4-methoxyphenylboronic acid, 2-methoxyphenylboronic acid, 4-dimethylaminophenylboronic acid, 1-naphthylboronic acid, 2-naphthylboronic acid, 4-cyanophenylboronic acid, 4-carboethoxyphenylboronic acid, and pentafluorophenylboronic acid.

Particularly preferred boron transfer-agents are 2-thienylboronic acid, 3,5-dimethylphenylboronic acid, 2,5-dimethylphenylboronic acid, 3,5-diisopropylphenylboronic acid, 3,5-di-tert-butylphenylboronic acid, and 1-naphthylboronic acid.

The cross-coupling reactions using organoboron transfer-agents (Suzuki-Miyaura reaction) require a base (an additive) in addition to $NaBPh_4$. Non-limiting examples of bases (additives) to be used include: potassium carbonate, sodium carbonate, lithium carbonate, cesium carbonate, rubidium carbonate, lit+hium hydroxide, sodium hydroxide, potassium hydroxide, sodium triphosphate, potassium triphosphate, sdium hydrocarbonate, calcium carbonate, calcium oxide, barioum carbonate, barium oxide, aluminium carbonate, aluminium oxide, yttrium carbonate, yttrium oxide, cerium carbonate, cerium oxide, barium hydroxide, calcium hydroxide, yttrium hydroxide, cerium hydroxide, aluminium hydroxide, sodium methylate, sodium ethylate, sodium isopropylate, sodium n-butoxide, sodium tert-butoxide, lithium ethylate, potassium ethylate.

Specific examples of suitable tin transfer-agents include but are not limited to tetramethyltin, teraethyltin, tetracyclohexyltin, 2-pyridyl-tri-n-butyltin, 4-pyridyl-tri-n-butyltin, 2-thienyl-tri-n-butyltin, 2-benzothienyl-tri-n-butyltin, 2-benzofiuryl-tri-n-butyltin, 3-(N-methylindolyl)-tri-n-butyltin, phenyl-tri-n-butyltin, phenyltrimethyltin, phenyltriethyltin, phenyltriisopropyltin, phenyltriisobutyltin, phenyltricyclohexyltin, tetraphenyltin, 2-methylphenyl-tri-n-butyltin, 3-methylphenyl-tri-n-butyltin, 4-methylphenyl-tri-n-butyltin, 4-tert-butylphenyl-tri-n-butyltin, 2,6-dimethylphenyl-tri-n-butyltin, 2,6-diisopropylphenyl-tri-n-butyltin, 3,5-dimethylphenyl-tri-n-butyltin, 2,5-dimethylphenyl-tri-n-butyltin, 3,5-diisopropylphenyl-tri-n-butyltin, 3,5-di-tert-butylphenyl-tri-n-butyltin, 2-isopropylphenyl-tri-n-butyltin, 3-trifluoromethylphenyl-tri-n-butyltin, 4-fluorophenyl-tri-n-butyltin, 4-methoxyphenyl-tri-n-butyltin, 2-methoxyphenyl-tri-n-butyltin, 4-dimethylaminophenyl-tri-n-butyltin, 1-naphthyl-tri-n-butyltin, 2-naphthyl-tri-n-butyltin, 4-cyanophenyl-tri-n-butyltin, 4-carboethoxyphenyl-tri-n-butyltin, pentafluorophenyl-tri-n-butyltin, phenyltin trichloride, phenyltin tribromide, phenyltin triiodide, phenyltin trifluoride, and phenyltin triethoxyde.

Particularly preferred tin transfer-agents are 2-thienyl-tri-n-butyltin, 3,5-dimethylphenyl-tri-n-butyltin, 2,5-dimethylphenyl-tri-n-butyltin, 3,5-diisopropylphenyl-tri-n-butyltin, 3,5-di-tert-butylphenyl-tri-n-butyltin, and 1-naphthyl-tri-n-butyltin.

The cross-coupling reactions using organotin transfer-agent (Stille reaction) require the use of a nucleophilic aid agent (an additive). Non-limiting examples of such aiding agents (additives) to be used include: lithium fluoride, sodium fluoride, potassium fluoride, rubidium fluoride, cesium fluoride, tetramethylammonium fluoride, tetraethylammonium fluoride, tetra-n-butylammonium fluoride, magnesium fluoride, calcium fluoride, barium fluoride, aluminium fluoride, tetramethylphosphonium fluoride, lithium chloride, sodium bromide, potassium chloride, rubidium chloride, cesium chloride, tetramethylammonium chloride, tetraethylammonium chloride, tetra-n-butylammonium chloride, magnesium chloride, calcium chloride, barium chloride, aluminium chloride, tetramethylphosphonium chloride, lithium hydroxide, sodium hydroxide, potassium hydroxide, rubidium hydroxide, cesium hydroxide, tetramethylammonium hydroxide, tetraethylammonium hydroxide, tetra-n-butylammonium hydroxide, magnesium hydroxide, calcium hydroxide, barium hydroxide, aluminium hydroxide, tetramethylphosphonium hydroxide, lithium methoxide, sodium methoxide, potassium methoxide, rubidium methoxide, cesium methoxide, magnesium methoxide, calcium methoxide, barium methoxide, aluminium methoxide, sodium ethoxide, sodium n-propoxide, sodium isopropoxide, sodium n-butoxide, sodium isobutoxide, sodium sec-butoxide, sodium phenoxide.

Specific examples of suitable copper transfer-agents include but are not limited to ethynylcopper, prop-1-ynylcopper, but-1-ynylcopper, (3-methylbut-1-ynyl)copper, (3,3-dimethylbut-1-ynyl)copper, (2-phenylethynyl)copper, (2-(3, 5-dimethylphenyl)ethynyl)copper, (2-(2,5-dimethylphenyl)ethynyl)copper, (2-(3,5-di-iso-propylphenyl)ethynyl)copper, (2-(3,5-di-tert-butyl-phenyl)ethynyl)copper, (2-mesitylethynyl)copper, and (2-(naphth-1-yl)ethynyl)copper.

Specific examples of suitable magnesium transfer-agents include but are not limited to methylmagnesium chloride, methylmagnesium bromide, methylmagnesium iodide, dimethylmagnesium, ethylmagnesium bromide, n-propylmagnesium chloride, isopropylmagnesium chloride, n-butylmagnesium chloride, sec-butylmagnesium chloride, isobutylmagnesium chloride, tert-butylmagnesium chloride, cyclopentylmagnesium chloride, cyclohexylmagnesium chloride, benzylmagnesium chloride, 4-methylbenzylmagnesium chloride, 4-methoxybenzylmagnesium chloride, 4-trifluoromethylmagnesium chloride, diphenylmethylmagnesium bromide, adamantylmagnesum bromide, cyclohexenylmagnesium chloride, isopropenylmagnesium chloride, 2-phenylethenylmagnesium bromide, trimethylsilylmethylmagnesium chloride, neopentylmagnesium chloride, methoxymethylmagnesium chloride, 3-methoxypropylmagnesium chloride, dimethylaminomethylmagnesium chloride, diphenylphosphinomethylmagnesium chloride, 2-pyridylmagnesium bromide, 4-pyridylmagnesium chloride, 2-thienylmagnesium bromide, 2-benzothienylmagnesium bromide, 2-benzofuirylmagnesium chloride, 3-(N-methylindolyl)magnesium bromide, phenylmagnesium bromide, 2-methylphenylmagnesium bromide, 3-methylphenylmagnesium bromide, 4-methylphenylmagnesium bromide, 4-tert-butylphenylmagnesium bromide, 2,6-dimethylphenylmagnesium bromide, 2,6-diisopropylphenylmagnesium bromide, 3,5-dimethylphenylmagnesium chloride, 2,5-dimethylphenylmagnesium chloride, 3,5-diisopropylphenylmagnesium chloride, 3,5-di-tert-butylphenylmagnesium chloride, 2-isopropylphenylmagnesium chloride, 3-trifluoromethylphenylmagnesium chloride, 4-fluorophenylmagnesium chloride, 4-methoxyphenylmagnesium chloride, 2-methoxyphenylmagnesium chloride, 4-dimethylaminophenylmagnesium chloride, 1-naphthylmagnesium chloride, 2-naphthylmagnesium chloride, and pentafluorophenylmagnesium bromide.

Particularly preferred magnesium transfer-agents are cyclopentylmagnesium chloride, cyclohexylmagnesium chloride, 2-thienylmagnesium bromide, 3,5-dimethylphenylmagnesium chloride, 2,5-dimethylphenylmagnesium chloride, 3,5-diisopropylphenylmagnesium chloride, 3,5-di-tert-butylphenylmagnesium chloride, and 1-naphthylmagnesium chloride.

Specific examples of suitable aluminum alkyl transfer-agents include but are not limited to (prop-i-enyl)diisobutylaluminum, (but-1-enyl)diisobutylaluminum, (pent-1-enyl)diisobutylaluminum, (hex-1-enyl)diisobutylaluminum, (3-methylbut-1-enyl)diisobutylaluminum, (3,3-dimethylbut-1-enyl)diisobutylaluminum, (4-methylpent-1-enyl)diisobutylaluminum, (3-methylpent-1-enyl)diisobutylaluminum, (styryl)diisobutylaluminum, (3,5-dimethylstyryl)diisobutylaluminum, (2,5-dimethylstyryl)diisobutylaluminum, (3,5-di-tert-butylstyryl)diisobutylaluminum, (2,4,6-trimethylstyryl)diisobutylaluminum, (2-(naphth-1-yl)vinyl)diisobutylaluminum, (but-2-en-2-yl)diisobutylaluminum, (pent-2-en-2-yl)diisobutylaluminum, (hex-2-en-2-yl)diisobutylaluminum, (hept-2-en-2-yl)diisobutylaluminum, (4-methylpent-2-en-2-yl)diisobutylaluminum, (4,4-dimethylpent-2-en-2-yl)diisobutylaluminum, (5-methylhex-1-enyl)diisobutylaluminum, (4-methylhex-2-en-2-yl)diisobutylaluminum, (1-phenyl-1-prop-2-enyl)diisobutylaluminum, (1-(3,5-dimethylphenyl)-1-prop-2-enyl)diisobutylaluminum, (1-(2,5-dimethylphenyl)-1-prop-2-enyl)diisobutylaluminum, (1-(3,5-di-tert-butyl-phenyl)-1-prop-2-enyl)diisobutylaluminum, (1-(2,4,6-trimethylphenyl)-1-prop-2-enyl)diisobutylaluminum, (1-(naphth-1-yl)prop-1-en-2yl)diisobutylaluminum, (2-methylprop-1-enyl)diisobutylaluminum, (2-methylbut-1-enyl)diisobutylaluminum, (2-methylpent-1-enyl)diisobutylaluminum, (2-methylhex-1-enyl)diisobutylaluminum, (2,3-dimethylbut-1-enyl)diisobutylaluminum, (2,3,3-trimethylbut-1-enyl)diisobutylaluminum, (2,4-dimethylpent-1-enyl)diisobutylaluminum, (2,3-dimethylpent-1-enyl)diisobutylaluminum, (2-phenylprop-1-enyl)diisobutylaluminum, (2-(3,5-dimethylphenyl)prop-1-enyl)diisobutylaluminum, (2-(2,5-dimethylphenyl)prop-1-enyl)diisobutylaluminum, (2-(3,5-di-tert-butylphenyl)prop-1-enyl)diisobutylaluminum, (2-(2,4,6-trimethylphenyl)prop-1-enyl)diisobutylaluminum, and (2-(naphth-1-yl)prop-1-enyl)diisobutylaluminum.

Specific examples of suitable lithium transfer-agents include but are not limited to methyllithium, ethyllithium, n-propyllithium, isopropyllithium, n-butyllithium, sec-butyllithium, isobutyllithium, tert-butyllithium, cyclopentyllithium, cyclohexyllithium, benzyllithium, 4-methylbenzyllithium, 4-methoxybenzyllithium, 4-trifluoromethyllithium, diphenylmethyllithium, adamantyllithium, cyclohexenyllithium, isopropenyllithium, 2-phenylethenyllithium, trimethylsilylmethyllithium, neopentyllithium, methoxymethyllithium, 3-methoxypropyllithium, dimethylaminomethyllithium, diphenylphosphinomethyllithium, 2-pyridyllithium, 4-pyridyllithium, 2-thienyllithium, 2-benzothienyllithium, 2-benzofuryllithium, 3-(N-methylindolyl)lithium, phenyllithium, 2-methylphenyllithium, 3-methylphenyllithium, 4-methylphenyllithium, 4-tert-butylphenyllithium, 2,6-dimethylphenyllithium, 2,6-diisopropylphenyllithium, 3,5-dimethylphenyllithium, 2,5-dimethylphenyllithium, 3,5-diisopropylphenyllithium, 3,5-di-tert-butylphenyllithium, 2-isopropylphenyllithium, 3-trifluoromethylphenyllithium, 4-fluorophenyllithium, 4-methoxyphenyllithium, 2-methoxyphenyllithium, 4-dimethylaminophenyllithium, 1-naphthyllithium, 2-naphthyllithium, and pentafluorophenyllithium.

Particularly preferred lithium transfer-agents are cyclopentyllithium, cyclohexyllithium, 2-thienyllithium, 3,5-dimethylphenyllithium, 2,5-dimethylphenyllithium, 3,5-diisopropylphenyllithium, 3,5-di-tert-butylphenyllithium, and 1-naphthyllithium.

Specific examples of suitable zirconium transfer-agents include but are not limited to (prop-l-enyl)dicyclopentadienylzirconium chloride, (but-1-enyl)dicyclopentadienylzirconium chloride, (pent-1-enyl)dicyclopentadienylzirconium chloride, (hex-1-enyl)dicyclopentadienylzirconium chloride, (3-methylbut-1-enyl)dicyclopentadienylzirconium chloride, (3,3-dimethylbut-1-enyl)dicyclopentadienylzirconium chloride, (4-methylpent-1-enyl)dicyclopentadienylzirconium chloride, (3-methylpent-1-enyl)dicyclopentadienylzirconium chloride, (styryl)dicyclopentadienylzirconium chloride, (3,5-dimethylstyryl)dicyclopentadienylzirconium chloride, (2,5-dimethylstyryl)dicyclopentadienylzirconium chloride, (3,5-di-tert-butylstyryl)dicyclopentadienylzirconium chloride, (2,4,6-trimethylstyryl)dicyclopentadienylzirconium chloride, (2-(naphth-1-yl)vinyl)dicyclopentadienylzirconium chloride, (but-2-en-2-yl)dicyclopentadienylzirconium chloride, (pent-2-en-2-yl)dicyclopentadienylzirconium chloride, (hex-2-en-2-yl)dicyclopentadienylzirconium chloride, (hept-2-en-2-yl)dicyclopentadienylzirconium chloride, (4-methylpent-2-en-2-yl)dicyclopentadienylzirconium chloride, (4,4-dimethylpent-2-en-2-yl)dicyclopentadienylzirconium chloride, (5-methylhex-1-enyl)dicyclopentadienylzirconium chloride, (4-methylhex-2-en-2-yl)dicyclopentadienylzirconium chloride, (1-phenyl-1-prop-2-enyl)dicyclopentadienylzirconium chloride, (1-(3,5-dimethylphenyl)-1-prop-2-enyl)dicyclopentadienylzirconium chloride, (1-(2,5-dimethylphenyl)-1-prop-2-enyl)

dicyclopentadienylzirconium chloride, (1-(3,5-di-tert-butyl-phenyl)-1-prop-2-enyl)dicyclopentadienylzirconium chloride, (1-(2,4,6-trimethylphenyl)-1-prop-2-enyl)dicyclopentadienylzirconium chloride, (1-(naphth-1-yl)prop-1-en-2yl)dicyclopentadienylzirconium chloride, (2-methylprop-1-enyl)dicyclopentadienylzirconium chloride, (2-methylbut-1-enyl)dicyclopentadienylzirconium chloride, (2-methylpent-1-enyl)dicyclopentadienylzirconium chloride, (2-methylhex-1-enyl)dicyclopentadienylzirconium chloride, (2,3-dimethylbut-1-enyl)dicyclopentadienylzirconium chloride, (2,3,3-trimethylbut-1-enyl)dicyclopentadienylzirconium chloride, (2,4-dimethylpent-1-enyl)dicyclopentadienylzirconium chloride, (2,3-dimethylpent-1-enyl)dicyclopentadienylzirconium chloride, (2-phenylprop-1-enyl)dicyclopentadienylzirconium chloride, (2-(3,5-dimethylphenyl)prop-1-enyl)dicyclopentadienylzirconium chloride, (2-(2,5-dimethylphenyl)prop-1-enyl)dicyclopentadienylzirconium chloride, (2-(3,5-di-tert-butylphenyl)prop-1-enyl)dicyclopentadienylzirconium chloride, (2-(2,4,6-trimethylphenyl)prop-1-enyl)dicyclopentadienylzirconium chloride, and (2-(naphth-1-yl)prop-1-enyl)dicyclopentadienylzirconium chloride.

Specific examples of suitable organosilane transfer-agents include but are not limited to phenyldimethylfluorosilane, 2-methylphenyldimethylfluorosilane, 3-methylphenyldimethylfluorosilane, 4-methylphenyldimethylfluorosilane, 4-tert-butylphenyldimethylfluorosilane, 2,6-dimethylphenyldimethylfluorosilane, 2,6-diisopropylphenyldimethylfluorosilane, 3,5-dimethylphenyldimethylfluorosilane, 2,5-dimethylphenyldimethylfluorosilane, 3,5-diisopropylphenyldimethylfluorosilane, 3,5-di-tert-butylphenyldimethylfluorosilane, 2-isopropylphenyldimethylfluorosilane, 3-trifluoromethylphenyldimethylfluorosilane, 4-fluorophenyldimethylfluorosilane, 4-methoxyphenyldimethylfluorosilane, 2-methoxyphenyldimethylfluorosilane, 4-dimethylaminophenyldimethylfluorosilane, 1-naphthyldimethylfluorosilane, 2-naphthyldimethylfluorosilane, pentafluorophenyldimethylfluorosilane, phenylethyldifluorosilane, 2-methylphenylethyldifluorosilane, 3-methylphenylethyldifluorosilane, 4-methylphenylethyldifluorosilane, 4-tert-butylphenylethyldifluorosilane, 2,6-dimethylphenylethyldifluorosilane, 2,6-diisopropylphenylethyldifluorosilane, 3,5-dimethylphenylethyldifluorosilane, 2,5-dimethylphenylethyldifluorosilane, 3,5-diisopropylphenylethyldifluorosilane, 3,5-di-tert-butylphenylethyldifluorosilane, 2-isopropylphenylethyldifluorosilane, 3-trifluoromethylphenylethyldifluorosilane, 4-fluorophenylethyldifluorosilane, 4-methoxyphenylethyldifluorosilane, 2-methoxyphenylethyldifluorosilane, 4-dimethylaminophenylethyldifluorosilane, 1-naphthylethyldifluorosilane, 2-naphthylethyldifluorosilane, pentafluorophenylethyldifluorosilane, phenylpropyldifluorosilane, 2-methylphenylpropyldifluorosilane, 3-methylphenylpropyldifluorosilane, 4-methylphenylpropyldifluorosilane, 4-tert-butylphenylpropyldifluorosilane, 2,6-dimethylphenylpropyldifluorosilane, 2,6-diisopropylphenylpropyldifluorosilane, 3,5-dimethylphenylpropyldifluorosilane, 2,5-dimethylphenylpropyldifluorosilane, 3,5-diisopropylphenylpropyldifluorosilane, 3,5-di-tert-butylphenylpropyldifluorosilane, 2-isopropylphenylpropyldifluorosilane, 3-trifluoromethylphenylpropyldifluorosilane, 4-fluorophenylpropyldifluorosilane, 4-methoxyphenylpropyldifluorosilane, 2-methoxyphenylpropyldifluorosilane, 4-dimethylaminophenylpropyldifluorosilane, 1-naphthylpropyldifluorosilane, 2-naphthylpropyldifluorosilane, pentafluorophenylpropyldifluorosilane, methyltrifluorosilane, ethyltrifluorosilane, n-propyltrifluorosilane, isopropyltrifluorosilane, n-butyltrifluorosilane, sec-butyltrifluorosilane, isobutyltrifluorosilane, tert-butyltrifluorosilane, cyclopentyltrifluorosilane, cyclohexyltrifluorosilane, benzyltrifluorosilane, 4-methylbenzyltrifluorosilane, 4-methoxybenzyltrifluorosilane, 4-trifluoromethyltrifluorosilane, diphenylmethyltrifluorosilane, adamantyltrifluorosilane, cyclohexenyltrifluorosilane, isopropenyltrifluorosilane, 2-phenylethenyltrifluorosilane, trimethylsilylmethyltrifluorosilane, neopentyltrifluorosilane, methoxymethyltrifluorosilane, and 3-methoxypropyltrifluorosilane.

Aliphatic, heteroaliphatic, aromatic, heteroaromatic, alkenyl, and heteroalkenyl organometallic compounds useful as the transfer-agents in the present coupling reactions are obtainable in a simple manner by standard methods of the prior art or can be purchased commercially. The synthesis of organozinc transfer-agents, of importance in Negishi reactions, is described, for example, in *Organozinc Reagents*, Ed. by P. Knochel, P. Jones, Oxford University Press, 1999. The synthesis of boronic acid transfer-agents, of importance in Suzuki-Miyaura reactions, is described, for example, in *Organic Synthesis, Collective Volume IV*, Wiley, 1963. The synthesis of organotin transfer-agents, of importance in Stille reactions, is described, for example, in V. Farina, V. Krishnamurthy, W. J. Scott, *The Stille Reaction*, Wiley, 1998 and the references cited therein. The synthesis of other organometallic transfer-agents of the formula (III) involves standard methods of organometallic chemistry and is described, for example, in *Organometallics in Synthesis*, Ed. By M. Schlosser, and in J. March, Advanced Organic Chemistry, $4^{th}$ Edition, 1992 and the references cited therein.

Catalysts for suitable for use in the present coupling reactions include but are not limited to (a) nickel complexes such as nickel(II) chloride, nickel(II) bromide, (2,2'-bipyridine)dibromonickel(II), dichlorobis(triphenylphosphine)nickel(II), dibromobis(triphenylphosphine)nickel(II), dichloro[1,2-bis(diphenylphosphino)ethane]nickel(II), dichloro[1,3-bis(diphenylphosphino)propane]nickel(II), dichloro[1,1'-bis(diphenylphosphino)ferrocene]nickel(II), bis(1,5-cyclooctadiene) nickel(0), tetrakis(triphenylphosphine)nickel(0), and nickel(II) acetylacetonato; (b) palladium-phoshine complexes such as bis(tri(tert-butyl)phosphine) palladium, bis(tricyclohexylphosphine)palladium, bis(tri(iso-propyl)phosphine)palladium, dichlorobis(tri(iso-propyl)phosphine)palladium(II), dichlorobis(tri(o-tolyl)phoshine)palladium(II), trans-dichlorobis(tricyclohexylphosphine) palladium(II), trans-dichlorobis(triphenylphosphine)palladium(II), trans-dichlorobis(tri-o-tolylphosphine)palladium(II), tetrakis(triphenylphosphine)palladium(0), tetrakis(tri(o-tolyl)phosphine)palladium(0), dichloro[1,1'-bis(diphenylphosphino)ferrocene]palladium (II), dichloro[1,2-bis(diphenylphosphino)ethane]palladium (II), dichloro[1,3-bis(diphenylphosphino)propane]palladium(II), dichloro[1,4-bis(diphenylphosphino)butane]palladium(II), dichlorobis(triphenylphosphine)palladium(II) polymer bound or tetrakis(triphenylphosphine)palladium(0) polymer bound (both are available from Aldrich Chemical Company where the polymer is a divinylbenzene crosslinked polystyrene), benzylbis(triphenylphosphine) palladium(II) chloride, trans-di(μ-acetato)bis[o-(di(o-tolyl)phosphino)benzyl]dipalladium(II), and trans-di(μ-acetato)bis[o-(di-mesityl-phosphino) benzyl]dipalladium(II); (c) palladium compounds such as palladium(II) acetate, palladium(0) dibenzylideneacetone, palladium(II) chloride, palladium(II) bromide, palladium(II) iodide, palladium(II) acetylacetonate, allylpalladium chloride dimer, bis(2-methylallyl)palladium chloride dimer, crotylpalladium chloride dimer, palladium(II) trifluoroacetate, dichloro(1,5-cyclooctadiene) palladium(II), dichlorobis(benzonitrile)palladium(II), dichlorobis(acetonitrile)palladium(II), and tris(dibenzylideneacetone)dipalladium(0); (d) copper catalysts such as copper(I) cyanide, copper(I) chloride, copper(I) iodide, copper(I) trifluoroacetate, copper(II) fluoride, copper(II) chloride, and copper(II) iodide; (e) silver catalysts such as silver(I) iodide; and (f) cobalt catalysts such as cobalt(II) bromide, and cobalt (II) acetylacetonate.

In most cases it is sufficient to use the particularly preferred catalyst Pd(OAc)$_2$ (OAc=O$_2$CCH$_3$) in combination with a phosphine or a phosphine-like ligand such as ligands A-N, or Pd(P$^t$Bu$_3$)$_2$ in an amount of 0.000001 to 5.0 mol % Pd, preferably 0.01 to 3.0 mol % Pd and most preferably about 1.0 to 2.5 mol % Pd, in each case based on the metallocene starting material. Most preferably, the coupling catalyst is 2.5 mol % Pd or less, relative to the transition metal starting material. Analogously, in most cases it is sufficient to use the particularly preferred coupling-catalyst NiCl$_2$(dppp)$_2$ (dppp=1,3-bis (diphenylphosphino)propane) or NiCl$_2$(PPh$_3$)$_2$ (Ph=phenyl) in an amount of 0.01 to 5 mol % Ni, preferably 1 to 3 mol % Ni and most preferably about 2 mol % Ni, in each case relative to the transition metal (typically a metallocene) starting material.

The molar ratio of transfer-agent to X* is preferably 1:1 to 4:1 and is dependent on the coupling reaction being used. For Negishi and Suzuki-Miyaura reations, the preferred molar ratio of transfer-agent to X* is from 1:1 to 2:1, preferably 1.0:1 to 1.5:1; more preferably 1.2:1 to 1.35:1 For the Heck reaction, the preferred molar ratio of transfer-agent to X* is 1:1 to 3:1, preferably 1.5:1 to 2.5:1, most preferably, 1.5:1 to 2:1. For all coupling reactions lower than stoichiometric ratios of transfer-agent to X* can be used, however, this is at the expense of lowering the yield of the final product.X* of the transistion metal compound (sometimes referred to as the first compound) can be selected from Cl, Br, I, OTs or OTf. In general, reactivity of X* decreases in the order of I>Br>OTf>Cl>OTs. While it is possible for X of the transition metal compound to undergo an exchange with ions generated in the reaction such as LiBr, ZnBrCl, etc, the cross-coupling reaction on the transition metal ligand (ligand-X*) still works to form the substituted transition metal ligand (ligand-R***). Some choices can be made to limit or prevent this side reaction. Typically, if X* is more reactive than X, then the side reaction is reduced, or entirely eliminated. If X* is the same as X, then the side reaction, even if it occurs, is inconsequential. For example, The cross-coupling reaction of (Cp)(Cp-X*)ZrCl2 where X* is Br or Cl with R*ZnCl, will produce (Cp)(Cp-R*)ZrCl2. Additionally, less harsh reaction conditions such are performing the Negishi reaction at room temperature and for shorter reaction times (hours vs. days) will lower or eliminate this type of side reaction.

Useful additives include but are not limited to (a) bases such as sodium methoxide, sodium ethoxide, potassium tert-butoxide, lithium hydroxide, sodium hydroxide, potassium hydroxide, barium hydroxide, thallium hydroxide, lithium bis(trimethylsilyl)amide, sodium bis(trimethylsilyl)amide, potassium bis(trimethylsilyl)amide, triethylamine, ethyldiisopropylamine, benzyldimethylaamine, propylamine, butylamine, diethylamine, diisopropylamine, sodium acetate, potassium acetate, sodium carbonate, potassium carbonate, cesium carbonate, calcium carbonate, thallium carbonate, sodium bicarbonate, potassium phosphate, pyridine, N-methylpyrrolidinone, piperidine, 2,2,5,5,6-pentamethylpiperidine, pyrrolidine, diaza[2.2.2]bicylcooctane, and any of the phosphines R'R"R'"P, where each R', R", and R'" is a hydrocarbyl or fluorocarbyl, and phosphine like reagents. Non-limiting examples of phosphine (A through G and N) and phosphine like reagents (H through M) are listed below.

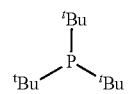

A

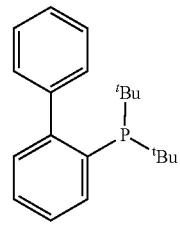

B

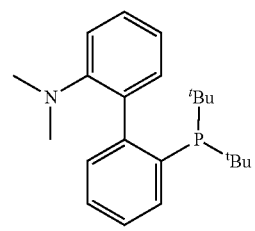

C

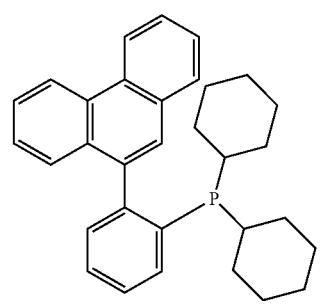

D

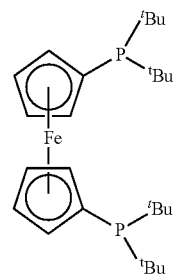

E

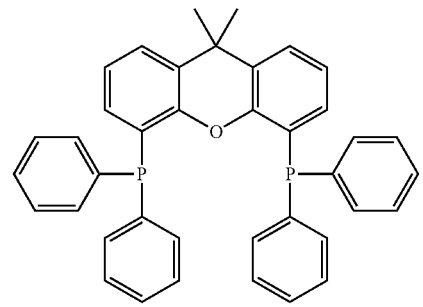

F

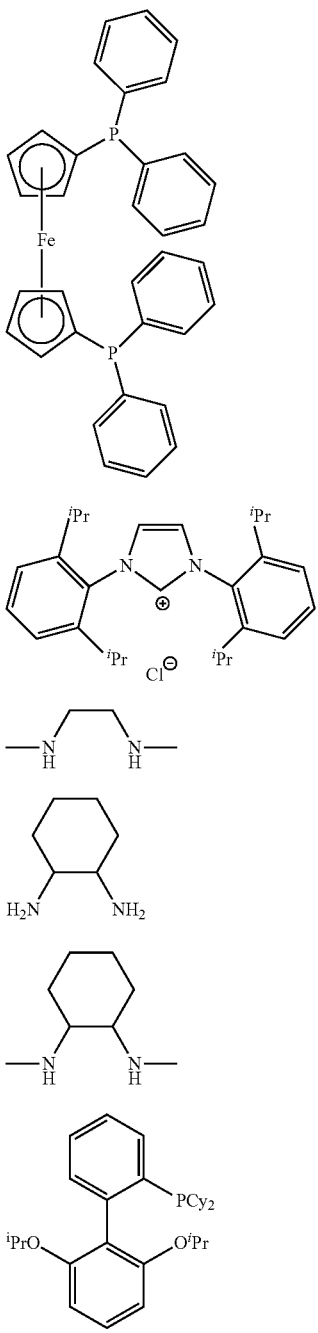

Additionally, polymeric bound or polymer supported phosphines may be used. Examples of commercially available polymeric bound phosphines include poly(ethylene glycol) triphenylphosphine; and dicyclohexylphenylphosphine, polymer-bound; (4-hydroxyphenyl)diphenylphosphine, polymer-bound; triphenylphosphine, polymer-supported; R-(+)-2,2'-bis(diphenylphosphino)-1,1'-binaphthalene, polymer-bound; S-(−)-2,2'-bis(diphenylphosphino)-1,1'-binaphthalene, polymer-bound (all available from Aldrich Chemical Company where the polymer-bound or polymer-supported is a divinylbenzene crosslinked polystyrene).

(b) salts such as lithium chloride, sodium chloride, potassium chloride, sodium bromide, sodium iodide, potassium fluoride, cesium fluoride, tetrabutylammonium fluoride, tetrabutylammonium chloride, tetrabutylammonium bromide, tetraethylammonium chloride, tetrapropylammonium bromide, benzyltriethylammonium bromide, benzyltrioctylammonium chloride, tris(diethylamino)sulfonium difluoro(trimethyl)silicate, nickel(I) bromide, silver(I) carbonate, silver(I) phosphate, silver(I) nitrate, silver(t) acetate, silver trifluoroacetate, silver(I) oxide, thallium(I) carbonate, thallium(I) acetate, zinc(I) chloride, zinc(I) bromide, copper(I) cyanide, copper(I) chloride, copper(I) bromide, copper(I) iodide, copper(II) chloride, and copper(II) oxide; and (c) other reagents such as chlorotrimethylsilane, 18-crown-6, triphenylarsine, and triphenylantimony.

Suitable solvents for the metal-catalyzed cross-coupling of the invention include, for example, aliphatic ethers such as diethyl ether, dibutyl ether, methyl tert-butyl ether, tetrahydrofuran, dioxane and dimethoxyethane, aliphatic hydrocarbons such as pentane, hexane and the like, aromatic hydrocarbons such as benzene, toluene, xylenes and the like. In many cases, other solvents can be used, such as dimethylformamide, water, acetone and the like. Mixtures of various solvents in various mixing ratios can also be used according to the present invention to match the solubility of the starting materials and end products to the reaction conditions in an optimal fashion. It should be noted that protic solvents such as water, alcohols and their mixtures with aprotic solvents can be also be used, but are typically used only when the starting materials, reagents, catalysts and additives cannot be decomposed (by hydrolysis) in such solvents. For example, the cross-coupling reaction of Br-substituted Cp2Ti(ORa)2 which can be definitely performed in the alcohol, RaOH, where Ra is a alkane radical.

Those of ordinary skill in the art will choose solvents or solvent mixtures appropriate to the specific substitution pattern of the starting compounds, the catalysts and reagents used by means of simple tests or on the basis of known solubilities and solvent properties.

In preferred embodiments of the process of the present invention, the metallocene starting material together with a sufficient amount of solvent are placed in the reaction vessel under an inert atmosphere. The coupling-catalyst, an optional ligand and an optional base or nucleophilic aid agent are subsequently added followed by the addition of a solution of the transfer-agent in a suitable solvent at room or lower (−78° C. to +10° C.) temperatures. The cross-coupling reaction can be carried out by vigorous stirring at room or elevated temperatures (10° C. to 180° C., preferably 20° C. to 100° C.) depending on the reaction under study, the reagents and the coupling-catalyst used. Addition of the metallocene starting material, coupling-catalyst and other additives can be performed in different orders. Those of ordinary skill in the art will choose an appropriate procedure depending on the reactivity and substitution of the individual reagents.

Suitable halogen substituted metallocene compounds that can be subjected to the cross-coupling reactions of the invention include, but are not limited to:
($\eta^5$-cyclopentadienyl)($\eta^5$-4-bromo-2-methylindenyl)zirconium dichloride,
($\eta^5$-3-tert-butylcyclopentadienyl)($\eta^5$-4-bromo-2-methylindenyl)zirconium dichloride,
($\eta^5$-3-trimethylsilylcyclopentadienyl)($\eta^5$-4-bromo-2-methylindenyl)zirconium dichloride,
($\eta^5$-pentamethylcyclopentadienyl)($\eta^5$-2-bromoindenyl)zirconium dichloride, ($\eta^5$-pentamethylcyclopentadienyl)($\eta^5$-2-bromo-4,7-dimethylindenyl)zirconium dichloride,
($\eta^5$-pentamethylcyclopentadienyl)($\eta^5$-4-bromo-2-methylindenyl)zirconium dichloride,
($\eta^5$-pentamethylcyclopentadienyl)($\eta^5$-4-chloro-2-methylindenyl)zirconium dichloride,
($\eta^5$-pentamethylcyclopentadienyl)($\eta^5$-4-fluoro-2-methylindenyl)zirconium dichloride,
($\eta^5$-pentamethylcyclopentadienyl)($\eta^5$-4-iodo-2-methylindenyl)zirconium dichloride,
($\eta^5$-pentamethylcyclopentadienyl)($\eta^5$-4-bromo-2-methylindenyl)zirconium dibromide,
($\eta^5$-pentamethylcyclopentadienyl)($\eta^5$-4-bromo-2-methylindenyl)zirconium diiodide,
($\eta^5$-pentamethylcyclopentadienyl)($\eta^5$-4-bromo-2-methylindenyl)zirconium difluoride,
($\eta^5$-pentamethylcyclopentadienyl)($\eta^5$-4-bromo-2-methylindenyl)zirconium dihydride,
($\eta^5$-pentamethylcyclopentadienyl)($\eta^5$-4-bromo-2-methylindenyl)dimethylzirconium,
($\eta^5$-pentamethylcyclopentadienyl)($\eta^5$-4-bromo-2-methylindenyl)diphenylzirconium,
($\eta^5$-pentamethylcyclopentadienyl)($\eta^5$-4-bromo-2-methylindenyl)dibenzylzirconium,
($\eta^5$-pentamethylcyclopentadienyl)($\eta^5$-4-bromo-2-methylindenyl)dimethoxyzirconium,
($\eta^5$-pentamethylcyclopentadienyl)($\eta^5$-4-bromo-2-methylindenyl)-bis(dimethylamino)zirconium,
($\eta^5$-1-dimethylaminoboratobenzene)($\eta^5$-4-bromo-2-methylindenyl)zirconium dichloride,
($\eta^5$-3-dimethylamino-1,3-azoboralide)($\eta^5$-4-bromo-2-methylindenyl)zirconium dichloride,
($\eta^5$-2-dimethylamino-1,2-oxaboralide)($\eta^5$-4-bromo-2-methylindenyl)zirconium dichloride,
($\eta^5$-2-dimethylamino-1,2-thiaboralide)($\eta^5$-4-bromo-2-methylindenyl)zirconium dichloride,
($\eta^5$-2,6-dimethyl-4-dimethylamino-1,4-phosphaboratobenzene)($\eta^5$-4-bromo-2-methylindenyl)zirconium dichloride,
($\eta^5$-2-dimethylamino-1,2-azaboratobenzene)($\eta^5$-4-bromo-2-methylindenyl)zirconium dichloride,
($\eta^5$-2,6-dimethyl-4-dimethylamino-1,4-phosphaboratobenzene)($\eta^5$-4-bromo-2-methylindenyl)zirconium dichloride,
($\eta^5$-3-[4-bromophenyl]-cyclopentadienyl)($\eta^5$-4-bromo-2-methylindenyl)zirconium dichloride,
($\eta^5$-3-[4-bromophenyl]-cyclopentadienyl)($\eta^5$-2-methylindenyl)zirconium dichloride,
($\eta^5$-cyclopentadienyl)($\eta^5$-2,7-dibromofluorenyl)zirconium dichloride,
($\eta^5$-3-[4-bromophenyl]-cyclopentadienyl)($\eta^5$-2,7-dibromofluorenyl)zirconium dichloride,
($\eta^5$-3-[4-bromophenyl]-cyclopentadienyl)($\eta^5$-fluorenyl)zirconium dichloride,
($\eta^5$-indenyl)($\eta^5$-2,7-dibromofluorenyl)zirconium dichloride,
($\eta^5$-4-bromo-2-methylindenyl)($\eta^5$-2,7-dibromofluorenyl)zirconium dichloride,
($\eta^5$-4-bromo-2-methylindenyl)($\eta^5$-fluorenyl)zirconium dichloride,
($\eta^5$-cyclopentadienyl)($\eta^5$-4-bromo-2-methylcyclopenta[b]naphthyl)zirconium dichloride,
($\eta^5$-cyclopentadienyl)($\eta^5$-8-bromo-6-methylindeno[5,6-d][1,3]dioxolyl)zirconium dichloride,
($\eta^5$-cyclopentadienyl)($\eta^5$-4-bromo-2,3,6-trimethylindeno[5,6-b]thienyl)zirconium dichloride,
($\eta^5$-cyclopentadienyl)($\eta^5$-2-bromo-4,6-dimethylindeno[5,6-b]thienyl)zirconium dichloride,
($\eta^5$-cyclopentadienyl)($\eta^5$-4-bromo-1,2,3,6-tetramethylcyclopenta[f]indolyl)zirconium dichloride,
($\eta^5$-cyclopentadienyl)($\eta^5$-4-bromo-1-phenyl-2,3,6-triamethylcyclopenta[f]indolyl)zirconium dichloride,
($\eta^5$-cyclopentadienyl)($\eta^5$-5-bromo-7-methylcyclopenta[g]quinolyl)zirconium dichloride,
($\eta^5$-cyclopentadienyl)($\eta^5$-2-bromo-5,7-dimethylcyclopenta[g]quinolyl)zirconium dichloride,
($\eta^5$-cyclopentadienyl)($\eta^5$-4,6-dibromo-2-methylindenyl)zirconium dichloride,
($\eta^5$-cyclopentadienyl)($\eta^5$-4,6-dichloro-2-methylindenyl)zirconium dichloride,
($\eta^5$-cyclopentadienyl)($\eta^5$-4,6-difluoro-2-methylindenyl)zirconium dichloride,
($\eta^5$-cyclopentadienyl)($\eta^5$-4-bromo-6-chloro-2-methylindenyl)zirconium dichloride,
($\eta^5$-cyclopentadienyl)($\eta^5$-4-bromo-6-fluoro-2-methylindenyl)zirconium dichloride,
($\eta^5$-cyclopentadienyl)($\eta^5$-5-bromo-2,4-dimethylindenyl)zirconium dichloride,
($\eta^5$-cyclopentadienyl)($\eta^5$-6-bromo-2,4-dimethylindenyl)zirconium dichloride,
($\eta^5$-cyclopentadienyl)($\eta^5$-7-bromo-2-methyl-4-phenylindenyl)zirconium dichloride,
($\eta^5$-5-methylcyclopenta[b]thienyl)($\eta^5$-4-bromo-2-methylindenyl)zirconium dichloride,
($\eta^5$-3-bromo-5-methylcyclopenta[b]thienyl)($\eta^5$-4-phenyl-2-methylindenyl)zirconium dichloride,
($\eta^5$-cyclopentadienyl)($\eta^5$-4-bromo-2-methylindenyl)zirconium dichloride,
($\eta^5$-cyclopentadienyl)($\eta^5$-3-bromo-5-methylcyclopenta[b]thienyl)zirconium dichloride,
($\eta^5$-cyclopentadienyl)($\eta^5$-1,3-dichlorocyclopenta[c]thienyl)zirconium dichloride,
($\eta^5$-cyclopentadienyl)($\eta^5$-8-bromo-2-methylcyclopenta[b][1]benzothienyl)zirconium dichloride,
($\eta^5$-cyclopentadienyl)($\eta^5$-8-chloro-2-methylcyclopenta[b][1]benzothienyl)zirconium dichloride,
($\eta^5$-cyclopentadienyl)($\eta^5$-8-iodo-2-methylcyclopenta[b][1]benzothienyl)zirconium dichloride,
($\eta^5$-cyclopentadienyl)($\eta^5$-8-fluoro-2-methylcyclopenta[b][1]benzothienyl)zirconium dichloride,
($\eta^5$-cyclopentadienyl)($\eta^5$-3-bromo-5-methylcyclopenta[b]furyl)zirconium dichloride,
($\eta^5$-cyclopentadienyl)($\eta^5$-2-bromo-1,5-dimethylcyclopenta[b]pyrrolyl)zirconium dichloride,
($\eta^5$-cyclopentadienyl)($\eta^5$-2-bromo-5-methyl-1-phenylcyclopenta[b]pyrrolyl)zirconium dichloride,
($\eta^5$-cyclopentadienyl)($\eta^5$-2-chloro-5-methyl-1-phenylcyclopenta[b]pyrrolyl)zirconium dichloride,
($\eta^5$-cyclopentadienyl)($\eta^5$-2-iodo-5-methyl-1-phenylcyclopenta[b]pyrrolyl)zirconium dichloride,
($\eta^5$-cyclopentadienyl)($\eta^5$-2-fluoro-5-methyl-1-phenylcyclopenta[b]pyrrolyl)zirconium dichloride,
($\eta^5$-cyclopentadienyl)($\eta^5$-2-bromo-1,5-dimethylcyclopenta[b]phospholyl)zirconium dichloride,
($\eta^5$-cyclopentadienyl)($\eta^5$-5-bromo-2,4-dimethylcyclopenta[b]indolyl)zirconium dichloride,
($\eta^5$-cyclopentadienyl)($\eta^5$-4-bromocyclopenta[b]pyridyl)zirconium dichloride,
($\eta^5$-cyclopentadienyl)($\eta^5$-4-bromocyclopenta[b]phosphoranyl)zirconium dichloride,
($\eta^5$-cyclopentadienyl)($\eta^5$-2,6-dibromo-1-dimethylamino-1-boratobenzene)zirconium dichloride, ($\eta^5$-cyclopentadienyl)($\eta^5$-4-bromo-3-dimethylamini-1,3-thiaborindenyl)zirconium dichloride,
($\eta^5$-cyclopentadienyl)($\eta^5$-4-bromo-3a,7a-azaborindenyl)zirconium dichloride,
($\eta^5$-cyclopentadienyl)($\eta^5$-7-bromo-2-dimethylamino-1,2-benzothiaboralide)zirconium dichloride,
($\eta^5$-cyclopentadienyl)($\eta^5$-3-bromo-2-dimethylamino-1,2-thiaborolide)zirconium dichloride,
($\eta^5$-cyclopentadienyl)($\eta^5$-2-[4-bromophenyl]-indenyl)zirconium dichloride,
($\eta^5$-cyclopentadienyl)($\eta^5$-2-[4-chlorophenyl]-indenyl)zirconium dichloride,
($\eta^5$-cyclopentadienyl)($\eta^5$-2-[4-iodophenyl]-indenyl)zirconium dichloride,
($\eta^5$-cyclopentadienyl)($\eta^5$-2-[4-fluorophenyl]-indenyl)zirconium dichloride,
($\eta^5$-cyclopentadienyl)($\eta^5$-2-[5-bromothien-2-yl]-indenyl)zirconium dichloride,
($\eta^5$-cyclopentadienyl)($\eta^5$-2-[4-bromopyridin-2-yl]-indenyl)zirconium dichloride,
($\eta^5$-cyclopentadienyl)($\eta^5$-2-bromoindenyl)zirconium dichloride,
($\eta^5$-cyclopentadienyl)($\eta^5$-3-bromoindenyl)zirconium dichloride,
($\eta^5$-cyclopentadienyl)($\eta^5$-2-chloroindenyl)zirconium dichloride,
($\eta^5$-cyclopentadienyl)($\eta^5$-2-bromofluorenyl)zirconium dichloride,
($\eta^5$-cyclopentadienyl)($\eta^5$-2-iodofluorenyl)zirconium dichloride,
($\eta^5$-cyclopentadienyl)($\eta^5$-2-chlorofluorenyl)zirconium dichloride,
($\eta^5$-cyclopentadienyl)($\eta^5$-2-fluorofluorenyl)zirconium dichloride,
($\eta^5$-cyclopentadienyl)($\eta^5$-2,7-dibromofluorenyl)zirconium dichloride,
($\eta^5$-cyclopentadienyl)($\eta^5$-7-bromoindeno[1,2-c]pyridinyl)zirconium dichloride,
($\eta^5$-cyclopentadienyl)($\eta^5$-3-bromoindeno[1,2-c]pyridinyl)zirconium dichloride,
($\eta^5$-cyclopentadienyl)($\eta^5$-7-bromoindeno[1,2-c]phosphoranyl)zirconium dichloride,
($\eta^5$-cyclopentadienyl)($\eta^5$-2-bromoindeno[1,2-b]thienyl)zirconium dichloride,
($\eta^5$-cyclopentadienyl)($\eta^5$-6-bromoindeno[2,1-b]thienyl)zirconium dichloride,
($\eta^5$-cyclopentadienyl)($\eta^5$-6-bromoindeno[1,2-c]thienyl)zirconium dichloride,
($\eta^5$-cyclopentadienyl)($\eta^5$-6-bromoindeno[1,2-b]thienyl)zirconium dichloride,
($\eta^5$-cyclopentadienyl)($\eta^5$-6-bromo-2,3-dimethylindeno[1,2-b]furanyl)zirconium dichloride,
($\eta^5$-cyclopentadienyl)($\eta^5$-2-bromoindeno[1,2-b][1]benzothienyl)zirconium dichloride,
($\eta^5$-cyclopentadienyl)($\eta^5$-8-bromoindeno[1,2-b][1]benzothienyl)zirconium dichloride,
($\eta^5$-cyclopentadienyl)($\eta^5$-8-bromoindeno[2,1-b][1]benzothienyl)zirconium dichloride,
($\eta^5$-cyclopentadienyl)($\eta^5$-3-bromo-6H-indeno[2,1-b][1]benzothienyl)zirconium dichloride,
($\eta^5$-cyclopentadienyl)($\eta^5$-2-bromo-5-methylindeno[1,2-b]indolyl)zirconium dichloride,
($\eta^5$-cyclopentadienyl)($\eta^5$-8-bromo-5-methylindeno[1,2-b]indolyl)zirconium dichloride,
($\eta^5$-cyclopentadienyl)($\eta^5$-8-bromo-5-methylindeno[2,1-b]indolyl)zirconium dichloride,
($\eta^5$-cyclopentadienyl)($\eta^5$-3-bromo-5-methylindeno[2,1-b]indolyl)zirconium dichloride,
($\eta^5$-pentamethylcyclopentadienyl)($\eta^5$-2-[5-bromonaphth-1-yl]indenyl)zirconium dichloride,
($\eta^5$-pentamethylcyclopentadienyl)($\eta^5$-2-[7-fluorobenzothien-2-yl]indenyl)zirconium dichloride,
($\eta^5$-pentamethylcyclopentadienyl)($\eta^5$-2-[2-chlorobenzothien-4-yl]indenyl)zirconium dichloride,
($\eta^5$-4-bromo-2-methylindenyl)zirconium trichloride,
($\eta^5$-2-bromoindenyl)zirconium trichloride,
($\eta^5$-4-bromo-2-methylindenyl)zirconium trichloride,
($\eta^5$-4-chloro-2-methylindenyl)zirconium trichloride,
($\eta^5$-4-fluoro-2-methylindenyl)zirconium trichloride,
($\eta^5$-4-iodo-2-methylindenyl)zirconium trichloride,
($\eta^5$-4-bromo-2-methylindenyl)zirconium tribromide,
($\eta^5$-4-bromo-2-methylindenyl)zirconium triiodide,
($\eta^5$-4-bromo-2-methylindenyl)zirconium trifluoride,
($\eta^5$-4-bromo-2-methylindenyl)zirconium trihydride,
($\eta^5$-4-bromo-2-methylindenyl)trimethylzirconium,
($\eta^5$-4-bromo-2-methylindenyl)triphenylzirconium,
($\eta^5$-4-bromo-2-methylindenyl)tribenzylzirconium,
($\eta^5$-4-bromo-2-methylindenyl)trimethoxyzirconium,
($\eta^5$-4-bromo-2-methylindenyl)-tris(dimethylamino)zirconium,
($\eta^5$-3-[4-bromophenyl]-cyclopentadienyl)zirconium trichloride,
($\eta^5$-4-bromo-2-methylcyclopenta[b]naphthyl)zirconium trichloride,
($\eta^5$-8-bromo-6-methylindeno[5,6-d][1,3]dioxolyl)zirconium trichloride,
($\eta^5$-4-bromo-2,3,6-trimethylindeno[5,6-b]thienyl)zirconium trichloride,
($\eta^5$-2-bromo-4,6-dimethylindeno[5,6-b]thienyl)zirconium trichloride,
($\eta^5$-4-bromo-1,2,3,6-tetramethylcyclopenta[f]indolyl)zirconium trichloride,
($\eta^5$-4-bromo-1-phenyl-2,3,6-triamethylcyclopenta[f]indolyl)zirconium trichloride,
($\eta^5$-5-bromo-7-methylcyclopenta[g]quinolyl)zirconium trichloride,
($\eta^5$-2-bromo-5,7-dimethylcyclopenta[g]quinolyl)zirconium trichloride,
($\eta^5$-4,6-dibromo-2-methylindenyl)zirconium trichloride,
($\eta^5$-4,6-dichloro-2-methylindenyl)zirconium trichloride,
($\eta^5$-4,6-difluoro-2-methylindenyl)zirconium trichloride,
($\eta^5$-4-bromo-6-chloro-2-methylindenyl)zirconium trichloride,
($\eta^5$-4-bromo-6-fluoro-2-methylindenyl)zirconium trichloride,
($\eta^5$-5-bromo-2,4-dimethylindenyl)zirconium trichloride,
($\eta^5$-6-bromo-2,4-dimethylindenyl)zirconium trichloride,
($\eta^5$-7-bromo-2-methyl-4-phenylindenyl)zirconium trichloride,
($\eta^5$-3-bromo-5-methylcyclopenta[b]thienyl)zirconium trichloride,
($\eta^5$-1,3-dichlorocyclopenta[c]thienyl)zirconium trichloride,
($\eta^5$-8-bromo-2-methylcyclopenta[b][1]benzothienyl)zirconium trichloride,
($\eta^5$-8-chloro-2-methylcyclopenta[b][1]benzothienyl)zirconium trichloride,
($\eta^5$-8-iodo-2-methylcyclopenta[b][1]benzothienyl)zirconium trichloride,
($\eta^5$-8-fluoro-2-methylcyclopenta[b][1]benzothienyl)zirconium trichloride,
($\eta^5$-3-bromo-5-methylcyclopenta[b]furyl)zirconium trichloride, ($\eta^5$-2-bromo-1,5-dimethylcyclopenta[b]pyrrolyl)zirconium trichloride,
($\eta^5$-2-bromo-5-methyl-1-phenylcyclopenta[b]pyrrolyl)zirconium trichloride,
($\eta^5$-2-chloro-5-methyl-1-phenylcyclopenta[b]pyrrolyl)zirconium trichloride,
($\eta^5$-2-iodo-5-methyl-1-phenylcyclopenta[b]pyrrolyl)zirconium trichloride,
($\eta^5$-2-fluoro-5-methyl-1-phenylcyclopenta[b]pyrrolyl)zirconium trichloride,
($\eta^5$-2-bromo-1,5-dimethylcyclopenta[b]phospholyl)zirconium trichloride,
($\eta^5$-5-bromo-2,4-dimethylcyclopenta[b]indolyl)zirconium trichloride,
($\eta^5$-4-bromocyclopenta[b]pyridyl)zirconium trichloride,
($\eta^5$-4-bromocyclopenta[b]phosphoranyl)zirconium trichloride,
($\eta^5$-2,6-dibromo-1-dimethylamino-1-boratobenzene)zirconium trichloride,
($\eta^5$-4-bromo-3-dimethylamino-1,3-thiaborindenyl)zirconium trichloride,
($\eta^5$-4-bromo-3a,7a-azaborindenyl)zirconium trichloride,
($\eta^5$-7-bromo-2-dimethylamino-1,2-benzothiaboralide)zirconium trichloride,
($\eta^5$-3-bromo-2-dimethylamino-1,2-thiaborolide)zirconium trichloride,
($\eta^5$-2-[4-bromophenyl]-indenyl)zirconium trichloride,
($\eta^5$-2-[4-chlorophenyl]-indenyl)zirconium trichloride,
($\eta^5$-2-[4-fluorophenyl]-indenyl)zirconium trichloride,
(?15-2-[4-iodophenyl]-indenyl)zirconium trichloride,
($\eta^5$-2-[5-bromothien-2-yl]-indenyl)zirconium trichloride,
($\eta^5$-2-[4-bromopyridin-2-yl]-indenyl)zirconium trichloride,
($\eta^5$-2-bromoindenyl)zirconium trichloride,
($\eta^5$-2-bromo-4,7-dimethylindenyl)zirconium trichloride,
($\eta^5$-3-bromoindenyl)zirconium trichloride,
($\eta^5$-2-chloroindenyl)zirconium trichloride,
($\eta^5$-2-bromofluorenyl)zirconium trichloride,
($\eta^5$-2-iodofluorenyl)zirconium trichloride,
($\eta^5$-2-chlorofluorenyl)zirconium trichloride,
($\eta^5$-2-fluorofluorenyl)zirconium trichloride,
($\eta^5$-2,7-dibromofluorenyl)zirconium trichloride,
($\eta^5$-7-bromoindeno[1,2-c]pyridinyl)zirconium trichloride,
($\eta^5$-3-bromoindeno[1,2-c]pyridinyl)zirconium trichloride,
($\eta^5$-7-bromoindeno[1,2-c]phosphoranyl)zirconium trichloride,
($\eta^5$-2-bromoindeno[1,2-b]thienyl)zirconium trichloride,
($\eta^5$-6-bromoindeno[2,1-b]thienyl)zirconium trichloride,
($\eta^5$-6-bromoindeno[1,2-c]thienyl)zirconium trichloride,
($\eta^5$-6-bromoindeno[1,2-b]thienyl)zirconium trichloride,
($\eta^5$-6-bromo-2,3-dimethylindeno[1,2-b]furanyl)zirconium trichloride,
($\eta^5$-2-bromoindeno[1,2-b][1]benzothienyl)zirconium trichloride,
($\eta^5$-8-bromoindeno[1,2-b][1]benzothienyl)zirconium trichloride,
($\eta^5$-8-bromoindeno[2,1-b][1]benzothienyl)zirconium trichloride,
($\eta^5$-3-bromo-6H-indeno[2,1-b][1]benzothienyl)zirconium trichloride,
($\eta^5$-2-bromo-5-methylindeno[1,2-b]indolyl)zirconium trichloride,
($\eta^5$-8-bromo-5-methylindeno[1,2-b]indolyl)zirconium trichloride,
($\eta^5$-8-bromo-5-methylindeno[2,1-b]indolyl)zirconium trichloride,
($\eta^5$-3-bromo-5-methylindeno[2,1-b]indolyl)zirconium trichloride,
($\eta^5$-2-[5-bromonaphth-1-yl]indenyl)zirconium tribromide,
($\eta^5$-2-[7-fluorobenzothien-2-yl]indenyl)zirconium tribromide,
($\eta^5$-2-[2-chlorobenzothien-4-yl]indenyl)zirconium tribromide,
rac-dimethylsilanediyl-bis($\eta^5$-4-bromo-2-methylinden-1-yl)zirconium dichloride,
rac-dimethylsilanediyl-bis($\eta^5$-4-bromoinden-1-yl)zirconium dichloride,
rac-dimethylsilanediyl-bis($\eta^5$-4-bromo-2-isopropylinden-1-yl)zirconium dichloride,
rac-dimethylsilanediyl-bis($\eta^5$-4-bromo-2-phenylinden-1-yl)zirconium dichloride,
rac-dimethylsilanediyl-bis($\eta^5$-4-bromo-2-[5-methyl-2-thienyl]inden-1-yl)zirconium dichloride,
rac-dimethylsilanediyl-bis($\eta^5$-4-bromo-2-[4-pyridinyl]inden-1-yl)zirconium dichloride,
rac-dimethylsilanediyl-bis($\eta^5$-4-fluoro-2-methylinden-1-yl)zirconium dichloride,
rac-dimethylsilanediyl-bis($\eta^5$-4-chloro-2-methylinden-1-yl)zirconium dichloride,
rac-dimethylsilanediyl-bis($\eta^5$-4-iodo-2-methylinden-1-yl)zirconium dichloride,
rac-dimethylsilanediyl-bis($\eta^5$-4-bromo-2-methylinden-1-yl)zirconium dibromide,
rac-dimethylsilanediyl-bis($\eta^5$-4-bromo-2-methylinden-1-yl)zirconium diiodide,
rac-dimethylsilanediyl-bis($\eta^5$-4-bromo-2-methylinden-1-yl)zirconium difluoride,
rac-dimethylsilanediyl-bis($\eta^5$-4-bromo-2-methylinden-1-yl)zirconium dihydride,
rac-dimethylsilanediyl-bis($\eta^5$-4-bromo-2-methylinden-1-yl)dimethylzirconium,
rac-dimethylsilanediyl-bis($\eta^5$-4-bromo-2-methylinden-1-yl)dibenzylzirconium,
rac-dimethylsilanediyl-bis($\eta^5$-4-bromo-2-methylinden-1-yl)diphenylzirconium,
rac-dimethylsilanediyl-bis($\eta^5$-4-bromo-2-methylinden-1-yl)-bis(dimethylamino)zirconium,
rac-dimethylsilanediyl-bis($\eta^5$-4-bromo-2-methylinden-1-yl)($N^1,N^3$-diphenyl-1,3-propanediamino)zirconium,
rac-dimethylsilanediyl-bis($\eta^5$-4-bromo-2-methylinden-1-yl)dimethoxyzirconium,
rac-dimethylsilanediyl-bis($\eta^5$-4-bromo-2-methylinden-1-yl)(3,3',5,5'-tetra-tert-butyl-[1,1'-biphenyl]-2,2'-dioxo)zirconium,
rac-dimethylsilanediyl-bis($\eta^5$-4-bromo-2,5-dmethylinden-1-yl)zirconium dichloride,
rac-dimethylsilanediyl-bis($\eta^5$-4-bromo-2-methyl-6-phenyl-inden-1-yl)zirconium dichloride,
rac-dimethylsilanediyl-bis($\eta^5$-4-bromo-2-methyl-6-[5-methyl-2-thienyl]inden-1-yl)zirconium dichloride,
rac-dimethylsilanediyl-bis($\eta^5$-4-bromo-2-methyl-6-[4-pyridinyl]inden-1-yl)zirconium dichloride,
rac-dimethylsilanediyl-bis($\eta^5$-4-bromo-6-isopropyl-2-methylinden-1-yl)zirconium dichloride,
rac-dimethylsilanediyl-bis($\eta^5$-4-bromo-2-methyl-5,6,7,8-tetrahydrocyclopenta[b]naphtha-1-yl)zirconium dichloride,
rac-dimethylsilanediyl-bis($\eta^5$-5-bromo-2-methyl-6,7,8,9-tetrahydrocyclopenta[a]naphth-3-yl)zirconium dichloride,
rac-dimethylsilanediyl-bis($\eta^5$-4-bromo-2-methylcyclopenta[b]naphth-1-yl)zirconium dichloride,
rac-dimethylsilanediyl-bis($\eta^5$-7-bromo-2,4-dimethylcyclopenta[b]naphth-1-yl)zirconium dichloride, rac-dimethylsilanediyl-bis($\eta^5$-8-bromo-6-methylindeno[5,6-d][1,3]dioxol-5-yl)zirconium dichloride,
rac-dimethylsilanediyl-bis($\eta^5$-4-bromo-2,3,6-trimethylindeno[5,6-b]thien-7-yl)zirconium dichloride,
rac-dimethylsilanediyl-bis($\eta^5$-2-bromo-4,6-dimethylindeno[5,6-b]thien-7-yl)zirconium dichloride,
rac-dimethylsilanediyl-bis($\eta^5$-4-bromo-1,2,3,6-tetramethylcyclopenta[f]indol-7-yl)zirconium dichloride,
rac-dimethylsilanediyl-bis($\eta^5$-4-bromo-1-phenyl-2,3,6-triamethylcyclopenta[f]indol-7-yl)zirconium dichloride,
rac-dimethylsilanediyl-bis($\eta^5$-5-bromo-7-methylcyclopenta[g]quinol-8-yl)zirconium dichloride,
rac-dimethylsilanediyl-bis($\eta^5$-2-bromo-5,7-dimethylcyclopenta[g]quinol-8-yl)zirconium dichloride,
rac-dimethylsilanediyl-bis($\eta^5$-4-bromo-6-trifluoromethyl-2-methylinden-1-yl)zirconium dichloride,
rac-dimethylsilanediyl-bis($\eta^5$-4-bromo-6-perfluorophenyl-2-methylinden-1-yl)zirconium dichloride,
rac-dimethylsilanediyl-bis($\eta^5$-4-bromo-6-methoxy-2-methylinden-1-yl)zirconium dichloride,
rac-dimethylsilanediyl-bis($\eta^5$-4-bromo-6-dimethylamino-2-methylinden-1-yl)zirconium dichloride,
rac-dimethylsilanediyl-bis($\eta^5$-4-bromo-6-methylsulfanyl-2-methylinden-1-yl)zirconium dichloride,
rac-dimethylsilanediyl-bis($\eta^5$-4-bromo-6-dimethylphosphino-2-methylinden-1-yl)zirconium dichloride,
rac-dimethylsilanediyl-bis($\eta^5$-4-bromo-6-trimethylsilyl-2-methylinden-1-yl)zirconium dichloride,
rac-dimethylsilanediyl-bis($\eta^5$-4-bromo-6-trimethylgermyl-2-methylinden-1-yl)zirconium dichloride,
rac-dimethylsilanediyl-bis($\eta^5$-4,6-dibromo-2-methylinden-1-yl)zirconium dichloride,
rac-dimethylsilanediyl-bis($\eta^5$-4,6-dichloro-2-methylinden-1-yl)zirconium dichloride,
rac-dimethylsilanediyl-bis($\eta^5$-4,6-difluoro-2-methylinden-1-yl)zirconium dichloride,
rac-dimethylsilanediyl-bis($\eta^5$-4-bromo-6-chloro-2-methylinden-1-yl)zirconium dichloride,
rac-dimethylsilanediyl-bis($\eta^5$-4-bromo-6-fluoro-2-methylinden-1-yl)zirconium dichloride,
rac-dimethylsilanediyl-bis($\eta^5$-5-bromo-2,4-dimethylinden-1-yl)zirconium dichloride,
rac-dimethylsilanediyl-bis($\eta^5$-6-bromo-2,4-dimethylinden-1-yl)zirconium dichloride,
rac-dimethylsilanediyl-bis($\eta^5$-7-bromo-2-methyl-4-phenyl-inden-1-yl)zirconium dichloride,
meso-dimethylsilanediyl-bis($\eta^5$-4-bromo-2-methylinden-1-yl)zirconium dichloride,
meso-dimethylsilanediyl-bis($\eta^5$-4-bromoinden-1-yl)zirconium dichloride,
rac-2,2'-propylidene-bis($\eta^5$-4-bromo-2-methylinden-1-yl)zirconium dichloride,
meso-2,2'-propylidene-bis($\eta^5$-4-bromo-2-methylinden-1-yl)zirconium dichloride,
rac-methylidene-bis($\eta^5$-4-bromo-2-methylinden-1-yl)zirconium dichloride,
rac-diphenylmethylidene-bis($\eta^5$-4-bromo-2-methylinden-1-yl)zirconium dichloride,
rac-1,2-ethylidene-bis($\eta^5$-4-bromo-2-methylinden-1-yl)zirconium dichloride,
meso-1,2-ethylidene-bis($\eta^5$-4-bromo-2-methylinden-1-yl)zirconium dichloride,
rac-dimethylgermanediyl-bis($\eta^5$-4-bromo-2-methylinden-1-yl)zirconium dichloride,
rac-methylboranediyl-bis($\eta^5$-4-bromo-2-methylinden-1-yl)zirconium dichloride,
rac-phenylboranediyl-bis($\eta^5$-4-bromo-2-methylinden-1-yl)zirconium dichloride,
rac-methylphosphinediyl-bis($\eta^5$-4-bromo-2-methylinden-1-yl)zirconium dichloride,
rac-methylphosphinediyl-bis($\eta^5$-4-bromoinden-1-yl)zirconium dichloride,
meso-methylphosphinediyl-bis($\eta^5$-4-bromoinden-1-yl)zirconium dichloride,
rac-phenylphosphinediyl-bis($\eta^5$-4-bromo-2-methylinden-1-yl)zirconium dichloride,
rac-dimethylsilanediyl-bis[$\eta^5$-2-(4-bromophenyl)inden-1-yl]zirconium dichloride,
meso-dimethylsilanediyl-bis[$\eta^5$-2-(4-bromophenyl)inden-1-yl]zirconium dichloride,
meso-dimethylsilanediyl-bis[7$^5$-2-(4-bromophenyl)inden-1-yl]zirconium dichloride,
rac-2,2'-propylidene-bis[$\eta^5$-2-(4-bromophenyl)inden-1-yl]zirconium dichloride,
rac-1,2-ethylidene-bis[$\eta^5$-2-(4-bromophenyl)inden-1-yl]zirconium dichloride,
rac-methylphosphinediyl-bis[$\eta^5$-2-(4-bromophenyl)inden-1-yl]zirconium dichloride,
rac-dimethylsilanediyl-bis[$\eta^5$-2-(4-bromo-2-pyridinyl)inden-1-yl]zirconium dichloride,
rac-dimethylsilanediyl-bis[$\eta^5$-2-(5-bromo-2-thienyl)inden-1-yl]zirconium dichloride,
rac-methyl(4-bromophenyl)silanediyl-bis($\eta^5$-2-methylinden-1-yl)zirconium dichloride,
meso-methyl(4-bromophenyl)silanediyl-bis($\eta^5$-2-methylinden-1-yl)zirconium dichloride,
rac-methyl(4-bromophenyl)silanediyl-bis($\eta^5$inden-1-yl)zirconium dichloride,
rac-methyl(4-bromophenyl)silanediyl-bis($\eta^5$-2-methyl-4-phenylinden-1-yl)zirconium dichloride,
rac-methyl(4-bromophenyl)silanediyl-bis($\eta^5$-2-methyl-4-naphthylinden-1-yl)zirconium dichloride,
rac-methyl(4-bromophenyl)silanediyl-bis($\eta^5$-2-isopropyl-4-phenylinden-1-yl)zirconium dichloride,
rac-methyl(4-bromophenyl)silanediyl-bis($\eta^5$-2-phenylinden-1-yl)zirconium dichloride,
rac-methyl(4-bromophenyl)silanediyl-bis($\eta^5$-2-methyl-4-phenylinden-1-yl)zirconium dibromide,
rac-methyl(4-bromophenyl)silanediyl-bis($\eta^5$-2-methyl-4-phenylinden-1-yl)zirconium diiodide,
rac-methyl(4-bromophenyl)silanediyl-bis($\eta^5$-2-methyl-4-phenylinden-1-yl)zirconium difluoride,
rac-methyl(4-bromophenyl)silanediyl-bis($\eta^5$-2-methyl-4-phenylinden-1-yl)zirconium dihydride,
rac-methyl(4-bromophenyl)silanediyl-bis($\eta^5$-2-methyl-4-phenylinden-1-yl)dimethylzirconium,
rac-methyl(4-bromophenyl)silanediyl-bis($\eta^5$-2-methyl-4-phenylinden-1-yl)dibenzylzirconium,
rac-methyl(4-bromophenyl)silanediyl-bis($\eta^5$-2-methyl-4-phenylinden-1-yl)diphenylzirconium,
rac-methyl(4-bromophenyl)silanediyl-bis($\eta^5$-2-methyl-4-phenylinden-1-yl)-bis(dimethylamino)zirconium,
rac-methyl(4-bromophenyl)silanediyl-bis($\eta^5$-2-methyl-4-phenylinden-1-yl)($N^1$,$N^3$-diphenyl-1,3-propanediamino)zirconium,
rac-methyl(4-bromophenyl)silanediyl-bis($\eta^5$-2-methyl-4-phenylinden-1-yl)dimethoxyzirconium,
rac-methyl(4-bromophenyl)silanediyl-bis($\eta^5$-2-methyl-4-phenylinden-1-yl)(3,3',5,5'-tetra-tert-butyl-[1,1'-biphenyl]-2,2'-dioxo)zirconium,
rac-methyl(4-bromophenyl)silanediyl-bis($\eta^5$-2-methyl-4-[5-methyl-2-thienyl]inden-1-yl)zirconium dichloride, rac-methyl(4-bromophenyl)silanediyl-bis($\eta^5$-2-methyl-4-[4-pyridinyl]inden-1-yl)zirconium dichloride,
rac-methyl(4-bromophenyl)silanediyl-bis($\eta^5$-2,3,6-trimethylindeno[5,6-b]thien-7-yl)zirconium dichloride,
rac-methyl(4-bromophenyl)silanediyl-bis($\eta^5$-1,2,3,6-tetramethylcyclopenta[f]indol-7-yl)zirconium dichloride,
rac-methyl(4-bromo-2-pyridinyl)silanediyl-bis($\eta^5$-2-methylinden-1-yl)zirconium dichloride,
rac-methyl(5-bromo-2-thienyl)silanediyl-bis($\eta^5$-2-methylinden-1-yl)zirconium dichloride,
rac-methyl(4-bromophenyl)germanediyl-bis($\eta^5$-2-methylinden-1-yl)zirconium dichloride,
rac-(4-bromophenyl)phosphinediyl-bis($\eta^5$-2-methylinden-1-yl)zirconium dichloride,
rac-1,1'-(4-bromophenylethylidene)-bis($\eta^5$-4-bromo-2-methylinden-1-yl)zirconium dichloride,
rac-methylidene-bis($\eta^5$-4-bromo-2-inden-1-yl)zirconium dichloride,
meso-methylidene-bis($\eta^5$-4-bromo-2-inden-1-yl)zirconium dichloride,
rac-methylidene-($\eta^5$-4-bromo-2-methylinden-1-yl)($\eta^5$-4-bromo-2-indenyl)zirconium dichloride,
meso-methylidene-($\eta^5$-4-bromo-2-methylinden-1-yl)($\eta^5$-4-bromo-2-methyl-2-indenyl)zirconium dichloride,
(4-bromophenyl)methylidene-bis($\eta^5$-2-inden-1-yl)zirconium dichloride,
bis(4-bromophenyl)methylidene-($\eta^5$-2-methylinden-1-yl)($\eta^5$-2-inden-1-yl)zirconium dichloride,
rac-dimethylsilanediyl-bis($\eta^5$-3-bromo-5-methylcyclopenta[b]thien-6-yl)zirconium dichloride,
meso-dimethylsilanediyl-bis($\eta^5$-3-bromo-5-methylcyclopenta[b]thien-6-yl)zirconium dichloride,
rac-dimethylsilanediyl-bis($\eta^5$-3-chloro-5-methylcyclopenta[b]thien-6-yl)zirconium dichloride,
rac-dimethylsilanediyl-bis($\eta^5$-3-fluoro-5-methylcyclopenta[b]thien-6-yl)zirconium dichloride,
rac-dimethylsilanediyl-bis($\eta^5$-3-bromo-5-methyl-2-phenylcyclopenta[b]thien-6-yl)zirconium dichloride,
rac-methylideno-bis($\eta^5$-3-bromo-5-methylcyclopenta[b]thien-6-yl)zirconium dichloride,
rac-2,2'-propylideno-bis($\eta^5$-3-bromo-5-methylcyclopenta[b]thien-6-yl)zirconium dichloride,
rac-1,2-ethylideno-bis($\eta^5$-3-bromo-5-methylcyclopenta[b]thien-6-yl)zirconium dichloride,
rac-methyl(4-bromophenyl)silanediyl-bis($\eta^5$-3-bromo-5-methylcyclopenta[b]thien-6-yl)zirconium dichloride,
rac-dimethylsilanediyl-bis($\eta^5$-3-bromo-5-methylcyclopenta[b]thien-6-yl)zirconium dibromide,
rac-dimethylsilanediyl-bis($\eta^5$-3-bromo-5-methylcyclopenta[b]thien-6-yl)zirconium diiodide,
rac-dimethylsilanediyl-bis($\eta^5$-3-bromo-5-methylcyclopenta[b]thien-6-yl)zirconium difluoride,
rac-dimethylsilanediyl-bis($\eta^5$-3-bromo-5-methylcyclopenta[b]thien-6-yl)zirconium dihydride,
rac-dimethylsilanediyl-bis($\eta^5$-3-bromo-5-methylcyclopenta[b]thien-6-yl)dimethylzirconium,
rac-dimethylsilanediyl-bis($\eta^5$-3-bromo-5-methylcyclopenta[b]thien-6-yl)diphenylzirconium,
rac-dimethylsilanediyl-bis($\eta^5$-3-bromo-5-methylcyclopenta[b]thien-6-yl)dibenzylzirconium,
rac-dimethylsilanediyl-bis($\eta^5$-3-bromo-5-methylcyclopenta[b]thien-6-yl)-bis(dimethylamino)zirconium,
rac-dimethylsilanediyl-bis($\eta^5$-3-bromo-5-methylcyclopenta[b]thien-6-yl)($N^1,N^3$-diphenyl-1,3-propanediamino)zirconium,
rac-dimethylsilanediyl-bis($\eta^5$-3-bromo-5-methylcyclopenta[b]thien-6-yl)dimethoxyzirconium,
rac-dimethylsilanediyl-bis($\eta^5$-3-bromo-5-methylcyclopenta[b]thien-6-yl)(3,3',5,5'-tetra-tert-butyl-[1,1'-biphenyl]-2,2'-dioxo)zirconium,
rac-dimethylsilanediyl-bis($\eta^5$-1,3-dichlorocyclopenta[c]thien-4-yl)zirconium dichloride,
rac-dimethylsilanediyl-bis($\eta^{75}$-8-bromo-2-methylcyclopenta[b][1]benzothien-3-yl)zirconium dichloride,
rac-dimethylsilanediyl-bis($\eta^5$-8-chloro-2-methylcyclopenta[b][1]benzothien-3-yl)zirconium dichloride,
rac-dimethylsilanediyl-bis($\eta^5$-8-iodo-2-methylcyclopenta[b][1]benzothien-3-yl)zirconium dichloride,
rac-dimethylsilanediyl-bis($\eta^5$-8-fluoro-2-methylcyclopenta[b][1]benzothien-3-yl)zirconium dichloride,
rac-dimethylsilanediyl-bis($\eta^5$-3-bromo-5-methylcyclopenta[b]far-6-yl)zirconium dichloride,
rac-dimethylsilanediyl-bis($\eta^5$-2-bromo-1,5-dimethylcyclopenta[b]pyrrol-4-yl)zirconium dichloride,
rac-dimethylsilanediyl-bis($\eta^5$-2-bromo-5-methyl-1-phenylcyclopenta[b]pyrrol-4-yl)zirconium dichloride,
rac-dimethylsilanediyl-bis($\eta^5$-2-chloro-5-methyl-i -phenylcyclopenta[b]pyrrol-4-yl)zirconium dichloride,
rac-dimethylsilanediyl-bis($\eta^5$-2-iodo-5-methyl-1-phenylcyclopenta[b]pyrrol-4-yl)zirconium dichloride,
rac-dimethylsilanediyl-bis($\eta^5$-2-fluoro-5-methyl-1-phenylcyclopenta[b]pyrrol-4-yl)zirconium dichloride,
rac-dimethylsilanediyl-bis($\eta^5$-2-bromo-1,5-dimethylcyclopenta[b]phosphol-4-yl)zirconium dichloride,
rac-dimethylsilanediyl-bis($\eta^5$-5-bromo-2,4-dimethylcyclopenta[b]indol-1-yl)zirconium dichloride,
rac-dimethylsilanediyl-bis($\eta^5$-4-bromocyclopenta[b]pyrid-7-yl)zirconium dichloride,
rac-dimethylsilanediyl-bis($\eta^5$-4-bromocyclopenta[b]phosphoran-7-yl)zirconium dichloride,
rac-dimethylsilanediyl-bis($\eta^5$-2,6-dibromo-1-dimethylamino-1-boratobenzene-4)zirconium dichloride,
rac-dimethylsilanediyl-bis($\eta^5$-4-bromo-3-dimethylamino-1,3-thiaborinden-2-yl)zirconium dichloride,
rac-dimethylsilanediyl-bis($\eta^5$-4-bromo-3a,7a-azaborinden-1-yl)zirconium dichloride,
rac-dimethylsilanediyl-bis($\eta^5$-7-bromo-2-dimethylamino-1,2-benzothiaboralide-3)zirconium dichloride,
rac-dimethylsilanediyl-bis( $\eta^5$-3-bromo-2-dimethylamino-1,2-thiaborolide-5)zirconium dichloride,
rac-dimethylsilanediyl-bis($\eta^5$-2-bromoinden-1-yl)zirconium dichloride,
rac-dimethylsilanediyl-bis($\eta^5$-3-bromoinden-1-yl)zirconium dichloride,
rac-dimethylsilanediyl-bis($\eta^5$-2-chloroinden-1-yl)zirconium dichloride,
rac-dimethylsilanediyl-bis($\eta^5$-2-bromofluoren-9-yl)zirconium dichloride,
meso-dimethylsilanediyl-bis($\eta^5$-2-bromofluoren-9-yl)zirconium dichloride,
rac-dimethylsilanediyl-bis($\eta^5$-2-iodofluoren-9-yl)zirconium dichloride,
rac-dimethylsilanediyl-bis($\eta^5$-2-chlorofluoren-9-yl)zirconium dichloride,
rac-dimethylsilanediyl-bis($\eta^5$-2-fluorofluoren-9-yl)zirconium dichloride,
dimethylsilanediyl-bis($\eta^5$-2,7-dibromofluoren-9-yl)zirconium dichloride,
rac-dimethylsilanediyl-bis($\eta^5$-7-bromoindeno [1,2-c]pyridin-5-yl)zirconium dichloride,
rac-dimethylsilanediyl-bis($\eta^5$-3-bromoindeno[1,2-c]pyridin-5-yl)zirconium dichloride,
rac-dimethylsilanediyl-bis($\eta^5$-7-bromoindeno[1,2-c]phosphoran-5-yl)zirconium dichloride, rac-dimethylsilanediyl-bis($\eta^5$-2-bromoindeno[1,2-b]thien-4-yl)zirconium dichloride,
rac-dimethylsilanediyl-bis($\eta^5$-6-bromoindeno[2,1-b]thien-8-yl)zirconium dichloride,
rac-dimethylsilanediyl-bis($\eta^5$-6-bromoindeno[1,2-c]thien-8-yl)zirconium dichloride,
rac-dimethylsilanediyl-bis($\eta^5$-6-bromoindeno[1,2-b]thien-4-yl)zirconium dichloride,
rac-dimethylsilanediyl-bis($\eta^5$-6-bromo-2,3-dimethylindeno[1,2-b]furan-4-yl)zirconium dichloride,
rac-dimethylsilanediyl-bis($\eta^5$-2-bromoindeno[1,2-b][1]benzothien-10-yl)zirconium dichloride,
rac-dimethylsilanediyl-bis($\eta^5$-8-bromoindeno[1,2-b][1]benzothien-10-yl)zirconium dichloride,
rac-dimethylsilanediyl-bis($\eta^5$-8-bromoindeno[2,1-b][1]benzothien-6-yl)zirconium dichloride,
rac-dimethylsilanediyl-bis($\eta^5$-3-bromo-6H-indeno[2,1-b][1]benzothien-6-yl)zirconium dichloride,
rac-dimethylsilanediyl-bis($\eta^5$-2-bromo-5-methylindeno[1,2-b]indol-10-yl)zirconium dichloride,
rac-dimethylsilanediyl-bis($\eta^5$-8-bromo-5-methylindeno[1,2-b]indol-10-yl)zirconium dichloride,
rac-dimethylsilanediyl-bis($\eta^5$-8-bromo-5-methylindeno[2,1-b]indol-6-yl)zirconium dichloride,
rac-dimethylsilanediyl-bis($\eta^5$-3-bromo-5-methylindeno[2,1-b]indol-6-yl)zirconium dichloride,
rac-methylideno-bis($\eta^5$-2-bromofluoren-9-yl)zirconium dichloride,
rac-2,2'-propylideno-bis($\eta^5$-2-bromofluoren-9-yl)zirconium dichloride,
rac-1,2-ethylideno-bis($\eta^5$-2-bromofluoren-9-yl)zirconium dichloride,
(4-bromophenyl)methylsilanediyl-bis($\eta^5$-fluoren-9-yl)zirconium dichloride,
(4-bromophenyl)methylidene-bis($\eta^5$-fluoren-9-yl)zirconium dichloride,
dimethylsilanediyl($\eta^5$-cyclopentadienyl)($\eta^5$-4-bromo-2-methylinden-1-yl)zirconium dichloride,
rac-dimethylsilanediyl($\eta^5$-3-tert-butylcyclopentadien-1-yl)($\eta^5$-4-bromo-2-methylinden-1-yl)zirconium dichloride,
dimethylsilanediyl($\eta^5$-2,3,4,5-teramethylcyclopentadien-1-yl)($\eta^5$-4-bromo-2-methylinden-1-yl)zirconium dichloride,
dimethylsilanediyl($\eta^5$-fluoren-9-yl)($\eta^5$-4-bromo-2-methylinden-1-yl)zirconium dichloride,
dimethylsilanediyl($\eta^5$-2-bromofluoren-9-yl)($\eta^5$-4-phenyl-2-methylinden-1-yl)zirconium dichloride,
dimethylsilanediyl($\eta^5$-cyclopentadienyl)($\eta^5$-2-bromofluoren-9-yl)zirconium dichloride,
dimethylsilanediyl($\eta^5$-cyclopentadienyl)($\eta^5$-3-[4-bromophenyl]-cyclopentadien-1-yl)zirconium dichloride,
dimethylsilanediyl($\eta^5$-fluoren-9-yl)($\eta^5$-2,7-dibromofluoren-9-yl)zirconium dichloride,
rac-dimethylsilanediyl($\eta^5$-3-trimethylsilylcyclopentadien-1-yl)($\eta^5$-4-bromo-2-methylinden-1-yl)zirconium dichloride,
rac-dimethylsilanediyl($\eta^5$-3-dimethylaminocyclopentadien-1-yl)($\eta^5$-4-bromo-2-methylinden-1-yl)zirconium dichloride,
rac-dimethylsilanediyl($\eta^5$-3-[4-bromophenyl]-cyclopentadien-1-yl)($\eta^5$-4-phenyl-2-methylinden-1-yl)zirconium dichloride,
methyl(4-bromophenyl)silanediyl($\eta^5$-cyclopentadienyl)($\eta^5$-4-phenyl-2-methylinden-1-yl)zirconium dichloride,
dimethylsilanediyl($\eta^5$-cyclopentadienyl)($\eta^5$-4-fluoro-2-methylinden-1-yl)zirconium dichloride,
dimethylsilanediyl($\eta^5$-cyclopentadienyl)($\eta^5$-4-chloro-2-methylinden-1-yl)zirconium dichloride,
dimethylsilanediyl($\eta^5$-cyclopentadienyl)($\eta^5$-4-iodo-2-methylinden-1-yl)zirconium dichloride,
dimethylsilanediyl($\eta^5$-cyclopentadienyl)($\eta^5$-4-bromo-2-methylinden-1-yl)zirconium dibromide,
dimethylsilanediyl($\eta^5$-cyclopentadienyl)($\eta^5$-4-bromo-2-methylinden-1-yl)zirconium diiodide,
dimethylsilanediyl($\eta^5$-cyclopentadienyl)($\eta^5$-4-bromo-2-methylinden-1-yl)zirconium difluoride,
dimethylsilanediyl($\eta^5$-cyclopentadienyl)($\eta^5$-4-bromo-2-methylinden-1-yl)zirconium dihydride,
dimethylsilanediyl($\eta^5$-cyclopentadienyl)($\eta^5$-4-bromo-2-methylinden-1-yl)dimethylzirconium,
dimethylsilanediyl($\eta^5$-cyclopentadienyl)($\eta^5$-4-bromo-2-methylinden-1-yl)dibenzylzirconium,
dimethylsilanediyl($\eta^5$-cyclopentadienyl)($\eta^5$-4-bromo-2-methylinden-1-yl)diphenylzirconium,
dimethylsilanediyl($\eta^5$-cyclopentadienyl)($\eta^5$-4-bromo-2-methylinden-1-yl)-bis-(dimethylamino)zirconium,
dimethylsilanediyl($\eta^5$-cyclopentadienyl)($\eta^5$-4-bromo-2-methylinden-1-yl)dimethoxyzirconium,
dimethylsilanediyl($\eta^5$-cyclopentadienyl)($\eta^5$-4-bromo-2,5-dmethylinden-1-yl)zirconium dichloride,
dimethylsilanediyl($\eta^5$-cyclopentadienyl)($\eta^5$-4-bromo-2-methylcyclopenta[b]naphth-1-yl)zirconium dichloride,
dimethylsilanediyl($\eta^5$-cyclopentadienyl)($\eta^5$-8-bromo-6-methylindeno[5,6-d][1,3]dioxol-5-yl)zirconium dichloride,
dimethylsilanediyl($\eta^5$-cyclopentadienyl)($\eta^5$-4-bromo-2,3,6-trimethylindeno[5,6-b]thien-7-yl)zirconium dichloride,
dimethylsilanediyl($\eta^5$-cyclopentadienyl)($\eta^5$-2-bromo-4,6-dimethylindeno[5,6-b]thien-7-yl)zirconium dichloride,
dimethylsilanediyl($\eta^5$-cyclopentadienyl)($\eta^5$-4-bromo-1,2,3,6-tetramethylcyclopenta[f]indol-7-yl)zirconium dichloride,
dimethylsilanediyl($\eta^5$-cyclopentadienyl)($\eta^5$-4-bromo-1-phenyl-2,3,6-trimethylcyclopenta[f]indol-7-yl)zirconium dichloride,
dimethylsilanediyl($\eta^5$-cyclopentadienyl)($\eta^5$-bromo-7-methylcyclopenta[g]quinol-8-yl)zirconium dichloride,
dimethylsilanediyl($\eta^5$-cyclopentadienyl)($\eta^5$-2-bromo-5,7-dimethylcyclopenta[g]quinol-8-yl)zirconium dichloride,
dimethylsilanediyl($\eta^5$-cyclopentadienyl)($\eta^5$-4,6-dibromo-2-methylinden-1-yl)zirconium dichloride,
dimethylsilanediyl($\eta^5$-cyclopentadienyl)($\eta^5$-4,6-dichloro-2-methylinden-1-yl)zirconium dichloride,
dimethylsilanediyl($\eta^5$-cyclopentadienyl)($\eta^5$-4,6-difluoro-2-methylinden-1-yl)zirconium dichloride,
dimethylsilanediyl($\eta^5$-cyclopentadienyl)($\eta^5$-4-bromo-6-chloro-2-methylinden-1-yl)zirconium dichloride,
dimethylsilanediyl($\eta^5$-cyclopentadienyl)($\eta^5$-4-bromo-6-fluoro-2-methylinden-1-yl)zirconium dichloride,
dimethylsilanediyl($\eta^5$-cyclopentadienyl)($\eta^5$-5-bromo-2,4-dimethylinden-1-yl)zirconium dichloride,
dimethylsilanediyl($\eta^5$-cyclopentadienyl)($\eta^5$-6-bromo-2,4-dimethylinden-1-yl)zirconium dichloride,
dimethylsilanediyl($\eta^5$-cyclopentadienyl)($\eta^5$-7-bromo-2-methyl-4-phenylinden-1-yl)zirconium dichloride,
rac-dimethylsilanediyl($\eta^5$-5-methyl-6-cyclopenta[b]thienyl)($\eta^5$-4-bromo-2-methylinden-1-yl)zirconium dichloride,
rac-dimethylsilanediyl($\eta^5$-3-bromo-5-methyl-6-cyclopenta[b]thienyl)($\eta^5$-4-phenyl-2-methylinden-1-yl)zirconium dichloride,
rac-methyl(5-bromonaphth-1-yl)silandiyl-bis($\eta^5$-2-methylinden-1-yl)zirconium dichloride, rac-methyl(7-fluorobenzothien-2-yl)silandiyl-bis($\eta^5$-2-methylinden-1-yl)zirconium dichloride,
rac-methyl(2-chlorobenzothien-4-yl)silandiyl-bis($\eta^5$-2-methylinden-1-yl)zirconium dichloride,
dimethylsilandiyl($\eta^5$-cyclopentadienyl)($\eta^5$-2-[5-bromonaphth-1-yl]inden-1-yl)zirconium dichloride,
dimethylsilandiyl($\eta^5$-cyclopentadienyl)($\eta^5$-2-[7-fluorobenzothien-2-yl]inden-1-yl)zirconium dichloride,
dimethylsilandiyl($\eta^5$-cyclopentadienyl)($\eta^5$-2-[2-chlorobenzothien-4-yl]inden-1-yl)zirconium dichloride,
4,4'-oxadiyl-bis($\eta^5$-7-bromo-1-phenylindenyl)zirconium dichloride,
4,4'-oxadiyl-bis($\eta^5$-7-chloro-1-phenylindenyl)zirconium dichloride,
4,4'-oxadiyl-bis($\eta^5$-7-fluoro-1-phenylindenyl)zirconium dichloride,
4,4'-oxadiyl-bis($\eta^5$-7-iodo-1-phenylindenyl)zirconium dichloride,
4,4'-sulfandiyl-bis($\eta^5$-7-bromo-1-phenylindenyl)zirconium dichloride,
4,4'-sulfandiyl-bis($\eta^5$-7-chloro-1-phenylindenyl)zirconium dichloride,
4,4'-sulfandiyl-bis($\eta^5$-7-fluoro-1-phenylindenyl)zirconium dichloride,
4,4'-sulfandiyl-bis($\eta^5$-7-iodo-1-phenylindenyl)zirconium dichloride,
4,4'-sulfandiyl-bis($\eta^5$-6-bromo-1-phenylindenyl)zirconium dichloride,
4,4'-sulfandiyl-bis($\eta^5$-5-bromo-1-phenylindenyl)zirconium dichloride,
4,4'-sulfandiyl-bis($\eta^5$-3-bromoindenyl)zirconium dichloride,
4,4'-sulfandiyl-bis($\eta^5$-2-bromoindenyl)zirconium dichloride,
4,4'-sulfandiyl-bis($\eta^5$-1-bromoindenyl)zirconium dichloride,
4,4'-sulfandiyl-bis($\eta^5$-7-bromo-1-phenylindenyl)zirconium dibromide,
4,4'-sulfandiyl-bis($\eta^5$-7-bromo-1-phenylindenyl)zirconium difluoride,
4,4'-sulfandiyl-bis($\eta^5$-7-bromo-1-phenylindenyl)zirconium diiodide,
4,4'-sulfandiyl-bis($\eta^5$-7-bromo-1-phenylindenyl)zirconium dihydride,
4,4'-sulfandiyl-bis($\eta^5$-7-bromo-1-phenylindenyl)dimethylzirconium,
4,4'-sulfandiyl-bis($\eta^5$-7-bromo-1-phenylindenyl)dimethoxyzirconium,
4,4'-sulfandiyl-bis($\eta^5$-7-bromo-1-phenylindenyl)bis(dimethylamino)zirconium,
4,4'-sulfandiyl-($\eta^5$-7-bromo-1-phenylindenyl)($\eta^5$-1-phenylindenyl)zirconium dichloride,
4,4'-sulfandiyl-($\eta^5$-7-chloro-1-phenylindenyl)($\eta^5$-1-phenylindenyl)zirconium dichloride,
4,4'-sulfandiyl-($\eta^5$-7-fluoro-1-phenylindenyl)($\eta^5$-1-phenylindenyl)zirconium dichloride,
4,4'-sulfandiyl-($\eta^5$-7-iodo-1-phenylindenyl)($\eta^5$-1-phenylindenyl)zirconium dichloride,
4,4'-sulfandiyl-($\eta^5$-6-bromo-1-phenylindenyl)($\eta^5$-1-phenylindenyl)zirconium dichloride,
4,4'-sulfandiyl-($\eta^5$-5-bromo-1-phenylindenyl)($\eta^5$-1-phenylindenyl)zirconium dichloride,
4,4'-sulfandiyl-($\eta^5$-3-bromoindenyl)($\eta^5$-1-phenylindenyl)zirconium dichloride,
4,4'-sulfandiyl-($\eta^5$-2-bromoindenyl)($\eta^5$-1-phenylindenyl)zirconium dichloride,
4,4'-sulfandiyl-($\eta^5$-1-bromoindenyl)($\eta^5$-1-phenylindenyl)zirconium dichloride,
4,4'-sulfandiyl-($\eta^5$-7-bromo-1-phenylindenyl)($\eta^5$-1-phenylindenyl)zirconium dibromide,
4,4'-sulfandiyl-($\eta^5$-7-bromo-1-phenylindenyl)($\eta^5$-1-phenylindenyl)zirconium difluoride,
4,4'-sulfandiyl-($\eta^5$-7-bromo-1-phenylindenyl)($\eta^5$-1-phenylindenyl)zirconium diiodide,
4,4'-sulfandiyl-($\eta^5$-7-bromo-1-phenylindenyl)($\eta^5$-1-phenylindenyl)zirconium dihydride,
4,4'-sulfandiyl-($\eta^5$-7-bromo-1-phenylindenyl)($\eta^5$-1-phenylindenyl)dimethylzirconium,
4,4'-sulfandiyl-($\eta^5$-7-bromo-1-phenylindenyl)($\eta^5$-1-phenylindenyl)dimethoxyzirconium,
4,4'-sulfandiyl-($\eta^5$-7-bromo-1-phenylindenyl)($\eta^5$-1-pyhenylindenyl)bis(dimethylamino)zirconium,
sulfandiyl-($\eta^5$-7-bromo-1-phenylinden-4-yl)($\eta^5$-2,3,4,5-tetramethylcyclopentadienyl)zirconium dichloride,
sulfandiyl-($\eta^5$-7-bromo-1-phenylinden-4-yl)($\eta^5$-cyclopentadienyl)zirconium dichloride,
sulfandiyl-($\eta^5$-7-bromo-1-phenylinden-4-yl)($\eta^5$-3-methylcyclopentadienyl)zirconium dichloride,
sulfandiyl-($\eta^5$-7-bromo-1-phenylinden-4-yl)($\eta^5$-3-tert-butylcyclopentadienyl)zirconium dichloride,
sulfandiyl-($\eta^5$-7-bromo-1-phenylinden-4-yl)($\eta^5$-3-trimethylsilylcyclopentadienyl)zirconium dichloride,
sulfandiyl-($\eta^5$-7-bromo-1-phenylinden-4-yl)($\eta^5$-3-phenylcyclopentadienyl)zirconium dichloride,
sulfandiyl-($\eta^5$-7-bromo-1-phenylinden-4-yl)($\eta^5$-3-[4-bromophenyl]cyclopentadienyl)zirconium dichloride,
sulfandiyl-($\eta^5$-inden-4-yl)($\eta^5$-3-[4-bromophenyl]cyclopentadienyl)zirconium dichloride,
sulfandiyl-($\eta^5$-7-bromoinden-4-yl)($\eta^5$-fluoren-1-yl)zirconium dichloride,
sulfandiyl-($\eta^5$-inden-4-yl)($\eta^5$-4-bromofluoren-1-yl)zirconium dichloride,
sulfandiyl-($\eta^5$-7-bromoinden-4-yl)($\eta^5$-fluoren-2-yl)zirconium dichloride,
sulfandiyl-($\eta^5$-7-bromoinden-4-yl)($\eta^5$-fluoren-3-yl)zirconium dichloride,
sulfandiyl-($\eta^5$-7-bromoinden-4-yl)($\eta^5$-fluoren-4-yl)zirconium dichloride,
sulfandiyl-($\eta^5$-inden-4-yl)($\eta^5$-1-bromofluoren-4-yl)zirconium dichloride,
sulfandiyl-($\eta^5$-inden-4-yl)($\eta^5$-2-bromofluoren-4-yl)zirconium dichloride,
4,1'-sulfandiyl-($\eta^5$-7-bromoindenyl)($\eta^5$-indenyl)zirconium dichloride,
4,2'-sulfandiyl-($\eta^5$-7-bromoindenyl)($\eta^5$-indenyl)zirconium dichloride,
4,1'-sulfandiyl-($\eta^5$-indenyl)($\eta^5$-2-bromoindenyl)zirconium dichloride,
4,1'-sulfandiyl-($\eta^5$-indenyl)($\eta^5$-2-chloroindenyl)zirconium dichloride,
4,1'-sulfandiyl-($\eta^5$-indenyl)($\eta^5$-2-fluoroindenyl)zirconium dichloride,
4,1'-sulfandiyl-($\eta^5$-indenyl)($\eta^5$-2-iodoindenyl)zirconium dichloride,
4,1'-sulfandiyl-($\eta^5$-indenyl)($\eta^5$-4-bromoindenyl)zirconium dichloride,
4,1'-sulfandiyl-($\eta^5$-indenyl)($\eta^5$-4-chloroindenyl)zirconium dichloride,
4,1'-sulfandiyl-($\eta^5$-indenyl)($\eta^5$-4-fluoroindenyl)zirconium dichloride,
4,1'-sulfandiyl-($\eta^5$-indenyl)($\eta^5$-4-iodoindenyl)zirconium dichloride, 4,1'-sulfandiyl-(η⁵-indenyl)(η⁵-2-[4-bromophenyl]indenyl) zirconium dichloride,
4,1'-sulfandiyl-(η⁵-indenyl)(η⁵-2-[4-chlorophenyl]indenyl) zirconium dichloride,
4,1'-sulfandiyl-(η⁵-indenyl)(η⁵-2-[4-fluorophenyl]indenyl) zirconium dichloride,
4,1'-sulfandiyl-(η⁵-indenyl)(η⁵-2-[4-iodophenyl]indenyl) zirconium dichloride,
4,4'-phenylphosphindiyl-bis(η⁵-7-bromo-1-phenylindenyl) zirconium dichloride,
4,4'-phenylphosphindiyl-bis(η⁵-7-chloro-1-phenylindenyl) zirconium dichloride,
4,4'-phenylphosphindiyl-bis(η⁵-7-iodo-1-phenylindenyl) zirconium dichloride,
4,4'-phenylphosphindiyl-bis(η⁵-7-fluoro-1-phenylindenyl) zirconium dichloride,
4,4'-(4-bromophenyl)phosphindiyl-bis(η⁵-1-phenylindenyl) zirconium dichloride,
4,4'-(4-iodohenyl)phosphindiyl-bis(η⁵-1-phenylindenyl)zirconium dichloride,
4,4'-(4-chlorophenyl)phosphindiyl-bis(η⁵-_1-phenylindenyl)zirconium dichloride,
4,4'-(4-fluorophenyl)phosphindiyl-bis(η⁵-1-phenylindenyl) zirconium dichloride,
4,4'-(4-bromophenyl)phosphindiyl-bis(η⁵-7-bromo-1-phenylindenyl)zirconium dichloride,
phenylphosphindiyl-(η⁵-7-bromo-1-phenylinden-4-yl)(η⁵-cyclopentadienyl)zirconium dichloride,
phenylphosphindiyl-(η⁵-7-bromo-1-phenylinden-4-yl)(η⁵-3-methylcyclopentadienyl)zirconium dichloride,
phenylphosphindiyl-(η⁵-7-bromo-1-phenylinden-4-yl)(η⁵-3-tert-butylcyclopentadienyl)zirconium dichloride,
phenylphosphindiyl-(η⁵-7-bromo-1-phenylinden-4-yl)(η⁵-3-trimethylsilylcyclopentadienyl)zirconium dichloride,
phenylphosphindiyl-(η⁵-7-bromo-1-phenylinden-4-yl)(η⁵-3-phenylcyclopentadienyl)zirconium dichloride,
phenylphosphindiyl-(η⁵-7-bromo-1-phenylinden-4-yl)(η⁵-3-[4-bromophenyl]cyclopentadienyl)zirconium dichloride,
phenylphosphindiyl-(η⁵-inden-4-yl)(η⁵-3-[4-bromophenyl]cyclopentadienyl)zirconium dichloride,
4,1'-phenylphosphindiyl-(η⁵-7-bromoindenyl)(η⁵-indenyl) zirconium dichloride,
4,2'-phenylphosphindiyl-(η⁵-7-bromoindenyl)(η⁵-indenyl) zirconium dichloride,
4,1'-phenylphosphindiyl-(η⁵-indenyl)(η⁵-2-bromoindenyl) zirconium dichloride,
4,1'-phenylphosphindiyl-(η⁵-indenyl)(η⁵-2-chloroindenyl) zirconium dichloride,
4,1'-phenylphosphindiyl-(η⁵-indenyl)(η⁵-2-fluoroindenyl) zirconium dichloride,
4,1'-phenylphosphindiyl-(η⁵-indeny)(η⁵-2-iodoindenyl)zirconium dichloride,
4,1'-phenylphosphindiyl-(η⁵-indenyl)(η⁵-4-bromoindenyl) zirconium dichloride,
4,1'-phenylphosphindiyl-(η⁵-indenyl)(η⁵-4-chloroindenyl) zirconium dichloride,
4,1'-phenylphosphindiyl-(η⁵-indenyl)(η⁵-4-fluoroindenyl) zirconium dichloride,
4,1'-phenylphosphindiyl-(η⁵-indenyl)(η⁵-4-iodoindenyl)zirconium dichloride,
4,1'-phenylphosphindiyl-(η⁵-indenyl)(η⁵-2-[4-bromophenyl]indenyl)zirconium dichloride,
4,1'-phenylphosphindiyl-(η⁵-indenyl)(η⁵-2-[4-chlorophenyl]indenyl)zirconium dichloride,
4,1'-phenylphosphindiyl-(η⁵-indenyl)(η⁵-2-[4-fluorophenyl]indenyl)zirconium dichloride,
4,1'-phenylphosphindiyl-(η⁵-indenyl)(η⁵-2-[4-iodophenyl]indenyl)zirconium dichloride,
4,4'-phenylphosphindiyl-bis(η⁵-7-bromo-1-phenylindenyl) zirconium dibromide,
4,4'-phenylphosphindiyl-bis(η⁵-7-bromo-1-phenylindenyl) zirconium difluoride,
4,4'-phenylphosphindiyl-bis(η⁵-7-bromo-1-phenylindenyl) zirconium diiodide,
4,4'-phenylphosphindiyl-bis(η⁵-7-bromo-1-phenylindenyl) zirconium dihydride,
4,4'-phenylphosphindiyl-bis(η⁵-7-bromo-1-phenylindenyl) dimethylzirconium,
4,4'-phenylphosphindiyl-bis(η⁵-7-bromo-1-phenylindenyl) dimethoxyzirconium,
4,4'-phenylphosphindiyl-bis(η⁵-7-bromo-1-phenylindenyl) bis(dimethylamino)zirconium,
4,4'-(4-bromophenyl)phosphindiyl-bis(η⁵-7-bromo-1-phenylindenyl)zirconium dichloride,
4,4'-(4-chlorophenyl)phosphindiyl-bis(η⁵-7-chloro-1-phenylindenyl)zirconium dichloride,
4,4'-(4-fluorophenyl)phosphindiyl-bis(η⁵-7-iodo-1-phenylindenyl)zirconium dichloride,
4,4'-(4-iodophenyl)phosphindiyl-bis(η⁵-7-fluoro-1-phenylindenyl)zirconium dichloride,
4,4'-sulfandiyl-bis(η⁵-7-bromo-2-methylindenyl)zirconium dichloride,
4,4'-sulfandiyl-bis(η⁵-7-bromoindenyl)zirconium dichloride,
4,4'-sulfandiyl-bis(η⁵-7-bromofluorenyl)zirconium dichloride,
4,4'-sulfandiyl-bis(η⁵-7-bromo-2,6-dimethylindenyl)zirconium dichloride,
4,4'-sulfandiyl-bis(η⁵-7-bromo-6-ethyl-2-methylindenyl) zirconium dichloride,
4,4'-sulfandiyl-bis(η⁵-7-bromo-5-phenylindenyl)zirconium dichloride,
4,4'-sulfandiyl-bis(η⁵-7-bromo-5-phenyl-2-methylindenyl) zirconium dichloride,
4,4'-sulfandiyl-bis(η⁵-7-bromo-2-methyl-6-o-tolylindenyl) zirconium dichloride,
4,4'-sulfandiyl-bis[η⁵-7-bromo-2-methyl-6-(5-methylthien-2-yl)indenyl]zirconium dichloride,
4,4'-sulfandiyl-bis[η⁵-7-bromo-2-methyl-6-(5-methylfur-2-yl)indenyl]zirconium dichloride,
4,4'-sulfandiyl-bis[η⁵-7-bromo-2-methyl-2-(2-benzothienyl)indenyl]zirconium dichloride,
4,4'-sulfandiyl-bis[η⁵-7-bromo-2-methyl-2-(2-benzofuryl) indenyl]zirconium dichloride,
4,4'-sulfandiyl-bis[η⁵-7-bromo-2-methyl-2-(4-fluorophenyl)indenyl]zirconium dichloride,
4,4'-sulfandiyl-bis[η⁵-7-bromo-2-methyl-2-(3-trifluoromethylphenyl)indenyl]zirconium dichloride,
4,4'-methylaza-bis(η⁵-7-bromo-1-phenylindenyl)zirconium dichloride,
4,4'-methylaza-bis(η⁵-7-chloro-1-phenylindenyl)zirconium dichloride,
4,4'-methylaza-bis(η⁵-7-fluoro-1-phenylindenyl)zirconium dichloride,
4,4'-methylaza-bis(η⁵-7-iodo-1-phenylindenyl)zirconium dichloride,
4,4'-phenylaza-bis(η⁵-7-bromo-1-phenylindenyl)zirconium dichloride,
4,4'-phenylaza-bis(η⁵-7-chloro-1-phenylindenyl)zirconium dichloride,
4,4'-phenylaza-bis(η⁵-7-fluoro-1-phenylindenyl)zirconium dichloride, 4,4'-phenylaza-bis($\eta^5$-7-iodo-1-phenylindenyl)zirconium dichloride,
4,4'-(thien-2-yl)aza-bis($\eta^5$-7-bromo-1-phenylindenyl)zirconium dichloride,
4,4'-(5-chlorothien-2-yl)aza-bis($\eta^5$-7-bromo-1-phenylindenyl)zirconium dichloride,
4,4'-(pyridin-2-yl)aza-bis($\eta^5$-7-bromo-1-phenylindenyl)zirconium dichloride,
4,4'-(4-bromopyridin-2-yl)aza-bis($\eta^5$-7-bromo-1-phenylindenyl)zirconium dichloride,
4,4'-(benzothien-3-yl)aza-bis($\eta^5$-7-bromo-1-phenylindenyl)zirconium dichloride,
5,5'-oxadiyl-bis($\eta^5$-7-bromo-1-phenylindenyl)zirconium dichloride,
5,5'-oxadiyl-bis($\eta^5$-7-chloro-1-phenylindenyl)zirconium dichloride,
5,5'-oxadiyl-bis($\eta^5$-7-fluoro-1-phenylindenyl)zirconium dichloride,
5,5'-oxadiyl-bis($\eta^5$-7-iodo-1-phenylindenyl)zirconium dichloride,
5,5'-sulfandiyl-bis($\eta^5$-7-bromo-1-phenylindenyl)zirconium dichloride,
5,5'-sulfandiyl-bis($\eta^5$-7-chloro-1-phenylindenyl)zirconium dichloride,
5,5'-sulfandiyl-bis($\eta^5$-7-fluoro-1-phenylindenyl)zirconium dichloride,
5,5'-sulfandiyl-bis($\eta^5$-7-iodo-1-phenylindenyl)zirconium dichloride,
5,5'-sulfandiyl-bis($\eta^5$-6-bromo-1-phenylindenyl)zirconium dichloride,
5,5'-sulfandiyl-bis($\eta^5$-5-bromo-1-phenylindenyl)zirconium dichloride,
5,5'-sulfandiyl-bis($\eta^5$-3-bromoindenyl)zirconium dichloride,
5,5'-sulfandiyl-bis($\eta^5$-2-bromoindenyl)zirconium dichloride,
5,5'-sulfandiyl-bis($\eta^5$-1-bromoindenyl)zirconium dichloride,
5,5'-sulfandiyl-bis($\eta^5$-7-bromo-1-phenylindenyl)zirconium dibromide,
5,5'-sulfandiyl-bis($\eta^5$-7-bromo-1-phenylindenyl)zirconium difluoride,
5,5'-sulfandiyl-bis($\eta^5$-7-bromo-1-phenylindenyl)zirconium diiodide,
5,5'-sulfandiyl-bis($\eta^5$-7-bromo-1-phenylindenyl)zirconium dihydride,
5,5'-sulfandiyl-bis($\eta^5$-7-bromo-1-phenylindenyl)dimethylzirconium,
5,5'-sulfandiyl-bis($\eta^5$-7-bromo-1-phenylindenyl)dimethoxyzirconium,
5,5'-sulfandiyl-bis($\eta^5$-7-bromo-1-phenylindenyl)bis(dimethylamino)zirconium,
5,5'-sulfandiyl-($\eta^5$-7-bromo-1-phenylindenyl)($\eta^5$-1-phenylindenyl)zirconium dichloride,
5,5'-sulfandiyl-($\eta^5$-7-chloro-1-phenylindenyl)($\eta^5$-1-phenylindenyl)zirconium dichloride,
5,5'-sulfandiyl-($\eta^5$-7-fluoro-1-phenylindenyl)($\eta^5$-1-phenylindenyl)zirconium dichloride,
5,5'-sulfandiyl-($\eta^5$-7-iodo-1-phenylindenyl)($\eta^5$-1-phenylindenyl)zirconium dichloride,
5,5'-sulfandiyl-($\eta^5$-6-bromo-1-phenylindenyl)($\eta^5$-1-phenylindenyl)zirconium dichloride,
5,5'-sulfandiyl-($\eta^5$-5-bromo-1-phenylindenyl)($\eta^5$-1-phenylindenyl)zirconium dichloride,
5,5'-sulfandiyl-($\eta^5$-3-bromoindenyl)($\eta^5$-1-phenylindenyl)zirconium dichloride,
5,5'-sulfandiyl-($\eta^5$-2-bromoindenyl)($\eta^5$-1-phenylindenyl)zirconium dichloride,
5,5'-sulfandiyl-($\eta^5$-1-bromoindenyl)($\eta^5$-1-phenylindenyl)zirconium dichloride,
5,5'-sulfandiyl-($\eta^5$-7-bromo-1-phenylindenyl)($\eta^5$-1-phenylindenyl)zirconium dibromide,
5,5'-sulfandiyl-($\eta^5$-7-bromo-1-phenylindenyl)($\eta^5$-1-phenylindenyl)zirconium difluoride,
5,5'-sulfandiyl-($\eta^5$-7-bromo-1-phenylindenyl)($\eta^5$-1-phenylindenyl)zirconium diiodide,
5,5'-sulfandiyl-($\eta^5$-7-bromo-1-phenylindenyl)($\eta^5$-1-phenylindenyl)zirconium dihydride,
5,5'-sulfandiyl-($\eta^5$-7-bromo-1-phenylindenyl)($\eta^5$-1-phenylindenyl)dimethylzirconium,
5,5'-sulfandiyl-($\eta^5$-7-bromo-1-phenylindenyl)($\eta^5$-1-phenylindenyl)dimethoxyzirconium,
5,5'-sulfandiyl-($\eta^5$-7-bromo-1-phenylindenyl)($\eta^5$-1-phenylindenyl)bis(dimethylamino)zirconium,
4,5'-oxadiyl-bis($\eta^5$-7-bromo-1-phenylindenyl)zirconium dichloride,
4,5'-oxadiyl-bis($\eta^5$-7-chloro-1-phenylindenyl)zirconium dichloride,
4,5'-oxadiyl-bis($\eta^5$-7-fluoro-1-phenylindenyl)zirconium dichloride,
4,5'-oxadiyl-bis($\eta^5$-7-iodo-1-phenylindenyl)zirconium dichloride,
4,5'-sulfandiyl-bis($\eta^5$-7-bromo-1-phenylindenyl)zirconium dichloride,
4,5'-sulfandiyl-bis($\eta^5$-7-chloro-1-phenylindenyl)zirconium dichloride,
4,5'-sulfandiyl-bis($\eta^5$-7-fluoro-1-phenylindenyl)zirconium dichloride,
4,5'-sulfandiyl-bis($\eta^5$-7-iodo-1-phenylindenyl)zirconium dichloride,
4,5'-sulfandiyl-bis($\eta^5$-6-bromo-1-phenylindenyl)zirconium dichloride,
4,5'-sulfandiyl-bis($\eta^5$-5-bromo-1-phenylindenyl)zirconium dichloride,
4,5'-sulfandiyl-bis($\eta^5$-3-bromoindenyl)zirconium dichloride,
4,5'-sulfandiyl-bis($\eta^5$-2-bromoindenyl)zirconium dichloride,
4,5'-sulfandiyl-bis($\eta^5$-1-bromoindenyl)zirconium dichloride,
4,5'-sulfandiyl-bis($\eta^5$-7-bromo-1-phenylindenyl)zirconium dibromide,
4,5'-sulfandiyl-bis($\eta^5$-7-bromo-1-phenylindenyl)zirconium difluoride,
4,5'-sulfandiyl-bis($\eta^5$-7-bromo-1-phenylindenyl)zirconium diiodide,
4,5'-sulfandiyl-bis($\eta^5$-7-bromo-1-phenylindenyl)zirconium dihydride,
4,5'-sulfandiyl-bis($\eta^5$-7-bromo-1-phenylindenyl)dimethylzirconium,
4,5'-sulfandiyl-bis($\eta^5$-7-bromo-1-phenylindenyl)dimethoxyzirconium,
4,5'-sulfandiyl-bis($\eta^5$-7-bromo-1-phenylindenyl)bis(dimethylamino)zirconium,
4,5'-sulfandiyl-($\eta^5$-7-bromo-1-phenylindenyl)($\eta^5$-1-phenylindenyl)zirconium dichloride,
4,5'-sulfandiyl-($\eta^5$-7-chloro-1-phenylindenyl)($\eta^5$-1-phenylindenyl)zirconium dichloride,
4,5'-sulfandiyl-($\eta^5$-7-fluoro-1-phenylindenyl)($\eta^5$-1-phenylindenyl)zirconium dichloride,
4,5'-sulfandiyl-($\eta^5$-7-iodo-1-phenylindenyl)($\eta^5$-1-phenylindenyl)zirconium dichloride, 4,5'-sulfandiyl-($\eta^5$-6-bromo-1-phenylindenyl)($\eta^5$-1-phenylindenyl)zirconium dichloride,
4,5'-sulfandiyl-($\eta^5$-bromo-1-phenylindenyl)($\eta^5$-1-phenylindenyl)zirconium dichloride,
4,5'-sulfandiyl-($\eta^5$-3-bromoindenyl)($\eta^5$-1-phenylindenyl)zirconium dichloride,
4,5'-sulfandiyl-($\eta^5$-2-bromoindenyl)($\eta^5$-1-phenylindenyl)zirconium dichloride,
4,5'-sulfandiyl-($\eta^5$-1-bromoindenyl)($\eta^5$-1-phenylindenyl)zirconium dichloride,
4,5'-sulfandiyl-($\eta^5$-7-bromo-1-phenylindenyl)($\eta^5$-1-phenylindenyl)zirconium dibromide,
4,5'-sulfandiyl-($\eta^5$-7-bromo-1-phenylindenyl)($\eta^5$-1-phenylindenyl)zirconium difluoride,
4,5'-sulfandiyl-($\eta^5$-7-bromo-1-phenylindenyl)($\eta^5$-1-phenylindenyl)zirconium diiodide,
4,5'-sulfandiyl-($\eta^5$-7-bromo-1-phenylindenyl)($\eta^5$-1-phenylindenyl)zirconium dihydride,
4,5'-sulfandiyl-($\eta^5$-7-bromo-1-phenylindenyl)($\eta^5$-1-phenylindenyl)dimethylzirconium,
4,5'-sulfandiyl-($\eta^5$-7-bromo-1-phenylindenyl)($\eta^5$-1-phenylindenyl)dimethoxyzirconium,
4,5'-sulfandiyl-($\eta^5$-7-bromo-1-phenylindenyl)($\eta^5$-1-phenylindenyl)bis(dimethylamino)zirconium,
sulfandiyl-($\eta^5$-7-bromo-2-methyinden-4-yl)($\eta^5$-2-bromo-5-methylcyclopenta[b]thien-3-yl)zirconium dichloride,
sulfandiyl-($\eta^5$-7-bromo-2-methyinden-4-yl)($\eta^5$-5-methylcyclopenta[b]thien-3-yl)zirconium dichloride,
sulfandiyl-($\eta^5$-2-methyinden-4-yl)($\eta^5$-2-bromo-5-methylcyclopenta[b]thien-3-yl)zirconium dichloride,
sulfandiyl-($\eta^5$-7-bromo-2-methyinden-4-yl)($\eta^5$-3-chlorocyclopenta[c]thien-1-yl)zirconium dichloride,
sulfandiyl-($\eta^5$-7-bromo-2-methyinden-4-yl)($\eta^5$-cyclopenta[b][1]benzothien-1-yl)zirconium dichloride,
sulfandiyl-($\eta^5$-7-bromo-2-methyinden-4-yl)($\eta^5$-5-methylcyclopenta[b]fur-3-yl)zirconium dichloride,
sulfandiyl-($\eta^5$-7-bromo-2-methyinden-4-yl)($\eta^5$-1,5-dimethylcyclopenta[b]pyrrol-3-yl)zirconium dichloride,
sulfandiyl-($\eta^5$-7-bromo-2-methyinden-4-yl)($\eta^5$-1,5-dimethylcyclopenta[b]phosphol-3-yl)zirconium dichloride,
sulfandiyl-($\eta^5$-7-bromo-2-methyinden-4-yl)($\eta^5$-5-bromo-4-methylcyclopenta[b]indol-1-yl)zirconium dichloride,
sulfandiyl-($\eta^5$-7-bromo-2-methyinden-4-yl)($\eta^5$-cyclopenta[b]pyridin-4-yl)zirconium dichloride,
4,4'-sulfandiyl-($\eta^5$-7-bromo-2-methyindenyl)($\eta^5$-1-dimethylamino-1-boratobenzene)zirconium dichloride,
4,4'-sulfandiyl-($\eta^5$-7-bromo-2-methyindenyl)($\eta^5$-3-dimethylamino-1,3-thiaborindenyl)zirconium dichloride,
sulfandiyl-($\eta^5$-7-bromo-2-methyinden-4-yl)($\eta^5$-2-dimethylamino-1,2-thiaborolide-3)zirconium dichloride,
3,3'-sulfandiyl-bis($\eta^5$-2-bromo-5-methylcyclopenta[b]thienyl)zirconium dichloride,
3,3'-sulfandiyl-bis($\eta^5$-2-chloro-5-methylcyclopenta[b]thienyl)zirconium dichloride,
3,3'-sulfandiyl-bis($\eta^5$-2-fluoro-5-methylcyclopenta[b]thienyl)zirconium dichloride,
3,3'-sulfandiyl-bis($\eta^5$-2-iodo-5-methylcyclopenta[b]thienyl)zirconium dichloride,
3,3'-sulfandiyl-bis($\eta^5$-2-bromo-5-methylcyclopenta[b]thienyl)zirconium dichloride,
3,3'-sulfandiyl-bis($\eta^5$-2-bromo-5-methylcyclopenta[b]thienyl)zirconium dibromide,
3,3'-sulfandiyl-bis($\eta^5$-2-bromo-5-methylcyclopenta[b]thienyl)zirconium diiodide,
3,3'-sulfandiyl-bis($\eta^5$-2-bromo-5-methylcyclopenta[b]thienyl)zirconium difluoride,
3,3'-sulfandiyl-bis($\eta^5$-2-bromo-5-methylcyclopenta[b]thienyl)zirconium dihydride,
3,3'-sulfandiyl-bis($\eta^5$-2-bromo-5-methylcyclopenta[b]thienyl)dimethylzirconium,
3,3'-sulfandiyl-bis($\eta^5$-2-bromo-5-methylcyclopenta[b]thienyl)diphenylzirconium,
3,3'-sulfandiyl-bis($\eta^5$-2-bromo-5-methylcyclopenta[b]thienyl)dibenzylzirconium,
3,3'-sulfandiyl-bis($\eta^5$-2-bromo-5-methylcyclopenta[b]thienyl)-bis(dimethylamino)zirconium,
3,3'-sulfandiyl-bis($\eta^5$-2-bromo-5-methylcyclopenta[b]thienyl)dimethoxyzirconium,
1,1'-sulfandiyl-bis($\eta^5$-3-chlorocyclopenta[c]thienyl)zirconium dichloride,
4,4'-sulfandiyl-bis($\eta^5$-7-bromoindeno[1,2-c]pyridinyl)zirconium dichloride,
4,4'-sulfandiyl-bis($\eta^5$-3-bromoindeno[1,2-c]pyridinyl)zirconium dichloride,
6,6'-sulfandiyl-bis($\eta^5$-7-bromoindeno[1,2-c]pyridinyl)zirconium dichloride,
6,6'-sulfandiyl-bis($\eta^5$-3-bromoindeno[1,2-c]pyridinyl)zirconium dichloride,
9,9'-sulfandiyl-bis($\eta^5$-7-bromoindeno[1,2-c]pyridinyl)zirconium dichloride,
9,9'-sulfandiyl-bis($\eta^5$-3-bromoindeno[1,2-c]pyridinyl)zirconium dichloride,
4,6'-sulfandiyl-bis($\eta^5$-7-bromoindeno[1,2-c]pyridinyl)zirconium dichloride,
4,6'-sulfandiyl-bis($\eta^5$-3-bromoindeno[1,2-c]pyridinyl)zirconium dichloride,
4,9'-sulfandiyl-bis($\eta^5$-7-bromoindeno[1,2-c]pyridinyl)zirconium dichloride,
4,9'-sulfandiyl-bis($\eta^5$-3-bromoindeno[1,2-c]pyridinyl)zirconium dichloride,
6,9'-sulfandiyl-bis($\eta^5$-7-bromoindeno[1,2-c]pyridinyl)zirconium dichloride,
6,9'-sulfandiyl-bis($\eta^5$-3-bromoindeno[1,2-c]pyridinyl)zirconium dichloride,
4,4'-sulfandiyl-bis($\eta^5$-7-bromoindeno[1,2-c]phosphoranyl)zirconium dichloride,
3,3'-sulfandiyl-bis($\eta^5$-2-bromoindeno[1,2-b]thienyl)zirconium dichloride,
3,3'-sulfandiyl-bis($\eta^5$-6-bromoindeno[1,2-b]thienyl)zirconium dichloride,
5,5'-sulfandiyl-bis($\eta^5$-2-bromoindeno[1,2-b]thienyl)zirconium dichloride,
5,5'-sulfandiyl-bis($\eta^5$-6-bromoindeno[1,2-b]thienyl)zirconium dichloride,
8,8'-sulfandiyl-bis($\eta^5$-2-bromoindeno[1,2-b]thienyl)zirconium dichloride,
8,8'-sulfandiyl-bis($\eta^5$-6-bromoindeno[1,2-b]thienyl)zirconium dichloride,
3,5'-sulfandiyl-bis($\eta^5$-2-bromoindeno[1,2-b]thienyl)zirconium dichloride,
3,5'-sulfandiyl-bis($\eta^5$-6-bromoindeno[1,2-b]thienyl)zirconium dichloride,
3,8'-sulfandiyl-bis($\eta^5$-2-bromoindeno[1,2-b]thienyl)zirconium dichloride,
3,8'-sulfandiyl-bis($\eta^5$-6-bromoindeno[1,2-b]thienyl)zirconium dichloride,
5,8'-sulfandiyl-bis($\eta^5$-2-bromoindeno[1,2-b]thienyl)zirconium dichloride,
5,8'-sulfandiyl-bis($\eta^5$-6-bromoindeno[1,2-b]thienyl)zirconium dichloride,
3,3'-sulfandiyl-bis($\eta^5$-2-bromoindeno[2,1-b]thienyl)zirconium dichloride, 3,3'-sulfandiyl-bis($\eta^5$-6-bromoindeno[2,1-b]thienyl)zirconium dichloride,
4,4'-sulfandiyl-bis($\eta^5$-2-bromoindeno[2,1-b]thienyl)zirconium dichloride,
4,4'-sulfandiyl-bis($\eta^5$-6-bromoindeno[2,1-b]thienyl)zirconium dichloride,
7,7'-sulfandiyl-bis($\eta^5$-2-bromoindeno[2,1-b]thienyl)zirconium dichloride,
7,7'-sulfandiyl-bis($\eta^5$-6-bromoindeno[2,1-b]thienyl)zirconium dichloride,
3,4'-sulfandiyl-bis($\eta^5$-2-bromoindeno[2,1-b]thienyl)zirconium dichloride,
3,4'-sulfandiyl-bis($\eta^5$-6-bromoindeno[2,1-b]thienyl)zirconium dichloride,
3,7'-sulfandiyl-bis($\eta^5$-2-bromoindeno[2,1-b]thienyl)zirconium dichloride,
3,7'-sulfandiyl-bis($\eta^5$-6-bromoindeno[2,1-b]thienyl)zirconium dichloride,
4,7'-sulfandiyl-bis($\eta^5$-2-bromoindeno[2,1-b]thienyl)zirconium dichloride,
4,7'-sulfandiyl-bis($\eta^5$-6-bromoindeno[2,1-b]thienyl)zirconium dichloride,
1,1'-sulfandiyl-bis($\eta^5$-3-bromoindeno[1,2-c]thienyl)zirconium dichloride,
1,1'-sulfandiyl-bis($\eta^5$-6-bromoindeno[1,2-c]thienyl)zirconium dichloride,
3,3'-sulfandiyl-bis($\eta^5$-1-bromoindeno[1,2-c]thienyl)zirconium dichloride,
3,3'-sulfandiyl-bis($\eta^5$-6-bromoindeno[1,2-c]thienyl)zirconium dichloride,
4,4'-sulfandiyl-bis($\eta^5$-3-bromoindeno[1,2-c]thienyl)zirconium dichloride,
4,4'-sulfandiyl-bis($\eta^5$-6-bromoindeno[1,2-c]thienyl)zirconium dichloride,
7,7'-sulfandiyl-bis($\eta^5$-3-bromoindeno[1,2-c]thienyl)zirconium dichloride,
7,7'-sulfandiyl-bis($\eta^5$-6-bromoindeno[1,2-c]thienyl)zirconium dichloride,
1,3'-sulfandiyl-bis($\eta^5$-6-bromoindeno[1,2-c]thienyl)zirconium dichloride,
1,4'-sulfandiyl-bis($\eta^5$-3-bromoindeno[1,2-c]thienyl)zirconium dichloride,
1,4'-sulfandiyl-bis($\eta^5$-6-bromoindeno[1,2-c]thienyl)zirconium dichloride,
1,7'-sulfandiyl-bis($\eta^5$-3-bromoindeno[1,2-c]thienyl)zirconium dichloride,
1,7'-sulfandiyl-bis($\eta^5$-6-bromoindeno[1,2-c]thienyl)zirconium dichloride,
3,4'-sulfandiyl-bis($\eta^5$-1-bromoindeno[1,2-c]thienyl)zirconium dichloride,
3,4'-sulfandiyl-bis($\eta^5$-6-bromoindeno[1,2-c]thienyl)zirconium dichloride,
3,7'-sulfandiyl-bis($\eta^5$-1-bromoindeno[1,2-c]thienyl)zirconium dichloride,
3,7'-sulfandiyl-bis($\eta^5$-6-bromoindeno[1,2-c]thienyl)zirconium dichloride,
4,7'-sulfandiyl-bis($\eta^5$-3-bromoindeno[1,2-c]thienyl)zirconium dichloride,
4,7'-sulfandiyl-bis($\eta^5$-6-bromoindeno[1,2-c]thienyl)zirconium dichloride,
3,3'-sulfandiyl-bis($\eta^5$-2-bromoindeno[1,2-b]furyl)zirconium dichloride,
3,3'-sulfandiyl-bis($\eta^5$-6-bromoindeno[1,2-b]furyl)zirconium dichloride,
5,5'-sulfandiyl-bis($\eta^5$-2-bromoindeno[1,2-b]fuiryl)zirconium dichloride,
5,5'-sulfandiyl-bis($\eta^5$-6-bromoindeno[1,2-b]fuiryl)zirconium dichloride,
8,8'-sulfandiyl-bis($\eta^5$-2-bromoindeno[1,2-b]furyl)zirconium dichloride,
8,8'-sulfandiyl-bis($\eta^5$-6-bromoindeno[1,2-b]fuiryl)zirconium dichloride,
3,5'-sulfandiyl-bis($\eta^5$-2-bromoindeno[1,2-b]furyl)zirconium dichloride,
3,5'-sulfandiyl-bis($\eta^5$-6-bromoindeno[1,2-b]fuiryl)zirconium dichloride,
3,8'-sulfandiyl-bis($\eta^5$-2-bromoindeno[1,2-b]fuiryl)zirconium dichloride,
3,8'-sulfandiyl-bis($\eta^5$-6-bromoindeno[1,2-b]fuiryl)zirconium dichloride,
5,8'-sulfandiyl-bis($\eta^5$-2-bromoindeno[1,2-b]furyl)zirconium dichloride,
5,8'-sulfandiyl-bis($\eta^5$-6-bromoindeno[1,2-b]furyl)zirconium dichloride,
6,6'-sulfandiyl-bis($\eta^5$-2-bromo-5-methylindeno[1,2-b]indolyl)zirconium dichloride,
6,6'-sulfandiyl-bis($\eta^5$-8-bromo-5-methylindeno[1,2-b]indolyl)zirconium dichloride,
9,9'-sulfandiyl-bis($\eta^5$-2-bromo-5-methylindeno[1,2-b]indolyl)zirconium dichloride,
9,9'-sulfandiyl-bis($\eta^5$-8-bromo-5-methylindeno[1,2-b]indolyl)zirconium dichloride,
6,9'-sulfandiyl-bis($\eta^5$-2-bromo-5-methylindeno[1,2-b]indolyl)zirconium dichloride,
6,9'-sulfandiyl-bis($\eta^5$-8-bromo-5-methylindeno[1,2-b]indolyl)zirconium dichloride,
7,7'-sulfandiyl-bis($\eta^5$-8-bromo-5-methylindeno[2,1-b]indolyl)zirconium dichloride,
7,7'-sulfandiyl-bis($\eta^5$-3-bromo-5-methylindeno[2,1-b]indolyl)zirconium dichloride,
10,10'-sulfandiyl-bis($\eta^5$-8-bromo-5-methylindeno[2,1-b]indolyl)zirconium dichloride,
10,10'-sulfandiyl-bis($\eta^5$-3-bromo-5-methylindeno[2,1-b]indolyl)zirconium dichloride,
7,10'-sulfandiyl-bis($\eta^5$-8-bromo-5-methylindeno[2,1-b]indolyl)zirconium dichloride,
7,10'-sulfandiyl-bis($\eta^5$-3-bromo-5-methylindeno[2,1-b]indolyl)zirconium dichloride,
3,3'-oxadiyl-bis($\eta^5$-2-bromo-5-methylcyclopenta[b]thienyl)zirconium dichloride,
3,3'-methylazadiyl-bis($\eta^5$-2-bromo-5-methylcyclopenta[b]thienyl)zirconium dichloride,
3,3'-phenylazadiyl-bis($\eta^5$-2-bromo-5-methylcyclopenta[b]thienyl)zirconium dichloride,
sulfandiyl-($\eta^5$-2-bromo-5-methylcyclopenta[b]thien-3-yl)($\eta^5$-cyclopentadienyl)zirconium dichloride,
sulfandiyl-($\eta^5$-2-bromo-5-methylcyclopenta[b]thien-3-yl)($\eta^5$-inden-1-yl)zirconium dichloride,
sulfandiyl-($\eta^5$-2-bromo-5-methylcyclopenta[b]thien-3-yl)($\eta^5$-inden-4-yl)zirconium dichloride,
sulfandiyl-($\eta^5$-2-bromo-5-methylcyclopenta[b]thien-3-yl)($\eta^5$-fluoren-9-yl)zirconium dichloride,
sulfandiyl-($\eta^5$-2-bromo-5-methylcyclopenta[b]thien-3-yl)($\eta^5$-fluoren-1-yl)zirconium dichloride,
sulfandiyl-($\eta^5$-2-bromo-5-methylcyclopenta[b]thien-3-yl)($\eta^5$-fluoren-4-yl)zirconium dichloride,
sulfandiyl-($\eta^5$-3-chlorocyclopenta[c]thien-1-yl)($\eta^5$-cyclopentadienyl)zirconium dichloride,
sulfandiyl-($\eta^5$-3-chlorocyclopenta[c]thien-1-yl)($\eta^5$-inden-1-yl)zirconium dichloride,
sulfandiyl-($\eta^5$-3-chlorocyclopenta[c]thien-1-yl)($\eta^5$-inden- 4-yl)zirconium dichloride,
sulfandiyl-(η⁵-3-chlorocyclopenta[c]thien-1-yl)(η⁵-fluoren-9-yl)zirconium dichloride,
sulfandiyl-(η⁵-3-chlorocyclopenta[c]thien-1-yl)(η⁵-fluoren-1-yl)zirconium dichloride,
sulfandiyl-(η⁵-3-chlorocyclopenta[c]thien-1-yl)(η⁵-fluoren-4-yl)zirconium dichloride,
sulfandiyl-(η⁵-7-bromoindeno[1,2-c]pyridine-4-yl)(η⁵-cyclopentadienyl)zirconium dichloride,
sulfandiyl-(η⁵-7-bromoindeno[1,2-c]pyridine-4-yl)(η⁵-inden-1-yl)zirconium dichloride,
sulfandiyl-(η⁵-7-bromoindeno[1,2-c]pyridine-4-yl)(η⁵-inden-4-yl)zirconium dichloride,
sulfandiyl-(η⁵-7-bromoindeno[1,2-c]pyridine-4-yl)(η⁵-fluoren-9-yl)zirconium dichloride,
sulfandiyl-(η⁵-7-bromoindeno[1,2-c]pyridine-4-yl)(η⁵-fluoren-1-yl)zirconium dichloride,
sulfandiyl-(η⁵-7-bromoindeno[1,2-c]pyridine-4-yl)(η⁵-fluoren-4-yl)zirconium dichloride,
sulfandiyl-(η⁵-7-bromoindeno[1,2-c]pyridine-6-yl)(η⁵-cyclopentadienyl)zirconium dichloride,
sulfandiyl-(η⁵-7-bromoindeno[1,2-c]pyridine-6-yl)(η⁵-inden-1-yl)zirconium dichloride,
sulfandiyl-(η⁵-7-bromoindeno[1,2-c]pyridine-6-yl)(η⁵-inden-4-yl)zirconium dichloride,
sulfandiyl-(η⁵-7-bromoindeno[1,2-c]pyridine-6-yl)(η⁵-fluoren-9-yl)zirconium dichloride,
sulfandiyl-(η⁵-7-bromoindeno[1,2-c]pyridine-6-yl)(e⁵-fluoren-1-yl)zirconium dichloride,
sulfandiyl-(η⁵-7-bromoindeno[1,2-c]pyridine-6-yl)(η⁵-fluoren-4-yl)zirconium dichloride,
sulfandiyl-(η⁵-7-bromoindeno[1,2-c]pyridine-9-yl)(η⁵-cyclopentadienyl)zirconium dichloride,
sulfandiyl-(η⁵-7-bromoindeno[1,2-c]pyridine-9-yl)(η⁵-inden-1-yl)zirconium dichloride,
sulfandiyl-(η⁵-7-bromoindeno[1,2-c]pyridine-9-yl)(η⁵-inden-4-yl)zirconium dichloride,
sulfandiyl-(η⁵-7-bromoindeno[1,2-c]pyridine-9-yl)(η⁵-fluoren-9-yl)zirconium dichloride,
sulfandiyl-(η⁵-7-bromoindeno[1,2-c]pyridine-9-yl)(η⁵-fluoren-1-yl)zirconium dichloride,
sulfandiyl-(η⁵-7-bromoindeno[1,2-c]pyridine-9-yl)(η⁵-fluoren-4-yl)zirconium dichloride,
sulfandiyl-(η⁵-7-bromoindeno[1,2-c]phosphoran-4-yl)(η⁵-cyclopentadienyl)zirconium dichloride,
sulfandiyl-(η⁵-7-bromoindeno[1,2-c]phosphoran-4-yl)(η⁵-inden-1-yl)zirconium dichloride,
sulfandiyl-(η⁵-7-bromoindeno[1,2-c]phosphoran-4-yl)(η⁵-inden-4-yl)zirconium dichloride,
sulfandiyl-(η⁵-7-bromoindeno[1,2-c]phosphoran-4-yl)(η⁵-fluoren-9-yl)zirconium dichloride,
sulfandiyl-(η⁵-7-bromoindeno[1,2-c]phosphoran-4-yl)(η⁵-fluoren-1-yl)zirconium dichloride,
sulfandiyl-(η⁵-7-bromoindeno[1,2-c]phosphoran-4-yl)(η⁵-fluoren-4-yl)zirconium dichloride,
sulfandiyl-(η⁵-2-bromoindeno[1,2-b]thien-3-yl)(η⁵-cyclopentadienyl)zirconium dichloride,
sulfandiyl-(η⁵-2-bromoindeno[1,2-b]thien-3-yl)( η⁵-inden-1-yl)zirconium dichloride,
sulfandiyl-(η⁵-2-bromoindeno[1,2-b]thien-3-yl)(η⁵-inden-4-yl)zirconium dichloride,
sulfandiyl-(η⁵-2-bromoindeno[1,2-b]thien-3-yl)(η⁵-fluoren-9-yl)zirconium dichloride,
sulfandiyl-(η⁵-2-bromoindeno[1,2-b]thien-3-yl)(η⁵-fluoren-1-yl)zirconium dichloride,
sulfandiyl-(η⁵-2-bromoindeno[1,2-b]thien-3-yl)(η⁵-fluoren-4-yl)zirconium dichloride,
sulfandiyl-(η⁵-2-bromoindeno[1,2-b]thien-5-yl)(η⁵-cyclopentadienyl)zirconium dichloride,
sulfandiyl-(η⁵-2-bromoindeno[1,2-b]thien-5-yl)(η⁵-inden-1-yl)zirconium dichloride,
sulfandiyl-(η⁵-2-bromoindeno[1,2-b]thien-5-yl)(η⁵-inden-4-yl)zirconium dichloride,
sulfandiyl-(η⁵-2-bromoindeno[1,2-b]thien-5-yl)(η⁵-fluoren-9-yl)zirconium dichloride,
sulfandiyl-(η⁵-2-bromoindeno[1,2-b]thien-5-yl)(η⁵-fluoren-1-yl)zirconium dichloride,
sulfandiyl-(η⁵-2-bromoindeno[1,2-b]thien-5-yl)(η⁵fluoren-4-yl)zirconium dichloride,
sulfandiyl-(η⁵-2-bromoindeno[1,2-b]thienyl)(η⁵-cyclopentadienyl)zirconium dichloride,
sulfandiyl-(η⁵-2-bromoindeno[1,2-b]thienyl)(η⁵-inden-1-yl)zirconium dichloride,
sulfandiyl-(η⁵-2-bromoindeno[1,2-b]thienyl)(η⁵-inden-4-yl)zirconium dichloride,
sulfandiyl-(η⁵-2-bromoindeno[1,2-b]thienyl)(η⁵-fluoren-9-yl)zirconium dichloride,
sulfandiyl-(η⁵-2-bromoindeno[1,2-b]thienyl)(η⁵-fluoren-1-yl)zirconium dichloride,
sulfandiyl-(η⁵-2-bromoindeno[1,2-b]thienyl)(η⁵-fluoren-4-yl)zirconium dichloride,
sulfandiyl-(η⁵-2-bromoindeno[2,1-b]thien-3-yl)(η⁵-cyclopentadienyl)zirconium dichloride,
sulfandiyl-(η⁵-2-bromoindeno[2,1-b]thien-3-yl)(η⁵-inden-1-yl)zirconium dichloride,
sulfandiyl-(η⁵-2-bromoindeno[2,1-b]thien-3-yl)(η⁵-inden-4-yl)zirconium dichloride,
sulfandiyl-(η⁵-2-bromoindeno[2,1-b]thien-3-yl)(η⁵-fluoren-9-yl)zirconium dichloride,
sulfandiyl-(η⁵-2-bromoindeno[2,1-b]thien-3-yl)(η⁵-fluoren-1-yl)zirconium dichloride,
sulfandiyl-(η⁵-2-bromoindeno[2,1-b]thien-3-yl)(η⁵-fluoren-4-yl)zirconium dichloride,
sulfandiyl-(η⁵-2-bromoindeno[2,1-b]thien-4-yl)(η⁵-cyclopentadienyl)zirconium dichloride,
sulfandiyl-(η⁵-2-bromoindeno[2,1-b]thien-4-yl)(η⁵-inden-1-yl)zirconium dichloride,
sulfandiyl-(η⁵-2-bromoindeno[2,1-b]thien-4-yl)(η⁵-inden-4-yl)zirconium dichloride,
sulfandiyl-(η⁵-2-bromoindeno[2,1-b]thien-4-yl)(η⁵-fluoren-9-yl)zirconium dichloride,
sulfandiyl-(η⁵-2-bromoindeno[2,1-b]thien-4-yl)(η⁵-fluoren-1-yl)zirconium dichloride,
sulfandiyl-(η⁵-2-bromoindeno[2,1-b]thien-4-yl)(η⁵-fluoren-4-yl)zirconium dichloride,
sulfandiyl-(η⁵-2-bromoindeno[2,1-b]thien-7-yl)(η⁵-cyclopentadienyl)zirconium dichloride,
sulfandiyl-(η⁵-2-bromoindeno[2,1-b]thien-7-yl)(η⁵-inden-1-yl)zirconium dichloride,
sulfandiyl-(η⁵-2-bromoindeno[2,1-b]thien-7-yl)(η⁵-inden-4-yl)zirconium dichloride,
sulfandiyl-(η⁵-2-bromoindeno[2,1-b]thien-7-yl)(η⁵-fluoren-9-yl)zirconium dichloride,
sulfandiyl-(η⁵-2-bromoindeno[2,1-b]thien-7-yl)(η⁵-fluoren-1-yl)zirconium dichloride,
sulfandiyl-(η⁵-2-bromoindeno[2,1-b]thien-7-yl)(η⁵-fluoren-4-yl)zirconium dichloride,
sulfandiyl-(η⁵-2-bromo-5-methylcyclopenta[b]thien-3-yl)(η⁵-cyclopentadienyl)zirconium dichloride,
sulfandiyl-(η⁷⁵-2-bromo-5-methylcyclopenta[b]thien-3-yl)(η⁵-inden-1-yl)zirconium dichloride,
sulfandiyl-(η⁵-2-bromo-5-methylcyclopenta[b]thien-3-yl)(η⁵-inden-4-yl)zirconium dichloride, sulfandiyl-($\eta^5$-2-bromo-5-methylcyclopenta[b]thien-3-yl)($\eta^5$-fluoren-9-yl)zirconium dichloride,
sulfandiyl-($\eta^5$-2-bromo-5-methylcyclopenta[b]thien-3-yl)($\eta^5$-fluoren-1-yl)zirconium dichloride,
sulfandiyl-($\eta^5$-2-bromo-5-methylcyclopenta[b]thien-3-yl)($\eta^5$-fluoren-4-yl)zirconium dichloride,
sulfandiyl-($\eta^5$-1-bromoindeno[1,2-c]thien-3-yl)($\eta^5$-cyclopentadienyl)zirconium dichloride,
sulfandiyl-($\eta^5$-bromoindeno[1,2-c]thien-3-yl)($\eta^5$-inden-1-yl)zirconium dichloride,
sulfandiyl-($\eta^5$-1-bromoindeno[1,2-c]thien-3-yl)($\eta^5$-inden-4-yl)zirconium dichloride,
sulfandiyl-($\eta^5$-1-bromoindeno[1,2-c]thien-3-yl)($\eta^5$-fluoren-9-yl)zirconium dichloride,
sulfandiyl-($\eta^5$-1-bromoindeno[1,2-c]thien-3-yl)($\eta^5$-fluoren-1-yl)zirconium dichloride,
sulfandiyl-($\eta^5$-1-bromoindeno[1,2-c]thien-3-yl)($\eta^5$-fluoren-4-yl)zirconium dichloride,
sulfandiyl-($\eta^5$-3-bromoindeno[1,2-c]thien-4-yl)($\eta^5$-cyclopentadienyl)zirconium dichloride,
sulfandiyl-($\eta^5$-3-bromoindeno[1,2-c]thien-4-yl)($\eta^5$-inden-1-yl)zirconium dichloride,
sulfandiyl-($\eta^5$-3-bromoindeno[1,2-c]thien-4-yl)($\eta^5$-inden-4-yl)zirconium dichloride,
sulfandiyl-($\eta^5$-3-bromoindeno[1,2-c]thien-4-yl)($\eta^5$-fluoren-9-yl)zirconium dichloride,
sulfandiyl-($\eta^5$-3-bromoindeno[1,2-c]thien-4-yl)($\eta^5$-fluoren-1-yl)zirconium dichloride,
sulfandiyl-($\eta^5$-3-bromoindeno[1,2-c]thien-4-yl)($\eta^5$-fluoren-4-yl)zirconium dichloride,
sulfandiyl-($\eta^5$-3-bromoindeno[1,2-c]thien-7-yl)($\eta^5$-cyclopentadienyl)zirconium dichloride,
sulfandiyl-($\eta^5$-3-bromoindeno[1,2-c]thien-7-yl)($\eta^5$-inden-1-yl)zirconium dichloride,
sulfandiyl-($\eta^5$-3-bromoindeno[1,2-c]thien-7-yl)($\eta^5$-inden-4-yl)zirconium dichloride,
sulfandiyl-($\eta^5$-3-bromoindeno[1,2-c]thien-7-yl)($\eta^5$-fluoren-9-yl)zirconium dichloride,
sulfandiyl-($\eta^5$-3-bromoindeno[1,2-c]thien-7-yl)($\eta^5$-fluoren-1-yl)zirconium dichloride,
sulfandiyl-($\eta^5$-3-bromoindeno[1,2-c]thien-7-yl)($\eta^5$-fluoren-4-yl)zirconium dichloride,
sulfandiyl-($\eta^5$-2-bromoindeno[1,2-b]furan-3-yl)($\eta^5$-cyclopentadienyl)zirconium dichloride,
sulfandiyl-($\eta^5$-2-bromoindeno[1,2-b]furan-3-yl)($\eta^5$-inden-1-yl)zirconium dichloride,
sulfandiyl-($\eta^5$-2-bromoindeno[1,2-b]furan-3-yl)($\eta^5$-inden-4-yl)zirconium dichloride,
sulfandiyl-($\eta^5$-2-bromoindeno[1,2-b]furan-3-yl)($\eta^5$-fluoren-9-yl)zirconium dichloride,
sulfandiyl-($\eta^5$-2-bromoindeno[1,2-b]furan-3-yl)($\eta^5$-fluoren-1-yl)zirconium dichloride,
sulfandiyl-($\eta^5$-2-bromoindeno[1,2-b]furan-3-yl)($\eta^{15}$-fluoren-4-yl)zirconium dichloride,
sulfandiyl-($\eta^5$-2-bromoindeno[1,2-b]furan-5-yl)($\eta^5$-cyclopentadienyl)zirconium dichloride,
sulfandiyl-($\eta^5$-2-bromoindeno [1,2-b]furan-5-yl)($\eta^5$-inden-1-yl)zirconium dichloride,
sulfandiyl-($\eta^5$-2-bromoindeno[1,2-b]furan-5-yl)($\eta^5$-inden-4-yl)zirconium dichloride,
sulfandiyl-($\eta^5$-2-bromoindeno[1,2-b]furan-5-yl)($\eta^5$-fluoren-9-yl)zirconium dichloride,
sulfandiyl-($\eta^5$-2-bromoindeno[1,2-b]furan-5-yl)($\eta^5$-fluoren-1-yl)zirconium dichloride,
sulfandiyl-($\eta^5$-2-bromoindeno[1,2-b]furan-5-yl)($\eta^5$-fluoren-4-yl)zirconium dichloride,
sulfandiyl-($\eta^5$-2-bromoindeno[1,2-b]furan-8-yl)($\eta^5$-cyclopentadienyl)zirconium dichloride,
sulfandiyl-($\eta^5$-2-bromoindeno[1,2-b]furan-8-yl)($\eta^5$-inden-1-yl)zirconium dichloride,
sulfandiyl-($\eta^5$-2-bromoindeno[1,2-b]furan-8-yl)($\eta^5$-inden-4-yl)zirconium dichloride,
sulfandiyl-($\eta^5$-2-bromoindeno[1,2-b]furan-8-yl)($\eta^5$-fluoren-9-yl)zirconium dichloride,
sulfandiyl-($\eta^5$-2-bromoindeno[1,2-b]furan-8-yl)($\eta^5$-fluoren-1-yl)zirconium dichloride,
sulfandiyl-($\eta^5$-2-bromoindeno[1,2-b]furan-8-yl)($\eta^5$-fluoren-4-yl)zirconium dichloride,
sulfandiyl-($\eta^5$-2-bromo-5-methylindeno[1,2-b]indol-6-yl)($\eta^5$-cyclopentadienyl)zirconium dichloride,
sulfandiyl-($\eta^5$-2-bromo-5-methylindeno[1,2-b]indol-6-yl)($\eta^5$-inden-1-yl)zirconium dichloride,
sulfandiyl-($\eta^5$-2-bromo-5-methylindeno[1,2-b]indol-6-yl)($\eta^5$-inden-4-yl)zirconium dichloride,
sulfandiyl-($\eta^5$-2-bromo-5-methylindeno[1,2-b]indol-6-yl)($\eta^5$-fluoren-9-yl)zirconium dichloride,
sulfandiyl-($\eta^5$-2-bromo-5-methylindeno[1,2-b]indol-6-yl)($\eta^5$-fluoren-1-yl)zirconium dichloride,
sulfandiyl-($\eta^5$-2-bromo-5-methylindeno[1,2-b]indol-6-yl)($\eta^5$-fluoren-4-yl)zirconium dichloride,
sulfandiyl-($\eta^5$-2-bromo-5-methylindeno[1,2-b]indol-9-yl)($\eta^5$-cyclopentadienyl)zirconium dichloride,
sulfandiyl-($\eta^5$-2-bromo-5-methylindeno[1,2-b]indol-9-yl)($\eta^5$-inden-1-yl)zirconium dichloride,
sulfandiyl-($\eta^5$-2-bromo-5-methylindeno[1,2-b]indol-9-yl)($\eta^5$-inden-4-yl)zirconium dichloride,
sulfandiyl-($\eta^5$-2-bromo-5-methylindeno[1,2-b]indol-9-yl)($\eta^5$-fluoren-9-yl)zirconium dichloride,
sulfandiyl-($\eta^5$-2-bromo-5-methylindeno[1,2-b]indol-9-yl)($\eta^5$-fluoren-1-yl)zirconium dichloride,
sulfandiyl-($\eta^5$-2-bromo-5-methylindeno[1,2-b]indol-9-yl)($\eta^5$-fluoren-4-yl)zirconium dichloride,
sulfandiyl-($\eta^5$-8-bromo-5-methylindeno[2,1-b]indol-7-yl)($\eta^5$-cyclopentadienyl)zirconium dichloride,
sulfandiyl-($\eta^5$-8-bromo-5-methylindeno[2,1-b]indol-7-yl)($\eta^5$-inden-1-yl)zirconium dichloride,
sulfandiyl-(4-8-bromo-5-methylindeno[2,1-b]indol-7-yl)($\eta^5$-inden-4-yl)zirconium dichloride,
sulfandiyl-($\eta^5$-8-bromo-5-methylindeno[2,1-b]indol-7-yl)($\eta^5$-fluoren-9-yl)zirconium dichloride,
sulfandiyl-($\eta^5$-8-bromo-5-methylindeno[2,1-b]indol-7-yl)($\eta^5$-fluoren-1-yl)zirconium dichloride,
sulfandiyl-($\eta^5$-8-bromo-5-methylindeno[2,1-b]indol-7-yl)($\eta^5$-fluoren-4-yl)zirconium dichloride,
sulfandiyl-($\eta^5$-8-bromo-5-methylindeno[2,1-b]indol-10-yl)($\eta^5$-cyclopentadienyl)zirconium dichloride,
sulfandiyl-($\eta^5$-8-bromo-5-methylindeno[2,1-b]indol-10-yl)($\eta^5$-inden-1-yl)zirconium dichloride,
sulfandiyl-($\eta^5$-8-bromo-5-methylindeno[2,1-b]indol-10-yl)($\eta^5$-inden-4-yl)zirconium dichloride,
sulfandiyl-($\eta^5$-8-bromo-5-methylindeno[2,1-b]indol-10-yl)($\eta^5$-fluoren-9-yl)zirconium dichloride,
sulfandiyl-($\eta^5$-8-bromo-5-methylindeno[2,1-b]indol-1 0-yl)($\eta^5$-fluoren-1-yl)zirconium dichloride,
sulfandiyl-($\eta^5$-8-bromo-5-methylindeno[2,1-b]indol-1 0-yl)($\eta^5$-fluoren-4-yl)zirconium dichloride,
sulfandiyl-($\eta^5$-2-bromo-5-methylcyclopenta[b]thien-3-yl)($\eta^5$-cyclopentadienyl)zirconium dichloride,
sulfandiyl-($\eta^5$-2-bromo-5-methylcyclopenta[b]thien-3-yl)($\eta^5$-inden-1-yl)zirconium dichloride,
sulfandiyl-($\eta^5$-2-bromo-5-methylcyclopenta[b]thien-3-yl)($\eta^5$-inden-4-yl)zirconium dichloride, sulfandiyl-(η⁵-2-bromo-5-methylcyclopenta[b]thien-3-yl)
(η⁵-fluoren-9-yl)zirconium dichloride,
sulfandiyl-(η⁵-2-bromo-5-methylcyclopenta[b]thien-3-yl)
(η⁵-fluoren-1-yl)zirconium dichloride,
sulfandiyl-(η⁵-2-bromo-5-methylcyclopenta[b]thien-3-yl)
(η⁵-fluoren-4-yl)zirconium dichloride,
4,4'-sulfandiyl-(η⁵-2-[5-bromonaphth-1-yl]indenyl)(η⁵-indenyl)zirconium dichloride,
4,4'-sulfandiyl-(η⁵-2-[7-fluorobenzothien-2-yl]indenyl)(η⁵-indenyl)zirconium dichloride,
4,4'-sulfandiyl-(η⁵-2-[2-chlorobenzothien-4-yl]indenyl)(η⁵-indenyl)zirconium dichloride,
(5-bromonaphth-1-yl)phosphindiyl-bis(η⁵-2-methylinden-4-yl)zirconium dichloride,
(7-fluorobenzothien-2-yl)phosphindiyl-bis(η⁵-2-methylinden-4-yl)zirconium dichloride,
(2-chlorobenzothien-4-yl)phosphindiyl-bis(η⁵-2-methylinden-4-yl)zirconium dichloride,
dimethylsilanediyl(η⁵-4-bromo-2-methylinden-1-yl)(tert-butylamido)zirconium dichloride,
dimethylsilanediyl(η⁵-4-chloro-2-methylinden-1-yl)(tert-butylamido)zirconium dichloride,
dimethylsilanediyl(η⁵-4-fluoro-2-methylinden-1-yl)(tert-butylamido)zirconium dichloride,
dimethylsilanediyl(η⁵-4-iodo-2-methylinden-1-yl)(tert-butylamido)zirconium dichloride,
dimethylsilanediyl(η⁵-4-bromo-2-methylinden-1-yl)(phenylamino)zirconium dichloride,
dimethylsilanediyl(η⁵-4-bromo-2-methylinden-1-yl)(4-bromophenylamido)zirconium dichloride,
dimethylsilanediyl(η⁵-2-methylinden-1-yl)(4-bromophenylamido)zirconium dichloride,
dimethylsilanediyl(η⁵-fluoren-9-yl)(4-bromophenylamido)zirconium dichloride,
dimethylsilanediyl(η⁵-2,3,4,5-teramethylcyclopentadien-1-yl)(4-bromophenylamido)zirconium dichloride,
dimethylsilanediyl(η⁵-cyclopentadienyl)(4-bromophenylamido)zirconium dichloride,
dimethylsilanediyl(η⁵-cyclopentadienyl)(4-chlorophenylamido)zirconium dichloride,
dimethylsilanediyl(η⁵-cyclopentadienyl)(4-fluorophenylamido)zirconium dichloride,
dimethylsilanediyl(η⁵-cyclopentadienyl)(4-iodophenylmido)zirconium dichloride,
dimethylsilanediyl(η⁵-2,3,4,5-tetramethycyclopentadien-1-yl)(4-bromophenylphosphido)zirconium dichloride,
dimethylgermandiyl(η⁵-2,3,4,5-tetramethycyclopentadien-1-yl)(4-bromophenylamido)zirconium dichloride,
2,2'-propylideno-(η⁵-2,3,4,5-tetramethycyclopentadien-1-yl)(4-bromophenylamido)zirconium dichloride,
methylideni-(η⁵-2,3,4,5-tetramethycyclopentadien-1-yl)(4-bromophenylamido)zirconium dichloride,
1,2-ethylideno-(η⁵-2,3,4,5-tetramethycyclopentadien-1-yl)(4-bromophenylamido)zirconium dichloride,
phenylmethylideno-(η⁵-2,3,4,5-tetramethycyclopentadien-1-yl)(4-bromophenylamido)zirconium dichloride,
(4-bromophenyl)methylideno-(η⁵-2,3,4,5-tetramethycyclopentadien-1-yl)(tert-butylamido)zirconium dichloride,
(4-chlorophenyl)methylideno-(η⁵-2,3,4,5-tetramethycyclopentadien-1-yl)(tert-butylamido)zirconium dichloride,
(4-fluorophenyl)methylideno-(η⁵-2,3,4,5-tetramethycyclopentadien-1-yl)(tert-butylamido)zirconium dichloride,
(4-iodophenyl)methylideno-(η⁵-2,3,4,5-tetramethycyclopentadien-1-yl)(tert-butylamido)zirconium dichloride,
dimethylsilanediyl(η⁵-2-bromoinden-1-yl)(tert-butylamido) zirconium dibromide,
dimethylsilanediyl(η⁵-2-bromoinden-1-yl)(tert-butylamido) zirconium diiodide,
dimethylsilanediyl(η⁵-2-bromoinden-1-yl)(tert-butylamido) zirconium difluoride,
dimethylsilanediyl(η⁵-2-bromoinden-1-yl)(tert-butylamido) zirconium dihydride,
dimethylsilanediyl(η⁵-2-bromoinden-1-yl)(tert-butylaiiido) dimethylzirconium,
dimethylsilanediyl(η⁵-2-bromoinden-1-yl)(tert-butylamido) dibenzylzirconium,
dimethylsilanediyl(η⁵-2-bromoinden-1-yl)(tert-butylamido) diphenylzirconium,
dimethylsilanediyl(η⁵-2-bromoinden-1-yl)(tert-butylamido) dimethoxyzirconium,
dimethylsilanediyl(η⁵-2-bromoinden-1-yl)(tert-butylamido) bis(dimethylamido)zirconium,
dimethylsilanediyl(η⁵-2-bromoinden-1-yl)(tert-butylamido) zirconium dichloride,
dimethylsilanediyl(η⁵-4-bromo-2-methylinden-1-yl)(tert-butylamido)zirconium dichloride,
dimethylsilanediyl(η⁵-4-chloro-2-methylindenyl)(tert-butylamido)zirconium dichloride,
dimethylsilanediyl(η⁵-4-fluoro-2-methylinden-1-yl)(tert-butylamido)zirconium dichloride,
dimethylsilanediyl(η⁵-4-iodo-2-methylinden-1-yl)(tert-butylamido)zirconium dichloride,
dimethylsilanediyl(η⁵-4-bromo-2-methylinden-1-yl)(tert-butylamido)zirconium tribromide,
dimethylsilanediyl(η⁵-4-bromo-2-methylinden-1-yl)(tert-butylamido)zirconium triiodide,
dimethylsilanediyl(η⁵-4-bromo-2-methylinden-1-yl)(tert-butylamido)zirconium trifluoride,
dimethylsilanediyl(η⁵-4-bromo-2-methylinden-1-yl)(tert-butylamido)zirconium trihydride,
dimethylsilanediyl(η⁵-4-bromo-2-methylinden-1-yl)(tert-butylamido)trimethylzirconium,
dimethylsilanediyl(η⁵-4-bromo-2-methylinden-1-yl)(tert-butylamido)triphenylzirconium,
dimethylsilanediyl(η⁵-4-bromo-2-methylinden-1-yl)(tert-butylamido)tribenzylzirconium,
dimethylsilanediyl(η⁵-4-bromo-2-methylinden-1-yl)(tert-butylamido)trimethoxyzirconium,
dimethylsilanediyl(η⁵-4-bromo-2-methylinden-1-yl)(tert-butylamido)-tris(dimethylamino)zirconium,
dimethylsilanediyl(η⁵-3-[4-bromophenyl]-cyclopentadien-1-yl)(tert-butylamido)zirconium dichloride,
dimethylsilanediyl(η⁵-4-bromo-2-methylcyclopenta[b] naphtha-1-yl)(tert-butylamido)zirconium dichloride,
dimethylsilanediyl(η⁵-8-bromo-6-methylindeno[5,6-d][1,3] dioxol-5-yl)(tert-butylamido)zirconium dichloride,
dimethylsilanediyl(η⁵-4-bromo-2,3,6-trimethylindeno[5,6-b]thien-7-yl)(tert-butylamido)zirconium dichloride,
dimethylsilanediyl(η⁵-2-bromo-4,6-dimethylindeno[5,6-b]thien-7-yl)(tert-butylamido)zirconium dichloride,
dimethylsilanediyl(η⁵-4-bromo-1,2,3,6-tetramethylcyclopenta[f]indol-7-yl)(tert-butylamido)zirconium dichloride,
dimethylsilanediyl(η⁵-4-bromo-1-phenyl-2,3,6-triamethylcyclopenta[f]indol-7-yl)(tert-butylamido)zirconium dichloride,
dimethylsilanediyl(η⁵-5-bromo-7-methylcyclopenta[g] quinol-8-yl)(tert-butylamido)zirconium dichloride,
dimethylsilanediyl(η⁵-2-bromo-5,7-dimethylcyclopenta[g] quinol-8-yl)(tert-butylamido)zirconium dichloride,
dimethylsilanediyl(η⁵-4,6-dibromo-2-methylinden-1-yl) (tert-butylamido)zirconium dichloride,
dimethylsilanediyl(η⁵-4,6-dichloro-2-methylinden-1-yl) (tert-butylamido)zirconium dichloride, dimethylsilanediyl($\eta^5$-4,6-difluoro-2-methylinden-1-yl)(tert-butylamido)zirconium dichloride,
dimethylsilanediyl($\eta^5$-4-bromo-6-chloro-2-methylinden-1-yl)(tert-butylamido)zirconium dichloride,
dimethylsilanediyl($\eta^5$-4-bromo-6-fluoro-2-methylinden-1-yl)(tert-butylamido)zirconium dichloride,
dimethylsilanediyl($\eta^5$-5-bromo-2,4-dimethylinden-1-yl)(tert-butylamido)zirconium dichloride,
dimethylsilanediyl($\eta^5$-6-bromo-2,4-dimethylinden-1-yl)(tert-butylamido)zirconium dichloride,
dimethylsilanediyl($\eta^5$-7-bromo-2-methyl-4-phenylinden-1-yl)(tert-butylamido)zirconium dichloride,
dimethylsilanediyl($\eta^5$-3-bromo-5-methylcyclopenta[b]thien-6-yl)(tert-butylamido)zirconium dichloride,
dimethylsilanediyl($\eta^5$-1-chlorocyclopenta[c]thien-4-yl)(tert-butylamido)zirconium dichloride,
dimethylsilanediyl($\eta^5$-8-bromo-2-methylcyclopenta[b][1]benzothien-1-zirconium dichloride,
dimethylsilanediyl($\eta^5$-8-chloro-2-methylcyclopenta[b][1]benzothien-1-yl)(tert-butylamido)zirconium dichloride,
dimethylsilanediyl($\eta^5$-8-iodo-2-methylcyclopenta[b][1]benzothien-1-yl)(tert-butylamido)zirconium dichloride,
dimethylsilanediyl($\eta^5$-8-fluoro-2-methylcyclopenta[b][1]benzothien-1-yl)(tert-butylamido)zirconium dichloride,
dimethylsilanediyl($\eta^5$-3-bromo-5-methylcyclopenta[b]fur-6yl)(tert-butylamido)zirconium dichloride,
dimethylsilanediyl($\eta^5$-2-bromo-1,5-dimethylcyclopenta[b]pyrrol-4yl)(tert-butylamido)zirconium dichloride,
dimethylsilanediyl($\eta^5$-2-bromo-5-methyl-1-phenylcyclopenta[b]pyrrol-4yl)(tert-butylamido)zirconium dichloride,
dimethylsilanediyl($\eta^5$-2-chloro-5-methyl-1-phenylcyclopenta[b]pyrrol-4yl)(tert-butylamido)zirconium dichloride,
dimethylsilanediyl($\eta^5$-2-iodo-5-methyl-1-phenylcyclopenta[b]pyrrol-4yl)(tert-butylamido)zirconium dichloride,
dimethylsilanediyl($\eta^5$-2-fluoro-5-methyl-1-phenylcyclopenta[b]pyrrol-4yl)(tert-butylamido)zirconium dichloride,
dimethylsilanediyl($\eta^5$-2-bromo-1,5-dimethylcyclopenta[b]phosphol-4-yl)(tert-butylamido)zirconium dichloride,
dimethylsilanediyl($\eta^5$-5-bromo-2,4-dimethylcyclopenta[b]indol-1-yl)(tert-butylamido)zirconium dichloride,
dimethylsilanediyl($\eta^5$-4-bromocyclopenta[b]pyrid-5-yl)(tert-butylamido)zirconium dichloride,
dimethylsilanediyl($\eta^5$-4-bromocyclopenta[b]phosphoran-5-yl)(tert-butylamido)zirconium dichloride,
dimethylsilanediyl($\eta^5$-2,6-dibromo-1-dimethylamino-1-boratobenzene-4)(tert-butylamido)zirconium dichloride,
dimethylsilanediyl($\eta^5$-4-bromo-3-dimethylamino-1,3-thiaborinden-5-yl)(tert-butylamido)zirconium dichloride,
dimethylsilanediyl($\eta^5$-4-bromo-3a,7a-azaborinden-1-yl)(tert-butylamido)zirconium dichloride,
dimethylsilanediyl($\eta^5$-3-bromo-2-dimethylamino-1,2-thiaborolide-4)(tert-butylamido)zirconium dichloride,
dimethylsilanediyl($\eta^5$-2-[4-bromophenyl]-inden-1-yl)(tert-butylamido)zirconium dichloride,
dimethylsilanediyl($\eta^5$-2-[4-chlorophenyl]-inden-1-yl)(tert-butylamido)zirconium dichloride,
dimethylsilanediyl($\eta^5$-2-[4-fluorophenyl]-inden-1-yl)(tert-butylamido)zirconium dichloride,
dimethylsilanediyl($\eta^5$-2-[4-iodophenyl]-inden-1-yl)(tert-butylamido)zirconium dichloride,
dimethylsilanediyl($\eta^5$-2-[5-bromothien-2-yl]-inden-1-yl)(tert-butylamido)zirconium dichloride,
dimethylsilanediyl($\eta^5$-2-[4-bromopyridin-2-yl]-inden-1-yl)(tert-butylamido)zirconium dichloride,
dimethylsilanediyl($\eta^5$-2-bromoinden-1-yl)(tert-butylamido)zirconium dichloride,
dimethylsilanediyl($\eta^5$-2-bromo-4,7-dimethylinden-1-yl)(tert-butylamido)zirconium dichloride,
dimethylsilanediyl($\eta^5$-3-bromoinden-1-yl)(tert-butylamido)zirconium dichloride,
dimethylsilanediyl($\eta^5$-2-chloroinden-1-yl)(tert-butylamido)zirconium dichloride,
dimethylsilanediyl($\eta^5$-2-bromofluorenyl)(tert-butylamido)zirconium dichloride,
dimethylsilanediyl($\eta^5$-2-iodofluorenyl)(tert-butylamido)zirconium dichloride,
dimethylsilanediyl($\eta^5$-2-chlorofluorenyl)(tert-butylamido)zirconium dichloride,
dimethylsilanediyl($\eta^5$-2-fluorofluorenyl)(tert-butylamido)zirconium dichloride,
dimethylsilanediyl($\eta^5$-2,7-dibromofluorenyl)(tert-butylamido)zirconium dichloride,
dimethylsilanediyl($\eta^5$-7-bromoindeno[1,2-c]pyridin-5-yl)(tert-butylamido)zirconium dichloride,
dimethylsilanediyl($\eta^5$-3-bromoindeno[1,2-c]pyridin-5-yl)(tert-butylamido)zirconium dichloride,
dimethylsilanediyl($\eta^5$-7-bromoindeno[1,2-c]phosphoran-5-yl)(tert-butylamido)zirconium dichloride,
dimethylsilanediyl($\eta^5$-2-bromoindeno[1,2-b]thien-4-yl)(tert-butylamido)zirconium dichloride,
dimethylsilanediyl($\eta^5$-6-bromoindeno[2,1-b]thien-8-yl)(tert-butylamido)zirconium dichloride,
dimethylsilanediyl($\eta^5$-6-bromoindeno[1,2-c]thien-8-yl)(tert-butylamido)zirconium dichloride,
dimethylsilanediyl($\eta^5$-6-bromo-2,3-dimethylindeno[1,2-b]furan-4-yl)(tert-butylamido)zirconium dichloride,
dimethylsilanediyl($\eta^5$-2-bromoindeno[1,2-b][1]benzothien-10-yl)(tert-butylamido)zirconium dichloride,
dimethylsilanediyl($\eta^5$-8-bromoindeno[1,2-b][1]benzothien-10-yl)(tert-butylamido)zirconium dichloride,
dimethylsilanediyl($\eta^5$-8-bromoindeno[2,1-b][1]benzothien-6-yl)(tert-butylamido)zirconium dichloride,
dimethylsilanediyl($\eta^5$-3-bromoindeno[2,1-b][1]benzothien-6-yl)(tert-butylamido)zirconium dichloride,
dimethylsilanediyl($\eta^5$-2-bromo-5-methylindeno[1,2-b]indol-10-yl)(tert-butylamido)zirconium dichloride,
dimethylsilanediyl($\eta^5$-8-bromo-5-methylindeno[1,2-b]indol-10-yl)(tert-butylamido)zirconium dichloride,
dimethylsilanediyl($\eta^5$-8-bromo-5-methylindeno[2,1-b]indol-6-yl)(tert-butylamido)zirconium dichloride,
dimethylsilanediyl($\eta^5$-3-bromo-5-methylindeno[2,1-b]indol-6-yl)(tert-butylamido)zirconium dichloride,
dimethylsilandiyl($\eta^5$-2-[5-bromonaphth-1-yl]inden-1-yl)(tert-butylamido)zirconium dichloride,
dimethylsilandiyl($\eta^5$-2-[7-fluorobenzothien-2-yl]inden-1-yl)(tert-butylamido)zirconium dichloride,
dimethylsilandiyl($\eta^5$-2-[2-chlorobenzothien-4-yl]inden-1-yl)(tert-butylamido)zirconium dichloride,
(5-bromonaphth-1-yl)methylideno-($\eta^5$-2,3,4,5-tetramethycyclopentadien-1-yl)(tert-butylamido)zirconium dichloride,
(7-fluorobenzothien-2-yl)methylideno-($\eta^5$-2,3,4,5-tetramethycyclopentadien-1-yl)(tert-butylamido)zirconium dichloride,
(2-chlorobenzothien-4-yl)methylideno-($\eta^5$-2,3,4,5-tetramethycyclopentadien-1-yl)(tert-butylamido)zirconium dichloride,
dimethylsilandiyl($\eta^5$-2,3,4,5-tetramethycyclopentadien-1-yl)(5-bromonaphth-1-yl)zirconium dichloride,
dimethylsilandiyl($\eta^5$-2,3,4,5-tetramethycyclopentadien-1-yl)(7-fluorobenzothien-2-y)zirconium dichloride, dimethylsilandiyl($\eta^5$-2,3,4,5-tetramethycyclopentadien-1-yl)(2-chlorobenzothien-4-yl)zirconium dichloride, and the hafnium and titanium analogs of the examples above.

Methods of synthesising the halogen substituted metallocene compounds listed above are disclosed in our copending U.S. patent application Ser. Nos. 11/302,798, 11/300,240, 11/300,032, 11/300,002, 11/300,054, 11/302,821, all filed concurrently herewith and all incorporated herein by reference.

A set of exemplary catalyst precursor prepared by coupling or cross-coupling reactions is set out below. These are by way of example only and are not intended to list every catalyst precursor that is within the scope of the invention.

Preferred compounds include:
($\eta^5$-2,4-dimethylindenyl)($\eta^5$-pentamethylcyclopentadienyl)zirconium dichloride,
($\eta^5$-2-methyl-4-phenylindenyl)($\eta^5$-pentamethylcyclopentadienyl)zirconium dichloride,
($\eta^5$-2-methyl-4-(p-tolyl)indenyl)($\eta^5$-pentamethylcyclopentadienyl)zirconium dichloride,
($\eta^5$-2-methyl-4-(m-tolyl)indenyl)($\eta^5$-pentamethylcyclopentadienyl)zirconium dichloride,
($\eta^5$-2-methyl-4-(o-tolyl)indenyl)($\eta^5$-pentamethylcyclopentadienyl)zirconium dichloride,
($\eta^5$-2-methyl-4-(4-t-butylphenyl)indenyl)($\eta^5$-pentamethylcyclopentadienyl)zirconium dichloride,
($\eta^5$-2-methyl-4-(4-fluorophenyl)indenyl)($\eta^5$-pentamethylcyclopentadienyl)zirconium dichloride,
($\eta^5$-2-methyl-4-(3-trifluoromethylphenyl)indenyl)($\eta^5$-pentamethylcyclopentadienyl)zirconium dichloride,
($\eta^5$-2-methyl-4-(2-methoxyphenyl)indenyl)($\eta^5$-pentamethylcyclopentadienyl)zirconium dichloride,
($\eta^5$-2-methyl-4-(4-biphenyl)bromoindenyl)($\eta^5$-pentamethylcyclopentadienyl)zirconium dichloride,
($\eta^5$-2-methyl-4-(1-naphthyl)indenyl)($\eta^5$-pentamethylcyclopentadienyl)zirconium dichloride,
($\eta^5$-2-methyl-4-(2-thienyl)indenyl)($\eta^5$-pentamethylcyclopentadienyl)zirconium dichloride,
($\eta^5$-2-methyl-4-(2-benzothienyl)indenyl)($\eta^5$-pentamethylcyclopentadienyl)zirconium dichloride,
($\eta^5$-2-methyl-4-(2-furyl)indenyl)($\eta^5$-pentamethylcyclopentadienyl)zirconium dichloride,
($\eta^5$-2-methyl-4-(2-benzofuryl)indenyl)($\eta^5$-pentamethylcyclopentadienyl)zirconium dichloride,
($\eta^5$-2-methyl-4-styrylindenyl)($\eta^5$-pentamethylcyclopentadienyl)zirconium dichloride (cis and trans),
($\eta^5$-2-methyl-4-(4-fluorostyryl)indenyl)($\eta^5$-pentamethylcyclopentadienyl)zirconium dichloride (trans),
($\eta^5$-2-methyl-4-(1,2-butoxyvinyl)indenyl)($\eta^5$-pentamethylcyclopentadienyl)zirconium dichloride,
($\eta^5$-2,4-dimethylindenyl)($\eta^5$-pentamethylcyclopentadienyl)hafnium dichloride,
($\eta^5$-2-methyl-4-phenylindenyl)($\eta^5$-pentamethylcyclopentadienyl)hafnium dichloride,
($\eta^5$-2-methyl-4-(p-tolyl)indenyl)($\eta^5$-pentamethylcyclopentadienyl)hafnium dichloride,
($\eta^5$-2-methyl-4-(m-tolyl)indenyl)($\eta^5$-pentamethylcyclopentadienyl)hafnium dichloride,
($\eta^5$-2-methyl-4-(o-tolyl)indenyl)($\eta^5$-pentamethylcyclopentadienyl)hafnium dichloride,
($\eta^5$-2-methyl-4-(4-t-butylphenyl)indenyl)($\eta^5$-pentamethylcyclopentadienyl)hafnium dichloride,
($\eta^5$-2-methyl-4-(4-fluorophenyl)indenyl)(5-pentamethylcyclopentadienyl)hafnium dichloride,
($\eta^5$-2-methyl-4-(3-trifluoromethylphenyl)indenyl)($\eta^5$-pentamethylcyclopentadienyl)hafnium dichloride,
($\eta^5$-2-methyl-4-(2-methoxyphenyl)indenyl)($\eta^5$-pentamethylcyclopentadienyl)hafnium dichloride,
($\eta^5$-2-methyl-4-(4-biphenyl)bromoindenyl)($\eta^5$-pentamethylcyclopentadienyl)hafnium dichloride,
($\eta^5$-2-methyl-4-(1-naphthyl)indenyl)($\eta^5$-pentamethylcyclopentadienyl)hafnium dichloride,
($\eta^5$-2-methyl-4-(2-thienyl)indenyl)($\eta^5$-pentamethylcyclopentadienyl)hafnium dichloride,
($\eta^5$-2-methyl-4-(2-benzothienyl)indenyl)($\eta^5$-pentamethylcyclopentadienyl)hafnium dichloride,
($\eta^5$-2-methyl-4-(2-furyl)indenyl)($\eta^5$-pentamethylcyclopentadienyl)hafnium dichloride,
($\eta^5$-2-methyl-4-(2-benzofuryl)indenyl)($\eta^5$-pentamethylcyclopentadienyl)hafnium dichloride,
($\eta^5$-2-methyl-4-styrylindenyl)($\eta^5$-pentamethylcyclopentadienyl)hafnium dichloride (cis and trans),
($\eta^5$-2-methyl-4-(4-fluorostyryl)indenyl)($\eta^5$-pentamethylcyclopentadienyl)hafnium dichloride (trans), and
($\eta^5$-2-methyl-4-(1,2-butoxyvinyl)indenyl)($\eta^5$-pentamethylcyclopentadienyl)hafnium dichloride.

Additional preferred compounds include:
($\eta^5$-2,4-dimethylindenyl)($\eta^5$-pentamethylcyclopentadienyl)hafnium dichloride,
($\eta^5$-2-methyl-4-(p-tolyl)indenyl)($\eta^5$-pentamethylcyclopentadienyl)hafnium dichloride,
($\eta^5$-2-methyl-4-(m-tolyl)indenyl)($\eta^5$-pentamethylcyclopentadienyl)hafnium dichloride,
($\eta^5$-2-methyl-4-(4-t-butylphenyl)indenyl)($\eta^5$-pentamethylcyclopentadienyl)hafnium dichloride, and
($\eta^5$-2-methyl-4-phenylindenyl)($\eta^5$-pentamethylcyclopentadienyl)hafnium dichloride.

Further preferred compounds include:
($\eta^5$-4,7-di-(3-trifluoromethylphenyl)inden-1-yl)($\eta^5$-pentamethylcyclopentadienyl)zirconium dichloride
($\eta^5$-4-(4-dimethylaminophenyl)-6-chloroindenyl)($\eta^5$-pentamethylcyclopentadienyl)zirconium dichloride,
($\eta^5$-4,7-di-(3-trifluoromethylphenyl)inden-1-yl)($\eta^5$-pentamethylcyclopentadienyl)hafnium dichloride, and
($\eta^5$-4-(4-dimethylaminophenyl)-6-chloroindenyl)($\eta^5$-pentamethylcyclopentadienyl)hafnium dichloride.

Additional preferred compounds include:
($\eta^5$-2,4-dimethylindenyl)($\eta^5$-cyclopentadienyl)zirconium dichloride,
($\eta^5$-2-methyl-4-phenylindenyl)($\eta^5$-cyclopentadienyl)zirconium dichloride,
($\eta^5$-2-methyl-4-(p-tolyl)indenyl)($\eta^5$-cyclopentadienyl)zirconium dichloride,
($\eta^5$-2-methyl-4-(m-tolyl)indenyl)($\eta^5$-cyclopentadienyl)zirconium dichloride,
($\eta^5$-2,4-dimethylindenyl)($\eta^5$-cyclopentadienyl)hafnium dichloride,
($\eta^5$-2-methyl-4-phenylindenyl)($\eta^5$-cyclopentadienyl)hafnium dichloride,
($\eta^5$-2-methyl-4-(p-tolyl)indenyl)($\eta^5$-cyclopentadienyl)hafnium dichloride, and
($\eta^5$-2-methyl-4-(m-tolyl)indenyl)($\eta^5$-cyclopentadienyl)hafnium dichloride.

Additional preferred compounds include:
d-/l-bis($\eta^5$-2-methyl-4-(4-t-butylphenyl)indenyl)zirconium dichloride,
meso-bis($\eta^5$-2-methyl-4-(4-t-butylphenyl)indenyl)zirconium dichloride,
d-/l-bis($\eta^5$-2-methyl-4-(4-t-butylphenyl)indenyl)hafnium dichloride, and
meso-bis($\eta^5$-2-methyl-4-(4-t-butylphenyl)indenyl)hafnium dichloride.

Additional preferred compounds include:
($\eta^5$-3,5-dimethylcyclopenta[b]thienyl)($\eta^5$-pentamethylcyclopentadienyl)zirconium dichloride,
($\eta^5$-3-phenyl-5-methylcyclopenta[b]thienyl)($\eta^5$-pentamethylcyclopentadienyl)zirconium dichloride,
($\eta^5$-3-p-tolyl)-5-methylcyclopenta[b]thienyl)($\eta^5$-pentamethylcyclopentadienyl)zirconium dichloride,
($\eta^5$-3-(m-tolyl)-5-methylcyclopenta[b]thienyl)($\eta^5$-pentamethylcyclopentadienyl)zirconium dichloride,
($\eta^5$-3-(4-t-butylphenyl)-5-methylcyclopenta[b]thienyl)($\eta^5$-pentamethylcyclopentadienyl)zirconium dichloride,
($\eta^5$-3,5-dimethylcyclopenta[b]thienyl)($\eta^5$-pentamethylcyclopentadienyl)hafnium dichloride,
($\eta^5$-3-phenyl-5-methylcyclopenta[b]thienyl)($\eta^5$-pentamethylcyclopentadienyl)hafnium dichloride,
($\eta^5$-3-p-tolyl)-5-methylcyclopenta[b]thienyl)($\eta^5$-pentamethylcyclopentadienyl)hafnium dichloride,
($\eta^5$-3-(m-tolyl)-5-methylcyclopenta[b]thienyl)($\eta^5$-pentamethylcyclopentadienyl)hafnium dichloride, and
($\eta^5$-3-(4-t-butylphenyl)-5-methylcyclopenta[b]thienyl)($\eta^5$-pentamethylcyclopentadienyl)hafnium dichloride.
Additional preferred compounds include:
d-/l-bis($\eta^5$-2-methyl-4-(p-tolyl)indenyl)zirconium dichloride,
meso-bis($\eta^5$-2-methyl-4-(p-tolyl)indenyl)zirconium dichloride,
d-/l-bis($\eta^5$-3,5-dimethylcyclopenta[b]thienyl)zirconium dichloride,
meso-bis($\eta^5$-3,5-dimethylcyclopenta[b]thienyl)zirconium dichloride,
d-/l-bis($\eta^5$-3-phenyl-5-methylcyclopenta[b]thienyl)zirconium dichloride,
meso-bis($\eta^5$-3-phenyl-5-methylcyclopenta[b]thienyl)zirconium dichloride,
d-/l-bis($\eta^5$-3-(p-tolyl)-5-methylcyclopenta[b]thienyl)zirconium dichloride,
meso-bis($\eta^5$-3-(p-tolyl)-5-methylcyclopenta[b]thienyl)zirconium dichloride,
d-/l-bis($\eta^5$-3-(m-tolyl)-5-methylcyclopenta[b]thienyl)zirconium dichloride,
meso-bis($\eta^5$-3-(m-tolyl)-5-methylcyclopenta[b]thienyl)zirconium dichloride,
d-/l-bis($\eta^5$-3-(4-t-butylphenyl)-5-methylcyclopenta[b]thienyl)zirconium dichloride,
meso-bis($\eta^5$-3-(4-t-butylphenyl)-5-methylcyclopenta[b]thienyl)zirconium dichloride,
d-/l-bis($\eta^5$-2-methyl-4-(p-tolyl)indenyl)hafnium dichloride,
meso-bis($\eta^5$-2-methyl-4-(p-tolyl)indenyl)hafnium dichloride,
d-/l-bis($\eta^5$-3,5-dimethylcyclopenta[b]thienyl)hafnium dichloride,
meso-bis($\eta^5$-3,5-dimethylcyclopenta[b]thienyl)hafnium dichloride,
d-/l-bis($\eta^5$-3-phenyl-5-methylcyclopenta[b]thienyl)hafnium dichloride,
meso-bis($\eta^5$-3-phenyl-5-methylcyclopenta[b]thienyl)hafnium dichloride,
d-/l-bis($\eta^5$-3-p-tolyl)-5-methylcyclopenta[b]thienyl)hafnium dichloride,
meso-bis($\eta^5$-3-(p-tolyl)-5-methylcyclopenta[b]thienyl)hafnium dichloride,
d-/l-bis($\eta^5$-3-(m-tolyl)-5-methylcyclopenta[b]thienyl)hafnium dichloride,
meso-bis($\eta^5$-3-(m-tolyl)-5-methylcyclopenta[b]thienyl)hafnium dichloride,
d-/l-bis($\eta^5$-3-(4-t-butylphenyl)-5-methylcyclopenta[b]thienyl)hafnium dichloride, and
meso-bis($\eta^5$-3-(4-t-butylphenyl)-5-methylcyclopenta[b]thienyl)hafnium dichloride.
Additional preferred compounds include:
rac-dimethylsilyl-bis($\eta^5$-4-(4-fluorophenyl)-2-methylinden-1-yl)zirconium dichloride,
rac-dimethylsilyl-bis($\eta^5$-4-(3-trimethylforophenyl)-2-methylinden-1-yl)zirconium dichloride,
rac-dimethylsilyl-bis($\eta^5$-4-(5-methyl-2-thienyl)-2-methylinden-1-yl)zirconium dichloride,
rac-dimethylsilyl-bis($\eta^5$-4-(5-methyl-2-furyl)-2-methylinden-1-yl)zirconium dichloride,
rac-dimethylsilyl-bis($\eta^5$-4-(2-benzothienyl)-2-methylinden-1-yl)zirconium dichloride,
rac-dimethylsilyl-bis($\eta^5$-4-(2-benzofuryl)-2-methylinden-1-yl)zirconium dichloride,
rac-dimethylsilyl-bis($\eta^5$-4-(2-methoxyphenyl)-2-methylinden-1-yl)zirconium dichloride,
rac-dimethylsilyl-bis($\eta^5$-4-(2-trifluoromethylphenyl)-2-methylinden-1-yl)zirconium dichloride,
rac-dimethylsilyl-bis($\eta^5$-4-(2-methylbenzothienyl)-2-methylinden-1-yl)zirconium dichloride,
rac-dimethylsilyl-bis($\eta^5$-4-(2,4-ditrifluoromethylphenyl)-2-methylinden-1-yl)zirconium dichloride,
rac-dimethylsilyl-bis($\eta^5$-4-(4-fluorophenyl)-2-methylinden-1-yl)hafnium dichloride,
rac-dimethylsilyl-bis($\eta^5$-4-(3-trimethylfuorophenyl)-2-methylinden-1-yl)hafnium dichloride,
rac-dimethylsilyl-bis($\eta^5$-4-(5-methyl-2-thienyl)-2-methylinden-1-yl)hafnium dichloride,
rac-dimethylsilyl-bis($\eta^5$-4-(5-methyl-2-furyl)-2-methylinden-1-yl)hafnium dichloride,
rac-dimethylsilyl-bis($\eta^5$-4-(2-benzothienyl)-2-methylinden-1-yl)hafnium dichloride,
rac-dimethylsilyl-bis($\eta^5$-4-(2-benzofuryl)-2-methylinden-1-yl)hafnium dichloride,
rac-dimethylsilyl-bis($\eta^5$-4-(2-methoxyphenyl)-2-methylinden-1-yl)hafnium dichloride,
rac-dimethylsilyl-bis($\eta^5$-4-(2-trifluoromethylphenyl)-2-methylinden-1-yl)hafnium dichloride,
rac-dimethylsilyl-bis($\eta^5$-4-(2-methylbenzothienyl)-2-methylinden-1-yl)hafnium dichloride, and
rac-dimethylsilyl-bis($\eta^5$-4-(2,4-ditrifluoromethylphenyl)-2-methylinden-1-yl)hafnium dichloride.
Additional preferred compounds include:
rac-dimethylsilyl-bis($\eta^5$-4-(4-biphenyl)-2,5-dimethylinden-1-yl)zirconium dichloride,
rac-dimethylsilyl-bis($\eta^5$-4-(p-tolyl)-2,5-dimethylinden-1-yl)zirconium dichloride,
rac-dimethylsilyl-bis($\eta^5$-4-(2-benzofuryl)-2,5-dimethylinden-1-yl)zirconium dichloride,
rac-dimethylsilyl-bis($\eta^5$-4-(2-benzothienyl)-2,5-dimethylinden-1-yl)zirconium dichloride,
rac-dimethylsilyl-bis($\eta^5$-4-(2-trifluoromethylphenyl)-2,5-dimethylinden-1-yl)zirconium dichloride,
rac-dimethylsilyl-bis($\eta^5$-4-(4-fluorophenyl)-2,5-dimethylinden-1-yl)zirconium dichloride,
rac-dimethylsilyl-bis($\eta^5$-4-(3-trifluoromethylphenyl)-2,5-dimethylinden-1-yl)zirconium dichloride,
rac-dimethylsilyl-bis($\eta^5$-4-(4-biphenyl)-2,5-dimethylinden-1-yl)hafnium dichloride,
rac-dimethylsilyl-bis($\eta^5$-4-(p-tolyl)-2,5-dimethylinden-1-yl)hafnium dichloride,
rac-dimethylsilyl-bis($\eta^5$-4-(2-benzofuryl)-2,5-dimethylinden-1-yl)hafnium dichloride,
rac-dimethylsilyl-bis($\eta^5$-4-(2-benzothienyl)-2,5-dimethylinden-1-yl)hafnium dichloride, rac-dimethylsilyl-bis($\eta^5$-4-(2-trifluoromethylphenyl)-2,5-dimethylinden-1-yl)hafnium dichloride,
rac-dimethylsilyl-bis($\eta^5$-4-(4-fluorophenyl)-2,5-dimethyl-inden-1-yl)hafnium dichloride, and
rac-dimethylsilyl-bis($\eta^5$-4-(3-trifluoromethylphenyl)-2,5-dimethylinden-1-yl)hafnium dichloride.
Additional preferred compounds include:
rac-dimethylsilyl-bis($\eta^5$-4-(4-fluorophenyl)-2,6-dimethyl-inden-1-yl)zirconium dichloride,
rac-dimethylsilyl-bis($\eta^5$-4-(3-trifluoromethylphenyl)-2,6-dimethylinden-1-yl)zirconium dichloride,
rac-dimethylsilyl-bis($\eta^5$-4-(p-tolyl)-2,6-dimethylinden-1-yl)zirconium dichloride,
rac-dimethylsilyl-bis($\eta^5$-4-(2-trifluoromethylphenyl)-2,6-dimethylinden-1-yl)zirconium dichloride,
rac-dimethylsilyl-bis($\eta^5$-4-(2,4-ditrifluoromethylphenyl)-2,6-dimethylinden-1-yl)zirconium dichloride,
rac-dimethylsilyl-bis($\eta^5$-4-(4-fluorophenyl)-2,6-dimethyl-inden-1-yl)hafnium dichloride,
rac-dimethylsilyl-bis($\eta^5$-4-(3-trifluoromethylphenyl)-2,6-dimethylinden-1-yl)hafnium dichloride,
rac-dimethylsilyl-bis($\eta^5$-4-(p-tolyl)-2,6-dimethylinden-1-yl)hafnium dichloride,
rac-dimethylsilyl-bis($\eta^5$-4-(2-trifluoromethylphenyl)-2,6-dimethylinden-1-yl)hafnium dichloride, and
rac-dimethylsilyl-bis($\eta^5$-4-(2,4-ditrifluoromethylphenyl)-2,6-dimethylinden-1-yl)hafnium dichloride.
Additional preferred compounds include:
rac-diethylsilyl-bis($\eta^5$-4-(4-fluorophenyl)-2-methylinden-1-yl)zirconium dichloride,
rac-diethylsilyl-bis($\eta^5$-4-(2-trifluoromethylphenyl)-2-methylinden-1-yl)zirconium dichloride,
rac-diethylsilyl-bis($\eta^5$-4-p-tolyl)-2-methylinden-1-yl)zirconium dichloride,
rac-diethylsilyl-bis($\eta^5$-4-(4-fluorophenyl)-2-methylinden-1-yl)hafnium dichloride,
rac-diethylsilyl-bis($\eta^5$-4-(2-trifluoromethylphenyl)-2-methylinden-1-yl)hafnium dichloride, and
rac-diethylsilyl-bis($\eta^5$-4-(p-tolyl)-2-methylinden-1-yl)hafnium dichloride.
Additional preferred compounds include:
isopropylidene-($\eta^5$-4-(2-trifluoromethylphenyl)-3-methyl-inden-1-yl)($\eta^5$-cyclopentadienyl)zirconium dichloride,
isopropylidene-($\eta^5$-4-(4-dimethylaminophenyl)-3-methyl-inden-1-yl)($\eta^5$-cyclopentadienyl)zirconium dichloride,
isopropylidene-($\eta^5$-4-(4-fluorophenyl)-3-methylinden-1-yl)($\eta^5$-cyclopentadienyl)zirconium dichloride,
isopropylidene-($\eta^5$-4-(3-trifluoromethylphenyl)-3-methyl-inden-1-yl)($\eta^5$-cyclopentadienyl)zirconium dichloride,
isopropylidene-($\eta^5$-4-(2,4-ditrifluoromethylphenyl)-3-methylinden-1-yl)($\eta^5$-cyclopentadienyl)zirconium dichloride,
isopropylidene-($\eta^5$-4-(2-trifluoromethylphenyl)-3-methyl-inden-1-yl)($\eta^5$-cyclopentadienyl)hafnium dichloride,
isopropylidene-($\eta^5$-4-(4-dimethylaminophenyl)-3-methyl-inden-1-yl)($\eta^5$-cyclopentadienyl)hafnium dichloride,
isopropylidene-($\eta^5$-4-(4-fluorophenyl)-3-methylinden 1-yl)($\eta^5$-cyclopentadienyl)hafnium dichloride,
isopropylidene-($\eta^5$-4-(3-trifluoromethylphenyl)-3-methyl-inden-1-yl)($\eta^5$-cyclopentadienyl)hafnium dichloride, and
isopropylidene-($\eta^5$-4-(2,4-ditrifluoromethylphenyl)-3-methylinden-1-yl)($\eta^5$-cyclopentadienyl)hafnium dichloride.
Additional preferred compounds include:
isopropylidene-($\eta^5$-2,7-di-(4-fluorophenyl)fluoren-9-yl)($\eta^5$-cyclopentadienyl)zirconium dichloride, and
isopropylidene-($\eta^5$-2,7-di-(4-fluorophenyl)fluoren-9-yl)($\eta^5$-cyclopentadienyl)hafnium dichloride.
Additional preferred compounds include:
rac-dimethylsilyl-bis($\eta^5$-3-phenyl-5-methylcyclopenta[b]thien-6-yl)zirconium dichloride,
rac-dimethylsilyl-bis($\eta^5$-3-(p-tolyl)-5-methylcyclopenta[b]thien-6-yl)zirconium dichloride,
rac-dimethylsilyl-bis($\eta^5$-3-(m-tolyl)-5-methylcyclopenta[b]thien-6-yl)zirconium dichloride,
rac-dimethylsilyl-bis($\eta^5$-3-(4-t-butylphenyl)-5-methylcyclopenta[b]thien-6-yl)zirconium dichloride,
rac-dimethylsilyl-bis($\eta^5$-3-phenyl-5-methylcyclopenta[b]thien-6-yl)hafnium dichloride,
rac-dimethylsilyl-bis($\eta^5$-3-(p-tolyl)-5-methylcyclopenta[b]thien-6-yl)hafnium dichloride,
rac-dimethylsilyl-bis($\eta^5$-3-(m-tolyl)-5-methylcyclopenta[b]thien-6-yl)hafnium dichloride, and
rac-dimethylsilyl-bis($\eta^5$-3-(4-t-butylphenyl)-5-methylcyclopenta[b]thien-6-yl)hafnium dichloride.
Additional preferred compounds include:
rac-dimethylsilyl-bis($\eta^5$-3-(p-tolyl)-2,5-dimethylcyclopenta[b]thien-6-yl)zirconium dichloride,
rac-dimethylsilyl-bis($\eta^5$-3-(m-tolyl)-2,5-dimethylcyclopenta[b]thien-6-yl)zirconium dichloride,
rac-dimethylsilyl-bis($\eta^5$-3-(4-fluorophenyl)-2,5-dimethyl-cyclopenta[b]thien-6-yl)zirconium dichloride,
rac-dimethylsilyl-bis($\eta^5$-3-(3-trifluoromethylphenyl)-2,5-dimethylcyclopenta[b]thien-6-yl)zirconium dichloride,
rac-dimethylsilyl-bis($\eta^5$-3-(4-dimethylaminophenyl)-2,5-dimethylcyclopenta[b]thien-6-yl)zirconium dichloride,
rac-dimethylsilyl-bis($\eta^5$-3-p-tolyl)-2,5-dimethylcyclopenta[b]thien-6-yl)hafnium dichloride,
rac-dimethylsilyl-bis($\eta^5$-3-(m-tolyl)-2,5-dimethylcyclopenta[b]thien-6-yl)hafnium dichloride,
rac-dimethylsilyl-bis($\eta^5$-3-(4-fluorophenyl)-2,5-dimethyl-cyclopenta[b]thien-6-yl)hafnium dichloride,
rac-dimethylsilyl-bis($\eta^5$-3-(3-trifluoromethylphenyl)-2,5-dimethylcyclopenta[b]thien-6-yl)hafnium dichloride, and
rac-dimethylsilyl-bis($\eta^5$-3-(4-dimethylaminophenyl)-2,5-dimethylcyclopenta[b]thien-6-yl)hafnium dichloride.
Additional preferred compounds include:
dimethylsilyl($\eta^5$-2,4-dimethylinden-1-yl)-($\eta^1$-tert-butylamido)zirconium dichloride,
dimethylsilyl($\eta^5$-2-methyl-4-(p-tolyl)inden-1-yl)-($\eta^1$-tert-butylamido)zirconium dichloride,
dimethylsilyl($\eta^5$-2-methyl-4-(m-tolyl)inden-1-yl)-($\eta^1$-tert-butylamido)zirconium dichloride,
dimethylsilyl($\eta^5$-2-methyl-4-(o-tolyl)inden-1-yl)-($\eta^1$-tert-butylamido)zirconium dichloride,
dimethylsilyl($\eta^5$-2-methyl-4-mesitylinden-1-yl)-($\eta^1$-tert-butylamido)zirconium dichloride,
dimethylsilyl($\eta^5$-2-methyl-4-(2,5-dimethylphenyl)inden-1-yl)-($\eta^1$-tert-butylamido)zirconium dichloride,
dimethylsilyl($\eta^5$-2-methyl-4-(4-fluorophenyl)inden-1-yl)-($\eta^1$-tert-butylamido)zirconium dichloride,
dimethylsilyl($\eta^5$-2-methyl-4-(3-trifluoromethylphenyl)inden-1-yl)-($\eta^1$-tert-butylamido)zirconium dichloride,
dimethylsilyl($\eta^5$-2-methyl-4-(4-biphenyl)inden-1-yl)-($\eta^1$-tert-butylamido)zirconium dichloride,
dimethylsilyl($\eta^5$-2,4-dimethylinden-1-yl)-($\eta^1$-tert-butylamido)hafnium dichloride,
dimethylsilyl($\eta^5$-2-methyl-4-(p-tolyl)inden-1-yl)-($\eta^1$-tert-butylamido)hafnium dichloride,
dimethylsilyl($\eta^5$-2-methyl-4-(m-tolyl)inden-1-yl)-($\eta^1$-tert-butylamido)hafnium dichloride,
dimethylsilyl($\eta^5$-2-methyl-4-(o-tolyl)inden-1-yl)-($\eta^1$-tert-butylamido)hafnium dichloride,
dimethylsilyl($\eta^5$-2-methyl-4-mesitylinden-1-yl)-($\eta^1$-tert-butylamido)hafnium dichloride, dimethylsilyl($\eta^5$-2-methyl-4-(2,5-dimethylphenyl)inden-1-yl)-($\eta^1$-tert-butylamido)hafnium dichloride,
dimethylsilyl($\eta^5$-2-methyl-4-(4-fluorophenyl)inden-1-yl)-($\eta^1$-tert-butylamido)hafnium dichloride,
dimethylsilyl($\eta^5$-2-methyl-4-(3-trifluoromethylphenyl)inden-1-yl)-($\eta^1$-tert-butylamido)hafnium dichloride,
dimethylsilyl($\eta^5$-2-methyl-4-(4-biphenyl)inden-1-yl)-($\eta^1$-tert-butylamido)hafnium dichloride,
dimethylsilyl($\eta^5$-2,4-dimethylinden-1-yl)-($\eta^1$-tert-butylamido)titanium dichloride,
dimethylsilyl($\eta^5$-2-methyl-4-(p-tolyl)inden-1-yl)-($\eta^1$-tert-butylamido)titanium dichloride,
dimethylsilyl($\eta^5$-2-methyl-4-(m-tolyl)inden-1-yl)-($\eta^7$-tert-butylamido)titanium dichloride,
dimethylsilyl($\eta^5$-2-methyl-4-(o-tolyl)inden-1-yl)-($\eta^7$-tert-butylamido)titanium dichloride,
dimethylsilyl($\eta^5$-2-methyl-4-mesitylinden-1-yl)-($\eta^7$-tert-butylamido)titanium dichloride,
dimethylsilyl($\eta^5$-2-methyl-4-(2,5-dimethylphenyl)inden-1-yl)-($\eta^5$-tert-butylamido)titanium dichloride,
dimethylsilyl($\eta^5$-2-methyl-4-(4-fluorophenyl)inden-1-yl)-($\eta^1$-tert-butylamido)titanium dichloride,
dimethylsilyl($\eta^5$-2-methyl-4-(3-trifluoromethylphenyl)inden-1-yl)-($\eta^1$-tert-butylamido)titanium dichloride, and
dimethylsilyl($\eta^2$-methyl-4-(4-biphenyl)inden-1-yl)-($\eta^7$-tert-butylamido)titanium dichloride.
Additional preferred compounds include:
dimethylsilyl($\eta^5$-2-methyl-4-(4-dimethylaminophenyl)inden-1-yl)-($\eta^1$-tert-butylamido)zirconium dichloride,
dimethylsilyl($\eta^5$-2-methyl-4-(2-methoxyphenyl)inden-1-yl)-($\eta^7$-tert-butylamido)zirconium dichloride,
dimethylsilyl($\eta^5$-2-methyl-4-(3-methoxy-2-methyl-2,3-dihydro-1H-inden-4-yl)inden-1-yl)-($\eta^1$-tert-butylamido)zirconium dichloride,
dimethylsilyl($\eta^5$-2-methyl-4-(5-methyl-2-furyl)inden-1-yl)-($\eta^1$-tert-butylamido)zirconium dichloride,
dimethylsilyl($\eta^5$-2-methyl-4-(5-methyl-2-thienyl)inden-1-yl)-($\eta^1$-tert-butylamido)zirconium dichloride,
dimethylsilyl($\eta^5$-2-methyl-4-(2-benzothienyl)inden-1-yl)-($\eta^1$-tert-butylamido)zirconium dichloride,
dimethylsilyl($\eta^5$-2-methyl-4-(2-benzofuryl)inden-1-yl)-($\eta^1$-tert-butylamido)zirconium dichloride,
dimethylsilyl($\eta^5$-2-methyl-4-(4-dimethylaminophenyl)inden-1-yl)-($\eta^1$-tert-butylamido)hafnium dichloride,
dimethylsilyl($\eta^5$-2-methyl-4-(2-methoxyphenyl)inden-1-yl)-($\eta^1$-tert-butylamido)hafnium dichloride,
dimethylsilyl($\eta^5$-2-methyl-4-(3-methoxy-2-methyl-2,3-dihydro-1H-inden-4-yl)inden-1-yl)-($\eta^1$-tert-butylamido)hafnium dichloride,
dimethylsilyl($\eta^5$-2-methyl-4-(5-methyl-2-fuiryl)inden-1-yl)-($\eta^1$-tert-butylamido)zirconium dichloride,
dimethylsilyl($\eta^5$-2-methyl-4-(5-methyl-2-thienyl)inden-1-yl)-($\eta^1$-tert-butylamido)hafnium dichloride,
dimethylsilyl($\eta^5$-2-methyl-4-(2-benzothienyl)inden-1-yl)-($\eta^1$-tert-butylamido)hafnium dichloride,
dimethylsilyl($\eta^5$-2-methyl-4-(2-benzofuryl)inden-1-yl)-($\eta^1$-tert-butylamido)hafnium dichloride,
dimethylsilyl($\eta^5$-2-methyl-4-(4-dimethylaminophenyl)inden-1-yl)-($\eta^1$-tert-butylamido)titanium dichloride,
dimethylsilyl($\eta^5$-2-methyl-4-(2-methoxyphenyl)inden-1-yl)-($\eta^1$-tert-butylamido)titanium dichloride,
dimethylsilyl($\eta^5$-2-methyl-4-(3-methoxy-2-methyl-2,3-dihydro-1H-inden-4-yl)inden-1-yl)-($\eta^1$-tert-butylamido)titanium dichloride,
dimethylsilyl($\eta^5$-2-methyl-4-(5-methyl-2-furyl)inden-1-yl)-($\eta^1$-tert-butylamido)titanium dichloride,
dimethylsilyl($\eta^5$-2-methyl-4-(5-methyl-2-thienyl)inden-1-yl)-($\eta^1$-tert-butylamido)titanium dichloride,
dimethylsilyl($\eta^5$-2-methyl-4-(2-benzothienyl)inden-1-yl)-($\eta^1$-tert-butylamido)titanium dichloride, and
dimethylsilyl($\eta^5$-2-methyl-4-(2-benzofuryl)inden-1-yl)-($\eta^1$-tert-butylamido)titanium dichloride.
Additional preferred compounds include:
dimethylsilyl($\eta^5$-tetramethylcyclopentadienyl)($\eta^1$-4-methyl-2,6-diisopropylphenylamido)zirconium dichloride,
dimethylsilyl($\eta^5$-tetramethylcyclopentadienyl)($\eta^1$-4-(p-tolyl)-2,6-diisopropylphenylamido)zirconium dichloride,
dimethylsilyl($\eta^5$-tetramethylcyclopentadienyl)($\eta^1$-4-(p-tolyl)-2,6-dimethylphenylamido)zirconium dichloride,
dimethylsilyl($\eta^5$-tetramethylcyclopentadienyl)($\eta^{1'}$-2,4,6-trimethylphenylamido)zirconium dichloride,
dimethylsilyl($\eta^5$-tetramethylcyclopentadienyl)($\eta^{1'}$-4-methyl-2,6-diisopropylphenylamido)hafnium dichloride,
dimethylsilyl($\eta^5$-tetramethylcyclopentadienyl)($\eta^1$-4-(p-tolyl)-2,6-diisopropylphenylamido)hafnium dichloride,
dimethylsilyl($\eta^5$-tetramethylcyclopentadienyl)($\eta^1$-4-(p-tolyl)-2,6-dimethylphenylamido)hafnium dichloride,
dimethylsilyl($\eta^5$-tetramethylcyclopentadienyl)($\eta^1$-2,4,6-trimethylphenylamido)hafnium dichloride,
dimethylsilyl($\eta^5$-tetramethylcyclopentadienyl)($\eta^1$-4-methyl-2,6-diisopropylphenylamido)titanium dichloride,
dimethylsilyl($\eta^5$-tetramethylcyclopentadienyl)($\eta^1$-4-(p-tolyl)-2,6-diisopropylphenylamido)titanium dichloride,
dimethylsilyl($\eta^5$-tetramethylcyclopentadienyl)($\eta^1$-4-(p-tolyl)-2,6-dimethylphenylamido)titanium dichloride, and
dimethylsilyl($\eta^5$-tetramethylcyclopentadienyl)($\eta^1$-2,4,6-trimethylphenylamido)titanium dichloride.
Additional preferred compounds include:
dimethylsilyl($\eta^5$-tetramethylcyclopentadienyl)($\eta^1$-4-(p-tolyl)phenylamido)zirconium dichloride,
dimethylsilyl($\eta^5$-tetramethylcyclopentadienyl)($\eta^1$-4-(4-biphenyl)phenylamido)zirconium dichloride,
dimethylsilyl($\eta^5$-tetramethylcyclopentadienyl)($\eta^1$-4-(4-dimethylaminophenyl)phenylamido)zirconium dichloride,
dimethylsilyl($\eta^5$-tetramethylcyclopentadienyl)($\eta^1$-4-(4-methoxyphenyl)phenylamido)zirconium dichloride,
dimethylsilyl($\eta^5$-tetramethylcyclopentadienyl)($\eta^1$-4-(3-trifluoromethylphenyl)phenylamido)zirconium dichloride,
dimethylsilyl($\eta^5$-tetramethylcyclopentadienyl)($\eta^1$-4-(4-fluorophenyl)phenylamido)zirconium dichloride,
dimethylsilyl($\eta^5$-tetramethylcyclopentadienyl)($\eta^1$-4-mesitylphenylamido)zirconium dichloride,
dimethylsilyl($\eta^5$-tetramethylcyclopentadienyl)($\eta^1$-4-(p-tolyl)phenylamido)hafnium dichloride,
dimethylsilyl($\eta^5$-tetramethylcyclopentadienyl)($\eta^1$-4-(4-biphenyl)phenylamido)hafnium dichloride,
dimethylsilyl($\eta^5$-tetramethylcyclopentadienyl)($\eta^{1'}$-4-(4-dimethylaminophenyl)phenylamido)hafnium dichloride,
dimethylsilyl($\eta^5$-tetramethylcyclopentadienyl)($\eta^{1'}$-4-(4-methoxyphenyl)phenylamido)hafnium dichloride,
dimethylsilyl($\eta^5$-tetramethylcyclopentadienyl)($\eta^1$-4-(3-trifluoromethylphenyl)phenylamido)hafnium dichloride,
dimethylsilyl($\eta^5$-tetramethylcyclopentadienyl)($\eta^1$-4-(4-fluorophenyl)phenylamido)hafnium dichloride,
dimethylsilyl($\eta^5$-tetramethylcyclopentadienyl)($\eta^1$-4-mesitylphenylamido)hafnium dichloride,
dimethylsilyl($\eta^5$tetramethylcyclopentadienyl)($\eta^1$-4-(p-tolyl)phenylamido)titanium dichloride,
dimethylsilyl($\eta^5$-tetramethylcyclopentadienyl)($\eta^1$-4-(4-biphenyl)phenylamido)titanium dichloride,
dimethylsilyl($\eta^5$-tetramethylcyclopentadienyl)($\eta^1$-4-(4-dimethylaminophenyl)phenylamido)titanium dichloride, dimethylsilyl($\eta^5$-tetramethylcyclopentadienyl)($\eta^1$-4-(4-methoxyphenyl)phenylamido)titanium dichloride,
dimethylsilyl($\eta^5$-tetramethylcyclopentadienyl)($\eta^1$-4-(3-trifluoromethylphenyl)phenylamido)titanium dichloride,
dimethylsilyl($\eta^5$-tetramethylcyclopentadienyl)($\eta^1$-4-(4-fluorophenyl)phenylamido)titanium dichloride, and
dimethylsilyl($\eta^5$-tetramethylcyclopentadienyl)($\eta^1$-4-mesitylphenylamido)titanium dichloride.

Additional preferred compounds include:
dimethylsilyl($\eta^5$-4,5-dimethylcyclopenta[b]thien-6-yl)($\eta^1$-4-(P-tolyl)-2,6-dimethylphenylamido)titanium dichloride,
dimethylsilyl($\eta^5$-4,5-dimethylcyclopenta[b]thien-6-yl)($\eta^1$-4-methyl-2,6-diisopropylphenylamido)titanium dichloride,
dimethylsilyl($\eta^5$-4,5-dimethylcyclopenta[b]thien-6-yl)($\eta^1$-4-(P-tolyl)-2,6-diisopropylphenylamido)titanium dichloride,
dimethylsilyl($\eta^5$-4,5-dimethylcyclopenta[b]thien-6-yl)($\eta^1$-4-(3-trifluoromethylphenyl)-2,6-diisopropylphenylamido)titanium dichloride,
dimethylsilyl($\eta^5$-4,5-dimethylcyclopenta[b]thien-6-yl)($\eta^1$-4-(4-dimethylaminophenyl)-2,6-diisopropylphenylamido)titanium dichloride,
dimethylsilyl($\eta^5$-4,5-dimethylcyclopenta[b]thien-6-yl)($\eta^{1'}$-4-(2-benzofuryl)-2,6-diisopropylphenylamido)titanium dichloride,
dimethylsilyl($\eta^5$-4,5-dimethylcyclopenta[b]thien-6-yl)($\eta^1$-2,4,6-trimethylphenylamido)titanium dichloride,
dimethylsilyl($\eta^5$-4,5-dimethylcyclopenta[b]thien-6-yl)($\eta^1$-4-(p-tolyl)-2,6-dimethylphenylamido)zirconium dichloride,
dimethylsilyl($\eta^5$-4,5-dimethylcyclopenta[b]thien-6-yl)($\eta^1$-4-methyl-2,6-diisopropylphenylamido)zirconium dichloride,
dimethylsilyl($\eta^5$-4,5-dimethylcyclopenta[b]thien-6-yl)($\eta^1$-4-(P-tolyl)-2,6-diisopropylphenylamido)zirconium dichloride,
dimethylsilyl($\eta^5$-4,5-dimethylcyclopenta[b]thien-6-yl)($\eta^1$-4-(3-trifluoromethylphenyl)-2,6-diisopropylphenylamido)zirconium dichloride,
dimethylsilyl($\eta^5$-4,5-dimethylcyclopenta[b]thien-6-yl)($\eta^1$-4-(4-dimethylaminophenyl)-2,6-diisopropylphenylamido)zirconium dichloride,
dimethylsilyl($\eta^5$-4,5-dimethylcyclopenta[b]thien-6-yl)($\eta^1$-4-(2-benzofuryl)-2,6-diisopropylphenylamido)zirconium dichloride,
dimethylsilyl($\eta^5$-4,5-dimethylcyclopenta[b]thien-6-yl)($\eta^1$-2,4,6-trimethylphenylamido)zirconium dichloride,
dimethylsilyl($\eta^5$-4,5-dimethylcyclopenta[b]thien-6-yl)($\eta^1$-4-p-tolyl)-2,6-dimethylphenylamido)hafnium dichloride,
dimethylsilyl($\eta^5$-4,5-dimethylcyclopenta[b]thien-6-yl)($\eta^1$-4-methyl-2,6-diisopropylphenylamido)hafnium dichloride,
dimethylsilyl($\eta^5$-4,5-dimethylcyclopenta[b]thien-6-yl)($\eta^1$-4-(p-tolyl)-2,6-diisopropylphenylamido)hafnium dichloride,
dimethylsilyl($\eta^5$-4,5-dimethylcyclopenta[b]thien-6-yl)($\eta^1$-4-(3-trifluoromethylphenyl)-2,6-diisopropylphenylamido)hafnium dichloride,
dimethylsilyl($\eta^5$-4,5-dimethylcyclopenta[b]thien-6-yl)($\eta^1$-4-(4-dimethylaminophenyl)-2,6-diisopropylphenylamido)hafnium dichloride,
dimethylsilyl ($\eta^5$-4,5-dimethylcyclopenta[b]thien-6-yl)($\eta^1$-4-(2-benzofuryl)-2,6-diisopropylphenylamido)hafnium dichloride, and
dimethylsilyl($\eta^5$-4,5-dimethylcyclopenta[b]thien-6-yl)($\eta^1$-2,4,6-trimethylphenylamido)hafnium dichloride.

In a preferred embodiment any of the catalyst precursors listed above (prepared by coupling or cross-coupling reactions) is combined with an activator to form a catalyst system. Prefereably such catalysts systems are used to polymerize olefins, such as ethylene and or propylene.

Activators and Catalyst Activation

The substituted metallocene compounds produced by the process described above are useful as catalyst precursors and, when activated with activators, such as methyl alumoxane or a non-coordinating anion, form active catalysts for the polymerization or oligomerization of olefins. Activators that may be used include alumoxanes such as methyl alumoxane, modified methyl alumoxane, ethyl alumoxane, iso-butyl alumoxane and the like; Lewis acid activators include triphenyl boron, tris-perfluorophenyl boron, tris-perfluorophenyl aluminum and the like; Ionic activators include dimethylanilinium tetrakis perfluorophenyl borate, triphenyl carbonium tetrakis perfluorophenyl borate, dimethylanilinium tetrakis perfluorophenyl aluminate, and the like.

A co-activator is a compound capable of alkylating the transition metal complex, such that when used in combination with an activator, an active catalyst is formed. Co-activators include alumoxanes such as methyl alumoxane, modified alumoxanes such as modified methyl alumoxane, and aluminum alkyls such as trimethyl aluminum, tri-isobutyl aluminum, triethyl aluminum, and tri-isopropyl aluminum. Co-activators are typically only used in combination with Lewis acid activators and ionic activators when the precatalyst is not a dihydrocarbyl or dihydride complex.

The alumoxane component useful as an activator typically is an oligomeric aluminum compound represented by the general formula ($R^x$—Al—O)$_n$, which is a cyclic compound, or $R^x(R^x$—Al—O)$_n$Al$R^x_2$, which is a linear compound. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst precursor ratio is 1:1 molar ratio.

Ionic activators (at times used in combination with a co-activator) may be used in the practice of this invention. Preferably, discrete ionic activators such as [Me$_2$PhNH][B(C$_6$F$_5$)$_4$], [Ph$_3$C][B(C$_6$F$_5$)$_4$], [Me$_2$PhNH][B((C$_6$H$_3$-3,5-(CF$_3$)$_2$))$_4$], [Ph$_3$C][B((C$_6$H$_3$-3,5-(CF$_3$)$_2$))$_4$], [NH$_4$][B(C$_6$H$_5$)$_4$] or Lewis acidic activators such as B(C$_6$F$_5$)$_3$ or B(C$_6$H$_5$)$_3$ can be used. Preferred co-activators, when used, are alumoxanes such as methyl alumoxane, modified alumoxanes such as modified methyl alumoxane, and aluminum alkyls such as tri-isobutyl aluminum, and trimethyl aluminum.

It is within the scope of this invention to use an ionizing or stoichiometric activator, neutral or ionic, such as tri (n-butyl) ammonium tetrakis (pentafluorophenyl) borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as $B(C_6F_6)_3$, which upon reaction with the hydrolyzable ligand (X') of the transition metal compound forms an anion, such as $([B(C_6F_5)_3(X')]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitrites and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

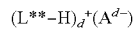

wherein L** is an neutral Lewis base;
H is hydrogen;
(L**-H)$^+$ is a Bronsted acid
A$^{d-}$ is a non-coordinating anion having the charge d−
d is an integer from 1 to 3.

The cation component, (L**-H)$_d^+$ may include Bronsted acids such as protons or protonated Lewis bases or reducible Lewis acids capable of protonating or abstracting a moiety, such as an alkyl or aryl, from the precatalyst after alkylation.

The activating cation (L-H)$_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation (L-H)$_d^+$may also be a moiety such as silver, tropylium, carbeniums, ferroceniums and mixtures, preferably carboniums and ferroceniums; most preferably triphenyl carbonium.

The anion component A$^{d-}$ include those having the formula $[M^{k+}Q_n]^{d-}$ wherein k is an integer from 1 to 3; n is an integer from 2-6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable A$^{d-}$ also include diboron compounds as disclosed in U.S. Pat. No. 5,447,895, which is fully incorporated herein by reference. [00141]Illustrative, but not limiting examples of boron compounds which may be used as an activating cocatalyst in combination with a co-activator in the preparation of the improved catalysts of this invention are tri-substituted ammonium salts such as:
trimethylammonium tetraphenylborate,
triethylammonium tetraphenylborate,
tripropylammonium tetraphenylborate,
tri(n-butyl)ammonium tetraphenylborate,
tri(tert-butyl)ammonium tetraphenylborate,
N,N-dimethylanilinium tetraphenylborate,
N,N-diethylanilinium tetraphenylborate,
N,N-dimethyl-(2,4,6-trimethylanilinium)tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate, N,N-dimethyl-(2,4,6-trimethylanilinium)tetrakis(pentafluorophenyl)borate,
trimethylammonium tetrakis-(2,3,4,6-tetrafluorophenyl)borate,
triethylammonium tetrakis-(2,3,4,6-tetrafluorophenyl)borate,
tripropylammonium tetrakis-(2,3,4,6-tetrafluorophenyl)borate,
tri(n-butyl)ammonium tetrakis-(2,3,4,6-tetrafluorophenyl)borate,
dimethyl(tert-butyl)ammonium tetrakis-(2,3,4,6-tetrafluorophenyl)borate,
N,N-dimethylanilinium tetrakis-(2,3,4,6-tetrafluorophenyl)borate,
N,N-diethylanilinium tetrakis-(2,3,4,6-tetrafluorophenyl)borate,
N,N-dimethyl-(2,4,6-trimethylanilinium)tetrakis-(2,3,4,6-tetrafluorophenyl)borate,
trimethylammonium tetrakis(perfluoronaphthyl)borate,
triethylammonium tetrakis(perfluoronaphthyl)borate,
tripropylammonium tetrakis(perfluoronaphthyl)borate,
tri(n-butyl)ammonium tetrakis(perfluoronaphthyl)borate,
tri(tert-butyl)ammonium tetrakis(perfluoronaphthyl)borate,
N,N-dimethylanilinium tetrakis(perfluoronaphthyl)borate,
N,N-diethylanilinium tetrakis(perfluoronaphthyl)borate,
N,N-dimethyl-(2,4,6-trimethylanilinium) tetrakis(perfluoronaphthyl)borate,
trimethylammonium tetrakis(perfluorobiphenyl)borate,
triethylammonium tetrakis(perfluorobiphenyl)borate,
tripropylammonium tetrakis(perfluorobiphenyl)borate,
tri(n-butyl)ammonium tetrakis(perfluorobiphenyl)borate,
tri(tert-butyl)ammonium tetrakis(perfluorobiphenyl)borate,
N,N-dimethylanilinium tetrakis(perfluorobiphenyl)borate,
N,N-diethylanilinium tetrakis(perfluorobiphenyl)borate,
N,N-dimethyl-(2,4,6-trimethylanilinium)tetrakis(perfluorobiphenyl)borate,
trimethylammonium tetrakis(3,5-bis(trifluoromethyl)phenyl)borate,
triethylammonium tetrakis(3,5-bis(trifluoromethyl)phenyl)borate,
tripropylammonium tetrakis(3,5-bis(trifluoromethyl)phenyl)borate,
tri(n-butyl)ammonium tetrakis(3,5-bis(trifluoromethyl)phenyl)borate,
tri(tert-butyl)ammonium tetrakis(3,5-bis(trifluoromethyl)phenyl)borate,
N,N-dimethylanilinium tetrakis(3,5-bis(trifluoromethyl)phenyl)borate,
N,N-diethylanilinium tetrakis(3,5-bis(trifluoromethyl)phenyl)borate,
N,N-dimethyl-(2,4,6-trimethylanilinium)tetrakis(3,5-bis(trifluoromethyl)phenyl)borate,
and dialkyl ammonium salts such as:
di-(iso-propyl)ammonium tetrakis(pentafluorophenyl)borate, and
dicyclohexylammonium tetrakis(pentafluorophenyl)borate;
and other salts such as:
tri(o-tolyl)phosphonium tetrakis(pentafluorophenyl)borate,
tri(2,6-dimethylphenyl)phosphonium tetrakis(pentafluorophenyl)borate,
tropillium tetraphenylborate,
triphenylcarbenium tetraphenylborate,
triphenylphosphonium tetraphenylborate,
triethylsilylium tetraphenylborate,
benzene(diazonium)tetraphenylborate,
tropillium tetrakis(pentafluorophenyl)borate,
triphenylcarbenium tetrakis(pentafluorophenyl)borate,
triphenylphosphonium tetrakis(pentafluorophenyl)borate,
triethylsilylium tetrakis(pentafluorophenyl)borate,
benzene(diazonium) tetrakis(pentafluorophenyl)borate,
tropillium tetrakis-(2,3,4,6-tetrafluorophenyl)borate,
triphenylcarbenium tetrakis-(2,3,4,6-tetrafluorophenyl)borate,
triphenylphosphonium tetrakis-(2,3,4,6-tetrafluorophenyl)borate,
triethylsilylium tetrakis-(2,3,4,6-tetrafluorophenyl)borate,
benzene(diazonium) tetrakis-(2,3,4,6-tetrafluorophenyl)borate,
tropillium tetrakis(perfluoronaphthyl)borate,
triphenylcarbenium tetrakis(perfluoronaphthyl)borate,
triphenylphosphonium tetrakis(perfluoronaphthyl)borate,
triethylsilylium tetrakis(perfluoronaphthyl)borate,
benzene(diazonium) tetrakis(perfluoronaphthyl)borate,
tropillium tetrakis(perfluorobiphenyl)borate,
triphenylcarbenium tetrakis(perfluorobiphenyl)borate,
triphenylphosphonium tetrakis(perfluorobiphenyl)borate,
triethylsilylium tetrakis(perfluorobiphenyl)borate,
benzene(diazonium) tetrakis(perfluorobiphenyl)borate,
tropillium tetrakis(3,5-bis(trifluoromethyl)phenyl)borate,
triphenylcarbenium tetrakis(3,5-bis(trifluoromethyl)phenyl)borate,
triphenylphosphonium tetrakis(3,5-bis(trifluoromethyl)phenyl)borate,
triethylsilylium tetrakis(3,5-bis(trifluoromethyl)phenyl)borate, and
benzene(diazonium) tetrakis(3,5-bis(trifluoromethyl)phenyl)borate.

Most preferably, the ionic stoichiometric activator (L**-H)$_d^+$ (A$^{d-}$) is N,N-dimethylanilinium tetrakis(perfluorophenyl)borate,
N,N-dimethylanilinium tetrakis(perfluoronaphthyl)borate,
N,N-dimethylanilinium tetrakis(perfluorobiphenyl)borate,
N,N-dimethylanilinium tetrakis(3,5-bis(trifluoromethyl)phenyl)borate,
triphenylcarbenium tetrakis(perfluoronaphthyl)borate,
triphenylcarbenium tetrakis(perfluorobiphenyl)borate,
triphenylcarbenium tetrakis(3,5-bis(trifluoromethyl)phenyl)borate, or
triphenylcarbenium tetra(perfluorophenyl)borate.

In a preferred embodiment, the activator is trispentafluorophenylborane.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst precursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

The present process also can employ cocatalyst compounds or activator compounds that are initially neutral Lewis acids but form a cationic metal complex and a noncoordinating anion, or a zwitterionic complex upon reaction with alkylated transition metal compounds. For example, tris (pentafluorophenyl) boron or aluminum acts to abstract a hydrocarbyl ligand to yield a cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", Chem. Rev., 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst precursor-to-activator molar ratio may be any ratio. Combinations of the described activator compounds may also be used for activation.

When an ionic or neutral stoichiometric activator is used, the catalyst precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl) boron, and mixtures of trimethyl aluminum with dimethylanilinium tetrakis(pentafluorophenyl)borate or tris (pentafluorophenyl)boron.

In some embodiments, scavenging compounds are used with stoichiometric activators. Typical aluminum or boron alkyl components useful as scavengers are represented by the general formula $R^x J''Z'''_2$ where J" is aluminum or boron, $R^x$ is as previously defined above, and each Z''' is independently $R^x$ or a different univalent anionic ligand such as halogen (Cl, Br, I), alkoxide ($OR^x$) and the like. Most preferred aluminum alkyls include triethylaluminum, diethylaluminum chloride, tri-iso-butylaluminum, tri-n-octylaluminum, tri-n-hexylaluminum, trimethylaluminum and the like. Preferred boron alkyls include triethylboron. Scavenging compounds may also be alumoxanes and modified alumoxanes including methylalumoxane and modified methylalumoxane.

Mixed Catalysts

The metallocene compounds of the invention can also be used in mixed catalyst systems where, for example, the invention catalyst is used in conjunction with a "second catalyst" in the same reactor or in a series of reactors and where the invention catalyst produces oligomers, macromers, or polymers with olefinic end-groups, and the "second catalyst" incorporates these oligomers, macromers, or polymers into a polymer backbone as a copolymer with other monomers, such as ethylene, propylene, butene, and other C2 to C20 olefins. Alternatively, the invention catalyst can be used in conjunction with a second catalyst in the same reactor or in a series of reactors where the second catalyst produces oligomers, macromers, or polymers with olefinic end-groups, and the invention catalyst incorporates these oligomers, macromers, or polymers into a polymer backbone as a copolymer with other monomers, such as ethylene, propylene, butene, and other C2 to C20 olefins. The "second catalyst" can be of the same family as the invention catalyst, or can be from a completely different catalyst family. Likewise, the invention catalyst can be used in conjunction with a "second catalyst" in the same reactor or in a series of reactors where the invention catalyst and the "second catalyst" produces mixtures or blends of polymers.

Suitable additional olefin polymerization catalysts for use as the "second catalyst" in a mixed catalyst system include any of the compositions well known in the art to catalyze the olefin to polyolefin reaction. For example, the "second catalyst" can include any Group 4-6 metallocene compound, such as the bridged and unbridged compounds containing one or two cyclopentadienyl-containing ligands. Typical catalysts and their precursors are well known in the art. Suitable description appears in the patent literature, for example U S. Pat. Nos. 4,871,705, 4,937,299, and 5,324,800, EP-A-0418044, EP-A-0591756, WO-A-92/00333 and WO-A-94/01471.

Mixed catalyst systems can also use non-cyclopentadienyl, Group 4 or 5 precursor compounds as the additional olefin polymerization catalyst. Non-cyclopentadienyl, Group 4 or 5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (II) Alkyne Derivatives", D. H. McConville, et al, Organometallics 1995, 14, 3154-3156. U.S. Pat. No. 5,318,935 describes bridged and unbridged, bis-amido catalyst compounds of Group 4 metals capable of a-olefins polymerization. Bridged bis(arylamido) Group 4 compounds for olefin polymerization are described by D. H. McConville, et al., in Organometallics 1995, 14, 5478-5480. In addition, D. H. McConville, et al, Macromolecules 1996, 29, 5241-5243, describe bridged bis(arylamido) Group 4 compounds that are polymerization catalysts for 1-hexene. Cationic Group-3- or Lanthanide olefin polymerization complexes are disclosed in U.S. Pat. No. 6,403,773.

Mixed catalyst systems can also use transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, J. Am. Chem. Soc., 1995, 117, 6414-6415, WO 96/23010 and WO 97/02298. See additionally the related bis(imino) Group 8 and 9 organometallic compounds described by V. C. Gibson and others in "Novel olefin polymerization catalysts based on iron and cobalt", Chem. Commun., 849-850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Supported Catalysts

The catalyst compounds of this invention may be placed on a support. To prepare uniform supported catalysts, the catalyst precursor is preferably dissolved in a suitable solvent and then the resultant solution is applied to or mixed with the support. The term "uniform supported catalyst" means that the catalyst precursor, the activator and or the activated catalyst approach uniform distribution upon the support's accessible surface area, including the interior pore surfaces of porous supports. Some embodiments of supported catalysts prefer uniform supported catalysts; other embodiments show no such preference.

Supported catalyst systems may be prepared by any method effective to support other coordination catalyst systems, effective meaning that the catalyst so prepared can be used for oligomerizing or polymerizing olefin in a heterogenous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100-200% of the pore volume). The mixture is optionally heated from 30-200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The catalyst precursor may also be supported absent the activator; in that case, the activator (and co-activator if needed) is added to a slurry process liquid phase. For example, a solution of catalyst precursor may be mixed with a support material for a period of about 1 minute to 10 hours. The resulting precatalyst mixture may be filtered from the solution and dried under vacuum, or evaporation alone removes the solvent. The total, catalyst-precursor-solution volume may be greater than the support's pore volume, but some embodiments limit the total solution volume below that needed to form a gel or slurry (about 90% to 400%, preferably about 100 to 200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 Jim is suitable for use in this invention.

Various embodiments select a porous support material, such as for example, talc, inorganic oxides, inorganic chlorides, for example magnesium chloride and resinous support materials such as polystyrene, polyolefin or polymeric compounds or any other organic support material and the like. Some embodiments select inorganic oxide materials as the support material including Group-2,-3,-4,-5,-13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

The catalyst supports used herein suitably have a surface area of from 10-700 $m^2/g$, a pore volume of 0.1-4.0 cc/g and an average particle size of 10-500 µm. Some embodiments select a surface area of 50-500 $m^2/g$, a pore volume of 0.5-3.5 cc/g, or an average particle size of 20-200 µm. Other embodiments select a surface area of 100-400 $m^2/g$, a pore volume of 0.8-3.0 cc/g, and an average particle size of 30-100 µm. Catalyst supports typically have a pore size of 10-1000 Angstroms, alternatively 50-500 Angstroms, or 75-350 Angstroms.

The catalyst precursors of the invention are generally deposited on a support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

Monomers

When activated with a conventional activator, the halogenated metallocene compounds of the invention can be used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1, 3-methylpentene-1,3,5,5-trimethylhexene-1, and 5-ethylnonene-1.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers can also be polymerized or oligomerized with the catalyst systems of the invention. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention include nitro substituted monomers including 6-nitro-1-hexene; amine substituted monomers including N-methylallylamine, N-allylcyclopentylamine, and N-allyl-hexylamine; ketone substituted monomers including methyl vinyl ketone, ethyl vinyl ketone, and 5-hexen-2-one; aldehyde substituted monomers including acrolein, 2,2-dimethyl-4-pentenal, undecylenic aldehyde, and 2,4-dimethyl-2,6-heptadienal; alcohol substituted monomers including allyl alcohol, 7-octen-1-ol, 7-octene-1,2-diol, 10-undecen-1-ol, 10-undecene-1,2-diol, 2-methyl-3-buten-1-ol; acetal, epoxide and or ether substituted monomers including 4-hex-5-enyl-2,2-dimethyl-[1,3]dioxolane, 2,2-dimethyl-4-non-8-enyl-[1,3]dioxolane, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, 11-methoxyundec-1-ene, and 8-methoxyoct-1-ene; sulfur containing monomers including allyl disulfide; acid and ester substituted monomers including acrylic acid, vinylacetic acid, 4-pentenoic acid, 2,2-dimethyl-4-pentenoic acid, 6-heptenoic acid, trans-2,4-pentadienoic acid, 2,6-heptadienoic acid, methyl acrylate, ethyl acrylate, tert-butyl acrylate, n-butyl acrylate, methacrylic acid, methyl methacrylate, ethyl methacrylate, tert-butyl methacrylate, n-butyl methacrylate, hydroxypropyl acrylate, acetic acid oct-7-enyl ester, non-8-enoic acid methyl ester, acetic acid undec-10-enyl ester, dodec-11-enoic acid methyl ester, propionic acid undec-10-enyl ester, dodec-11-enoic acid ethyl ester, and nonylphenoxypolyetheroxy acrylate; siloxy containing monomers including trimethyloct-7-enyloxy silane, and trimethylundec-10-enyloxy silane, polar functionalized norbornene monomers including 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo[9.5.1.1$^{3,9}$.1$^{5,15}$.1$^{7,13}$]octasiloxane, 2-benzoyl-5-norbornene, 2-acetyl-5-norbornene, 7-syn methoxymethyl-5-norbornen-2-one, 5-norbornen-2-ol, and 5-norbornen-2-yloxy-trimethylsilane, and partially fluorinated monomers including nonafluoro-1-hexene, allyl-1,1,2,2,-tetrafluoroethyl ether, 2,2,3,3-tetrafluoro-non-8-enoic acid ethyl ester, 1,1,2,2-tetrafluoro-2-(1,1,2,2-tetrafluoro-oct-7-enyloxy)-ethanesulfonyl fluoride, acrylic acid 2,2,3,3,4,4,5,5,6,6,7,7,8,8,8-pentadecafluoro-octyl ester, and 1,1,2,2-tetrafluoro-2-(1,1,2,2,3,3,4,4-octafluoro-dec-9-enyloxy)-ethanesulfonyl fluoride.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably any $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the homopolymers or copolymers described, additionally comprise one or more diolefin comonomers, preferably one or more $C_4$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methylpentene-1,3-methylpentene-1,3,5,5-trimethylhexene-1, cyclopentene, 4-methylcyclopentene, cyclohexene, and 4-methylcyclohexene.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methylpentene-1,3-methylpentene-1, and 3,5,5-trimethylhexene-1.

In a preferred embodiment, the polymer produced herein is a homopolymer of norbornene or a copolymer of norbornene and a substituted norbornene, including polar functionalized norbornenes.

In a preferred embodiment the copolymers described herein comprise at least 50 mole % of a first monomer and up to 50 mole % of other monomers.

In another embodiment, the polymer comprises:
(a) a first monomer present at from 40 to 95 mole %, preferably 50 to 90 mole %, preferably 60 to 80 mole %, and
(b) a comonomer present at from 5 to 60 mole %, preferably 10 to 40 mole %, more preferably 20 to 40 mole %, and
(c) a termonomer present at from 0 to 10 mole %, more preferably from 0.5 to 5 mole %, more preferably 1 to 3 mole %.

In a preferred embodiment the first monomer (a) comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclopentene, cyclohexene, cyclooctene, hexadiene, cyclohexadiene and the like.

In a preferred embodiment the comonomer (b) comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the termnonomer (c) comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1,3-methylpentene-1,4-methylpentene-1, cyclopentadiene, and cyclohexene.

In a preferred embodiment the monomers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Polymerization Processes

Invention catalyst complexes are useful in polymerizing unsaturated monomers conventionally known to undergo metallocene-catalyzed polymerization such as solution, slurry, gas-phase, and high-pressure polymerization. Typically one or more transition metal compounds, one or more activators, and one or more monomers are contacted to produce polymer. These catalysts may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The transition metal compound, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69-6895 kPa) and the polymerization diluent temperature will typically be between −10 and 160° C. The process can be carried out in a stirred tank reactor or a tubular reactor, or more than one reactor operated in series or in parallel. See the disclosure of U.S. Pat. No. 5,001,205 for general process conditions. All documents are incorporated by reference for description of polymerization processes, ionic activators and useful scavenging compounds.

The invention catalyst compositions can be used individually or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group 13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-phenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ where perfluorophenyl=pfp=$C_6F_5$.

In terms of polymer density, the polymers capable of production in accordance the invention, can range from about 0.85 to about 0.95, preferably from 0.87 to 0.93, more preferably 0.89 to 0.920. Polymer molecular weights can range from about 3000 Mn to about 2,000,000 Mn or greater. Molecular weight distributions can range from about 1.1 to about 50.0, with molecular weight distributions from 1.2 to about 5.0 being more typical. Pigments, antioxidants and other additives, as is known in the art, may be added to the polymer.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.).

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment when high density polyethylene is desired then the reactor temperature is typically between 70 and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr ( 45,500 Kg/hr).

Other gas phase processes contemplated by the process of the invention include those described in U.S. Pat. Nos. 5,627,242, 5,665,818 and 5,677,375, and European publications EP-A-0794 200, EP-A-0 802 202 and EP-B-634 421 all of which are herein fully incorporated by reference.

In another preferred embodiment the catalyst system is in liquid form and is introduced into the gas phase reactor into a resin particle lean zone. For information on how to introduce a liquid catalyst system into a fluidized bed polymerization into a particle lean zone, see U.S. Pat. No. 5,693,727, which is incorporated by reference herein.

Slurry Phase Polymerization

A slurry polymerization process generally operates between 1 to about 50 atmosphere pressure range (15 psig to 735 psig, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

In a further embodiment the process, preferably a slurry or gas phase process, is operated in the absence of or essentially free of any scavengers, such as triethylaluminum, trimethylaluminum, tri-iso-butylaluminum and tri-n-hexylaluminum and diethyl aluminum chloride, dibutyl zinc and the like. This process is described in International Patent Publication No. WO 96/08520 and U.S. Pat. No. 5,712,352, which are herein fully incorporated by reference.

In another embodiment the process is run with scavengers. Typical scavengers include trimethyl aluminum, tri-iso-butyl aluminum and an excess of alumoxane or modified alumoxane.

In a preferred embodiment, hydrogen or other chain termination agent (such as phenylsilane) are added to the slurry polymerization.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, International Patent Publication Nos. WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For a medium pressure process, the temperature within which the polymerization reaction occurs is at least 80° C. and typically ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S. Pat. Nos. 5,084,534, 5,408,017, 6,127,497, 6,255,410, which are incorporated herein by reference.

In another embodiment this invention relates to:

1. A process for producing a substituted metallocene compound, the process comprising:
   (a) providing a first compound represented by the formula (1):

$AMX_{n-1}$ wherein:
   M is a transition metal atom having a coordination number of n selected from Group 3, 4, 5 or 6 of the Periodic Table of Elements, or a lanthanide metal atom, or actinide metal atom;
   A is a monocyclic or polycyclic ligand that is pi-bonded to M and is substituted with at least one halogen or sulfonate substituent directly bonded to any $sp^2$ carbon atom at a bondable ring position of the ligand; and
   each X is, independently, a univalent anionic ligand, or two X are joined and bound to the metal atom to form a metallocycle ring, or two X are joined to form a chelating ligand, a diene ligand, or an alkylidene ligand; and
   (b) reacting said first compound with a transfer-agent which comprises a hydrocarbyl, substituted hydrocarbyl, halocarbyl, substituted halocarbyl, silylcarbyl, or germylcarbyl radical capable of replacing said at least one halogen or sulfonate substituent of said first compound under reaction conditions.

2. The process of paragraph 1 wherein A comprises a substituted monocyclic arenyl ligand or a substituted polycyclic arenyl ligand.

3. The process of paragraph 1 wherein A includes one or more ring heteroatoms selected from boron, a Group 14 atom that is not carbon, a Group 15 atom, and a Group 16 atom.

4. The process of paragraph 1 wherein said A is a substituted cyclopentadienyl, substituted heterocyclopentadienyl, substituted indenyl, substituted heteroindenyl, substituted-fluorenyl, substituted heterofluorenyl, substituted cyclopentanaphthyl, substitutedheterocyclopentanaphthyl, substituted heterophenyl, substituted heterocyclopentapentalenyl, substituted heterocyclopentaindenyl, or substituted heterobenzocyclopentaindenyl ligand.

5. A process for producing a substituted metallocene compound, the process comprising:
   (a) providing a first compound represented by the formula (2):

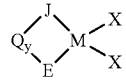

wherein
   M is a group 3, 4, 5 or 6 transition metal atom, or a lanthanide metal atom, or actinide metal atom;
   each of J and E is independently a substituted or unsubstituted, monocyclic or polycyclic ligand pi-bonded to M, wherein at least one of J and E includes at least one halogen or sulfonate substituent directly bonded to an $sp^2$ carbon atom at a bondable ring position of the ligand;
   Q is an optional bridging group that is bonded to E and J, and is present when y is one and absent when y is zero;
   y is zero or one; and
   each X is, independently, a univalent anionic ligand, or two X are joined and bound to the metal atom to form a metallocycle ring, or two X are joined to form a chelating ligand, a diene ligand, or an alkylidene ligand; and
   (b) reacting said first compound with a transfer-agent which comprises a hydrocarbyl, substituted hydrocarbyl, halocarbyl, substituted halocarbyl, silylcarbyl, germylcarbyl radical capable of replacing said at least one halogen or sulfonate substituent of said first compound under reaction conditions in the presence of a coupling catalyst.

6. The process of paragraph 5 wherein at least one of J and E comprises a substituted or unsubstituted, monocyclic or polycyclic arenyl ligand.

7. The process of paragraph 5 wherein at least one of J and E includes one or more ring heteroatoms selected from boron, a Group 14 atom that is not carbon, a Group 15 atom, and a Group 16 atom.

8. The process of paragraph 5 wherein each of J and E is independently a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, or a substituted or unsubstituted fluorenyl ligand, a substituted or unsubstituted heterofluorenyl ligand, and a substituted or unsubstituted cyclopentanaphthyl, or a substituted or unsubstituted heterocyclopentanaphthyl ligand, or a substituted or unsubstituted heterophenyl ligand, or a substituted or unsubstituted heterocyclopentapentalenyl ligand, or a substituted or unsubstituted heterocyclopentaindenyl ligand, or a substituted or unsubstituted heterobenzocyclopentaindenyl ligand.

9. The process of any of paragraphs 5 to 8 wherein y is 1 and Q is selected from the group consisting of: P(=S)R', P(=Se)R', P(=O)R!, R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$GeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'$_2$C—O—CR'$_2$, R'$_2$CR'$_2$C—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR=$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C=P=CR', R'$_2$C—PR'—CR'$_2$, O, S, Se, Te, NR', PR', AsR', SbR', O—O, S—S, R'N—NR', R'P—PR', O—S, O—NR', O—PR', S—NR', S—PR', and R'N—PR' where R' is hydrogen or a C$_1$-C$_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

10. The process of any of paragraphs 5 to 8 wherein y is 1 and Q is selected from the group consisting of: CH$_2$, CH$_2$CH$_2$, CH(CH$_3$)$_2$, SiMe$_2$, SiPh$_2$, SiMePh, Si(CH$_2$)$_3$, Si(CH$_2$)$_4$, O, S, NPh, PPh, NMe, PMe, NEt, NPr, NBu, PEt, PPr, and PBu, where Me is methyl, Ph is phenyl, Et is ethyl, Pr is propyl, and Bu is butyl.

11. A process for producing a substituted metallocene compound, the process comprising:

(a) providing a first compound represented by the formula (3):

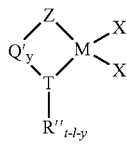

wherein

M is a Group 3, 4, 5 or 6 transition metal atom, or a lanthanide metal atom, or actinide metal atom;

Z is a substituted or unsubstituted, monocyclic or polycyclic ligand that is pi-bonded to M;

Q' is an optional bridging group that is bonded to Z and T, and is present when y is one and absent when y is zero;

y is zero or one; and

T is a heteroatom with a coordination number of three from Group 15 or with a coordination number of two from Group 16 of the Periodic Table of Elements;

R" is selected from a C$_3$-C$_{100}$ substituted or unsubstituted monocyclic or polycyclic ring structure substituent that is partially unsaturated, unsaturated or aromatic; or a C$_2$-C$_{100}$ substituted or unsubstituted, unsaturated or partially unsaturated, linear or branched alicyclic hydrocarbyl substituent; or a C$_1$-C$_{100}$ substituted or unsubstituted saturated hydrocarbyl radical;

t is the coordination number of the heteroatom T (2 or 3) where "t-1-y" indicates the number of R– substituents bonded to T; and each X is, independently, a univalent anionic ligand, or two X are joined and bound to the metal atom to form a metallocycle ring, or two X are joined to form a chelating ligand, a diene ligand, or an alkylidene ligand;

provided that Z is substituted with at least one halogen or sulfonate substituent directly bonded to any sp$^2$ carbon atom at a bondable ring position of the ligand Z, or that R" is substituted with at least one halogen or sulfonate substituent bonded to an sp$^2$ carbon atom, or both.

(b) reacting said first compound with a transfer-agent which comprises a hydrocarbyl, substituted hydrocarbyl, halocarbyl, substituted halocarbyl, silylcarbyl, germylcarbyl radical capable of replacing said at least one halogen or sulfonate substituent of said first compound under reaction conditions in the presence of a coupling catalyst.

12. The process of paragraph 11 wherein Z comprises a monocyclic or polycyclic arenyl ligand.

13. The process of paragraph 11 wherein Z includes one or more ring heteroatoms selected from boron, a Group 14 atom that is not carbon, a Group 15 atom, and a Group 16 atom.

14. The process of paragraph 11 wherein Z is independently a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, or a substituted or unsubstituted fluorenyl ligand, a substituted or unsubstituted heterofluorenyl ligand, and a substituted or unsubstituted cyclopentanaphthyl, or a substituted or unsubstituted heterocyclopentanaphthyl ligand, or a substituted or unsubstituted heterophenyl ligand, or a substituted or unsubstituted heterocyclopentapentalenyl ligand, or a substituted or unsubstituted heterocyclopentaindenyl ligand, or a substituted or unsubstituted heterobenzocyclopentaindenyl ligand.

15. The process of any one of paragraphs 11 to 13 wherein t-1-y is equal to 1.

16. The process of any one of paragraphs 11 to 15 wherein T is nitrogen.

17. The process of any one of paragraphs 11 to 16 wherein R" is selected from methyl, ethyl, all propyl isomers, all butyl isomers, phenyl, benzyl, phenethyl, 1-adamantyl, cyclododecyl, cyclohexyl and norbornyl.

18. The process of any one of paragraphs 11 to 17 wherein the halogen or sulfonate substituent is on R", and R" is selected from the group consisting of 2-bromophenyl, 3-bromophenyl, 4-bromophenyl, 2,6-diisopropyl-4-bromophenyl, 2,6-dimethyl-4-bromophenyl, 2,4,6-trimethyl-3-bromophenyl, 2-bromo-4,6-dimethylphenyl, 2-bromo-4-methylphenyl, 2-bromo-3,4,6-trimethylphenyl, 2-bromo-4-fluorophenyl, 2-bromo-4,6-difluorophenyl, 2,6-dibromophenyl, 2,6-dibromo-4-methylphenyl, 2,6-dibromo-4-fluorophenyl, 2,5-dibromophenyl, and 2,4-dibromophenyl.

19. The process of any one of paragraphs 11 to 18 wherein y is 1 and Q' is selected from the group consisting of: P(=S)R', P(=Se)R', P(=O)R', R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C=P=CR', and R'$_2$C—PR'—CR'$_2$ where R' is hydrogen or a C$_1$-C$_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent 20. The process of any one of paragraphs 11 to 18 wherein y is 1 and Q' is selected from the group consisting of CH$_2$, CH$_2$CH$_2$, CH(CH$_3$)$_2$, SiMe$_2$, SiPh$_2$, SiMePh, Si(CH$_2$)$_3$, and Si(CH$_2$)$_4$, where Me is methyl, and Ph is phenyl.

21. The process of any one of paragraphs 5 to 10 wherein y is 1 and Q is a bridging group containing at least one Group 13, 14, 15, or 16 element.
22. The process of any one of paragraphs 11 to 20 wherein y is 1 and Q' is a bridging group containing boron or a Group 14, 15 or 16 element.
23. The process of any preceding paragraphs 1 to 22 wherein the halogen or sulfonate substituent is a chloro, bromo, iodo, tosylate or triflate substituent.
24. The process of any preceding paragraphs 1 to 23 wherein the halogen substituent is a chloro or bromo substituent.
25. The process of any preceding paragraphs 1 to 24 wherein M is titanium, zirconium or hafnium.
26. The process of any preceding paragraphs 1 to 25 wherein the transfer-agent is an organometallic compound.
27. The process of paragraph 26 wherein the metal of the organometallic compound is selected from boron, tin, copper, magnesium, zinc, aluminum, lithium and zirconium.
28. A substituted metallocene compound prepared by the process of any preceding paragraphs 1 to 27.
29. A catalyst system comprising the substituted metallocene compound of paragraph 28 and an activator.
30. A process for polymerizing olefins comprising contacting a metallocene compound prepared by the process of any of paragraphs 1 to 27 with an activator and at least one olefin.
31. The process of paragraph 30 wherein said at least one olefin comprises ethylene and/or propylene.

Experimental—Synthesis

All manipulations with air and moisture sensitive compounds were performed either in an atmosphere of thoroughly purified argon using a standard Schlenk technique or in a controlled atmosphere Glove Box (Vacuum Atmospheres Co.). Tetrahydrofuran (THF, Merck=Merck KGaA, Darmstadt, Germany) and diethyl ether (Merck) were purified by distillation over LiAlH$_4$, and stored over sodium benzophenone ketyl under an inert atmosphere; prior to use, the solvents were distilled from the benzophenone ketyl. Hydrocarbon solvents such as benzene (Merck), toluene (Merck), and hexanes (Merck) and including benzene-d$_6$ (Cambridge Isotope Laboratories, Inc., for NMR measurements) were typically distilled over CaH$_2$, and were stored over Na/K alloy under an inert atmosphere; prior to use, the solvents were distilled from the Na/K alloy. Methylene chloride (Merck) (and CCl$_2$D$_2$ for NMR measurements, Cambridge Isotope Laboratories, Inc.) was distilled and stored over CaH$_2$ under an inert atmosphere; prior to use, the solvent was distilled from the CaH$_2$. Chloroform-d (Merck) was distilled over P$_4$O$_{10}$ (Merck) and stored over molecular sieves (3 Å). Thiophene (Merck), 2-methylthiophene (Fluka Chemical Corp.=Fluka), furan (Merck), 2-methylfuran (Aldrich=Aldrich Chemical Co.), benzothiophene (Aldrich), benzofuran (Aldrich), 2.0 M $^n$BuLi in hexanes (Chemetall=Chemetall Chemical Products), 2.0 M 4-tert-butylbromophenylmagnesium bromide in ether (Aldrich), 2.0 M methylzinc chloride in THF (Aldrich), 1.0 M phenylmagnesium bromide in THF (Aldrich), 1.0 M p-tolylmagnesium bromide in THF (Aldrich), 1.0 M m-tolylmagnesium chloride in THF (Aldrich), 0.5 M dimethylaminophenylmagnesium bromide in THF (Aldrich), 1.0 M 2-methoxyphenylmagnesium bromide in THF (Aldrich), 4-bromobiphenyl (Aldrich), mesityl bromide (Acros=Acros Organics), 2-bromotoluene (Acros), 2-bromoanisole (Acros), 3-bromobenzotrifluoride (Acros), 4-fluorobromobenzene (Acros), 1-bromonaphthalene (Acros), lithium bis(trimethylsilyl)amide (Aldrich), styrene (Acros), 4-fluorostyrene (Aldrich), NaBPh$_4$ (Acros), n-butyl vinyl ether (Acros), 0.5 M ZnCl$_2$ in THF (Aldrich), and Pd(P$^t$Bu$_3$)$_2$ (Strem=Strem Chemical Co.), dibromobis(triphenylphosphine)nickel(II) (Aldrich), 2,5-dimethylphenylmagnesium bromide (0.5 M in THF, Aldrich), and 4-biphenylmagnesium bromide (0.5 M in THF, Aldrich) were used as obtained. Solutions of Grignard reagents (4-phenylphenylmagnesium bromide, 4-tert-butylphenylmagnesium bromide, 2-methylphenylmagnesium bromide, mesitylmagnesium bromide, 4-fluorophenylmagnesium bromide, 3-trifluoromethylphenylmagnesium bromide, 2-tolylmagnesium bromide, and 1-naphthylmagnesium bromide) in THF were obtained from magnesium turnings (Aldrich) and the respective arylbromides in THF at reflux. Trichloromethylsilane (Merck) was distilled in the presence of quinoline in argon to eliminate HCl. Celite 503 (Fluka) was dried in vacuum for 20 hour at 200° C.

$^1$H and $^{13}$C NMR spectra were recorded with a Varian VXR 400 or Brucker DPX-300 for 0.1-5% solutions in deuterated solvents. Chemical shifts for $^1$H and $^{13}$C were measured relative to TMS. In $^1$H NMR spectra, the assignment was made on the evidence of double resonance and NOE experiments. C, H microanalyses were done using CHN—O-Rapid analyzer (Heracus).

The synthesis of the halogen substituted catalyst precursors listed below are disclosed in our copending U.S. patent application Ser. Nos. 11/302,798, 11/300,240, 11/300,032, 11/300,002, 11/300,054, 11/302,821, all filed concurrently herewith and all incorporated herein by reference, and were used to prepare the catalysts listed on Table 1, using the indicated cross-coupling reaction:

($\eta^5$-2-methyl-4-bromoindenyl)($\eta^5$-pentamethylcyclopentadienyl)zirconium dichloride (1), ($\eta^5$-2-methyl-4-bromoindenyl)($\eta^5$-pentamethylcyclopentadienyl)hafnium dichloride (2), ($\eta^5$-2-methyl-4-bromoindenyl)($\eta^5$-cyclopentadienyl)zirconium dichloride (3), mixture of d-ll- and meso-bis($\eta^5$-2-methyl-4-bromoindenyl) zirconium dichlorides (4), bis($\eta^5$-2-bromoindenyl)zirconium dichloride (5), ($\eta^5$-3-bromo-5-methylcyclopenta[b]thienyl)($\eta^5$-pentamethylcyclopentadienyl)zirconium dichloride (6), mixture of d-ll- and meso-bis($\eta^5$-3-bromo-5-methylcyclopenta[b]thienyl)zirconium dichlorides (7), rac-dimethylsilyl-bis($\eta^5$-4-bromo-2-methylinden-1-yl)zirconium dichloride (rac-8), meso-dimethylsilyl-bis($\eta^5$-4-bromo-2-methylinden-1-yl) zirconium dichloride (meso-8), rac-dimethylsilyl-bis($\eta^5$-3-bromo-5-methylcyclopenta[b] thien-6-yl)zirconium dichloride (rac-9), 4,4'-sulfandiyl-bis($\eta^5$-7-bromo-2-methylindenyl)zirconium dichloride (10), dimethylsilyl($\eta^5$-2-methyl-4-bromoinden-1-yl)-($\eta^1$-tert-butylamido)zirconium dichloride (11), dimethylsilyl($\eta^5$-tetramethylcyclopentadienyl)($\eta^1$-4-bromo-2,6-diisopropylphenylamido)zirconium dichloride (12), rac-dimethylsilyl-bis($\eta^5$-4-bromo-2,5-dimethylinden-1-yl) zirconium dichloride (13), dimethylsilyl($\eta^5$-tetramethylcyclopentadienyl)($\eta^1$-4-bromophenylamido)zirconium dichloride (14), rac-dimethylsilyl-bis($\eta^5$-4-bromo-6-isopropyl-2-methylinden-1-yl)zirconium dichloride (15), rac-dimethylsilyl-bis($\eta^5$-3-bromo-2,5-dimethylcyclopenta [b]thien-6-yl)zirconium dichloride (16), dimethylsilyl($\eta^5$-2-methyl-4-bromoinden-1-yl)($\eta^1$-tert-butylamido)titanium dichloride (17), dimethylsilyl($\eta^5$-4,5-dimethylcyclopenta[b]thien-6-yl)($\eta^1$-4-bromo-2,6-dimethylphenylamido)titanium dichloride (18), rac-dimethylsilyl-bis($\eta^5$-4-bromo-2,6-dimethylinden-1-yl)zirconium dichloride (19), dimethylsilyl($\eta^5$-tetramethylcyclopentadienyl)($\eta^1$-4-bromophenylamido)titanium dichloride (20), dimethylsilyl($\eta^5$-tetramethylcyclopentadienyl)($\eta^1$-4-bromo-2,6-diisopropylphenylamido)titanium dichloride (21), rac-diethylsilyl-bis($\eta^5$-4-bromo-2-methylinden-1-yl)zirconium dichloride (22), dimethylsilyl($\eta^5$-tetramethylcyclopentadienyl)($\eta^1$-4-bromo-2,6-dimethylphenylamido)zirconium dichloride (23), dimethylsilyl($\eta^5$-4,5-dimethylcyclopenta[b]thien-6-yl)($\eta^1$-4-bromo-2,6-dimethylphenylamido)zirconium dichloride (24), dimethylsilyl($\eta^5$-4,5-dimethylcyclopenta[b]thien-6-yl)($\eta^1$-4-bromo-2,6-diisopropylphenylamido)zirconium dichloride (25), dimethylsilyl($\eta^5$-4,5-dimethylcyclopenta[b]thien-6-yl)($\eta^1$-4-bromo-2,6-diisopropylphenylamido)titanium dichloride (26), 4,4'-tolylazandiyl-bis($\eta^5$-7-bromo-2-methylindenyl)zirconium dichloride (27), 4,4'-oxadiyl-bis($\eta^5$-7-bromo-2-methylindenyl)zirconium dichloride (28), ($\eta^5$-4-bromo-6-chloroindenyl)($\eta^5$-pentamethylcyclopentadienyl)zirconium dichloride (29), rac-dimethylsilyl-bis($\eta^5$-4-bromo-2-isopropylinden-1-yl)zirconium dichloride (30), isopropylidene-($\eta^5$-4-bromo-3-methylinden-1-yl)($\eta^5$-cyclopentadienyl)zirconium dichloride (31), isopropylidene-($\eta^5$-2,7-dibromofluoren-9-yl)($\eta^5$-cyclopentadienyl)zirconium dichloride (32), dimethylsilyl($\eta^5$-tetramethylcyclopentadienyl)($\eta^1$-4-bromo-2,6-dimethylphenylamido)titanium dichloride (33), and ($\eta^5$-4,7-dibromoinden-1-yl)($\eta^5$-pentamethylcyclopentadienyl)zirconium dichloride (34).

TABLE 1

Precatalyst Prepared from Halogen-Substituted Metallocenes

| Ex. | Prec.[a] | Precatalyst | Rxn[b] |
|---|---|---|---|
| 1a | 1 | ($\eta^5$-2,4-di-Me-indenyl)($\eta^5$-Me$_5$Cp)ZrCl$_2$ (1a) | N |
| 1b | 1 | ($\eta^5$-2-Me-4-Ph-indenyl)($\eta^5$-Me$_5$Cp)ZrCl$_2$ (1b) | N |
| 1b2 | 1 | ($\eta^5$-2-Me-4-Ph-indenyl)($\eta^5$-Me$_5$Cp)ZrCl$_2$ (1b) | S |
| 1c/1c' | 1 | ($\eta^5$-2-Me-4-(4-MeC$_6$H$_4$)-indenyl)($\eta^5$-Me$_5$Cp)ZrCl$_2$ (1c) | N |
| 1d | 1 | ($\eta^5$-2-Me-4-(3-MeC$_6$H$_4$)-indenyl)($\eta^5$-Me$_5$Cp)ZrCl$_2$ (1d) | N |
| 1e | 1 | ($\eta^5$-2-Me-4-(2-MeC$_6$H$_4$)-indenyl)($\eta^5$-Me$_5$Cp)ZrCl$_2$ (1e) | N |
| 1f | 1 | ($\eta^5$-2-Me-4-(4-tBuC$_6$H$_4$)-indenyl)($\eta^5$-Me$_5$Cp)ZrCl$_2$ (1f) | N |
| 1g | 1 | ($\eta^5$-2-Me-4-(4-FC$_6$H$_4$)-indenyl)($\eta^5$-Me$_5$Cp)ZrCl$_2$ (1g) | N |
| 1h | 1 | ($\eta^5$-2-Me-4-(3-CF$_3$C$_6$H$_4$)-indenyl)($\eta^5$-Me$_5$Cp)ZrCl$_2$ (1h) | N |
| 1i | 1 | ($\eta^5$-2-Me-4-(2-MeOC$_6$H$_4$)-indenyl)($\eta^5$-Me$_5$Cp)ZrCl$_2$ (1i) | N |
| 1k | 1 | ($\eta^5$-2-Me-4-(4-PhC$_6$H$_4$)-lindenyl)($\eta^5$-Me$_5$Cp)ZrCl$_2$ (1k) | N |
| 1l | 1 | ($\eta^5$-2-Me-4-(1-naphthyl)-indenyl)($\eta^5$-Me$_5$Cp)ZrCl$_2$ (1l) | N |
| 1m | 1 | ($\eta^5$-2-Me-4-(2-thienyl)-indenyl)($\eta^5$-Me$_5$Cp)ZrCl$_2$ (1m) | N |
| 1n | 1 | ($\eta^5$-2-Me-4-(2-benzothienyl)-indenyl)($\eta^5$-Me$_5$Cp)ZrCl$_2$ (1n) | N |
| 1o | 1 | ($\eta^5$-2-Me-4-(2-furyl)-indenyl)($\eta^5$-Me$_5$Cp)ZrCl$_2$ (1o) | N |
| 1p | 1 | ($\eta^5$-2-Me-4-(2-benzofuryl)-indenyl)($\eta^5$-Me$_5$Cp)ZrCl$_2$ (1p) | N |
| 1q | 1 | cis- and trans- isomers of ($\eta^5$-2-Me-4-styrylindenyl)($\eta^5$-Me$_5$Cp)ZrCl$_2$ (1q) | H |
| 1r | 1 | trans-($\eta^5$-2-Me-4-(4-F-styryl)-indenyl)($\eta^5$-Me$_5$Cp)ZrCl$_2$ (1r) | H |
| 1s | 1 | cis- and trans- isomers of ($\eta^5$-2-Me-4-(1,2-butoxyvinyl)indenyl)($\eta^5$-Me$_5$Cp)ZrCl$_2$ (1s) | H |
| 2a | 2 | ($\eta^5$-2,4-di-Me-indenyl)($\eta^5$-Me$_5$Cp)HfCl$_2$ (2a) | N |
| 2b | 2 | ($\eta^5$-2-Me-4-(4-MeC$_6$H$_4$)-indenyl)($\eta^5$-Me$_5$Cp)HfCl$_2$ (2b) | N |
| 2c | 2 | ($\eta^5$-2-Me-4-(3-MeC$_6$H$_4$)-indenyl)($\eta^5$-Me$_5$Cp)HfCl$_2$ (2c) | N |
| 2d | 2 | ($\eta^5$-2-Me-4-(4-tBuC$_6$H$_4$)-indenyl)($\eta^5$-Me$_5$Cp)HfCl$_2$ (2d) | N |
| 2e | 2 | ($\eta^5$-2-Me-4-Ph-indenyl)($\eta^5$-Me$_5$Cp)HfCl$_2$ (2e) | N |
| 3a | 3 | ($\eta^5$-2,4-di-Me-indenyl)($\eta^5$-Cp)ZrCl$_2$ (3a) | N |
| 3b | 3 | ($\eta^5$-2-Me-4-Ph-indenyl)($\eta^5$-Cp)ZrCl$_2$ (3b) | N |
| 3c | 3 | ($\eta^5$-2-Me-4-(4-MeC$_6$H$_4$)-indenyl)($\eta^5$-Cp)ZrCl$_2$ (3c) | N |
| 3d | 3 | ($\eta^5$-2-Me-4-(3-MeC$_6$H$_4$)-indenyl)($\eta^5$-Cp)ZrCl$_2$ (3d) | N |
| 4a | 4 | d-/l- and meso-bis($\eta^5$-2,4-di-Me-indenyl)ZrCl$_2$ (4a) | N |
| 4b | 4 | d-/l- and meso-bis($\eta^5$-2-Me-(4-MeC$_6$H$_4$)-indenyl)ZrCl$_2$ (4b) | N |
| 4c | 4 | d-/l- and meso-bis($\eta^5$-2-Me-4-(4-tBuC$_6$H$_4$)-indenyl)ZrCl$_2$ (4c) | N |
| 5a | 5 | bis($\eta^5$-2-(4-MeC$_6$H$_4$)indenyl)ZrCl$_2$ (5a) | N |
| 6a | 6 | ($\eta^5$-3,5-di-Me-cyclopenta[b]thienyl))($\eta^5$-Cp)ZrCl$_2$ (6a) | N |
| 6b | 6 | ($\eta^5$-3-Ph-5-Me-cyclopenta[b]thienyl))($\eta^5$-Cp)ZrCl$_2$ (6b) | N |
| 6c | 6 | ($\eta^5$-3-(4-MeC$_6$H$_4$)-5-Me-cyclopenta[b]thienyl))($\eta^5$-Cp)ZrCl$_2$ (6c) | N |
| 6d | 6 | ($\eta^5$-3-(3-MeC$_6$H$_4$)-5-Me-cyclopenta[b]thienyl))($\eta^5$-Cp)ZrCl$_2$ (6d) | N |
| 6e | 6 | ($\eta^5$-3-(4-tBuC$_6$H$_4$)-5-Me-cyclopenta[b]thienyl))($\eta^5$-Cp)ZrCl$_2$ (6e) | N |
| 7a | 7 | d-/l- and meso-bis($\eta^5$-3,5-di-Me-cyclopenta[b]thienyl)ZrCl$_2$ (7a) | N |
| 7b | 7 | d-/l- and meso-bis($\eta^5$-3-Ph-5-Me-cyclopenta[b]thienyl)ZrCl$_2$ (7b) | N |
| 7c | 7 | d-/l- and meso-bis($\eta^5$-3-(4-MeC$_6$H$_4$)-5-Me-cyclopenta[b]thienyl)ZrCl$_2$ (7c) | N |
| 7d | 7 | d-/l- and meso-bis($\eta^5$-3-(3-MeC$_6$H$_4$)-5-Me-cyclopenta[b]thienyl)ZrCl$_2$ (7d) | N |
| 7e | 7 | d-/l- and meso-bis($\eta^5$-3-(4-tBuC$_6$H$_4$)-5-Me-cyclopenta[b]thienyl)ZrCl$_2$ (7e) | N |
| rac-8a | rac-8 | rac-Me$_2$Si($\eta^5$-2,4-di-Me-inden-1-yl)ZrCl$_2$ (rac-8a) | N |
| rac-8b | rac-8 | rac-Me$_2$Si($\eta^5$-4-(4-MeC$_6$H$_4$)-2-Me-inden-1-yl)ZrCl$_2$ (rac-8b) | N |
| rac-8c | rac-8 | rac-Me$_2$Si($\eta^5$-4-(3-MeC$_6$H$_4$)-2-Me-inden-1-yl)ZrCl$_2$ (rac-8c) | N |
| rac-8d | rac-8 | rac-Me$_2$Si($\eta^5$-4-(2-MeC$_6$H$_4$)-2-Me-inden-1-yl)ZrCl$_2$ (rac-8d) | N |
| rac-8e | rac-8 | rac-Me$_2$Si($\eta^5$-4-(4-tBuC$_6$H$_4$)-2-Me-inden-1-yl)ZrCl$_2$ (rac-8e) | N |
| rac-8f | rac-8 | rac-Me$_2$Si($\eta^5$-4-(4-FC$_6$H$_4$)-2-Me-inden-1-yl)ZrCl$_2$ (rac-8f) | N |

TABLE 1-continued

Precatalyst Prepared from Halogen-Substituted Metallocenes

| Ex. | Prec.[a] | Precatalyst | Rxn[b] |
|---|---|---|---|
| rac-8g | rac-8 | rac-Me$_2$Si($\eta^5$-4-(3-CF$_3$C$_6$H$_4$)-2-Me-inden-1-yl)ZrCl$_2$ (rac-8g) | N |
| rac-8h | rac-8 | rac-Me$_2$Si($\eta^5$-4-(2,4,6-tri-Me-C$_6$H$_2$)-2-Me-inden-1-yl)ZrCl$_2$ (rac-8h) | N |
| rac-8i | rac-8 | rac-Me$_2$Si($\eta^5$-4-(5-Me-2-thienyl)-2-Me-inden-1-yl)ZrCl$_2$ (rac-8i) | N |
| rac-8k | rac-8 | rac-Me$_2$Si($\eta^5$-4-(5-Me-2-furyl)-2-Me-inden-1-yl)ZrCl$_2$ (rac-8k) | N |
| rac-8l | rac-8 | rac-Me$_2$Si($\eta^5$-4-(2-benzothienyl)-2-Me-inden-1-yl)ZrCl$_2$ (rac-8l) | N |
| rac-8m | rac-8 | rac-Me$_2$Si($\eta^5$-4-(2-benzofuryl)-2-Me-inden-1-yl)ZrCl$_2$ (rac-8m) | N |
| rac-8n | rac-8 | rac-Me$_2$Si($\eta^5$-4-(1-naphthyl)-2-Me-inden-1-yl)ZrCl$_2$ (rac-8n) | N |
| rac-8o | rac-8 | rac-Me$_2$Si($\eta^5$-4-(4-PhC$_6$H$_4$)-2-Me-inden-1-yl)ZrCl$_2$ (rac-8o) | N |
| rac-8p | rac-8 | rac-Me$_2$Si($\eta^5$-4-(4-Me$_2$NC$_6$H$_4$)-2-Me-inden-1-yl)ZrCl$_2$ (rac-8p) | N |
| rac-8q | rac-8 | rac-Me$_2$Si($\eta^5$-4-(2-MeOC$_6$H$_4$)-2-Me-inden-1-yl)ZrCl$_2$ (rac-8q) | N |
| rac-8r | rac-8 | rac-Me$_2$Si($\eta^5$-4-(2-PhC$_6$H$_4$)-2-Me-inden-1-yl)ZrCl$_2$ (rac-8r) | N |
| rac-8s | rac-8 | rac-Me$_2$Si($\eta^5$-4-(3,5-di-tBu-C$_6$H$_3$)-2-Me-inden-1-yl)ZrCl$_2$ (rac-8s) | N |
| rac-8t | rac-8 | rac-Me$_2$Si($\eta^5$-4-(2-CF$_3$C$_6$H$_4$)-2-Me-inden-1-yl)ZrCl$_2$ (rac-8t) | N |
| rac-8u | rac-8 | rac-Me$_2$Si($\eta^5$-4-(3-(2-Me-benzothienyl))-2-Me-inden-1-yl)ZrCl$_2$ (rac-8u) | N |
| rac-8v | rac-8 | rac-Me$_2$Si($\eta^5$-4-di-(2,4-di-CF$_3$—C$_6$H$_3$)-2-Me-inden-1-yl)ZrCl$_2$ (rac-8v) | N |
| meso-8b | meso-8 | meso-Me$_2$Si($\eta^5$-4-(4-MeC$_6$H$_4$)-2-Me-inden-1-yl)ZrCl$_2$ (meso-8b) | N |
| meso-8d | meso-8 | meso-Me$_2$Si($\eta^5$-4-(2-MeC$_6$H$_4$)-2-Me-inden-1-yl)ZrCl$_2$ (meso-8d) | N |
| rac-9a | rac-9 | rac-Me$_2$Si($\eta^5$-3,5-di-Me-cyclopenta[b]thien-6-yl)$_2$ZrCl$_2$ (rac-9a) | N |
| rac-9b | rac-9 | rac-Me$_2$Si($\eta^5$-3-Ph-5-Me-cyclopenta[b]thien-6-yl)$_2$ZrCl$_2$ (rac-9b) | N |
| rac-9c | rac-9 | rac-Me$_2$Si($\eta^5$-3-(4-MeC$_6$H$_4$)-5-Me-cyclopenta[b]thien-6-yl)$_2$ZrCl$_2$ (rac-9c) | N |
| rac-9d | rac-9 | rac-Me$_2$Si($\eta^5$-3-(3-MeC$_6$H$_4$)-5-Me-cyclopenta[b]thien-6-yl)$_2$ZrCl$_2$ (rac-9d) | N |
| rac-9e | rac-9 | rac-Me$_2$Si($\eta^5$-3-(4-tBuC$_6$H$_4$)-5-Me-cyclopenta[b]thien-6-yl)$_2$ZrCl$_2$ (rac-9e) | N |
| 10a | 10 | 4,4'-S-($\eta^5$-2,7-di-Me-indenyl)$_2$ZrCl$_2$ (10a) | N |
| 10b | 10 | 4,4'-S-($\eta^5$-7-Ph-2-Me-indenyl)$_2$ZrCl$_2$ (10b) | N |
| 10c | 10 | 4,4'-S-($\eta^5$-7-(4-MeC$_6$H$_4$)-2-Me-indenyl)$_2$ZrCl$_2$ (10c) | N |
| 10d | 10 | 4,4'-S-($\eta^5$-7-(3-MeC$_6$H$_4$)-2-Me-indenyl)$_2$ZrCl$_2$ (10d) | N |
| 10e | 10 | 4,4'-S-($\eta^5$-7-(4-tBuC$_6$H$_4$)-2-Me-indenyl)$_2$ZrCl$_2$ (10e) | N |
| 10f | 10 | 4,4'-S-($\eta^5$-7-(2,4,6-tri-Me-C$_6$H$_2$)-2-Me-indenyl)$_2$ZrCl$_2$ (10f) | N |
| 10g | 10 | 4,4'-S-($\eta^5$-7-(5-Me-2-thienyl)-2-Me-indenyl)$_2$ZrCl$_2$ (10g) | N |
| 10h | 10 | 4,4'-S-($\eta^5$-7-(5-Me-2-furyl)-2-Me-indenyl)$_2$ZrCl$_2$ (10h) | N |
| 10i | 10 | 4,4'-S-($\eta^5$-7-(2-benzothienyl)-2-Me-indenyl)$_2$ZrCl$_2$ (10i) | N |
| 10k | 10 | 4,4'-S-($\eta^5$-7-(2-benzofuryl)-2-Me-indenyl)$_2$ZrCl$_2$ (10k) | N |
| 10l | 10 | 4,4'-S-($\eta^5$-7-(4-FC$_6$H$_4$)-2-Me-indenyl)$_2$ZrCl$_2$ (10l) | N |
| 10m | 10 | 4,4'-S-($\eta^5$-7-(3-CF$_3$C$_6$H$_4$)-2-Me-indenyl)$_2$ZrCl$_2$ (10m) | N |
| 10n | 10 | 4,4'-S-($\eta^5$-7-(2,5-di-Me-C$_6$H$_3$)-2-Me-indenyl)$_2$ZrCl$_2$ (10n) | N |
| 10o | 10 | 4,4'-S-($\eta^5$-7-(4-PhC$_6$H$_4$)-2-Me-indenyl)$_2$ZrCl$_2$ (10o) | N |
| 11a | 11 | Me$_2$Si($\eta^5$-2,4-di-Me-inden-1-yl)($\eta^1$-tert-butylamido)ZrCl$_2$ (11a) | N |
| 11b | 11 | Me$_2$Si($\eta^5$-2-Me-4-(4-MeC$_6$H$_4$)-inden-1-yl)($\eta^1$-tert-butylamido)ZrCl$_2$ (11b) | N |
| 11c | 11 | Me$_2$Si($\eta^5$-2-Me-4-(3-MeC$_6$H$_4$)-inden-1-yl)($\eta^1$-tert-butylamido)ZrCl$_2$ (11c) | N |
| 11d | 11 | Me$_2$Si($\eta^5$-2-Me-4-(2-MeC$_6$H$_4$)-inden-1-yl)($\eta^1$-tert-butylamido)ZrCl$_2$ (11d) | N |
| 11e | 11 | Me$_2$Si($\eta^5$-2-Me-4-(2,4,6-tri-Me-C$_6$H$_2$)-inden-1-yl)($\eta^1$-tert-butylamido)ZrCl$_2$ (11e) | N |
| 11f | 11 | Me$_2$Si($\eta^5$-2-Me-4-(2,5-di-Me-C$_6$H$_3$)-inden-1-yl)($\eta^1$-tert-butylamido)ZrCl$_2$ (11f) | N |
| 11g | 11 | Me$_2$Si($\eta^5$-2-Me-4-(4-FC$_6$H$_4$)-inden-1-yl)($\eta^1$-tert-butylamido)ZrCl$_2$ (11g) | N |
| 11h | 11 | Me$_2$Si($\eta^5$-2-Me-4-(3-CF$_3$C$_6$H$_4$)-inden-1-yl)($\eta^1$-tert-butylamido)ZrCl$_2$ (11h) | N |
| 11i | 11 | Me$_2$Si($\eta^5$-2-Me-4-(4-PhC$_6$H$_4$)-inden-1-yl)($\eta^1$-tert-butylamido)ZrCl$_2$ (11i) | N |
| 11k | 11 | Me$_2$Si($\eta^5$-2-Me-4-(4-Me$_2$NC$_6$H$_4$)-inden-1-yl)($\eta^1$-tert-butylamido)ZrCl$_2$ (11k) | N |
| 11l | 11 | Me$_2$Si($\eta^5$-2-Me-4-(2-MeOC$_6$H$_4$)-inden-1-yl)($\eta^1$-tert-butylamido)ZrCl$_2$ (11l) | N |
| 11m | 11 | Me$_2$Si($\eta^5$-2-Me-4-(3-MeO-2-Me-2,3-dihydro-1H-inden-4-yl)-inden-1-yl)($\eta^1$-tert-butylamido)ZrCl$_2$ (11m) | N |
| 11n | 11 | Me$_2$Si($\eta^5$-2-Me-4-(5-Me-2-furyl)-inden-1-yl)($\eta^1$-tert-butylamido)ZrCl$_2$ (11n) | N |
| 11o | 11 | Me$_2$Si($\eta^5$-2-Me-4-(5-Me-2-thienyl)-inden-1-yl)($\eta^1$-tert-butylamido)ZrCl$_2$ (11o) | N |
| 11p | 11 | Me$_2$Si($\eta^5$-2-Me-4-(2-benzothienyl)-inden-1-yl)($\eta^1$-tert-butylamido)ZrCl$_2$ (11p) | N |
| 11r | 11 | Me$_2$Si($\eta^5$-2-Me-4-(2-benzofuryl)-inden-1-yl)($\eta^1$-tert-butylamido)ZrCl$_2$ (11r) | N |
| 12a | 12 | Me$_2$Si($\eta^5$-Me$_4$Cp)($\eta^1$-4-Me-2,6-diisopropylphenylamido)ZrCl$_2$ (12a) | N |
| 12b | 12 | Me$_2$Si($\eta^5$-Me$_4$Cp)($\eta^1$-4-(4-MeC$_6$H$_4$)-2,6-diisopropylphenylamido)ZrCl$_2$ (12b) | N |
| 13a | 13 | rac-Me$_2$Si($\eta^5$-4-(4-PhC$_6$H$_4$)-2,5-dimethylinden-1-yl)$_2$ZrCl$_2$ (13a) | N |
| 13b | 13 | rac-Me$_2$Si($\eta^5$-4-(4-MeC$_6$H$_4$)-2,5-dimethylinden-1-yl)$_2$ZrCl$_2$ (13b) | N |
| 13c | 13 | rac-Me$_2$Si($\eta^5$-4-(2-benzofuryl)-2,5-dimethylinden-1-yl)$_2$ZrCl$_2$ (13c) | N |
| 13d | 13 | rac-Me$_2$Si($\eta^5$-4-(2-benzothienyl)-2,5-dimethylinden-1-yl)$_2$ZrCl$_2$ (13d) | N |
| 13e | 13 | rac-Me$_2$Si($\eta^5$-4-(3,5-di-tBu-C$_6$H$_3$)-2,5-dimethylinden-1-yl)$_2$ZrCl$_2$ (13e) | N |
| 13f | 13 | rac-Me$_2$Si($\eta^5$-4-(2-CF$_3$C$_6$H$_4$)-2,5-dimethylinden-1-yl)$_2$ZrCl$_2$ (13f) | N |
| 13g | 13 | rac-Me$_2$Si($\eta^5$-4-(4-FC$_6$H$_4$)-2,5-dimethylinden-1-yl)$_2$ZrCl$_2$ (13g) | N |
| 13h | 13 | rac-Me$_2$Si($\eta^5$-4-(3-CF$_3$C$_6$H$_4$)-2,5-dimethylinden-1-yl)$_2$ZrCl$_2$ (13h) | N |
| 13i | 13 | rac-Me$_2$Si($\eta^5$-4-Ph-2,5-dimethylinden-1-yl)$_2$ZrCl$_2$ (13i) | N |
| 13i2 | 13 | rac-Me$_2$Si($\eta^5$-4-Ph-2,5-dimethylinden-1-yl)$_2$ZrCl$_2$ (13i) | S |
| 14a | 14 | Me$_2$Si($\eta^5$-Me$_4$Cp)($\eta^1$-4-Me-phenylamido)ZrCl$_2$ (14a) | N |
| 14b | 14 | Me$_2$Si($\eta^5$-Me$_4$Cp)($\eta^1$-4-(4-MeC$_6$H$_4$)-phenylamido)ZrCl$_2$ (14b) | N |
| 14c | 14 | Me$_2$Si($\eta^5$-Me$_4$Cp)($\eta^1$-4-(4-PhC$_6$H$_4$)-phenylamido)ZrCl$_2$ (14c) | N |
| 14d | 14 | Me$_2$Si($\eta^5$-Me$_4$Cp)($\eta^1$-4-(4-Me$_2$NC$_6$H$_4$)-phenylamido)ZrCl$_2$ (14d) | N |
| 14e | 14 | Me$_2$Si($\eta^5$-Me$_4$Cp)($\eta^1$-4-(4-MeOC$_6$H$_4$)-phenylamido)ZrCl$_2$ (14e) | N |
| 14f | 14 | Me$_2$Si($\eta^5$-Me$_4$Cp)($\eta^1$-4-(3-CF$_3$C$_6$H$_4$)-phenylamido)ZrCl$_2$ (14f) | N |
| 14g | 14 | Me$_2$Si($\eta^5$-Me$_4$Cp)($\eta^1$-4-(4-FC$_6$H$_4$)-phenylamido)ZrCl$_2$ (14g) | N |
| 14h | 14 | Me$_2$Si($\eta^5$-Me$_4$Cp)($\eta^1$-4-(2,4,6-tri-Me—C$_6$H$_2$)-phenylamido)ZrCl$_2$ (14h) | N |
| 15a | 15 | rac-Me$_2$Si($\eta^5$-4-Ph-6-isopropyl-2-Me-inden-1-yl)$_2$ZrCl$_2$ (15a) | N |
| 15a2 | 15 | rac-Me$_2$Si($\eta^5$-4-Ph-6-isopropyl-2-Me-inden-1-yl)$_2$ZrCl$_2$ (15a) | S |
| 16a | 16 | rac-Me$_2$Si($\eta^5$-3-(4-MeC$_6$H$_4$)-2,5-di-Me-cyclopenta[b]thien-6-yl)$_2$ZrCl$_2$ (16a) | N |

TABLE 1-continued

Precatalyst Prepared from Halogen-Substituted Metallocenes

| Ex. | Prec.[a] | Precatalyst | Rxn[b] |
|---|---|---|---|
| 16b | 16 | rac-Me$_2$Si($\eta^5$-3-(3-MeC$_6$H$_4$)-2,5-di-Me-cyclopenta[b]thien-6-yl)ZrCl$_2$ (16b) | N |
| 16c | 16 | rac-Me$_2$Si($\eta^5$-3-(2-MeC$_6$H$_4$)-2,5-di-Me-cyclopenta[b]thien-6-yl)ZrCl$_2$ (16c) | N |
| 16d | 16 | rac-Me$_2$Si($\eta^5$-3-(4-FC$_6$H$_4$)-2,5-di-Me-cyclopenta[b]thien-6-yl)ZrCl$_2$ (16d) | N |
| 16e | 16 | rac-Me$_2$Si($\eta^5$-3-(3-CF$_3$C$_6$H$_4$)-2,5-di-Me-cyclopenta[b]thien-6-yl)ZrCl$_2$ (16e) | N |
| 16f | 16 | rac-Me$_2$Si($\eta^5$-3-(4-Me$_2$NC$_6$H$_4$)-2,5-di-Me-cyclopenta[b]thien-6-yl)ZrCl$_2$ (16f) | N |
| 17a | 17 | Me$_2$Si($\eta^5$-2,4-di-Me-inden-1-yl)($\eta^1$-tert-butylamido)TiCl$_2$ (17a) | N |
| 17b | 17 | Me$_2$Si($\eta^5$-2-Me-4-(4-MeC$_6$H$_4$)-inden-1-yl)($\eta^1$-tert-butylamido)TiCl$_2$ (17b) | N |
| 17c | 17 | Me$_2$Si($\eta^5$-2-Me-4-(2-MeC$_6$H$_4$)-inden-1-yl)($\eta^1$-tert-butylamido)TiCl$_2$ (17c) | N |
| 17d | 17 | Me$_2$Si($\eta^5$-2-Me-4-(2,4,6-tri-Me—C$_6$H$_2$)-inden-1-yl)($\eta^1$-tert-butylamido)TiCl$_2$ (17d) | N |
| 17e | 17 | Me$_2$Si($\eta^5$-2-Me-4-(2,5-di-Me—C$_6$H$_3$)-inden-1-yl)($\eta^1$-tert-butylamido)TiCl$_2$ (17e) | N |
| 17f | 17 | Me$_2$Si($\eta^5$-2-Me-4-(3-CF$_3$C$_6$H$_4$)-inden-1-yl)($\eta^1$-tert-butylamido)TiCl$_2$ (17f) | N |
| 17g | 17 | Me$_2$Si($\eta^5$-2-Me-4-(4-FC$_6$H$_4$)-inden-1-yl)($\eta^1$-tert-butylamido)TiCl$_2$ (17g) | N |
| 17h | 17 | Me$_2$Si($\eta^5$-2-Me-4-(4-Me$_2$NC$_6$H$_4$)-inden-1-yl)($\eta^1$-tert-butylamido)TiCl$_2$ (17h) | N |
| 17i | 17 | Me$_2$Si($\eta^5$-2-Me-4-(2-MeOC$_6$H$_4$)-inden-1-yl)($\eta^1$-tert-butylamido)TiCl$_2$ (17i) | N |
| 18a | 18 | Me$_2$Si($\eta^5$-4,5-dimethylcyclopenta[b]thien-6-yl)($\eta^1$-2,4,6-tri-Me-phenylamido)TiCl$_2$ (18a) | N |
| 18b | 18 | Me$_2$Si($\eta^5$-4,5-dimethylcyclopenta[b]thien-6-yl)($\eta^1$-4-(4-MeC$_6$H$_4$)-2,6-di-Me-phenylamido)TiCl$_2$ (18b) | N |
| 19a | 19 | rac-Me$_2$Si($\eta^5$-4-(4-FC$_6$H$_4$)-2,6-di-Me-inden-1-yl)$_2$ZrCl$_2$ (19a) | N |
| 19b | 19 | rac-Me$_2$Si($\eta^5$-4-(3-CF$_3$C$_6$H$_4$)-2,6-di-Me-inden-1-yl)$_2$ZrCl$_2$ (19b) | N |
| 19c | 19 | rac-Me$_2$Si($\eta^5$-4-(4-MeC$_6$H$_4$)-2,6-di-Me-inden-1-yl)$_2$ZrCl$_2$ (19c) | N |
| 19d | 19 | rac-Me$_2$Si($\eta^5$-4-(2-CF$_3$C$_6$H$_4$)-2,6-di-Me-inden-1-yl)$_2$ZrCl$_2$ (19d) | N |
| 19e | 19 | rac-Me$_2$Si($\eta^5$-4-(2,4-di-CF$_3$—C$_6$H$_3$)-2,6-di-Me-inden-1-yl)$_2$ZrCl$_2$ (19e) | N |
| 20a | 20 | Me$_2$Si($\eta^5$-Me$_4$Cp)($\eta^1$-4-Me-phenylamido)TiCl$_2$ (20a) | N |
| 20b | 20 | Me$_2$Si($\eta^5$-Me$_4$Cp)($\eta^1$-4-(4-MeC$_6$H$_4$)-phenylamido)TiCl$_2$ (20b) | N |
| 21a | 21 | Me$_2$Si($\eta^5$-Me$_4$Cp)($\eta^1$-4-Me-2,6-diisopropylphenylamido)TiCl$_2$ (21a) | N |
| 22a | 22 | rac-Et$_2$Si($\eta^5$-4-(4-FC$_6$H$_4$)-2-Me-inden-1-yl)$_2$ZrCl$_2$ (22a) | N |
| 22b | 22 | rac-Et$_2$Si($\eta^5$-4-(3-CF$_3$C$_6$H$_4$)-2-Me-inden-1-yl)$_2$ZrCl$_2$ (22b) | N |
| 22c | 22 | rac-Et$_2$Si($\eta^5$-4-(4-MeC$_6$H$_4$)-2-Me-inden-1-yl)$_2$ZrCl$_2$ (22c) | N |
| 23a | 23 | Me$_2$Si($\eta^5$-Me$_4$Cp)($\eta^1$-4-(4-MeC$_6$H$_4$)-2,6-di-Me-phenylamido)ZrCl$_2$ (23a) | N |
| 24a | 24 | Me$_2$Si($\eta^5$-4,5-di-Me-cyclopenta[b]thien-6-yl)($\eta^1$-4-(4-MeC$_6$H$_4$)-2,6-di-Me-phenylamido)ZrCl$_2$ (24a) | N |
| 25a | 25 | Me$_2$Si($\eta^5$-4,5-di-Me-cyclopenta[b]thien-6-yl)($\eta^1$-4-Me-2,6-diisopropylphenylamido)ZrCl$_2$ (25a) | N |
| 25b | 25 | Me$_2$Si($\eta^5$-4,5-di-Me-cyclopenta[b]thien-6-yl)($\eta^1$-4-(4-MeC$_6$H$_4$)-2,6-diisopropylphenylamido)ZrCl$_2$ (25b) | N |
| 26a | 26 | Me$_2$Si($\eta^5$-4,5-di-Me-cyclopenta[b]thien-6-yl)($\eta^1$-4-Me-2,6-diisopropylphenylamido)TiCl$_2$ (26a) | N |
| 26b | 26 | Me$_2$Si($\eta^5$-4,5-di-Me-cyclopenta[b]thien-6-yl)($\eta^1$-4-(4-MeC$_6$H$_4$)-2,6-diisopropylphenylamido)TiCl$_2$ (26b) | N |
| 26c | 26 | Me$_2$Si($\eta^5$-4,5-di-Me-cyclopenta[b]thien-6-yl)($\eta^1$-4-(3-CF$_3$C$_6$H$_4$)-2,6-diisopropylphenylamido)TiCl$_2$ (26c) | N |
| 26d | 26 | Me$_2$Si($\eta^5$-4,5-di-Me-cyclopenta[b]thien-6-yl)($\eta^1$-4-(4-Me$_2$NC$_6$H$_4$)-2,6-diisopropylphenylamido)TiCl$_2$ (26d) | N |
| 26e | 26 | Me$_2$Si($\eta^5$-4,5-di-Me-cyclopenta[b]thien-6-yl)($\eta^1$-4-(2-benzofuryl)-2,6-diisopropylphenylamido)TiCl$_2$ (26e) | N |
| 27a | 27 | 4,4'-(4-MeC$_6$H$_4$)N-($\eta^5$-2,7-di-Me-indenyl)$_2$ZrCl$_2$ (27a) | N |
| 27b | 27 | 4,4'-(4-MeC$_6$H$_4$)N-($\eta^5$-7-(4-MeC$_6$H$_4$)-2-Me-indenyl)$_2$ZrCl$_2$ (27b) | N |
| 28a | 28 | 4,4'-O-($\eta^5$-2,7-di-Me-indenyl)$_2$ZrCl$_2$ (28a) | N |
| 28b | 28 | 4,4'-O-($\eta^5$-7-(4-MeC$_6$H$_4$)-2-Me-indenyl)$_2$ZrCl$_2$ (28b) | N |
| 28c | 28 | 4,4'-O-($\eta^5$-7-(4-Me$_2$NC$_6$H$_4$)-2-Me-indenyl)$_2$ZrCl$_2$ (28c) | N |
| 28d | 28 | 4,4'-O-($\eta^5$-7-(2-benzofuryl)-2-Me-indenyl)$_2$ZrCl$_2$ (28d) | N |
| 28e | 28 | 4,4'-O-($\eta^5$-7-(2-benzothienyl)-2-Me-indenyl)$_2$ZrCl$_2$ (28e) | N |
| 29a | 29 | ($\eta^5$-4-(4-Me$_2$NC$_6$H$_4$)-6-Cl-indenyl)($\eta^5$-Me$_5$Cp)$_2$ZrCl$_2$ (29a) | N |
| 30a | 30 | rac-Me$_2$Si($\eta^5$-4-(2-PhC$_6$H$_4$)-2-isopropylinden-1-yl)$_2$ZrCl$_2$ (30a) | N |
| 31a | 31 | Me$_2$C($\eta^5$-4-(2-CF$_3$C$_6$H$_4$)-3-methylinden-1-yl)($\eta^5$-Cp)ZrCl$_2$ (31a) | N |
| 31b | 31 | Me$_2$C($\eta^5$-4-(4-Me$_2$NC$_6$H$_4$)-3-methylinden-1-yl)($\eta^5$-Cp)ZrCl$_2$ (31b) | N |
| 31c | 31 | Me$_2$C($\eta^5$-4-(4-FC$_6$H$_4$)-3-methylinden-1-yl)($\eta^5$-Cp)ZrCl$_2$ (31c) | N |
| 31d | 31 | Me$_2$C($\eta^5$-4-(3-CF$_3$C$_6$H$_4$)-3-methylinden-1-yl)($\eta^5$-Cp)ZrCl$_2$ (31d) | N |
| 31e | 31 | Me$_2$C($\eta^5$-4-(2,4-di-CF$_3$—C$_6$H$_3$)-3-methylinden-1-yl)($\eta^5$-Cp)ZrCl$_2$ (31e) | N |
| 32a | 32 | Me$_2$C($\eta^5$-2,7-di-(4-FC$_6$H$_4$)-fluoren-9-yl)($\eta^5$-Cp)ZrCl$_2$ (32a) | N |
| 33a | 33 | Me$_2$Si($\eta^5$-Me$_4$Cp)($\eta^1$-2,4,6-tri-Me-phenylamido)TiCl$_2$ (33a) | N |
| 34a | 34 | ($\eta^5$-4,7-di-(3-CF$_3$C$_6$H$_4$)-inden-1-yl)($\eta^5$-Me$_5$Cp)ZrCl$_2$ (34a) | N |
| 35a | 29a* | ($\eta^5$-4-(4-Me$_2$NC$_6$H$_4$)-6-(2-CF$_3$C$_6$H$_4$)-indenyl)($\eta^5$-Me$_5$Cp)$_2$ZrCl$_2$ (35a) | N |

[a]Halogen-substituted precursor.
[b]Indicates the type of reaction used to prepare the precatalsyts where N is the Negishi cross-coupling reaction, S is the Suzuki-Miyaura cross-coupling reaction, and H is the Heck cross-coupling reaction.
29a* is ($\eta^5$-4-(4-Me$_2$NC$_6$H$_4$)-6-Cl-indenyl)($\eta^5$-Me$_5$Cp)$_2$ZrCl$_2$, the product of reaction 29a in this table.

Examples showing how these cross-coupling reactions were carried out follow.

EXAMPLES 1a-1p

Negishi coupling applying ($\eta^5$-2-methyl-4-bromoindenyl)($\eta^5$-pentamethylcyclopentadienyl)zirconium dichloride (1)

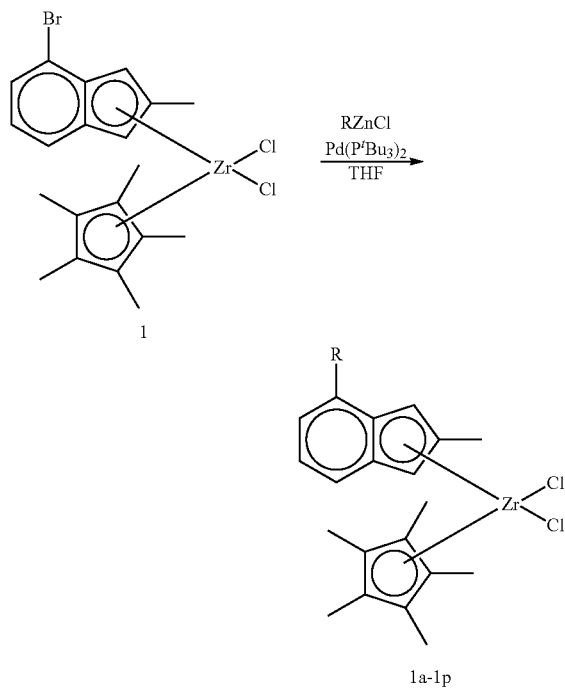

R = Me(1a), C$_6$H$_5$(1b), 4-MeC$_6$H$_4$(1c), 3-MeC$_6$H$_4$(1d),
2-MeC$_6$H$_4$(1e), 4-$^t$BuC$_6$H$_4$(1f), 4-FC$_6$H$_4$(1g), 3-CF$_3$C$_6$H$_4$(1h),
2-MeOC$_6$H$_4$(1i), 4-biphenyl(1k), 1-naphthyl(1l), 2-thienyl(1m),
2-benzothienyl(1n), 2-furyl(1o), 2-benzofuryl(1p).

EXAMPLE 1a ($\eta^5$-2,4-dimethylindenyl)($\eta^5$-pentamethylcyclopentadienyl)zirconium dichloride (1a)

In a 16 ml vial equipped with a PTFE coated stir bar, to a suspension of 300 mg (0.59 mmol) of 1 in 8.0 ml of THF, 0.39 ml of 2.0 M MeZnCl (0.78 mmol) in THF and 0.59 ml of 0.02 M (0.012 mmol) Pd(P$^t$Bu$_3$)$_2$ in THF were added by a dosing pipette. The reaction mixture was stirred for 4 hours at room temperature and then evaporated to dryness. To the residue, a solution of 1.0 ml of MeSiCl$_3$ in 10 ml of dry dichloromethane was added to eliminate an excess of the organozinc reagent. The resulting mixture was stirred at ambient temperature for 1 hour and then evaporated to dryness. In order to eliminate THF contamination, the residue was treated with hot toluene (20 ml), then, the suspension was evaporated to dryness. The residue was additionally treated with 60 ml of hot toluene, and the resulting suspension was filtered through Celite 503. The toluene extract was evaporated to dryness. The obtained solid was washed with 3×15 ml of hexanes and dried in vacuum. Yield 144 mg (54%) of yellowish solid.

Anal. calc. for C$_{21}$H$_{26}$Cl$_2$Zr: C, 57.25; H, 5.95. Found: C, 57.30; H, 5.99. $^1$H NMR (C$_6$D$_6$): δ 6.99 (m, 1H, 5-H in indenyl), 6.90 (m, 1H, 7-H in indenyl), 6.82 (dd, J=8.2 Hz, J=6.7 Hz, 1H, 6-H in indenyl), 6.54 (m, 1H, 1-H in indenyl), 5.57 (d, J=2.2 Hz, 1H, 3-H in indenyl), 2.43 (s, 3H, 4-Me in indenyl), 2.05 (s 3H, 2-Me in indenyl), 1.77 (s, 15H, C$_5$M$_5$). $^{13}$C{$^1$H} NMR (C$_6$D$_6$): δ 135.7, 134.8, 132.4, 125.4, 125.2, 124.6, 120.9, 119.1, 111.1, 100.9, 20.1, 16.8, 12.7.

EXAMPLE 1c ($\eta^5$-2-methyl-4-p-tolylindenyl)($\eta^5$-pentamethylcyclopentadienyl)zirconium dichloride (1c)

In a 16 ml vial equipped with a PTFE coated stir bar, 0.79 ml of 1.0 M (0.79 mmol) p-tolylmagnesium bromide in THF was added by a dosing pipette to a mixture of 1.73 ml of 0.5 M (0.87 mmol) ZnCl$_2$ in THF and 5 ml of THF by vigorous stirring at ambient temperature. This organozinc reagent was additionally stirred for 1 hour and then added to a mixture of 306 mg (0.61 mmol) of 1, 0.61 ml of 0.02 M (0.012 mmol) Pd(P$^t$Bu$_3$)$_2$ in THF, and 2 ml of THF placed in a separate 16 ml vial equipped with a PTFE coated stir bar. The reaction mixture was stirred for 4 hours at room temperature and then evaporated to dryness. To the residue, a solution of 1.0 ml of MeSiCl$_3$ in 10 ml of dry dichloromethane was added to eliminate an excess of the organozinc reagent. The resulting mixture was stirred at ambient temperature for 1 hour and then evaporated to dryness. In order to eliminate THF contamination, the residue was treated with hot toluene (20 ml). The suspension was evaporated to dryness. The residue was additionally treated with 60 ml of hot toluene, and the suspension formed was filtered through Celite 503. The toluene extract was evaporated to dryness. The obtained solid was washed with 3×15 ml of hexanes and dried in vacuum. Yield 261 mg (83%) of yellowish solid.

Anal. calc. for C$_{27}$H$_{30}$Cl$_2$Zr: C, 62.77; H, 5.85. Found: C, 62.86; H, 5.92. $^1$H NMR (CD$_2$Cl$_2$): δ 7.54 (m, 2H, 3,5-H in p-tolyl), 7.31 (dt, J=8.4 Hz, J=0.9 Hz, 1H, 7-H in indenyl), 7.24 (m, 2H, 2,6-H in p-tolyl), 7.21 (dd, J=7.0 Hz, J=0.9 Hz, 1H, 5-H in indenyl), 7.07 (dd, J=8.4 Hz, J=7.0 Hz, 1H, 6-H in indenyl), 6.69 (m, 1H, 1-H in indenyl), 6.19 (m, 1H, 3-H in indenyl), 2.37 (s, 3H, 4-Me in p-tolyl), 2.15 (s, 3H, 2-Me in indenyl), 1.97 (s, 15H, C$_5$Me$_5$). $^{13}$C{$^1$H} NMR (CD$_2$Cl$_2$): δ 139.2, 139.1, 138.5, 133.6, 132.4, 130.7, 130.2, 126.9, 126.6, 126.4, 122.3, 115.7, 107.3, 102.3, 22.5, 17.3, 13.9.

EXAMPLE 1c'

($\eta^5$-2-methyl-4-p-tolylindenyl)($\eta^5$-pentamethylcyclopentadienyl)zirconium dichloride (1c)

In a 16 ml vial equipped with a PTFE coated stir bar, 0.79 ml of 1.0 M (0.79 mmol) p-tolylmagnesium bromide in THF was added by a dosing pipette to a mixture of 1.73 ml of 0.5 M (0.87 mmol) ZnCl$_2$ in THF and 5 ml of THF by vigorous stirring at ambient temperature. This organozinc reagent was additionally stirred for 1 hour and then added to a mixture of 306 mg (0.61 mmol) of 1, 9 mg (0.012 mmol) of NiBr$_2$(PPh$_3$)$_2$, and 3 ml of THF placed in a separate 16 ml vial equipped with a PTFE coated stir bar. The reaction mixture was stirred for 48 hours at room temperature and then evaporated to dryness. To the residue, a solution of 1.0 ml of MeSiCl$_3$ in 10 ml of dry dichloromethane was added to eliminate an excess of the organozinc reagent. The resulting mixture was stirred at ambient temperature for 1 hour and then evaporated to dryness. In order to eliminate THF contamination, the residue was treated with hot toluene (20 ml). The suspension was evaporated to dryness. The residue was additionally treated with 60 ml of hot toluene, and the suspension formed was filtered through Celite 503. The toluene extract was evaporated to dryness. The obtained solid was washed with 3×15 ml of hexanes and dried in vacuum. Yield 277 mg (88%) of yellowish solid of 1c. $^1$H and $^{13}$C{$^1$H} NMR spectra were identical to those for the sample obtained in the example 1c above.

Anal. calc. for $C_{27}H_{30}Cl_2Zr$: C, 62.77; H, 5.85. Found: C, 62.86; H, 5.92.

EXAMPLE 1b ($\eta^5$-2-methyl-4-phenylindenyl)($\eta^5$-pentamethylcyclopentadienyl)zirconium dichloride (1b)

Following the procedure described for 1c, 0.90 ml of 1.0 M (0.90 mmol) phenylmagnesium bromide in TBF, 1.98 ml of 0.5 M (0.99 mmol) $ZnCl_2$ in THF, 350 mg (0.69 mmol) of 1, and 0.69 ml of 0.02 M (0.014 mmol) Pd(P$^t$Bu$_3$)$_2$ in THF gave yellowish solid. Yield 290 mg (83%).

Anal. calc. for $C_{26}H_{28}Cl_2Zr$: C, 62.13; H, 5.61. Found: C, 62.34; H, 5.71. $^1$H NMR (CD$_2$Cl$_2$): δ 7.62-7.69 (m, 2H, 2,6-H in Ph), 7.28-7.47 (m, 4H, 7-H in indenyl and 3,4,5-H in Ph), 7.23 (dd, J=7.0 Hz, J=0.9 Hz, 1H, 5-H in indenyl), 7.08 (dd, J=8.5 Hz, J=7.0 Hz, 1H, 6-H in indenyl), 6.70 (m, 1H, 1-H in indenyl), 6.21 (d, J=2.3 Hz, 1H, 3-H in indenyl), 2.05 (s, 3H, 2-Me in indenyl), 1.88 (s, 15H, C$_5$M$_5$). $^{13}$C{$^1$H} NMR (CD$_2$Cl$_2$): δ 142.6, 140.3, 134.7, 133.7, 131.5, 131.2, 130.3, 128.1, 128.0, 127.7, 123.8, 123.7, 116.9, 103.6, 18.5, 15.1.

EXAMPLES 1b2

Suzuki-Miyaura reaction of metallocene 1 to produce ($\eta^5$-2-methyl-4-phenylindenyl)($\eta^5$-pentamethylcyclopentadienyl)zirconium dichloride (1b)

In a 16 ml vial equipped with PTFE coated stir bar, to a solution of 200 mg (0.40 mmol) of 1 in 10 ml of toluene, 153 mg (0.45 mmol) of NaBPh$_4$ and 4 mg (0.008 mmol) of Pd(P$^t$Bu$_3$)$_2$ were added. The reaction mixture was stirred for 12 hours at 90° C. The obtained suspension was filtered through Celite 503. Crystals that precipitated from the filtrate at −30° C. were collected, washed with 5 ml of hexanes, and dried in vacuum. Yield 130 mg (65%) of yellowish solid.

Anal. calc. for $C_{26}H_{28}Cl_2Zr$: C, 62.13; H, 5.61. Found: C, 62.29; H, 5.70. $^1$H NMR (CD$_2$Cl$_2$): δ 7.62-7.69 (m, 2H, 2,6-H in Ph), 7.28-7.47 (m, 4H, 7-H in indenyl and 3,4,5-H in Ph), 7.23 (dd, J=7.0 Hz, J=0.9 Hz, 1H, 5-H in indenyl), 7.08 (dd, J=8.5 Hz, J=7.0 Hz, 1H, 6-H in indenyl), 6.70 (m, 1H, 1-H in indenyl), 6.21 (d, J=2.3 Hz, 1H, 3-H in indenyl), 2.05 (s, 3H, 2-Me in indenyl), 1.88 (s, 15H, C$_5$M$_5$). $^{13}$C{$^1$H} NMR (CD$_2$Cl$_2$): δ 142.6, 140.3, 134.7, 133.7, 131.5, 131.2, 130.3, 128.1, 128.0, 127.7, 123.8, 123.7, 116.9, 103.6, 18.5, 15.1.

EXAMPLE 1d ($\eta^5$-2-methyl-4-m-tolylindenyl)($\eta^5$-pentamethylcyclopentadienyl)zirconium dichloride (1d)

Following the procedure described for 1c, 0.90 ml of 1.0 M (0.90 mmol) m-tolylmagnesium chloride in THF, 1.98 ml of 0.5 M (0.99 mmol) $ZnCl_2$ in THF, 350 mg (0.69 mmol) of 1, and 0.69 ml of 0.02 M (0.014 mmol) Pd(P$^t$Bu$_3$)$_2$ in THF gave yellowish solid. Yield 272 mg (76%).

Anal. calc. for $C_{27}H_{30}Cl_2Zr$: C, 62.77; H, 5.85. Found: C, 62.95; H, 6.00. $^1$H NMR (CD$_2$Cl$_2$): δ 7.27-7.48 (m, 4H, 2,4,5,6-H in m-tolyl), 7.22 (dd, J=7.1 Hz, J=1.0 Hz, 1H, 5-H in indenyl), 7.16 (m, 1H, 7-H in indenyl), 7.07 (dd, J=8.4 Hz, J=7.1 Hz, 1H, 6-H in indenyl), 6.70 (m, 1H, 1-H in indenyl), 6.20 (d, J=2.2 Hz, 1H, 3-H in indenyl), 2.38 (s, 3H, 3-Me im m-tolyl), 2.15 (s, 3H, 2-Me in indenyl), 1.97 (s, 15H, C$_5$Me$_5$).

EXAMPLE 1e ($\eta^5$-2-methyl-4-o-tolylindenyl)($\eta^5$-pentamethylcyclopentadienyl-$\eta^5$)zirconium dichloride (1e)

Following the procedure described for 1c, 0.59 ml of 0.83 M (0.49 mmol) o-tolylmagnesium bromide in THF, 1.08 ml of 0.5 M (0.54 mmol) $ZnCl_2$ in THF, 190 mg (0.38 mmol) of 1, and 0.38 ml of 0.02 M (0.008 mmol) Pd(P$^t$Bu$_3$)$_2$ in THF gave yellowish solid. Yield 150 mg (77%).

Anal. calc. for $C_{27}H_{30}Cl_2Zr$: C, 62.77; H, 5.85. Found: C, 62.85; H, 5.97. $^1$H NMR (CD$_2$Cl$_2$): δ 7.65 (br.s, 1H, 5-H in indenyl), 7.32 (m, 1H, 7-H in indenyl), 7.16-7.27 (m, 3H, 3,4,5-H in o-tolyl), 7.03-7.14 (m, 2H, 6-H in indenyl and 6-H in o-tolyl), 6.28 (br.s, 1H, 1-H in indenyl), 6.19 (d, J=2.3 Hz, 1H, 3-H in indenyl), 2.13 (s, 3H, 2-Me in o-tolyl), 2.02 (s, 3H, 2-Me in indenyl), 1.98 (s, 15H, C$_5$Me$_5$). $^{13}$C{$^1$H} NMR (CD$_2$Cl$_2$): δ 138.3, 137.6, 137.4, 131.7 (br.s), 131.5, 131.4, 130.8, 130.6, 129.7, 129.0, 128.7, 128.3, 127.1, 126.7, 126.4, 122.6, 21.5, 17.3, 14.0.

EXAMPLE 1f

[$\eta^5$-2-methyl-4-(4-tert-butylphenyl)indenyl]($\eta^5$-pentamethylcyclopentadienyl)zirconium dichloride (1f)

Following the procedure described for 1c, 1.14 ml of 0.80 M (0.91 mmol) 4-tert-butylphenylmagnesium bromide in ether, 2.00 ml of 0.5 M (1.00 mmol) $ZnCl_2$ in TBF, 354 mg (0.70 mmol) of 1, and 0.70 ml of 0.02 M (0.014 mmol) Pd(P$^t$Bu$_3$)$_2$ in THF gave yellowish solid. Yield 327 mg (84%).

Anal. calc. for $C_{30}H_{36}Cl_2Zr$: C, 64.49; H, 6.49. Found: C, 64.72; H, 6.62. $^1$H NMR (CD$_2$Cl$_2$): δ 7.60 (m, 2H, 2,6-H in C$_6$H$_4$), 7.46 (m, 2H, 3,5-H in C$_6$H$_4$), 7.31 (dt, J=8.4 Hz, J=0.9 Hz, 1H, 7-H in indenyl), 7.22 (dd, J=7.0 Hz, J=0.9 Hz, 1H, 5-H in indenyl), 7.07 (dd, J=8.4 Hz, J=7.0 Hz, 1H, 6-H in indenyl), 6.72 (m, 1H, 1-H in indenyl), 6.20 (d, J=2.2 Hz, 1H, 3-H in indenyl), 2.15 (s, 3H, 2-Me in indenyl), 1.97 (s, 15H, C$_5$Me$_5$), 1.33 (s, 9H, $^t$Bu). $^{13}$C{$^1$H} NMR (CD$_2$Cl$_2$): δ 138.0, 137.9, 137.3, 132.3, 131.2, 129.3, 128.8, 125.9, 125.6, 125.3, 121.3, 121.1, 114.7, 101.1, 34.9, 31.5, 16.1, 12.8.

EXAMPLE 1g

[$\eta^5$-2-methyl-4-(4-fluorophenyl)indenyl]($\eta^5$-pentamethylcyclopentadienyl)zirconium dichloride (1g)

Following the procedure described for 1c, 0.65 ml of 1.18 M (0.77 mmol) 4-fluorophenylmagnesium bromide in THF, 1.70 ml of 0.5 M (0.75 mmol) $ZnCl_2$ in THF, 300 mg (0.59 mmol) of 1, and 0.59 ml of 0.02 M (0.012 mmol) Pd(P$^t$Bu$_3$)$_2$ in THF gave yellowish solid. Yield 271 mg (87%).

Anal. calc. for $C_{26}H_{27}Cl_2FZr$: C, 59.98; H, 5.23. Found: C, 60.03; H, 5.32. $^1$H NMR (CD$_2$Cl$_2$): δ 7.65 (m, 2H, 2,6-H in C$_6$H$_4$), 7.35 (m, 1H, 5-H in indenyl), 7.02-7.23 (m, 4H, 6,7-H in indenyl and 3,5-H in C$_6$H$_4$), 6.65 (m, 1H, 1-H in indenyl), 6.21 (d, J=2.2 Hz, 1H, 3-H in indenyl), 2.16 (s, 3H, 2-Me in indenyl), 1.99 (s, 15H, C$_5$Me$_5$). $^{13}$C{$^1$H} NMR (CD$_2$Cl$_2$): δ

138.2, 133.6, 132.7, 132.1, 132.0, 127.0, 126.8, 126.6, 123.0, 122.8, 122.5, 117.0, 116.8, 102.4, 17.4, 14.0.

EXAMPLE 1h

[$\eta^5$-2-methyl-4-(3-trifluoromethylphenyl)indenyl] ($\eta^5$-pentamethylcyclopentadienyl) zirconium dichloride (1h)

Following the procedure described for 1c, 0.76 ml of 1.02 M (0.78 mmol) 3-trifluoromethylphenylmagnesium bromide in THF, 1.70 ml of 0.5 M (0.85 mmol) $ZnCl_2$ in THF, 300 mg (0.59 mmol) of 1, and 0.59 ml of 0.02 M (0.012 mmol) Pd(P$^t$Bu$_3$)$_2$ in THF gave yellowish solid. Yield 245 mg (72%).

Anal. calc. for $C_{27}H_{27}Cl_2F_3Zr$: C, 56.83; H, 4.77. Found: C, 56.84; H, 4.88. $^1$H NMR (CD$_2$Cl$_2$): δ 7.92 (m, 2H, 2,6-H in C$_6$H$_4$), 7.68 (m, 2H, 5,4-H in C$_6$H$_4$), 7.38 (m, 1H, 5-H in indenyl), 7.26 (m, 1H, 7-H in indenyl), 7.11 (dd, J=8.4 Hz, J=7.0 Hz, 6-H in indenyl), 6.64 (m, 1H, 1-H in indenyl), 6.23 (d, J=2.1 Hz, 3-H in indenyl), 2.17 (s, 3H, 2-Me in indenyl), 1.98 (s, 15H, C$_5$Me$_5$).

EXAMPLE 1i

[$\eta^5$-2-methyl-4-(2-methoxyphenyl)indenyl]($\eta^5$-pentamethylcyclopentadienyl)zirconium dichloride (1i)

Following the procedure described for 1c, 0.42 ml of 0.86 M (0.36 mmol) 2-methoxyphenylmagnesium bromide in THF, 0.79 ml of 0.5 M (0.40 mmol) $ZnCl_2$ in THF, 140 mg (0.69 mmol) of 1, and 0.28 ml of 0.02 M (0.013 mmol) Pd(P$^t$Bu$_3$)$_2$ in THF gave yellowish solid. Yield 40 mg (27%).

Anal. calc. for $C_{27}H_{30}Cl_2OZr$: C, 60.88; H, 5.68. Found: C, 61.01; H, 5.75. $^1$H NMR (CD$_2$Cl$_2$): δ 7.65 (dd, J=7.6 Hz, J=1.8 Hz, 1H, 3-H in C$_6$H$_4$), 7.30-7.37 (m, 2H, 5,6-H in C$_6$H$_4$), 7.22 (dd, J=7.0 Hz, J=1.0 Hz, 1H, 5-H in indenyl), 7.07 (dd, J=8.4 Hz, J=7.0 Hz, 1H, 6-H in indenyl), 7.02 (dt, J=7.6 Hz, J=1.1 Hz, 1H, 4-H in C$_6$H$_4$), 6.98 (dd, J=8.4 Hz, J=1.0 Hz, 1H, 7-H in indenyl), 6.37 (m, 1H, 1-H in indenyl), 6.17 (dd, J=2.3 Hz, J=0.5 Hz, 1H, 3-H), 3.70 (s, 3H, OMe), 2.14 (s, 3H, 2-Me in indenyl), 1.97 (s, 15H, C$_5$Me$_5$). $^{13}$C{$^1$H} NMR (CD$_2$Cl$_2$): δ 135.8, 134.7, 133.1, 132.9, 132.4, 132.1, 130.6, 130.09, 129.8, 126.83, 126.3, 122.7, 122.1, 118.4, 112.5, 101.9, 56.9, 17.3, 13.9.

EXAMPLE 1k

[$\eta^5$-2-methyl-4-(4-biphenyl)indenyl]($\eta^5$-pentamethylcyclopentadienyl)zirconium dichloride (1k)

Following the procedure described for 1c, 1.33 ml of 0.31 M (0.41 mmol) 4-biphenylmagnesium bromide in THF, 0.90 ml of 0.5 M (0.45 mmol) $ZnCl_2$ in THF, 350 mg (0.69 mmol) of 1, and 0.69 ml of 0.02 M (0.014 mmol) Pd(P$^t$Bu$_3$)$_2$ in THF gave yellowish solid. Yield 61 mg (33%).

Anal. calc. for $C_{32}H_{32}Cl_2Zr$: C, 66.41; H, 5.57. Found: C, 66.67; H, 5.60. $^1$H NMR (CD$_2$Cl$_2$): δ 7.15-7.84 (m, 11H, C$_6$H$_5$, C$_6$H$_4$ and 5,7-H in indenyl), 7.12 (dd, J=8.4 Hz, J=7.1 Hz, 1H, 6-H in indenyl), 6.79 (m, 1H, 1-H in indenyl), 6.23 (d, J=2.1 Hz, 1H, 3-H in indenyl), 2.19 (s, 3H, 2-Me in indenyl), 2.01 (s, 15H, C$_5$Me$_5$). $^{13}$C{$^1$H} NMR (CD$_2$Cl$_2$): δ 142.7, 142.3, 141.8, 140.5, 138.7, 133.4, 132.6, 130.8, 130.4, 130.3, 128.8, 128.7, 128.6, 126.8, 126.5, 122.7, 115.7, 102.4, 17.4, 14.0.

EXAMPLE 1l

[$\eta^5$-2-methyl-4-(1-naphthyl)indenyl]($\eta^5$-pentamethylcyclopentadienyl)zirconium dichloride (1l)

Following the procedure described for 1c, 2.23 ml of 0.15 M (0.33 mmol) 1-naphthylmagnesium bromide in THF, 0.74 ml of 0.5 M (0.37 mmol) $ZnCl_2$ in THF, 130 mg (0.26 mmol) of 1, and 0.26 ml of 0.02 M (0.005 mmol) Pd(P$^t$Bu$_3$)$_2$ in THF gave yellowish solid. Yield 92 mg (65%).

Anal. calc. for $C_{30}H_{30}Cl_2Zr$: C, 65.19; H, 5.47. Found: C, 65.53; H, 5.56. $^1$H NMR (CD$_2$Cl$_2$): δ 7.10-7.97 (m, 7H, 5,6,7-H in indenyl and naphthyl), 6.22 (dd, J=2.3 Hz, J=0.5 Hz, 1H, 3-H in indenyl), 6.19 (m, 1H, 1-H in indenyl), 2.08 (s, 3H, 2-Me in indenyl), 2.00 (s, 15H, C$_5$Me$_5$). $^{13}$C{$^1$H} NMR (CD$_2$Cl$_2$): δ 139.6, 135.8, 133.1, 133.0, 132.1, 130.52, 130.56 (two resonances), 130.1, 129.8 (two resonances), 126.8, 126.3, 122.7, 122.1, 116.4, 112.5, 101.7, 17.2, 14.0.

EXAMPLE 1m

[$\eta^5$-2-methyl-4-(2-thienyl)indenyl]($\eta^5$-pentamethylcyclopentadienyl)zirconium dichloride (1m)

In a 16 ml vial equipped with a PTFE coated stir bar to 2.16 ml of 0.30 M (0.64 mmol) of thiophene in THF, 1.29 ml of 0.5 M (1.29 mmol) $^n$BuLi in hexanes was added by a dosing pipette by vigorous stirring at −80° C. This mixture was stirred and slowly warmed (for ca. 1 h) to 0° C. Then, 1.42 ml of 0.5 M (0.71 mmol) $ZnCl_2$ in THF was added at −80° C., and the obtained mixture was stirred and slowly warmed to ambient temperature and then evaporated to dryness. In a separate 16 ml vial equipped with a PTFE coated stir bar, to a mixture of 250 mg (0.50 mmol) of 1, 0.50 ml of 0.02 M (0.010 mmol) Pd(P$^t$Bu$_3$)$_2$ in THF, and 4 ml of THF the above described organozinc reagent were added. This mixture was stirred for 4 hours at room temperature and then evaporated to dryness. To the residue, a solution of 1.0 ml of MeSiCl$_3$ in 10 ml of dry dichloromethane was added to eliminate an excess of the organozinc reagent. The resulting mixture was stirred at ambient temperature for 1 hour and then evaporated to dryness. In order to eliminate THF contamination, the residue was treated with hot toluene (20 ml). The suspension was evaporated to dryness. The residue was additionally treated with 60 ml of hot toluene, and the suspension formed was filtered through Celite 503. The toluene extract was evaporated to dryness. The obtained solid was washed with 3×15 ml of hexanes and dried in vacuum. Yield 192 mg (76%) of yellowish solid.

Anal. calc. for $C_{24}H_{26}Cl_2SZr$: C, 56.67; H, 5.15. Found: C, 56.95; H, 5.27. $^1$H NMR (CD$_2$Cl$_2$): δ 7.43 (dd, J=3.6 Hz, J=1.1 Hz, 1H, 5-H in thienyl), 7.30-7.36 (m, 3H, 5,7-H in indenyl and 4-H in thienyl), 7.11 (dd, J=5.1 Hz, J=3.6 Hz, 1H, 3-H in thienyl), 7.03 (dd, J=8.5 Hz, J=7.0 Hz, 1H, 6-H in indenyl), 6.87 (m, 1H, 1-H in indenyl), 6.20 (d, J=2.2 Hz, 1H, 3-H in indenyl), 2.18 (s, 3H, 2-Me in indenyl), 1.96 (s, 15H, $C_5Me_5$). $^{13}C\{^1H\}$ NMR ($CD_2Cl_2$): δ 143.8, 133.0, 132.5, 132.4, 129.3, 129.0, 127.5, 126.8, 126.6, 126.5, 126.3, 122.9, 115.4, 102.7, 17.5, 13.9.

EXAMPLE 1n

[η⁵-2-methyl-4-(2-benzothienyl)indenyl](η⁵-pentamethylcyclopentadienyl)zirconium dichloride (1n)

Following the procedure described for 1m, 2.02 ml of 0.52 M (1.05 mmol) of benzothiophene, 2.11 ml of 0.5 M "BuLi (1.06 mmol), 2.32 ml of 0.5 M (1.16 mmol) $ZnCl_2$ in THF, 410 mg (0.81 mmol) of 1, and 0.81 ml of 0.02 M (0.016 mmol) Pd(P$^t$Bu$_3$)$_2$ in THF gave yellowish solid. Yield 143 mg (31%).

Anal. calc. for $C_{28}H_{28}Cl_2SZr$: C, 60.19; H, 5.05. Found: C, 60.34; H, 5.20. $^1H$ NMR ($CD_2Cl_2$): δ 7.76-7.85 (m, 2H, 4,7-H in benzothienyl), 7.66 (s, 1H, 3-H in benzothienyl), 7.26-7.48 (m, 4H, 5,7-H in indenyl and 5,6-H in benzothienyl), 7.08 (dd, J=8.5 Hz, J=7.1 Hz, 1H, 6-H in indenyl), 6.98 (m, 1H, 1-H in indenyl), 6.23 (d, J=2.1 Hz, 1H, 3-H in indenyl), 2.21 (s, 3H, 2-Me in indenyl), 1.98 (s, 15H, $C_5Me_5$). $^{13}C\{^1H\}$ NMR ($CD_2Cl_2$): δ 142.1, 141.1, 133.4, 132.6, 132.4, 128.9, 127.4, 126.8, 126.0, 125.9, 126.7, 126.4, 125.9, 125.4, 124.1, 123.7, 123.61, 123.58, 115.4, 102.7, 17.5, 14.0.

EXAMPLE 1o

[η⁵-2-methyl-4-(2-furyl)indenyl](η⁵-pentamethylcyclopentadienyl)zirconium dichloride (1o)

Following the procedure described for 1m, 1.19 ml of 0.37 M (0.44 mmol) of furan, 0.88 ml of 0.5 M "BuLi (0.44 mmol), 0.96 ml of 0.5 M (0.48 mmol) $ZnCl_2$ in THF, 170 mg (0.34 mmol) of 1, and 0.34 ml of 0.02 M (0.007 mmol) Pd(P$^t$Bu$_3$)$_2$ in THF gave yellowish solid. Yield 80 mg (48%).

Anal. calc. for $C_{24}H_{26}Cl_2OZr$: C, 58.52; H, 5.32. Found: C, 58.66; H, 5.37. $^1H$ NMR ($CD_2Cl_2$): δ 7.51-7.55 (m, 2H, 5-H in indenyl and 5-H in furyl), 7.32 (dt, J=8.5 Hz, J=0.9 Hz, 1H, 7-H in indenyl), 7.06 (dd, J=8.5 Hz, J=7.2 Hz 1H, 6-H in indenyl), 6.94 (m, 1H, 1-H in indenyl), 6.81 (dd, J=3.4 Hz, J=0.7 Hz, 1H, 4-H in furyl), 6.52 (dd, J=3.4 Hz, J=1.8 Hz, 1H, 3-H in furyl, 6.19 (d, J=2.2 Hz, 1H, 3-H in indenyl), 2.07 (s, 3H, 2-Me in indenyl), 1.94 (s, 15H, $C_5Me_5$).

EXAMPLE 1p

[η⁵-2-methyl-4-(2-benzofuryl)indenyl](η⁵-pentamethylcyclopentadienyl)zirconium dichloride (1p)

Following the procedure described for 1m, 3.10 ml of 0.42 M (1.30 mmol) of benzofuran, 2.62 ml of 0.5 M "BuLi (1.31 mmol), 2.89 ml of 0.5 M (1.45 mmol) $ZnCl_2$ in THF, 510 mg (1.01 mmol) of 1, and 1.01 ml of 0.02 M (0.016 mmol) Pd(P$^t$Bu$_3$)$_2$ in THF gave yellowish solid. Yield 374 mg (68%).

Anal. calc. for $C_{28}H_{28}Cl_2OZr$: C, 61.97; H, 5.20. Found: C, 62.05; H, 5.22. $^1H$ NMR ($C_6D_6$): δ 7.91 (dd, J=7.2 Hz, J=0.8 Hz, 1H, 5-H in indenyl), 7.32-7.41 (m, 3H, 3,4,7-H in benzothienyl), 7.18 (m, 1H, 1-H in indenyl), 7.03-7.08 (m, 3H, 7-H in indenyl and 5,6-H in benzothienyl), 6.92 (dd, J=8.6 Hz, J=7.2 Hz, 1H, 6-H in indenyl), 5.70 (d, J=2.2 Hz, 1H, 3-H in indenyl), 2.05 (s, 3H, 2-Me in indenyl), 1.77 (s, 15H, $C_5Me_5$).

EXAMPLE 1q

Heck reaction of metallocene 1 to produce cis- and trans-isomers of (2-methyl-4-styrylindenyl)(pentamethylcyclopentadienyl)zirconium dichloride (1q)

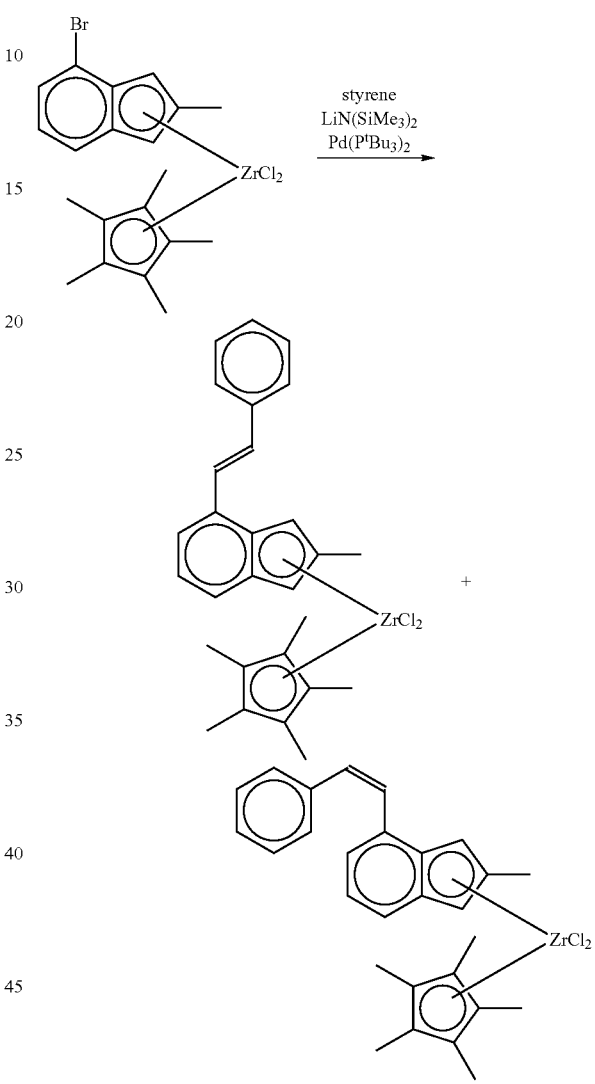

To a solution of 200 mg (0.40 mmol) of 1 in 5 ml of toluene, 45.5 mg (0.45 mmol) of freshly distilled styrene, 199 mg (1.19 mmol) of LiN(SiMe$_3$)$_2$, and 0.40 ml of 0.02 M (0.0079 mmol, 2%) of Pd(P$^t$Bu$_3$)$_2$ in toluene were added. This mixture was stirred for 20 hours at ambient temperature; then, for 20 hours at 90° C. The resulting mixture was evaporated to dryness. To the residue, a solution of 1.0 ml of MeSiCl$_3$ in 10 ml of methylene chloride was added. This mixture was stirred for 1 hour at room temperature, then, evaporated to dryness. To the residue, 20 ml of toluene was added. The resulting mixture was filtered through a glass frit (G4). The filtrate was evaporated to dryness. The crude product was washed with 3×15 ml of hexanes and dried in vacuum. Yield, 170 mg (81%) of yellowish solid. The product is a mixture of trans- and cis-isomers, ca. 3 to 1 based on the NMR spectra.

Anal. calc. for $C_{28}H_{30}Cl_2Zr$: C, 63.61; H, 5.72. Found: C, 63.88; H, 5.80. $^1H$ NMR ($CD_2Cl_2$): δ 7.56-7.61 (m, 2H, 2,6-H in Ph), 7.21-7.45 (m, 6H, 3,4,5-H in Ph and 5,6,7-H in indenyl), 7.03-7.12 (m, 2H, CH=CH), 6.81 and 6.84 (two m, 1H, 3-H in indenyl), 6.19 and 6.22 (two m, 1H, 1-H in indenyl), 2.20-2.25 (m, 3H, 2-Me in indenyl), 1.99-2.07 (m, 15H, $C_5Me_5$).

EXAMPLE 1r

Heck Reaction of Metallocene 1 to Produce trans-(2-methyl4-(4-fluorostyryl)indenyl)(pentamethylcyclopentadienyl)zirconium dichloride (1q)

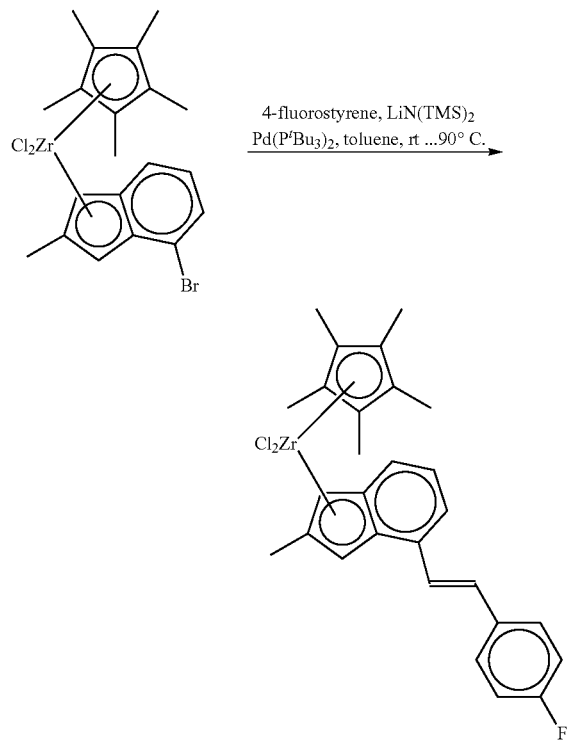

In a 16 ml vial equipped with PTFE coated stir bar, to a solution of 200 mg (0.40 mmol) of 1 in 10 ml of toluene, 58 mg (0.48 mmol) of 4-fluorostyrene, 199 mg (1.19 mmol) of LiN(SiMe$_3$)$_2$, and 0.40 ml (0.008 mmol) of 0.02 M solution of Pd(P$^t$Bu$_3$)$_2$ in toluene were added. The reaction mixture was stirred for 20 h at room temperature and then for 24 h at 90° C. The reaction mixture was cooled to ambient temperature, and 172 mg (1.58 mmol) of Me$_3$SiCl was added. The resulting mixture was stirred for 10 h at room temperature and then evaporated to dryness. The residue was washed with 4×8 ml of hexanes on a glass frit (G4). The combined filtrate was evaporated to dryness, and the residue was dried in vacuum. Yield 66 mg (30%) of yellow solid of pure trans-isomer.

Anal. calc. for $C_{28}H_{29}Cl_2FZr$: C, 61.52; H, 5.35. Found: C, 61.75; H, 5.48. $^1$H NMR (CD$_2$Cl$_2$): δ 7.56 (m, 2H, 3,5-H in C$_6$H$_4$F), 7.41 (m, 1H, 5-H in indenyl), 7.36 (m, 1H, 7-H in indenyl), 7.26 (m, 2H, 2,6-H in C$_6$H$_4$F), 7.10 (m, 1H, 6-H in indenyl), 7.04-7.08 (m, 2H, CH=CH), 6.83 (m, 1H, 1-H in indenyl), 6.19 (d, J=2.1 Hz, 3-H in indenyl), 2.25 (s, 3H, 2-Me in indenyl), 1.99 (s, 15H, $C_5Me_5$).

EXAMPLE 1s

Heck Reaction of Metallocene 1 to Produce cis- and trans-isomers of (2-methyl-4-(1,2-n-butoxyvinyl)indenyl)(pentamethylcyclopentadienyl)zirconium dichloride (1s)

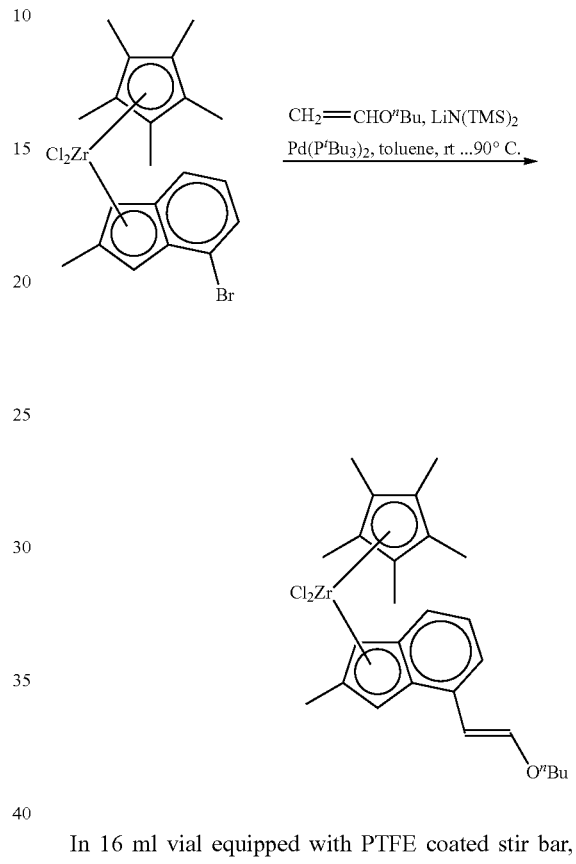

In 16 ml vial equipped with PTFE coated stir bar, to a solution of 200 mg (0.40 mmol) of 1 in 10 ml of toluene, 48 mg (0.48 mmol) of n-butyl vinyl ether, 199 mg (1.19 mmol) of LiN(SiMe$_3$)$_2$, and 0.40 ml (0.008 mmol) of 0.02 M solution of Pd(P$^t$Bu$_3$)$_2$ in toluene were added. The reaction mixture was stirred for 20 h at room temperature and then 20 h at 90° C. The reaction mixture was cooled to ambient temperature, and 172 mg (1.58 mmol) of Me$_3$SiCl was added. The resulting mixture was stirred for 10 h at room temperature and then evaporated to dryness. The residue was washed with 50 ml of hexanes on glass frit (G4). The filtrate was evaporated to dryness, and the residue was dried in vacuum. Yield 82 mg (39%) of yellowish solid of a ca. 1:2 mixture of cis- and trans-isomers.

Anal. calc. for $C_{26}H_{34}Cl_2OZr$: C, 59.52; H, 6.53. Found: C, 59.82; H, 6.69. $^1$H NMR (CD$_2$Cl$_2$): δ 7.27-7.57 (m, 1H, CH=CHOCH$_2$), 6.91-7.24 (m, 3H, 5,6,7-H in indenyl), 6.56-6.63 (m, 1H, 1-H in indenyl), 6.08-6.12 (m, 1H, 3-H in indenyl), 6.01 and 6.43 (two m, 1H, CH=CHOCH$_2$), 3.85-4.04 (m, 2H, OCH$_2$CH$_2$CH$_2$Me), 2.20 and 2.21 (two s, 3H, 2-Me in indenyl), 1.97 and 1.96 (two s, 15H, $C_5Me_5$), 1.71 (m, 2H, OCH$_2$CH$_2$CH$_2$Me), 1.46 (m, 2H, OCH$_2$CH$_2$CH$_2$Me), 0.97 (m, 3H, OCH$_2$CH$_2$CH$_2$Me).

EXAMPLES 2a-2d

Negishi Coupling Applying ($\eta^5$-2-methyl-4-bromoindenyl)($\eta^5$-pentamethylcyclopentadienyl) hafnium dichloride (2)

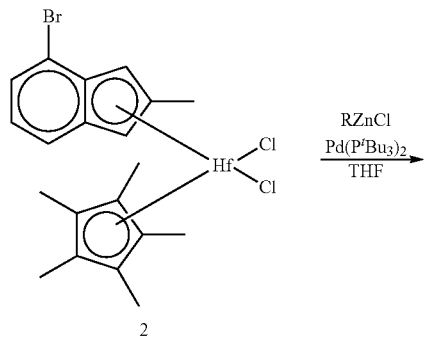

R=Me (2a), 4-MeC$_6$H$_4$ (2b), 3-MeC$_6$H$_4$ (2c), 4-$^t$BuC$_6$H$_4$ (2d).

EXAMPLE 2a

Negishi Reaction of Metallocene 2 to Produce ($\eta^5$-2,4-dimethylindenyl)($\eta^5$-pentamethylcyclopentadienyl) hafnium dichloride (2a)

Following the procedure described for 1a, 600 mg (1.01 mmol) of 2, 0.66 ml of 2.0 M MeZnCl (1.32 mmol) in THF, and 1.01 ml of 0.02 M (0.020 mmol) Pd(P$^t$Bu$_3$)$_2$ in THF gave yellowish solid. Yield 482 mg (90%).

Anal. calc. for C$_{21}$H$_{26}$Cl$_2$Hf: C, 47.79; H, 4.96. Found: C, 47.87; H, 5.02. $^1$H NMR (C$_6$D$_6$): δ 7.02 (m, 1H, 5-H in indenyl), 6.88 (m, 1H, 7-H in indenyl), 6.80 (dd, J=8.2 Hz, J=6.8 Hz, 1H, 6-H in indenyl), 6.45 (m, 1H, 1-H in indenyl), 5.56 (d, J=2.2 Hz, 1H, 3-H in indenyl), 2.42 (s, 3H, 4-Me in indenyl), 2.11 (s 3H, 2-Me in indenyl), 1.85 (s, 15H, C$_5$M$_5$). $^{13}$C{$^1$H} NMR (C$_6$D$_6$): δ 135.3, 134.4, 130.9, 126.3, 125.1, 122.5, 119.5, 119.3, 109.5, 99.0, 20.1, 16.7, 12.5.

EXAMPLE 2b ($\eta^5$-2-methyl-4-p-tolylindenyl)($\eta^5$-pentamethylcyclopentadienyl)hafnium dichloride (2b)

Following the procedure described for 1c, 0.66 ml of 1.0 M (0.66 mmol) p-tolylmagnesium bromide in THF, 1.45 ml of 0.5 M (0.73 mmol) ZnCl$_2$ in THF, 300 mg (0.51 mmol) of 2, and 0.51 ml of 0.02 M (0.010 mmol) Pd(P$^t$Bu$_3$)$_2$ in THF gave yellowish solid. Yield 219 mg (72%).

Anal. calc. for C$_{27}$H$_{30}$Cl$_2$Zr: C, 53.70; H, 5.01. Found: C, 53.96; H, 5.13. $^1$H NMR (CD$_2$Cl$_2$): δ 7.53 (m, 2H, 2,6-H in p-tolyl), 7.31 (dt, J=8.5 Hz, J=0.8 Hz, 1H, 7-H in indenyl), 7.23 (m, 2H, 3,5-H in p-tolyl), 7.18 (dd, J=6.9 Hz, J=0.8 Hz, 1H, 5-H in indenyl), 7.03 (ddd, J=8.5 Hz, J=6.9 Hz, J=0.6 Hz, 1H, 6-H in indenyl), 6.60 (m, 1H, 1-H in indenyl), 6.15 (d, J=2.2 Hz, 1H, 3-H in indenyl), 2.36 (s, 3H, 4-Me in p-tolyl), 2.20 (s, 3H, 2-Me in indenyl), 2.03 (s, 15H, C$_5$Me$_5$).

EXAMPLE 2c ($\eta^5$-2-methyl-4-m-tolylindenyl)($\eta^5$-pentamethylcyclopentadienyl)hafnium dichloride (2c)

Following the procedure described for 1c, 1.10 ml of 1.0 M (1.10 mmol) m-tolylmagnesium chloride in THF, 2.41 ml of 0.5 M (1.21 mmol) ZnCl$_2$ in THF, 500 mg (0.84 mmol) of 2, and 0.84 ml of 0.02 M (0.017 mmol) Pd(P$^t$Bu$_3$)$_2$ in THF gave yellowish solid. Yield 384 mg (75%).

Anal. calc. for C$_{27}$H$_{30}$Cl$_2$Zr: C, 53.70; H, 5.01. Found: C, 54.05; H, 5.22. $^1$H NMR (CD$_2$Cl$_2$): δ 7.27-7.48 (m, 4H, 2,4,5,6-H in m-tolyl), 7.20 (dd, J=7.0 Hz, J=1.0 Hz, 1H, 5-H in indenyl), 7.16 (m, 1H, 7-H in indenyl), 7.04 (dd, J=8.5 Hz, J=7.0 Hz, 1H, 6-H in indenyl), 6.62 (m, 1H, 1-H in indenyl), 6.16 (d, J=2.3 Hz, 1H, 3-H in indenyl), 2.38 (s, 3H, 3-Me im m-tolyl), 2.21 (s, 3H, 2-Me in indenyl), 2.04 (s, 15H, C$_5$Me$_5$). $^{13}$C{$^1$H} NMR (CD$_2$Cl$_2$): δ 140.2, 138.6, 138.0, 132.1, 129.9, 129.6, 128.7, 126.2, 125.6, 125.3, 125.1, 123.6, 123.2 (two resonances), 121.4, 112.9, 99.3, 21.7, 16.1, 12.5.

EXAMPLE 2d

[$\eta^5$-2-methyl-4-(tert-butylphenyl)indenyl]($\eta^5$-pentamethylcyclopentadienyl)hafnium dichloride (2d)

Following the procedure described for 1c, 0.86 ml of 0.80 M (0.69 mmol) 4-tert-butylphenylmagnesium bromide in ether, 1.52 ml of 0.5 M (0.76 mmol) ZnCl$_2$ in THF, 315 mg (0.53 mmol) of 2, and 0.53 ml of 0.02 M (0.011 mmol) Pd(P$^t$Bu$_3$)$_2$ in THF gave yellowish solid. Yield 229 mg (67%).

Anal. calc. for C$_{30}$H$_{36}$Cl$_2$Zr: C, 55.78; H, 5.62. Found: C, 55.91; H, 5.70. $^1$H NMR (CD$_2$Cl$_2$): δ 7.60 (m, 2H, 2,6-H in C$_6$H$_4$), 7.46 (m, 2H, 3,5-H in C$_6$H$_4$), 7.32 (m, 1H, 7-H in indenyl), 7.20 (m, 1H, 5-H in indenyl), 7.04 (dd, J=8.4 Hz, J=7.0 Hz, 1H, 6-H in indenyl), 6.65 (m, 1H, 1-H in indenyl), 6.17 (d, J=2.2 Hz, 1H, 3-H in indenyl), 2.21 (s, 3H, 2-Me in indenyl), 2.05 (s, 15H, C$_5$Me$_5$), 1.34 (s, 9H, $^t$Bu). $^{13}$C{$^1$H} NMR (CD$_2$Cl$_2$): δ 138.8, 138.7, 138.6, 133.3, 130.8, 130.5, 129.9, 129.6, 128.0, 127.0, 124.4, 122.5, 114.2, 100.5, 36.1, 32.7, 17.3, 13.7.

EXAMPLES 3a-3d

Negishi Coupling Applying ($\eta^5$-2-methyl-4-bromoindenyl)($\eta^5$-cyclopentadienyl)zirconium dichloride (3)

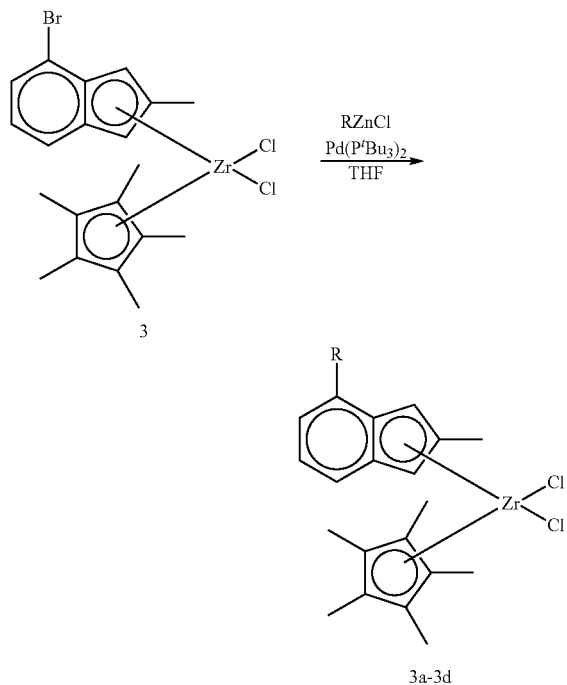

R = Me (3a), C$_6$H$_5$ (3b), 4-MeC$_6$H$_4$ (3c), 3-MeC$_6$H$_4$ (3d).

EXAMPLE 3a ($\eta^5$-2,4-dimethylindenyl)($\eta^5$-cyclopentadienyl)zirconium dichloride (3a)

Following the procedure described for 1a, 300 mg (0.69 mmol) of 3, 0.45 ml of 2.0 M MeZnCl (0.90 mmol) in THF, and 0.69 ml of 0.02 M (0.014 mmol) Pd(P$^t$Bu$_3$)$_2$ in THF gave yellowish solid. Yield 150 mg (59%).

Anal. calc. for C$_{16}$H$_{16}$Cl$_2$Zr: C, 51.88; H, 4.35. Found: C, 52.10; H, 4.47. $^1$H NMR (CD$_2$Cl$_2$): δ 6.99 (dq, J=8.4 Hz, J=1.0 Hz, 1H, 5-H in indenyl), 7.10 (dd, J=8.4 Hz, J=6.9 Hz, 1H, 6-H in indenyl), 6.97 (dt, J=6.9 Hz, J=1.0 Hz 1H, 7-H in indenyl), 6.40 (d, J=2.2 Hz, 1H, 1-H in indenyl), 6.21 (d, J=2.2 Hz, 1H, 3-H in indenyl), 6.05 (s, 5H, C$_5$H$_5$), 2.48 (s, 3H, 4-Me in indenyl), 2.31 (s 3H, 2-Me in indenyl).

EXAMPLE 3b ($\eta^5$-2-methyl-4-phenylindenyl)($\eta^5$-cyclopentadienyl) zirconium dichloride (3b)

Following the procedure described for 1c, 1.10 ml of 1.0 M (1.10 mmol) phenylmagnesium bromide in THF, 2.41 ml of 0.5 M (1.21 mmol) ZnCl$_2$ in THF, 500 mg (0.84 mmol) of 3, and 0.84 ml of 0.02 M (0.017 mmol) Pd(P$^t$Bu$_3$)$_2$ in THF gave yellowish solid. Yield 348 mg (70%).

Anal. calc. for C$_{21}$H$_{18}$Cl$_2$Zr: C, 58.32; H, 4.19. Found: C, 52.68; H, 4.36. $^1$H NMR (CD$_2$Cl$_2$): δ 7.66-7.72 (m, 2H, 2,6-H in Ph), 7.05-7.56 (m, 6H, 5,6,7-H in indenyl and 3,4,5-H in Ph), 6.51 (s, 2H, 1,3-H in indenyl), 6.03 (s, 5H, C$_5$H$_5$), 2.32 (s, 3H, 2-Me in indenyl).

EXAMPLE 3c ($\eta^5$-2-methyl-4-p-tolylindenyl)($\eta^5$-cyclopentadienyl) zirconium dichloride (3c)

Following the procedure described for 1c, 0.66 ml of 1.0 M (0.66 mmol) p-tolylmagnesium bromide in THF, 1.45 ml of 0.5 M (0.73 mmol) ZnCl$_2$ in THF, 300 mg (0.51 mmol) of 3, and 0.51 ml of 0.02 M (0.010 mmol) Pd(P$^t$Bu$_3$)$_2$ in THF gave yellowish solid. Yield 220 mg (72%).

Anal. calc. for C$_{22}$H$_{20}$Cl$_2$Zr: C, 59.18; H, 4.51. Found: C, 59.47; H, 4.68. $^1$H NMR (C$_6$D$_6$): δ 7.50 (m, 2H, 2,6-H in p-tolyl), 7.27 (dt, J=8.4 Hz, J=0.9 Hz, 1H, 7-H in indenyl), 7.08 (m, 2H, 3,5-H in p-tolyl), 7.03 (dd, J=7.0 Hz, J=0.9 Hz, 1H, 5-H in indenyl), 6.90 (dd, J=8.4 Hz, J=7.0 Hz, 1H, 6-H in indenyl), 6.30 (d, J=2.2 Hz, 1H, 1-H in indenyl), 6.17 (d, J=2.2 Hz, 1H, 3-H in indenyl), 5.73 (s, 5H, C$_5$H$_5$), 2.17 (s, 3H, 4-Me in p-tolyl), 2.14 (s, 3H, 2-Me in indenyl).

EXAMPLE 3d ($\eta^5$-2-methyl-4-m-tolylindenyl)($\eta^5$-cyclopentadienyl)zirconium dichloride (3d)

Following the procedure described for 1c, 1.10 ml of 1.0 M (1.10 mmol) m-tolylmagnesium chloride in THF, 2.41 ml of 0.5 M (1.21 mmol) ZnCl$_2$ in THF, 500 mg (0.84 mmol) of 3, and 0.84 ml of 0.02 M (0.017 mmol) Pd(P$^t$Bu$_3$)$_2$ in THF gave yellowish solid. Yield 383 mg (75%).

Anal. calc. for C$_{22}$H$_{20}$Cl$_2$Zr: C, 59.18; H, 4.51. Found: C, 59.31; H, 4.60. $^1$H NMR (CD$_2$Cl$_2$): δ 7.05-7.65 (m, 7H, 5,6,7-H in indenyl and 2,4,5,6-H in m-tolyl), 6.51 (s, 2H, 1,3-H in indenyl), 6.02 (s, 5H, C$_5$H$_5$), 2.43 (s, 3H, 3-Me im m-tolyl), 2.32 (s, 3H, 2-Me in indenyl).

EXAMPLES 4a-4c

Negishi Coupling Applying a Mixture of d-/l-and meso-bis($\eta^5$-2-methyl-4-bromoindenyl) zirconium dichlorides

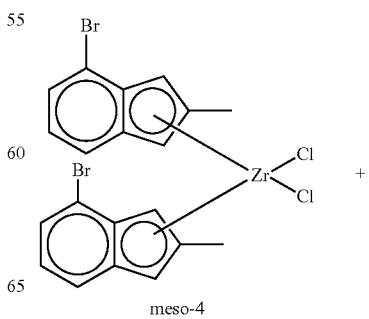

meso-4

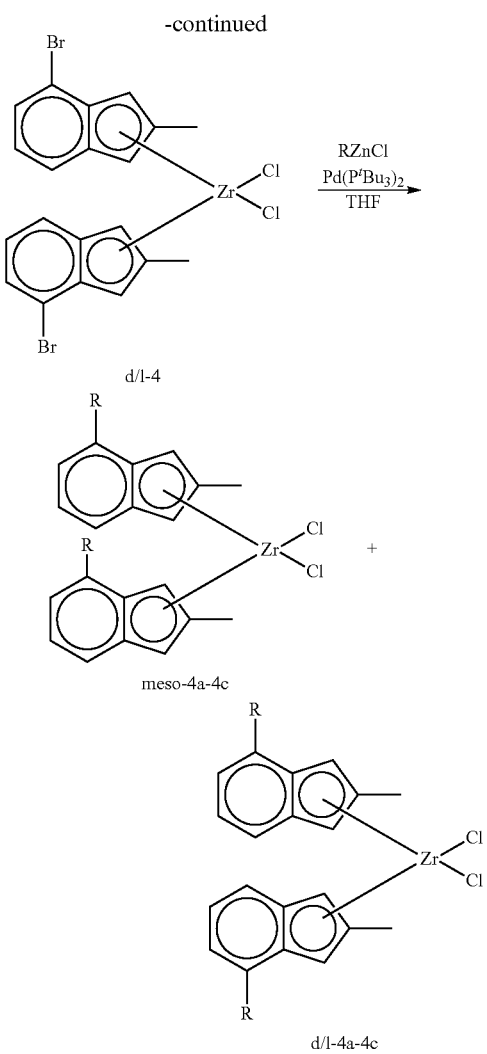

R = Me(4a), 4-MeC₆H₄(4b), 4-ᵗBuC₆H₄(4c).

EXAMPLE 4a

A mixture of d-/l-and meso-bis($\eta^5$-2,4-dimethylindenyl)zirconium dichloride (4a)

Following the procedure described for 1a, 400 mg (0.69 mmol) of a mixture of d/l-and meso-4, 0.90 ml of 2.0 M MeZnCl (1.80 mmol) in THF, and 1.38 ml of 0.02 M (0.028 mmol) Pd(P$^t$Bu$_3$)$_2$ in THF gave a mixture of d/l-and meso-complexes (1:1) for 2 hours at 70° C. Yield 239 mg (77%).

Anal. calc. for $C_{22}H_{22}Cl_2Zr$: C, 58.91; H, 4.94. Found: C, 58.99; H, 4.97. $^1$H NMR (CD$_2$Cl$_2$): δ 7.23 (m, 2H, 5,5'-H), 6.95 (dd, J=8.1 Hz, J=6.9 Hz, 2H, 6,6'-H), 6.89 (dt, J=6.9 Hz, J=1.0 Hz, 2H, 7,7'-H), 6.30 (m, 2H, 1,1'-H), 6.16 (d, J=2.2 Hz, 2H, 3,3'-H), 2.39 (s, 6H, 4,4'-Me), 2.15 (s, 6H, 2,2'-Me).

EXAMPLE 4b

A mixture of d-/l-and meso-bis($\eta^5$-2-methyl-4-p-tolylindenyl)zirconium dichloride (4b)

Following the procedure described for 1c, 1.80 ml of 1.0 M (1.80 mmol) p-tolylmagnesium bromide in THF, 3.96 ml of 0.5 M (1.98 mmol) ZnCl$_2$ in THF, 400 mg (0.69 mmol) a mixture of d/l-and meso-4, and 1.38 ml of 0.02 M (0.028 mmol) Pd(P$^t$Bu$_3$)$_2$ in THF gave a mixture of d/l-and meso-complexes (1:1) for 2 hours at 70° C. Yield 170 mg (41%).

Anal. calc. for $C_{34}H_{30}Cl_2Zr$: C, 67.98; H, 5.03. Found: C, 68.11; H, 5.10. $^1$H NMR (C$_6$D$_6$): δ 7.57-7.68 (m, 4H, 2,2',6,6'-H in p-tolyl), 6.98-7.20 (m, 6H, 7,7'-H in indenyl and 3,3',5,5'-H in p-tolyl), 6.89 (dd, J=8.5 Hz, J=6.9 Hz, 2H, 6,6'-H), 6.54 (d, J=2.2 Hz, 2H, 1,1'-H), 5.87 (d, J=2.2 Hz, 2H, 3,3'-H), 2.15 (s, 6H, 4,4'-Me in p-tolyl), 1.93 (s, 6H, 2,2'-Me in indenyl).

EXAMPLE 4c

A Mixture of d-/l-and meso-bis[$\eta^5$-2-methyl-4-(4-tert-butylphenyl)indenyl]zirconium dichloride (4c)

Following the procedure described for 1c, 1.91 ml of 0.80 M (1.53 mmol) 4-tert-butylphenylmagnesium bromide in ether, 1.68 ml of 0.5 M (0.84 mmol) ZnCl$_2$ in THF, 340 mg (0.59 mmol) a mixture of d/l-and meso-4, and 1.18 ml of 0.02 M (0.024 mmol) Pd(P$^t$Bu$_3$)$_2$ in THF gave of a mixture of d/l-and meso-complexes (1:1) for 2 hours at 70° C. Yield 177 mg (44%).

Anal. calc. for $C_{40}H_{42}Cl_2Zr$: C, 70.15; H, 6.18. Found: C, 70.33; H, 6.25. $^1$H NMR (CD$_2$Cl$_2$): δ 7.06-7.71 (m, 14H, 5,5',6,6',7,7'-H in indenyl and 2,2',3,3',5,5',6,6'-H in C$_6$H$_4$), 6.44 (d, J=2.2 Hz, 2H, 1,1'-H in indenyl), 6.17 (d, J=2.2 Hz, 2H, 3,3'-H in indenyl), 2.06 (s, 6H, 2,2'-Me in indenyl), 1.39 (s, 18H, $^t$Bu).

EXAMPLE 5a

Negishi Reaction of Metallocene 5 to Produce bis($\eta^5$-2-p-tolylindenyl)zirconium dichloride (5a)

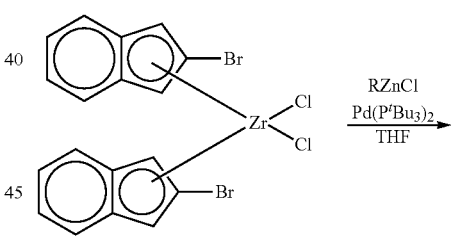

R = 4-MeC₆H₄(5a)

Following the procedure described for 1c, 2.55 ml of 1.0 M (2.55 mmol) p-tolylmagnesium bromide in THF, 5.61 ml of 0.5 M (2.81 mmol) ZnCl$_2$ in THF, 540 mg (0.98 mmol) of 5, and 1.96 ml of 0.02 M (0.039 mmol) Pd(P$^t$Bu$_3$)$_2$ in THF gave yellowish solid for 2 hours at 70° C. Yield 225 mg (40%).

Anal. calc. for $C_{32}H_{26}Cl_2Zr$: C, 67.11; H, 4.58. Found: C, 67.38; H, 4.65. $^1$H NMR (CD$_2$Cl$_2$): δ 7.34-7.39 (m, 4H, 2,2',6,6'-H in p-tolyl), 7.19-7.25 (m, 8H, 4,4',7,7'-H in indenyl and 3,3',5,5'-H in p-tolyl), 7.09 (dd, J=6.5 Hz, J=3.1 Hz, 4H, 5,5',6,6'-H in indenyl), 6.54 (s, 4H, 1,1',3,3'-H in indenyl), 2.41 (s, 6H, 4,4'-Me in p-tolyl).

EXAMPLE 6a-6e

Negishi Coupling Applying ($\eta^5$-3-bromo-5-methyl-cyclopenta[b]thienyl)($\eta^5$-pentamethylcyclopentadienyl)zirconium dichloride (6)

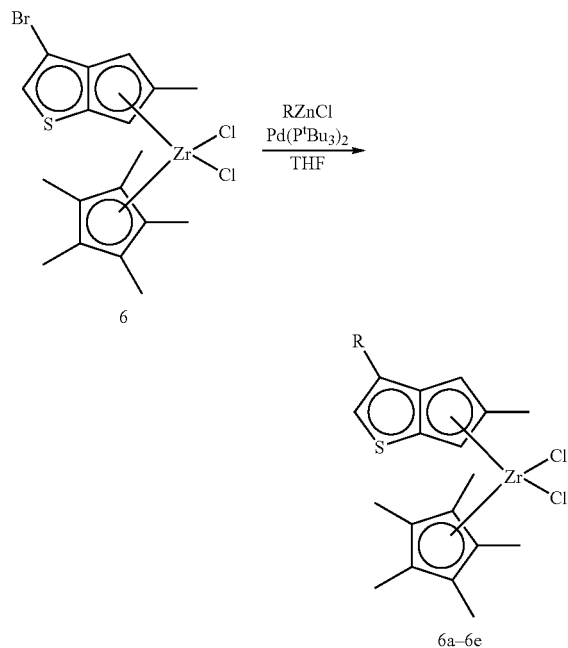

R=Me (6a), $C_6H_5$ (6b), 4-$MeC_6H_4$ (6c), 3-$MeC_6H_4$ (6d), 4-$^tBuC_6H_4$ (6e).

EXAMPLE 6a ($\eta^5$-3,5-dimethylcyclopenta[b]thienyl)($\eta^5$-pentamethylcyclopentadienyl) zirconium dichloride (6a)

Following the procedure described for 1a, 300 mg (0.59 mmol) of 6, 0.38 ml of 2.0 M MeZnCl (0.72 mmol) in THF, and 0.59 ml of 0.02 M (0.012 mmol) Pd(P$^t$Bu$_3$)$_2$ in THF gave yellowish solid. Yield 122 mg (46%).

Anal. calc. for $C_{19}H_{24}Cl_2SZr$: C, 51.10; H, 5.42. Found: C, 51.22; H, 5.49. $^1$H NMR (CD$_2$Cl$_2$): δ 6.25 (q, J=1.3 Hz, 1H, 5-H in cyclopentathienyl), 5.86 (s, 1H, 3-H in cyclopentathienyl), 5.85 (s, 1H, 1-H in cyclopentathienyl), 2.24 (d, J=1.3 Hz, 3H, 4-Me in cyclopentathienyl), 2.11 (s, 3H, 2-Me in cyclopentathienyl), 1.95 (s, 15H, C$_5$Me$_5$).

EXAMPLE 6b ($\eta^5$-3-phenyl-5-methylcyclopenta[b]thienyl)($\eta^5$-pentamethylcyclopentadienyl) zirconium dichloride (6b)

Following the procedure described for 1c, 1.53 ml of 1.0 M (1.53 mmol) phenylmagnesium bromide in THF, 3.36 ml of 0.5 M (1.68 mmol) ZnCl$_2$ in THF, 600 mg (1.17 mmol) of 6, and 1.17 ml of 0.02 M (0.023 mmol) Pd(P$^t$Bu$_3$)$_2$ in THF gave yellowish solid. Yield 368 mg (62%).

Anal. calc. for $C_{24}H_{26}Cl_2SZr$: C, 56.67; H, 5.15. Found: C, 56.84; H, 5.23. $^1$H NMR (CD$_2$Cl$_2$): δ 7.61-7.65 (m, 2H, 2,6-H in Ph), 7.36-7.42 (m, 2H, 3,5-H in Ph), 7.26-7.32 (m, 2H, 5-H in cyclopentathienyl and 4-H in Ph), 6.58 (dq, J=1.9 Hz, J=0.5 Hz, 1H, 3-H in cyclopentathienyl), 5.97 (dq, J=1.9 Hz, J=0.5 Hz, 1H, 1-H in cyclopentathienyl), 2.15 (t, J=0.5 Hz, 3H, 2-Me in cyclopentathienyl), 1.99 (s, 15H, C$_5$Me$_5$).

EXAMPLE 6c ($\eta^5$-3-p-tolyl-5-methylcyclopenta[b]thienyl)($\eta^5$-pentamethylcyclopentadienyl) zirconium dichloride (6c)

Following the procedure described for 1c, 1.53 ml of 1.0 M (1.53 mmol) p-tolylmagnesium bromide in THF, 3.36 ml of 0.5 M (1.68 mmol) ZnCl$_2$ in THF, 600 mg (1.17 mmol) of 6, and 1.17 ml of 0.02 M (0.023 mmol) Pd(P$^t$Bu$_3$)$_2$ in THF gave yellowish solid. Yield 315 mg (51%).

Anal. calc. for $C_{25}H_{28}Cl_2SZr$: C, 57.45; H, 5.40. Found: C, 57.57; H, 5.50. $^1$H NMR (CD$_2$Cl$_2$): δ 7.50-7.54 (m, 2H, 2,6-H in p-tolyl), 7.24 (s, 1H, 5-H in cyclopentathienyl), 7.18-7.22 (m, 2H, 3,5-H in p-tolyl), 6.56 (dq, J=1.9 Hz, J=0.5 Hz, 1H, 3-H in cyclopentathienyl), 5.96 (dq, J=1.9 Hz, J=0.5 Hz, 1H, 1-H in cyclopentathienyl), 2.34 (s, 3H, 4-Me in p-tolyl), 2.14 (t, J=0.5 Hz, 3H, 2-Me in cyclopentathienyl), 1.99 (s, 15H, C$_5$Me$_5$). $^{13}$C{$^1$H} NMR (CD$_2$Cl$_2$): δ 139.1, 136.1, 133.8, 132.6, 131.0, 128.6, 127.6, 126.3, 123.2, 112.2, 109.3, 101.6, 22.6, 17.8, 13.7.

EXAMPLE 6d ($\eta^5$-3-m-tolyl-5-methylcyclopenta[b]thienyl)($\eta^5$-pentamethylcyclopentadienyl)zirconium dichloride (6d)

Following the procedure described for 1c, 1.53 ml of 1.0 M (1.53 mmol) m-tolylmagnesium chloride in THF, 3.36 ml of 0.5 M (1.68 mmol) ZnCl$_2$ in THF, 600 mg (1.17 mmol) of 6, and 1.17 ml of 0.02 M (0.023 mmol) Pd(P$^t$Bu$_3$)$_2$ in THF gave yellowish solid. Yield 290 mg (47%).

Anal. calc. for $C_{25}H_{28}Cl_2SZr$: C, 57.45; H, 5.40. Found: C, 57.61; H, 5.52. $^1$H NMR (CD$_2$Cl$_2$): δ 7.41-7.46 (m, 2H, 2,6-H in m-tolyl), 7.25-7.30 (m, 2H, 5-H in cyclopentathienyl and 5-H in m-tolyl), 7.10-7.14 (m, 1H, 4-H in m-tolyl), 6.57 (m, 1H, 3-H in cyclopentathienyl), 5.97 (d, J=2.0 Hz, 1H, 1-H in cyclopentathienyl), 2.36 (s, 3H, 3-Me in m-tolyl), 2.15 (s, 3H, 2-Me in cyclopentathienyl), 1.99 (s, 15H, C$_5$Me$_5$). $^{13}$C{$^1$H} NMR (CD$_2$Cl$_2$): δ 139.9, 136.5, 136.2, 132.5, 130.1, 129.9, 129.3, 128.1, 126.3, 125.8, 123.1, 112.2, 103.2, 101.6, 31.7, 22.8, 17.7, 13.7.

EXAMPLE 6e

[$\eta^5$-3-(4-tert-butylphenyl)-5-methylcyclopenta[b]thienyl]($\eta^5$-pentamethylcyclopentadienyl)-zirconium dichloride (6e)

Following the procedure described for 1c, 0.95 ml of 0.80 M (0.76 mmol) 4-tert-butylphenylmagnesium bromide in ether, 1.68 ml of 0.5 M (0.84 mmol) ZnCl$_2$ in THF, 300 mg (0.59 mmol) of 6, and 0.59 ml of 0.02 M (0.012 mmol) Pd(P$^t$Bu$_3$)$_2$ in THF gave yellowish solid. Yield 138 mg (39%).

Anal. calc. for $C_{28}H_{34}Cl_2SZr$: C, 59.55; H, 6.07. Found: C, 59.70; H, 6.16. $^1$H NMR (CD$_2$Cl$_2$): δ 7.53-7.60 (m, 2H, 2,6-H in p-tolyl), 7.39-7.47 (m, 2H, 3,5-H in p-tolyl), 6.58 (s, 1H, 5-H in cyclopentathienyl), 6.57 (d, J=2.0 Hz, 1H, 3-H in cyclopentathienyl), 5.97 (d, J=2.0 Hz, 1H, 1-H in cyclopentathienyl), 2.15 (s, 3H, 2-Me in cyclopentathienyl), 1.99 (s, 15H, $C_5Me_5$), 1.31 (s, 9H, $^tBu$).

EXAMPLES 7a-7e

Negishi Coupling Applying a Mixture of d-/l-and meso-bis($\eta^5$-3-bromo-5-methylcyclopenta[b]thienyl)zirconium dichlorides (d-/l-and meso-7)

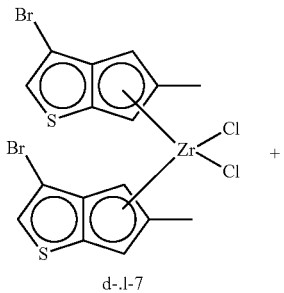

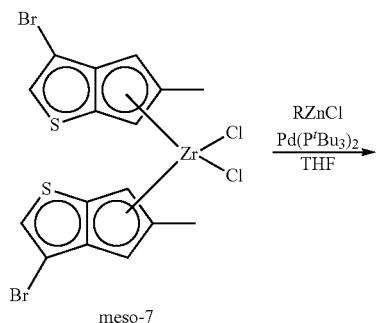

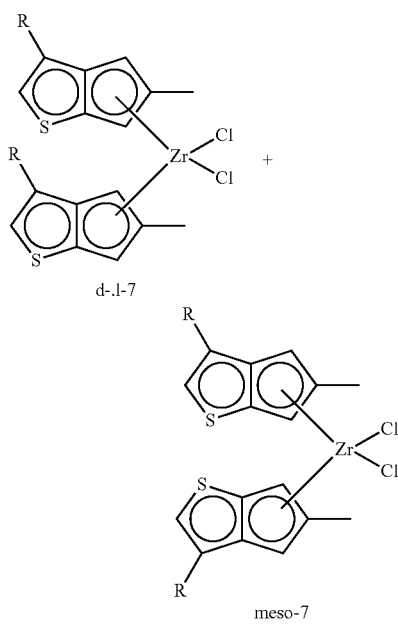

R = Me(7a), $C_6H_5$(7b), 4-Me$C_6H_4$(7c), 3-Me$C_6H_4$(7d), 4-$^tBuC_6H_4$(7e).

EXAMPLE 7a

A mixture of d-/l- and meso-bis($\eta^5$-3,5-dimethylcyclopenta[b]thienyl)zirconium dichloride (7a)

Following the procedure described for 1a, 226 mg (0.38 mmol) of a mixture of d/l-and meso-7, 0.50 ml of 2.0 M MeZnCl (1.00 mmol) in THF, and 0.77 ml of 0.02 M (0.015 mmol) Pd(P$^t$Bu$_3$)$_2$ in THF gave a mixture of d/l-and meso-complexes (1:1) for 2 hours at 70° C. Yield 164 mg (91%).

Anal. calc. for $C_{18}H_{18}Cl_2S_2Zr$: C, 46.94; H, 3.94. Found: C, 47.31; H, 4.11. $^1$H NMR (CD$_2$Cl$_2$): δ 6.90 (q, J=0.8 Hz, 2H, 5,5'-H in d/l- or meso-complex), 6.81 (q, J=0.8 Hz, 2H, 5,5'-H in meso- or d/l-complex), 6.16 (d, J=1.7 Hz, 2H, 3,3'-H in d/l- or meso-complex), 6.13 (d, J=1.7 Hz, 2H, 3,3'-H in meso- or d/l-complex), 5.98 (d, J=1.7 Hz, 2H, 1,1'-H in d/l- or meso-complex), 5.10 (d, J=1.7 Hz, 2H, 1,1'-H in meso- or d/l-complex), 2.26 (d, J=0.8 Hz, 6H, 4,4'-Me in d/l- or meso-complex), 2.21 (d, J=0.8 Hz, 6H, 4,4'-Me in meso- or d/l-complex), 2.19 (s, 6H, 2,2'-Me in d/l- or meso-complex), 2.11 (s, 6H, 2,2'-Me in meso- or d/l-complex). $^{13}$C{$^1$H} NMR (CD$_2$Cl$_2$): δ 139.7, 136.4, 130.2, 128.8, 128.44, 128.38, 127.6, 123.7, 120.5, 114.4, 108.9, 108.0, 104.5, 103.7, 26.9, 18.7, 16.2, 16.1.

EXAMPLE 7b

A mixture of d-/l-and meso-bis($\eta^5$-3-phenyl-5-methylcyclopenta[b]thienyl)zirconium dichloride (7b)

Following the procedure described for 1c, 0.83 ml of 1.0 M (0.83 mmol) phenylmagnesium bromide in THF, 1.83 ml of 0.5 M (0.92 mmol) ZnCl$_2$ in THF, 189 mg (0.32 mmol) of a mixture of d/l-and meso-7, and 0.64 ml of 0.02 M (0.013 mmol) Pd(P$^t$Bu$_3$)$_2$ in THF gave a mixture of d/l- and meso-complexes (1:1) for 2 hours at 70° C. Yield 126 mg (69%).

Anal. calc. for $C_{28}H_{22}Cl_2S_2Zr$: C, 57.51; H, 3.79. Found: C, 57.69; H, 3.85. $^1$H NMR (CD$_2$Cl$_2$): δ 7.59-7.70 (m, 8H, 2,2',6,6'-H of Ph in d/l-and meso-complexes), 7.27-7.50 (m, 16H, 5,5'-H of cyclopentathienyl and 3,3',4,4',5,5'-H of Ph in d/l-and meso-complexes), 6.42 (d, J=1.6 Hz, 2H, 3,3'-H in d/l- or meso-complex), 6.38 (d, J=1.6 Hz, 2H, 3,3'-H in meso- or d/l-complex), 6.06 (d, J=1.6 Hz, 2H, 1,1'-H in d/l- or meso-complex), 5.87 (d, J=1.6 Hz, 2H, 1,1'-H in meso- or d/l-complex), 2.14 (s, 6H, 2,2'-Me in d/l- or meso-complex), 2.11 (s, 6H, 2,2'-Me in meso- or d/l-complex).

EXAMPLE 7c

A Mixture of d-/l-and meso-bis($\eta^5$-3-p-tolyl-5-methylcyclopenta[b]thienyl)zirconium dichloride (7c)

Following the procedure described for 1c, 0.76 ml of 1.0 M (0.76 mmol) p-tolylmagnesium bromide in THF, 1.68 ml of 0.5 M (0.84 mmol) ZnCl$_2$ in THF, 173 mg (0.29 mmol) of a mixture of d/l-and meso-7, and 0.59 ml of 0.02 M (0.012 mmol) Pd(P$^t$Bu$_3$)$_2$ in THF gave a mixture of d/l-and meso-complexes (1:1) for 2 hours at 70° C. Yield 58 mg (32%).

Anal. calc. for $C_{30}H_{26}Cl_2S_2Zr$: C, 58.80; H, 4.28. Found: C, 58.92; H, 4.35. $^1$H NMR (CD$_2$Cl$_2$): δ 7.48-7.62 (m, 8H, 2,2',6,6'-H of p-tolyl in d/l-and meso-complexes), 7.34 (s, 4H, 5,5'-H in cyclopentathienyl of d/l- or meso-complexes), 7.32 (s, 4H, 5,5'-H in cyclopentathienyl of meso- or d/l-complexes), 7.19-7.31 (m, 8H, 3,3',5,5'-H of p-tolyl in d/l-and meso-complexes), 6.39 (m, 2H, 3,3'-H in d/l- or meso-complex), 6.37 (m, 2H, 3,3'-H in meso- or d/l-complex), 6.03 (m, 2H, 1,1'-H in d/l- or meso-complex), 5.85 (m, 2H, 1,1'-H in meso- or d/l-complex), 2.38 (s, 6H, 4,4'-Me of p-tolyl in d/l- or meso-complex), 2.34 (s, 6H, 4,4'-Me of p-tolyl in meso- or d/l-complex), 2.12 (s, 6H, 2,2'-Me in d/l- or meso-complex), 2.09 (s, 6H, 2,2'-Me in meso- or d/l-complex).

EXAMPLE 7d

A Mixture of d-/l-and meso-bis($\eta^5$-3-m-tolyl-5-methylcyclopenta[b]thienyl)zirconium dichloride (7d)

Following the procedure described for 1c, 0.79 ml of 1.0 M (0.79 mmol) m-tolylmagnesium chloride in THF, 1.74 ml of 0.5 M (0.87 mmol) $ZnCl_2$ in THF, 180 mg (0.31 mmol) of a mixture of d/l-and meso-7, and 0.61 ml of 0.02 M (0.012 mmol) $Pd(P^tBu_3)_2$ in THF gave a mixture of d/l-and meso-complexes (1:1) for 2 hours at 70° C. Yield 161 mg (86%).

Anal. calc. for $C_{30}H_{26}Cl_2S_2Zr$: C, 58.80; H, 4.28. Found: C, 59.14; H, 4.39. $^1H$ NMR ($CD_2Cl_2$): δ 7.10-7.52 (m, 20H, 5,5'-H in cyclopentathienyl and 2,2',4,4',5,5',6,6'-H of m-tolyl in d/l-and meso-complexes), 6.42 (d, J=1.9 Hz, 2H, 3,3'-H in d/l- or meso-complex), 6.41 (d, J=1.9 Hz, 2H, 3,3'-H in meso- or d/l-complex), 6.04 (d, 2H, 1,1'-H in d/l- or meso-complex), 5.84 (d, 2H, 1,1'-H in meso- or d/l-complex), 2.39 (s, 6H, 3,3'-Me of m-tolyl in d/l- or meso-complex), 2.37 (s, 6H, 4,4'-Me of p-tolyl in meso- or d/l-complex), 2.14 (s, 12H, 2,2'-Me in d/l-and meso-complex).

EXAMPLE 7e

A Mixture of d-/l-and meso-bis[$\eta^5$-3-(4-tert-butylphenyl)-5-methylcyclopenta[b]thienyl)zirconium dichloride (7e)

Following the procedure described for 1c, 1.05 ml of 1.0 M (1.05 mmol) 4-tert-butylphenylmagnesium bromide in ether, 1.85 ml of 0.5 M (0.93 mmol) $ZnCl_2$ in THF, 191 mg (0.32 mmol) of a mixture of d/l-and meso-7, and 0.65 ml of 0.02 M (0.013 mmol) $Pd(P^tBu_3)_2$ in THF gave a mixture of d/l-and meso-complexes (1:1) for 2 hours at 70° C. Yield 84 mg (37%).

Anal. calc. for $C_{36}H_{38}Cl_2S_2Zr$: C, 62.04; H, 5.50. Found: C, 62.19; H, 5.57. $^1H$ NMR ($CD_2Cl_2$): δ 7.39-7.64 (m, 8H, 2,2',6,6'-H of p-tolyl in d/l-and meso-complexes), 7.39-7.52 (m, 8H, 3,3',5,5'-H of p-tolyl in d/l-and meso-complexes), 7.36 (s, 4H, 5,5'-H in cyclopentathienyl of d/l- or meso-complexes), 7.33 (s, 4H, 5,5'-H in cyclopentathienyl of meso- or d/l-complexes), 6.42 (d, J=1.6 Hz, 2H, 3,3'-H in d/l- or meso-complex), 6.39 (d, J=1.6 Hz, 2H, 3,3'-H in meso- or d/l-complex), 6.07 (d, J=1.6 Hz, 2H, 1,1'-H in d/l- or meso-complex), 5.88 (d, J=1.6 Hz, 2H, 1,1'-H in meso- or d/l-complex), 2.14 (s, 6H, 2,2'-Me in d/l- or meso-complex), 2.12 (s, 6H, 2,2'-Me in meso- or d/l-complex), 1.34 (s, 9H, $^tBu$ in d/l- or meso-complex), 1.31 (s, 9H, $^tBu$ in meso- or d/l-complex).

EXAMPLES rac-8a-rac-8n

Negishi Coupling Applying rac-dimethylsilyl-bis($\eta^5$-4-bromo-2-methylinden-1-yl)zirconium dichloride (rac-8)

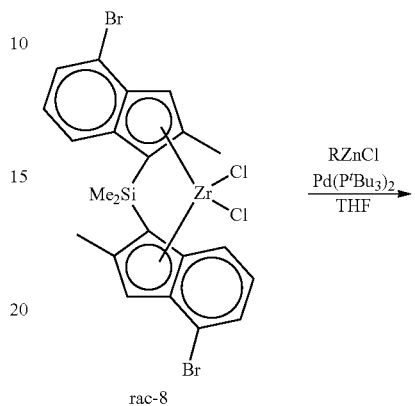

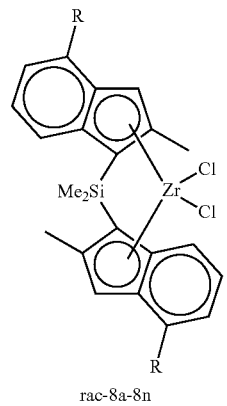

R=Me (rac-8a), 4-$MeC_6H_4$ (rac-8b), 3-$MeC_6H_4$ (rac-8c), 2-$MeC_6H_4$ (rac-8d), 4-$^tBuC_6H_4$ (rac-8e), 4-$FC_6H_4$ (rac-8f), 3-$CF_3C_6H_4$ (rac-8g), 2,4,6-$Me_3C_6H_2$ (rac-8h), 5-methyl-2-thienyl (rac-8i), 5-methyl-2-furyl (rac-8k), 2-benzothienyl (rac-8l), 2-benzofuryl (rac-8m), 1-naphthyl (rac-8n).

EXAMPLE rac-8a rac-Dimethylsilyl-bis($\eta^5$-2,4-dimethylinden-1-yl) zirconium dichloride (rac-8a)

Following the procedure described for 1a, 270 mg (0.43 mmol) of rac-8, 0.55 ml of 2.0 M MeZnCl (1.10 mmol) in THF, and 0.85 ml of 0.02 M (0.017 mmol) $Pd(P^tBu_3)_2$ in THF for 2 hours at 70° C. gave yellow solid. Yield 199 mg (93%).

Anal. calc. for $C_{24}H_{26}Cl_2SiZr$: C, 57.12; H, 5.19. Found: C, 57.34; H, 4.90. $^1H$ NMR ($CD_2Cl_2$): δ 7.35-7.41 (m, 2H, 7,7'-H), 6.99-7.04 (m, 2H, 5,5'-H), 6.80-6.87 (m, 2H, 6,6'-H), 6.73 (s, 2H, 3,3'-H), 2.31 (s, 6H, 4,4'-Me), 2.11 (s, 6H, 2,2'-Me), 0.92 (s, 6H, $SiMe_2$).

EXAMPLE rac-8b rac-Dimethylsilyl-bis($\eta^5$-2-methyl-4-p-tolylinden-1-yl)zirconium dichloride (rac-8b)

In 16 ml vial equipped with PTFE coated stir bar, 0.62 ml of 1.0 M (0.62 mmol) p-tolylmagnesium bromide in THF was added by a dosing pipette to a mixture of 1.35 ml of 0.5 M (0.68 mmol) $ZnCl_2$ in THF and 5 ml of THF by vigorous stirring at ambient temperature. This organozinc reagent was additionally stirred for 1 hour and then added to a mixture of 150 mg (0.24 mmol) of rac-8, 0.47 ml of 0.02 M (0.009 mmol) Pd(P$^t$Bu$_3$)$_2$ in THF, and 2 ml of THF placed in a separate 16 ml vial equipped with PTFE coated stir bar. The reaction mixture was stirred for 2 hours at 70° C. and then evaporated to dryness. To the residue 5 ml of dry dichloromethane was added, then, this mixture was stirred for 10 min and filtered through glass frit (G4). The precipitate was washed by 3×5 ml of THF, 3×5 ml of cold $CH_2Cl_2$, and 10 ml of hexanes and then dried in vacuum. Yield 70 mg (45%) of yellow solid.

Anal. calc. for $C_{36}H_{34}Cl_2SiZr$: C, 65.83; H, 5.22. Found: C, 65.94; H, 5.00. $^1$H NMR (CD$_2$Cl$_2$): δ 7.63 (d, J=8.7 Hz, 2H, 7,7'-H of indenyl), 7.46 (m, 4H, 2,2',6,6'-H of p-tolyl), 7.30 (d, J=7.0 Hz, 2H, 5,5'-H of indenyl), 7.21 (m, 4H, 3,3', 5,5'-H of p-tolyl), 7.06 (dd, J=8.7 Hz, J=7.0 Hz, 2H, 6,6'-H of indenyl), 6.86 (s, 2H, 3,3'-H of indenyl), 2.33 (s, 6H, 4,4'-Me of p-tolyl), 2.20 (s, 6H, 2,2'-Me of indenyl), 1.30 (s, 6H, SiMe$_2$).

EXAMPLE rac-8c rac-Dimethylsilyl-bis($\eta^5$-2-methyl-4-m-tolylinden-1-yl)zirconium dichloride (rac-8c)

Following the procedure described for 1c, 0.62 ml of 1.0 M (0.62 mmol) m-tolylmagnesium chloride in THF, 1.35 ml of 0.5 M (0.68 mmol) $ZnCl_2$ in THF, 150 mg (0.24 mmol) of rac-8, and 0.47 ml of 0.02 M (0.009 mmol) Pd(P$^t$Bu$_3$)$_2$ in THF gave yellow solid for 2 hours at 70° C. Yield 81 mg (52%).

Anal. calc. for $C_{36}H_{34}Cl_2SiZr$: C, 65.83; H, 5.22. Found: C, 66.11; H, 5.04. $^1$H NMR (CD$_2$Cl$_2$): δ 7.65 (d, J=8.7 Hz, 2H, 7,7'-H of indenyl), 7.11-7.49 (m, 10H, 5,5'-H of indenyl and 2,2',4,4',5,5',6,6'-H of m-tolyl), 7.08 (dd, J=8.7 Hz, J=7.0 Hz, 2H, 6,6'-H of indenyl), 6.89 (s, 2H, 3,3'-H of indenyl), 2.34 (s, 6H, 3,3'-Me of m-tolyl), 2.21 (s, 6H, 2,2'-Me of indenyl), 1.31 (s, 6H, SiMe$_2$). $^{13}$C{$^1$H} NMR (CD$_2$Cl$_2$): δ 141.1, 140.0, 137.7, 136.9, 133.8, 130.8, 130.1, 130.0, 129.3, 128.0, 127.4, 127.2, 126.0, 123.8, 72.4, 22.8, 20.0, 3.9.

EXAMPLE rac-8d rac-Dimethylsilyl-bis($\eta^5$-2-methyl-4-o-tolylinden-1-yl)zirconium dichloride (rac-8d)

Following the procedure described for 1c. 0.74 ml of 0.83 M (0.59 mmol) o-tolylmagnesium bromide in THF, 1.35 ml of 0.5 M (0.68 mmol) $ZnCl_2$ in THF, 150 mg (0.24 mmol) of rac-8, and 0.47 ml of 0.02 M (0.009 mmol) Pd(P$^t$Bu$_3$)$_2$ in THF gave yellow solid for 2 hours at 70° C. Yield 120 mg (77%).

Anal. calc. for $C_{36}H_{34}Cl_2SiZr$: C, 65.83; H, 5.22. Found: C, 66.05; H, 5.04. $^1$H NMR (CD$_2$Cl$_2$): δ 7.64 (m, 2H, 7,7'-H of indenyl), 7.19-7.52 (m, 10H, 3,3',4,4',5,5',6,6'-H of o-tolyl), 7.16 (m, 2H, 5,5'-H of indenyl), 7.05 (dd, J=8.7 Hz, J=7.0 Hz, 2H, 6,6'-H of indenyl), 6.44 (br.s, 2H, 3,3'-H of indenyl), 2.20 (s, 6H, 2,2'-Me of indenyl), 2.03 (br.s, 6H, 2,2'-Me of o-tolyl), 1.30 (s, 6H, SiMe$_2$).

EXAMPLE rac-8e rac-Dimethylsilyl-bis[$\eta^5$-2-methyl-4-(4-tert-butylphenyl)inden-1-yl]zirconium dichloride (rac-8e)

Following the procedure described for rac-8b, 0.77 ml of 0.83 M (0.64 mmol) 4-tert-butylphenylmagnesium bromide in ether, 1.35 ml of 0.5 M (0.68 mmol) $ZnCl_2$ in THF, 150 mg (0.24 mmol) of rac-8, and 0.47 ml of 0.02 M (0.009 mmol) Pd(P$^t$Bu$_3$)$_2$ in THF gave yellow solid. Yield 81 mg (46%).

Anal. calc. for $C_{42}H_{46}Cl_2SiZr$: C, 68.07; H, 6.26. Found: C, 68.22; H, 6.05. $^1$H NMR (CD$_2$Cl$_2$): δ 7.64 (m, 2H, 7,7'-H of indenyl), 7.50-7.56 (m, 4H, 2,2',6,6'-H of $C_6H_4$), 7.41-7.47 (m, 4H, 3,3',5,5'-H of $C_6H_4$) 7.33 (dd, J=7.0 Hz, J=0.8 Hz, 2H, 5,5'-H of indenyl), 7.08 (dd, J=8.7 Hz, J=7.0 Hz, 2H, 6,6'-H of indenyl), 6.91 (m, 2H, 3,3'-H of indenyl), 2.21 (d, J=0.4 Hz, 6H, 2,2'-Me of indenyl), 1.31 (s, 6H, SiMe$_2$), 1.30 (s, 18H, $^t$Bu).

EXAMPLE rac-8f rac-Dimethylsilyl-bis[$\eta^5$-2-methyl-4-(4-fluorophenyl)inden-1-yl]zirconium dichloride (rac-8f)

Following the procedure described for 1c, 0.52 ml of 1.18 M (0.61 mmol) 4-fluorophenylmagnesium bromide in THF, 1.35 ml of 0.5 M (0.68 mmol) $ZnCl_2$ in THF, 150 mg (0.24 mmol) of rac-8, and 0.47 ml of 0.02 M (0.009 mmol) Pd(P$^t$Bu$_3$)$_2$ in THF gave yellow solid for 2 hours at 70° C. Yield 142 mg (89%).

Anal. calc. for $C_{34}H_{28}Cl_2F_2SiZr$: C, 61.43; H, 4.25. Found: C, 61.31; H, 4.01. $^1$H NMR (CD$_2$Cl$_2$): δ 7.66 (m, 2H, 7,7'-H of indenyl), 7.52-7.64 (m, 4H, 2,2',6,6'-H of $C_6H_4$), 7.30 (m, 2H, 5,5'-H of indenyl), 7.02-7.16 (m, 6H, 6,6'-H of indenyl and 3,3',5,5'-H of $C_6H_4$), 6.83 (s, 2H, 3,3'-H of indenyl), 2.21 (s, 6H, 2,2'-Me of indenyl), 1.32 (s, 6H, SiMe$_2$). $^{13}$C{$^1$H} NMR (CD$_2$Cl$_2$): δ 142.3 (d, J=293.3 Hz), 139.0, 137.7, 131.8 (d, J=9.9 Hz), 129.3, 128.1, 127.4, 126.2, 124.2, 123.8, 123.5, 117.0 (d, J=22.3 Hz), 72.4, 20.0, 3.8.

EXAMPLE rac-8g rac-Dimethylsilyl-bis[$\eta^5$-2-methyl-4-(3-trifluoromethylphenyl)inden-1-yl]zirconium dichloride (rac-8g)

Following the procedure described for 1c, 0.60 ml of 1.02 M (0.61 mmol) 3-trifluoromethylphenylmagnesium bromide in THF, 1.35 ml of 0.5 M (0.68 mmol) $ZnCl_2$ in THF, 150 mg (0.24 mmol) of rac-8, and 0.47 ml of 0.02 M (0.009 mmol) Pd(P$^t$Bu$_3$)$_2$ in THF gave yellow solid for 2 hours at 70° C. Yield 173 mg (94%).

Anal. calc. for $C_{36}H_{28}Cl_2F_6SiZr$: C, 56.53; H, 3.69. Found: C, 56.50; H, 3.52. $^1$H NMR (CD$_2$Cl$_2$): δ 7.81-7.90 (m, 4H, 2,2',6,6'-H of $C_6H_4$), 7.69-7.74 (m, 2H, 7,7'-H of indenyl), 7.51-7.63 (m, 4H, 5,5',4,4'-H of $C_6H_4$), 7.37 (dd, J=7.0 Hz, J=0.6 Hz, 2H, 5,5'-H of indenyl), 7.12 (dd, J=8.7 Hz, J=7.0 Hz, 2H, 6,6'-H of indenyl), 6.84 (s, 2H, 3,3'-H of indenyl), 2.22 (s, 6H, 2,2'-Me of indenyl), 1.33 (s, 6H, SiMe$_2$).

EXAMPLE rac-8h rac-Dimethylsilyl-bis($\eta^5$-2-methyl-4-mesitylinden-1-yl)zirconium dichloride (rac-8h)

Following the procedure described for 1c, 0.93 ml of 0.88 M (0.82 mmol) mesitylmagnesium bromide in THF, 1.80 ml of 0.5 M (0.90 mmol) ZnCl$_2$ in THF, 200 mg (0.32 mmol) of rac-8, and 0.63 ml of 0.02 M (0.013 mmol) Pd(P$^t$Bu$_3$)$_2$ in THF gave yellow solid for 2 hours at 70° C. Yield 215 mg (96%).

Anal. calc. for C$_{40}$H$_{42}$Cl$_2$SiZr: C, 67.38; H, 5.94. Found: C, 67.65; H, 5.79. $^1$H NMR (CD$_2$Cl$_2$): δ 7.63 (dt, J=8.6 Hz, J=0.9 Hz, 2H, 7,7'-H of indenyl), 7.10 (dd, J=6.9 Hz, J=0.9 Hz, 2H, 5,5'-H of indenyl), 7.02 (dd, J=8.6 Hz, J=6.9 Hz, 2H, 6,6'-H of indenyl), 6.89 (s, 2H, 3,3'-H of mesityl), 6.80 (s, 2H, 5,5'-H of mesityl), 6.35 (s, 2H, 3,3'-H of indenyl), 2.32 (s, 6H, 2,2'-Me of mesityl), 2.29 (s, 6H, 4,4'-Me of mesityl), 2.25 (s, 6H, 6,6'-Me of mesityl), 1.52 (s, 6H, 2,2'-Me), 1.28 (s, 6H, SiMe$_2$). $^{13}$C{$^1$H} NMR (CD$_2$Cl$_2$): δ 139.3, 138.6, 138.5, 138.2, 137.5, 137.4, 137.1, 128.4, 72.5, 23.0, 22.2, 21.6, 20.2, 3.7.

EXAMPLE rac-8i rac-Dimethylsilyl-bis[η$^5$-2-methyl-4-(5-methyl-2-thienyl)inden-1-yl]zirconium dichloride (rac-8i)

Following the procedure described for 1m, 1.61 ml of 0.51 M (0.82 mmol) of 2-methylthiophene, 1.64 ml of 0.5 M $^n$BuLi (0.82 mmol), 1.80 ml of 0.5 M (0.90 mmol) ZnCl$_2$ in THF, 200 mg (0.32 mmol) of rac-8, and 0.63 ml of 0.02 M (0.013 mmol) Pd(P$^t$Bu$_3$)$_2$ in THF gave yellow solid. Yield 204 mg (96%).

Anal. calc. for C$_{32}$H$_{30}$Cl$_2$S$_2$SiZr: C, 57.46; H, 4.52. Found: C, 57.78; H, 4.67. $^1$H NMR (CD$_2$Cl$_2$): δ 7.60 (dt, J=8.7 Hz, J=0.8 Hz, 2H, 7,7'-H of indenyl), 7.38 (dd, J=7.1 Hz, J=0.7 Hz, 2H, 5,5'-H of indenyl), 7.15 (d, J=3.6. Hz, 3,3'-H of thienyl), 7.08 (m, 2H, 3,3'-H of indenyl), 7.02 (dd, J=8.7 Hz, J=7.1 Hz, 2H, 6,6'-H of indenyl), 6.73 (m, 2H, 4,4'-H of thienyl), 2.46 (m, 6H, 5,5'-Me of thienyl), 2.21 (s, 6H, 2,2'-Me of indenyl), 1.30 (s, 6H, SiMe$_2$).

EXAMPLE rac-8k rac-Dimethylsilyl-bis[η$^5$-2-methyl-4-(5-methyl-2-furyl)inden-1-yl]zirconium dichloride (rac-8k)

Following the procedure described for 1m, 1.35 ml of 0.61 M (0.82 mmol) of 2-methylfuran, 1.64 ml of 0.5 M $^n$BuLi (0.82 mmol), 1.80 ml of 0.5 M (0.90 mmol) ZnCl$_2$ in THF, 200 mg (0.32 mmol) of rac-8, and 0.63 ml of 0.02 M (0.013 mmol) Pd(P$^t$Bu$_3$)$_2$ in THF gave yellow solid. Yield 167 mg (83%).

Anal. calc. for C$_{32}$H$_{30}$Cl$_2$O$_2$SiZr: C, 60.36; H, 4.75. Found: C, 60.65; H, 4.59. $^1$H NMR (CD$_2$Cl$_2$): δ 7.59 (dd, J=7.1 Hz, J=0.5 Hz, 2H, 5,5'-H of indenyl), 7.57 (dt, J=8.7 Hz, J=0.9 Hz, 2H, 7,7'-H of indenyl), 7.11 (m, 2H, 3,3'-H of indenyl), 7.04 (dd, J=8.7 Hz, J=7.2 Hz, 2H, 6,6'-H of indenyl), 6.63 (d, J=3.2 Hz, 3,3'-H of furyl), 6.06 (m, 2H, 4,4'-H of furyl), 2.33 (m, 6H, 5,5'-Me of furyl), 2.23 (s, 6H, 2,2'-Me of indenyl), 1.29 (s, 6H, SiMe$_2$).

EXAMPLE rac-8l rac-Dimethylsilyl-bis[η$^5$-2-methyl-4-(2-benzothienyl)inden-1-yl]zirconium dichloride (rac-8l)

In a 16 ml vial equipped with a PTFE coated stir bar, to 1.57 ml of 0.30 M (0.82 mmol) of thiophene in THF, 1.64 ml of 0.5 M (0.82 mmol) $^n$BuLi in hexanes was added by a dosing pipette by vigorous stirring at −80° C. This mixture was stirred and slowly warmed (for ca. 1 h) to 0° C. Then, 1.80 ml of 0.5 M (0.90 mmol) ZnCl$_2$ in THF was added at −80° C., and the obtained mixture was stirred and slowly warmed to ambient temperature and then evaporated to dryness. In a separate 16 ml vial equipped with PTFE coated stir bar, to a mixture of 200 mg (0.32 mmol) of rac-8, 0.63 ml of 0.02 M (0.013 mmol) Pd(P$^t$Bu$_3$)$_2$ in THF, and 4 ml of THF the above described organozinc reagent was added. This mixture was stirred for 2 hours at 70° C. and then evaporated to dryness. To the residue, 5 ml of dry dichloromethane was added, then, this mixture was filtered through a glass frit (G4). The precipitate was washed with 3×5 ml of THF, 3×5 ml of CH$_2$Cl$_2$, 10 ml of hexanes and then dried in vacuum. Yield 180 mg (77%) of yellow solid.

Anal. calc. for C$_{38}$H$_{30}$Cl$_2$S$_2$SiZr: C, 61.59; H, 4.08. Found: C, 61.83; H, 3.82. $^1$H NMR (CD$_2$Cl$_2$): δ 7.77 (m, 4H, 4,4',7,7'-H of benzothienyl), 7.71 (d, J=8.7 Hz, 2H, 7,7'-H of indenyl), 7.60 (s, 2H, 3,3'-H of benzothienyl), 7.57 (d, J=7.1 Hz, 2H, 5,5'-H of indenyl), 7.29 (m, 4H, 5,5',6,6'-H of benzothienyl), 7.21 (s, 2H, 3,3'-H of indenyl), 7.11 (dd, J=8.7 Hz, J=7.1 Hz, 2H, 6,6'-H of indenyl), 2.26 (s, 6H, 2,2'-Me of indenyl), 1.34 (s, 6H, SiMe$_2$). $^{13}$C{$^1$H} NMR (CD$_2$Cl$_2$): δ 144.7, 138.3, 138.1, 137.6, 135.6, 133.3, 130.2, 130.1, 128.3, 128.1 (two resonances), 127.4 (three resonances), 121.8, 120.6, 72.4, 20.7, 0.7.

EXAMPLE rac-8m rac-Dimethylsilyl-bis[η$^5$-2-methyl-4-(2-benzofuryl)inden-1-yl]zirconium dichloride (rac-8m)

Following the procedure described for rac-8l, 1.64 ml of 0.50 M (0.82 mmol) of benzofuran in THF, 1.64 ml of 0.5 M $^n$BuLi (0.82 mmol) in hexanes, 1.80 ml of 0.5 M (0.90 mmol) ZnCl$_2$ in THF, 200 mg (0.32 mmol) of 8, and 0.63 ml of 0.02 M (0.013 mmol) Pd(P$^t$Bu$_3$)$_2$ in THF gave an orange solid. Yield 66 mg (30%).

Anal. calc. for C$_{38}$H$_{30}$Cl$_2$O$_2$SiZr: C, 64.39; H, 4.27. Found: C, 64.16; H, 4.29. $^1$H NMR (CD$_2$Cl$_2$): δ 7.80 (m, 2H, 5,5'/6,6'-H of benzofuryl), 7.74 (m, 2H, 6,6'/5,5'-H of benzofuryl), 7.71 (m, 2H, 7,7'-H of indenyl), 7.60 (s, 2H, 3,3'-H of benzofuryl), 7.57 (dd, J=7.1 Hz, J=0.6 Hz, 2H, 5,5'-H of indenyl), 7.29 (m, 4H, 4,4',7,7'-H of benzofuryl), 7.21 (s, 2H, 3,3'-H of indenyl), 7.11 (dd, J=8.7 Hz, J=7.1 Hz, 2H, 6,6'-H of indenyl), 2.26 (s, 6H, 2,2'-Me of indenyl), 1.34 (s, 6H, SiMe$_2$).

EXAMPLE rac-8n rac-Dimethylsilyl-bis[η$^5$-2-methyl-4-(1-naphthyl)inden-1-yl]zirconium dichloride (rac-8n)

In 16 ml vial equipped with PTFE coated stir bar and containing 8.80 ml of 0.25 M (2.20 mmol) ZnCl$_2$ in THF, 2.00 ml of 1.0 M (2.00 mmol) 1-naphthylmagnesium bromide in THF was added at room temperature. This mixture was stirred for 1 hour. Then, in a separate 16 ml vial equipped with PTFE coated stir bar containing a suspension of 200 mg (0.32 mmol) of rac-8 in 2.0 ml of THF, 4.42 ml of the solution of the above obtained organozinc reagent and 0.65 ml of 0.02 M (0.013 mmol) Pd(P$^t$Bu$_3$)$_2$ in THF were added by a dosing pipette. The reaction mixture was stirred for 2 hours at 70° C. End then evaporated to dryness. To the residue, 10 ml of dry dichloromethane and 1.0 ml of MeSiCl$_3$ were added. This mixture was stirred for 1 hour and then evaporated to dryness. To the residue, 20 ml of toluene was added. This mixture was refluxed for 10 min, cooled and evaporated to dryness. Then, 60 ml of toluene was added, and the resulted suspension was filtered through glass frit (G4). The filtrate was evaporated to dryness. The residue was washed by 3×15 ml of hexanes and dried in vacuum. Yield 106 mg (46%) of yellow-orange solid.

Anal. calc. for $C_{42}H_{34}Cl_2SiZr$: C, 69.20; H, 4.70. Found: C, 68.99; H, 4.82. $^1H$ NMR ($CD_2Cl_2$): δ 7.87 (m, 4H, 5,5',8,8'-H in naphthyl), 7.74 (m, 2H, 3,3'-H in naphthyl), 7.71 (m, 2H, 4,4'-H in naphthyl), 7.53 (dd, J=8.2 Hz, J=7.0 Hz, 2H, 7,7'-H of indenyl), 7.48 (m, 2H, 5,5'-H of indenyl), 7.42 (m, 2H, 6,6'-H in naphthyl), 7.28 (m, 2H, 7,7'-H in naphthyl), 7.12 (dd, J=8.7 Hz, J=7.0 Hz, 2H, 6,6'-H of indenyl), 6.38 (s, 2H, 3,3'-H of indenyl), 2.17 (s, 6H, 2,2'-Me in indenyl), 1.34 (s, 6H, $Me_2Si$).

EXAMPLES meso-8b

Negishi Coupling Applying meso-dimethylsilyl-bis($\eta^5$-4-bromo-2-methylinden-1-yl)zirconium dichloride (meso-8); synthesis of meso-dimethylsilyl-bis($\eta^5$-2-methyl4-p-tolylinden-1-yl)zirconium dichloride (meso-8b)

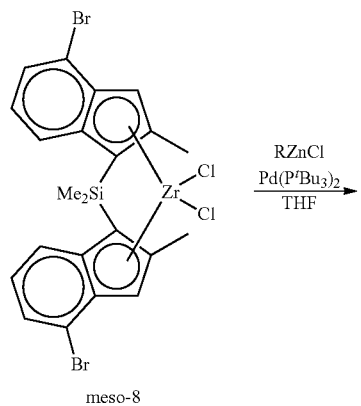

meso-8

R = 4-$MeC_6H_4$(meso-8b).

Following the procedure described for 1c, 1.80 ml of 1.0 M (1.80 mmol) p-tolylmagnesium bromide in THF, 3.97 ml of 0.5 M (1.99 mmol) $ZnCl_2$ in THF, 440 mg (0.69 mmol) of meso-8, and 1.39 ml of 0.02 M (0.028 mmol) $Pd(P^tBu_3)_2$ in THF gave yellow solid for 2 hours at 70° C. Yield 377 mg (83%).

Anal. calc. for $C_{36}H_{34}Cl_2SiZr$: C, 65.83; H, 5.22. Found: C, 66.14; H, 5.07. $^1H$ NMR ($CD_2Cl_2$): δ 7.64 (m, 2H, 7,7'-H in indenyl), 7.37-7.42 (m, 4H, 2,2',6,6'-H in p-tolyl), 7.17-7.22 (m, 4H, 3,3',5,5'-H in p-tolyl), 7.06 (dd, J=7.0 Hz, J=0.8 Hz, 2H, 5,5'-H in indenyl), 6.84 (dd, J=8.7 Hz, J=7.0 Hz, 2H, 6,6'-H in indenyl), 2.41 (s, 6H, 4-Me in p-tolyl), 2.34 (s, 6H, 2-Me in indenyl), 1.45 (s, 3H, SiMe), 1.23 (s, 3H, SiMe').

EXAMPLES rac-9a-rac-9e

Negishi Coupling Applying rac-dimethylsilyl-bis($\eta^5$-3-bromo-5-methylcyclopenta[b]thien-6-yl)zirconium dichloride (rac-9)

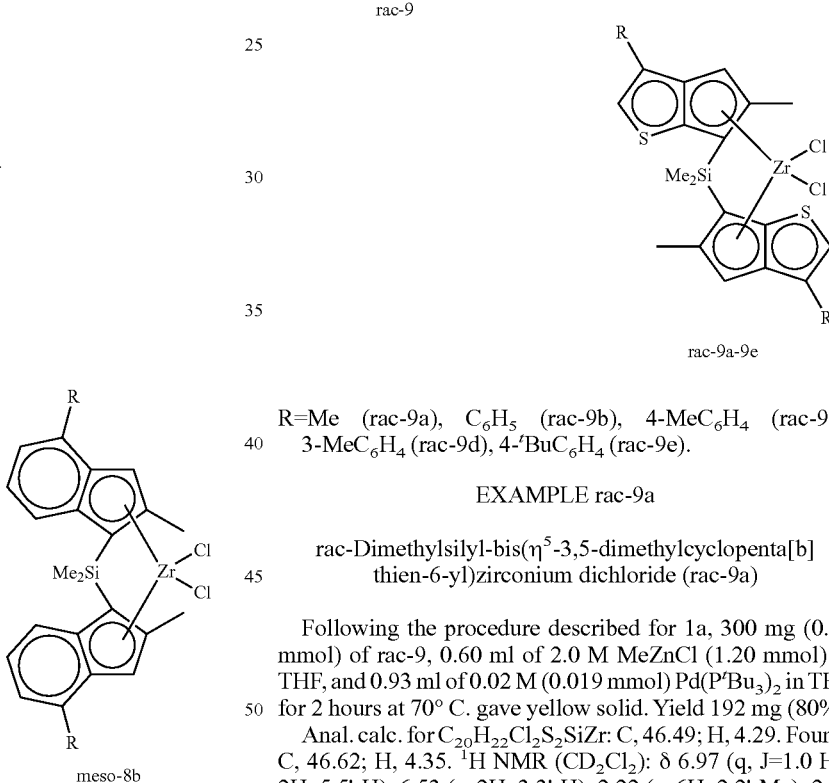

R=Me (rac-9a), $C_6H_5$ (rac-9b), 4-$MeC_6H_4$ (rac-9c), 3-$MeC_6H_4$ (rac-9d), 4-$^tBuC_6H_4$ (rac-9e).

EXAMPLE rac-9a rac-Dimethylsilyl-bis($\eta^5$-3,5-dimethylcyclopenta[b]thien-6-yl)zirconium dichloride (rac-9a)

Following the procedure described for 1a, 300 mg (0.46 mmol) of rac-9, 0.60 ml of 2.0 M MeZnCl (1.20 mmol) in THF, and 0.93 ml of 0.02 M (0.019 mmol) $Pd(P^tBu_3)_2$ in THF for 2 hours at 70° C. gave yellow solid. Yield 192 mg (80%).

Anal. calc. for $C_{20}H_{22}Cl_2S_2SiZr$: C, 46.49; H, 4.29. Found: C, 46.62; H, 4.35. $^1H$ NMR ($CD_2Cl_2$): δ 6.97 (q, J=1.0 Hz, 2H, 5,5'-H), 6.53 (s, 2H, 3,3'-H), 2.22 (s, 6H, 2,2'-Me), 2.16 (d, J=1.0 Hz, 6H, 4,4'-Me), 1.01 (s, 6H, $SiMe_2$). $^{13}C\{^1H\}$ NMR ($CD_2Cl_2$): δ 135.7, 130.5, 128.5, 127.3, 122.5, 117.6, 71.4, 19.4, 14.6, −0.6.

EXAMPLE rac-9b rac-Dimethylsilyl-bis($\eta^5$-3-phenyl-5-methylcyclopenta[b]thien-6-yl)zirconium dichloride (rac-9b)

Following the procedure described for 1c, 0.76 ml of 1.0 M (0.76 mmol) phenylmagnesium bromide in THF, 1.67 ml of 0.5 M (0.84 mmol) $ZnCl_2$ in THF, 189 mg (0.29 mmol) of rac-9, and 0.59 ml of 0.02 M (0.012 mmol) $Pd(P^tBu_3)_2$ in THF gave yellow solid for 2 hours at 70° C. Yield 130 mg (69%).

Anal. calc. for $C_{30}H_{26}Cl_2S_2SiZr$: C, 56.22; H, 4.09. Found: C, 56.34; H, 4.18. $^1$H NMR ($CD_2Cl_2$): δ 7.54-7.62 (m, 4H, 2,2',6,6'-H of Ph), 7.49 (s, 2H, 3,3'-H of cyclopentathienyl), 7.34-7.43 (m, 4H, 3,3',5,5'-H of Ph), 7.25-7.34 (m, 2H, 4,4'-H of Ph), 6.86 (s, 2H, 3,3'-H of cyclopentathienyl), 2.32 (s, 6H, 2,2'-Me of cyclopentathienyl), 1.09 (s, 6H, SiMe$_2$). $^{13}$C{$^1$H} NMR ($CD_2Cl_2$): δ 144.7, 137.7, 136.2, 135.7, 130.8, 130.4, 129.4, 128.6, 121.4, 120.4, 72.5, 20.7, 0.7.

EXAMPLE rac-9c rac-Dimethylsilyl-bis($\eta^5$-3-p-tolyl-5-methylcyclopenta[b]thien-6-yl)zirconium dichloride (rac-9c)

Following the procedure described for 1c, 0.80 ml of 1.0 M (0.80 mmol) phenylmagnesium bromide in THF, 1.77 ml of 0.5 M (0.89 mmol) ZnCl$_2$ in THF, 200 mg (0.31 mmol) of rac-9, and 0.62 ml of 0.02 M (0.012 mmol) Pd(P$^t$Bu$_3$)$_2$ in THF gave yellow solid for 2 hours at 70° C. Yield 197 mg (95%).

Anal. calc. for $C_{32}H_{30}Cl_2S_2SiZr$: C, 57.46; H, 4.52. Found: C, 57.70; H, 4.66. $^1$H NMR ($CD_2Cl_2$): δ 7.41-7.52 (m, 6H, 5,5'-H of cyclopentathienyl and 2,2',6,6'-H of p-tolyl), 7.16-7.24 (m, 4H, 3,3',5,5'-H of p-tolyl), 6.83 (s, 2H, 3,3'-H of cyclopentathienyl), 2.32 (s, 6H, 4,4'-Me of p-tolyl), 2.31 (s, 6H, 2,2'-Me of cyclopentathienyl), 1.08 (s, 6H, SiMe$_2$). $^{13}$C{$^1$H} NMR ($CD_2Cl_2$): δ 145.8, 144.8, 139.4, 138.2, 133.4, 131.1, 130.0, 128.4, 121.5, 120.5, 72.4, 22.5, 20.7, 0.8.

EXAMPLE rac-9d rac-Dimethylsilyl-bis($\eta^5$-3-m-tolyl-5-dimethylcyclopenta[b]thien-6-yl)zirconium dichloride (rac-9d)

Following the procedure described for 1c, 0.76 ml of 1.0 M (0.76 mmol) m-tolylmagnesium chloride in THF, 1.68 ml of 0.5 M (0.84 mmol) ZnCl$_2$ in THF, 190 mg (0.29 mmol) of rac-9, and 0.59 ml of 0.02 M (0.012 mmol) Pd(P$^t$Bu$_3$)$_2$ in THF gave yellow solid for 2 hours at 70° C. Yield 124 mg (63%).

Anal. calc. for $C_{32}H_{30}Cl_2S_2SiZr$: C, 57.46; H, 4.52. Found: C, 57.61; H, 4.59. $^1$H NMR ($CD_2Cl_2$): δ 7.47 (s, 2H, 5,5'-H of cyclopentathienyl), 7.06-7.44 (m, 8H, 2,2',4,4',5,5=,6,6'-H of m-tolyl), 6.85 (m, 2H, 3,3'-H of cyclopentathienyl), 2.34 (s, 6H, 3,3'-Me of m-tolyl), 2.32 (s, 6H, 2,2'-Me of cyclopentathienyl), 1.09 (s, 6H, SiMe$_2$). $^{13}$C{$^1$H} NMR ($CD_2Cl_2$): δ 144.7, 140.1, 137.6, 136.1, 135.9, 130.6, 130.3, 130.1, 129.1, 125.6, 121.5, 120.4, 72.5, 22.8, 20.7, 0.7.

EXAMPLE rac-9e rac-dimethylsilyl-bis[$\eta^5$-3-(4-tert-butylphenyl)-5-dimethylcyclopenta[b]thien-6-yl]zirconium dichloride (rac-9e)

Following the procedure described for 1c, 1.00 ml of 0.80 M (0.80 mmol) 4-tert-butylphenylmagnesium bromide in ether, 1.75 ml of 0.5 M (0.88 mmol) ZnCl$_2$ in THF, 198 mg (0.31 mmol) of rac-9, and 0.61 ml of 0.02 M (0.012 mmol) Pd(P$^t$Bu$_3$)$_2$ in THF gave yellow solid for 2 hours at 70° C. Yield 185 mg (79%).

Anal. calc. for $C_{38}H_{42}Cl_2S_2SiZr$: C, 60.60; H, 5.62. Found: C, 60.86; H, 5.75. $^1$H NMR ($CD_2Cl_2$): δ 7.37-7.61 (m, 10H, 5,5'-H of cyclopentathienyl and 2,2',3,3',5,5',6,6'-H of C$_6$H$_4$), 6.85 (s, 2H, 3,3'-H of cyclopentathienyl), 2.31 (s, 6H, 2,2'-Me of cyclopentathienyl), 1.29 (s, 18H, $^t$Bu), 1.09 (s, 6H, SiMe$_2$). $^{13}$C{$^1$H} NMR ($CD_2Cl_2$): δ 138.3, 138.1, 137.6, 135.6, 133.3, 130.1, 128.1, 127.4, 121.5, 120.6, 72.5, 36.1, 32.6, 20.7, 0.7.

EXAMPLES 10a-10o

Negishi Coupling Using 4,4'-sulfandiyl-bis($\eta^5$-7-bromo-2-methylindenyl)zirconium dichloride (10)

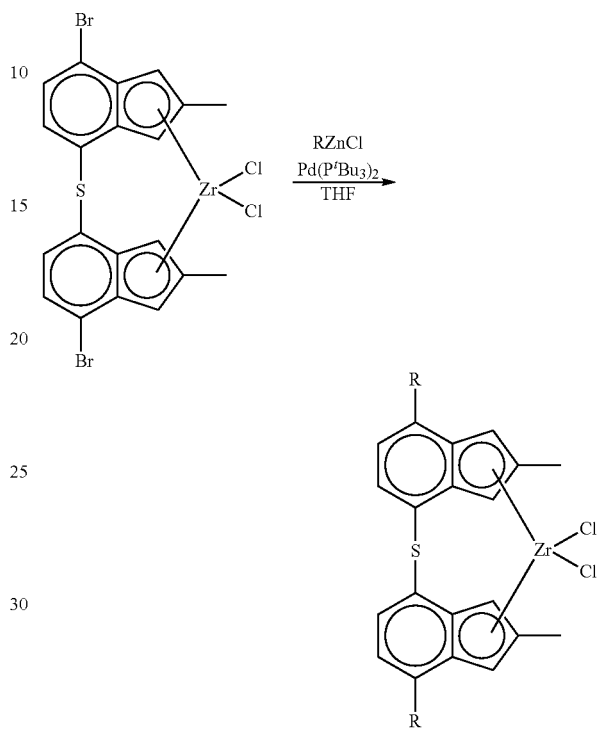

R=Me (10a), Ph (10b) 4-MeC$_6$H$_4$ (10c), 3-MeC$_6$H$_4$ (10d), 4-$^t$BuC$_6$H$_4$ (10e), 2,4,6-Me$_3$C$_6$H$_2$ (10f), 5-methyl-2-thienyl (10g), 5-methyl-2-furyl (10h), 2-benzothienyl (10i), 2-benzofuryl (10k), 4-FC$_6$H$_4$ (10l), 3-CF$_3$C$_6$H$_4$ (10m), 2,5-dimethylphenyl (10n), 4-biphenyl (10o).

EXAMPLE 10a 4,4'-Sulfandiyl-bis($\eta^5$-2,7-dimethylindenyl)zirconium dichloride (10a)

Under a nitrogen atmosphere, in a 16 ml vial equipped with PTFE coated stir bar and a suspension of 286 mg (0.47 mmol) of 10 in 8.0 ml of THF, 0.61 ml of 2.0 M MeZnCl (1.22 mmol) in THF and 0.94 ml of 0.02 M (0.019 mmol) Pd(P$^t$Bu$_3$)$_2$ in THF were added by a dosing pipette. The reaction mixture was stirred for 2 hours at 70° C. and then evaporated to dryness. To the residue, a solution of 1.0 ml of MeSiCl$_3$ in 10 ml of dry dichloromethane was added to eliminate an excess of the organozinc reagent. The resulting mixture was stirred at ambient temperature for 1 hour and then evaporated to dryness. In order to eliminate THF contamination, toluene (20 ml) was added and the mixture was vigorously stirred and brought to reflux; then the suspension was evaporated to dryness. This procedure was repeated a second time using 60 ml of toluene, and the resulting suspension was filtered through Celite 503. The resulting toluene filtrate was evaporated to dryness. The obtained solid was washed with 3×15 ml of hexanes and dried in vacuum. Yield, 210 mg (93%) of a yellow solid.

Anal. calc. for $C_{22}H_{20}Cl_2SZr$: C, 55.21; H, 4.21. Found: C, 55.35; H, 4.16. $^1H$ NMR (300 MHz, $CD_2Cl_2$): δ 7.51 (d, J=7.1 Hz, 2H, 5,5'-H), 6.95 (m, 2H, 6,6'-H), 6.39 (d, J=2.3 Hz, 2H, 1,1'-H), 4.52 (d, J=2.3 Hz, 2H, 3,3'-H), 2.52 (s, 6H, 7,7'-Me), 2.06 (s, 6H, 2,2'-Me). $^{13}C\{^1H\}$ NMR (75 MHz, $CD_2Cl_2$): δ 143.6, 143.2, 132.8, 130.3, 127.0, 125.3, 110.9, 106.4, 105.1, 21.3, 18.6.

EXAMPLE 10b 4,4'-Sulfandiyl-bis($\eta^5$-7-phenyl-2-methylindenyl) zirconium dichloride (10b)

Under a nitrogen atmosphere, in a 16 ml vial equipped with a PTFE coated stir bar, 0.57 ml of 1.0 M (0.57 mmol) phenylmagnesium bromide in THF was added by a dosing pipette to a mixture of 1.25 ml of 0.5 M (0.63 mmol) $ZnCl_2$ in THF and 5 ml of THF with vigorous stirring at ambient temperature. This organozinc reagent was additionally stirred for 1 hour and then added to a mixture of 133 mg (0.22 mmol) of 10, 0.44 ml of 0.02 M (0.009 mmol) $Pd(P^tBu_3)_2$ in THF, and 2 ml of THF placed in a separate 16 ml vial equipped with a PTFE coated stir bar. The reaction mixture was stirred for 2 hours at 70° C. and then evaporated to dryness. To the residue, a solution of 1.0 ml of $MeSiCl_3$ in 10 ml of dry dichloromethane was added to eliminate an excess of the organozinc reagent. The resulting mixture was stirred at ambient temperature for 1 hour and then evaporated to dryness. In order to eliminate THF contamination, toluene (20 ml) was added and the mixture was vigorously stirred and brought to reflux; then the suspension was evaporated to dryness. This procedure was repeated a second time using 60 ml of toluene, and the resulting suspension was filtered through Celite 503. The resulting toluene filtrate was evaporated to dryness. The obtained solid was washed with 3×15 ml of hexanes and dried in vacuum. Yield, 50 mg (38%) of a yellow solid.

Anal. calc. for $C_{32}H_{24}Cl_2SZr$: C, 63.77; H, 4.01. Found: C, 63.94; H, 3.92. $^1H$ NMR (300 MHz, $CD_2Cl_2$): δ 7.74 (d, J=7.2 Hz, 2H, 5,5'-H), 7.62-7.69 (m, 4H, 2,2',6,6'-H in Ph), 7.33-7.49 (m, 6H, 3,3',4,4',5,5'-H in Ph), 7.23 (d, J=7.2 Hz, 2H, 6,6'-H), 6.59 (d, J=2.2 Hz, 2H, 1,1'-H), 4.80 (d, J=2.2 Hz, 2H, 3,3'-H), 2.08 (s, 6H, 2,2'-Me).

EXAMPLE 10c 4,4'-Sulfandiyl-bis($\eta^5$-2-methyl-7-p-tolyl-indenyl) zirconium dichloride (10c)

Under a nitrogen atmosphere, following the procedure described for 10b, 0.79 ml of 1.0 M (0.79 mmol) p-tolylmagnesium bromide in THF, 1.74 ml of 0.5 M (0.87 mmol) $ZnCl_2$ in THF, 185 mg (0.30 mmol) of 10, and 0.61 ml of 0.02 M (0.012 mmol) $Pd(P^tBu_3)_2$ in THF gave a yellow solid for 2 hours at 70° C. Yield, 104 mg (54%).

Anal. calc. for $C_{34}H_{28}Cl_2SZr$: C, 64.74; H, 4.47. Found: C, 64.89; H, 4.40. $^1H$ NMR (300 MHz, $CD_2Cl_2$): δ 7.72 (d, J=7.4 Hz, 2H, 5,5'-H), 7.52-7.58 (m, 4H, 2,2',6,6'-H in p-tolyl), 7.23-7.29 (m, 4H, 3,3',5,5'-H in p-tolyl), 7.21 (d, J=7.4 Hz, 2H, 6,6'-H), 6.59 (d, J=2.5 Hz, 2H, 1,1'-H), 4.77 (d, J=2.5 Hz, 2H, 3,3'-H), 2.37 (s, 6H, 4,4'-Me in p-tolyl), 2.07 (s, 6H, 2,2'-Me). $^{13}C\{^1H\}$ NMR (75 MHz, $CD_2Cl_2$): δ 143.4, 139.6, 139.3, 137.9, 135.6, 130.7, 130.5, 130.0, 127.0, 122.9, 110.5, 106.1, 103.3, 22.5, 18.5.

EXAMPLE 10d 4,4'-Sulfandiyl-bis($\eta^5$-2-methyl-7-m-tolylindenyl) zirconium dichloride (10d)

Under a nitrogen atmosphere, following the procedure described for 10b, 0.53 ml of 1.0 M (0.53 mmol) m-tolylmagnesium chloride in THF, 1.16 ml of 0.5 M (0.58 mmol) $ZnCl_2$ in THF, 123 mg (0.20 mmol) of 10, and 0.40 ml of 0.02 M (0.008 mmol) $Pd(P^tBu_3)_2$ in THF gave yellow solid for 2 hours at 70° C. Yield, 85 mg (67%).

Anal. calc. for $C_{34}H_{28}Cl_2SZr$: C, 64.74; H, 4.47. Found: C, 65.03; H, 4.55. $^1H$ NMR (300 MHz, $CD_2Cl_2$): δ 7.73 (d, J=7.3 Hz, 2H, 5,5'-H), 7.16-7.52 (m, 10H, 6,6'-H in indenyl and 2,2',4,4',5,5',6,6'-H in m-tolyl), 6.60 (d, J=2.2 Hz, 2H, 1,1'-H), 4.79 (d, J=2.2 Hz, 2H, 3,3'-H), 2.39 (s, 6H, 4,4'-Me in p-tolyl), 2.09 (s, 6H, 2,2'-Me). $^{13}C\{^1H\}$ NMR (75 MHz, $CD_2Cl_2$): δ 143.5, 138.7, 138.6, 136.2, 135.9, 131.3, 130.3, 130.0 (two resonances), 127.8, 127.2, 124.6, 110.7, 106.1, 103.3, 22.8, 18.5.

EXAMPLE 10e 4,4'-Sulfandiyl-bis[$\eta^5$-2-methyl-7-(4-tert-butylphenyl)indenyl]zirconium dichloride (10e)

Under a nitrogen atmosphere, in a 16 ml vial equipped with PTFE coated stir bar, 0.98 ml of 0.8 M (0.78 mmol) 4-tert-butylphenylmagnesium bromide in ether was added by a dosing pipette to a mixture of 0.87 ml of 0.5 M (0.44 mmol) $ZnCl_2$ in THF and 5 ml of THF with vigorous stirring at ambient temperature. This organozinc reagent was additionally stirred for 1 hour and then added to a mixture of 184 mg (0.30 mmol) of 10, 0.61 ml of 0.02 M (0.012 mmol) $Pd(P^tBu_3)_2$ in THF, and 2 ml of THF placed in a separate 16 ml vial equipped with PTFE coated stir bar. The reaction mixture was stirred for 2 hours at 70° C. and then evaporated to dryness. The product was extracted with 3×30 ml of hexanes. The yellow solution was evaporated to dryness, and the residue was washed with 10 ml of cold hexanes and dried in vacuum. Yield, 176 mg (81%) of a yellow solid.

Anal. calc. for $C_{40}H_{40}Cl_2SZr$: C, 67.20; H, 5.64. Found: C, 67.48; H, 5.74. $^1H$ NMR (300 MHz, $CD_2Cl_2$): δ 7.72 (d, J=7.3 Hz, 2H, 5,5'-H), 7.59-7.67 (m, 4H, 2,2',6,6'-H in $C_6H_4$), 7.40-7.48 (m, 4H, 3,3',5,5'-H in $C_6H_4$), 7.23 (d, J=7.3 Hz, 2H, 6,6'-H), 6.62 (d, J=2.3 Hz, 2H, 1,1'-H), 4.80 (d, J=2.3 Hz, 2H, 3,3'-H), 2.08 (s, 6H, 2,2'-Me), 1.33 (s, 18H, $^tBu$). $^{13}C\{^1H\}$ NMR (75 MHz, $CD_2Cl_2$): δ 143.5, 139.3, 138.6, 137.9, 135.6, 130.3, 130.0, 128.1, 127.0, 118.2, 110.7, 106.2, 104.6, 36.2, 32.7, 18.5.

EXAMPLE 10f 4,4'-Sulfandiyl-bis($\eta^5$-7-mesityl-2-methylindenyl) zirconium dichloride (10f)

Under a nitrogen atmosphere, following the procedure described for 10b, 0.97 ml of 0.88 M (0.85 mmol) mesitylmagnesium bromide in THF, 1.88 ml of 0.5 M (0.94 mmol) $ZnCl_2$ in THF, 200 mg (0.33 mmol) of 10, and 0.66 ml of 0.02 M (0.013 mmol) $Pd(P^tBu_3)_2$ in THF gave yellow solid for 2 hours at 70° C. Yield, 214 mg (95%).

Anal. calc. for $C_{38}H_{36}Cl_2SZr$: C, 66.45; H, 5.28. Found: C, 66.11; H, 5.39. $^1$H NMR (300 MHz, $CD_2Cl_2$): δ 7.71 (d, J=7.3 Hz, 2H, 5,5'-H of indenyl), 7.06 (d, J=7.3 Hz, 2H, 6,6'-H of indenyl), 6.96 (m, 2H, 3,3'-H of mesityl), 6.91 (m, 2H, 3,3'-H of mesityl), 6.04 (m, 2H, 1,1'-H of indenyl), 4.87 (m, 2H, 3,3'-H of indenyl), 2.29 (s, 6H, 2,2'-Me of mesityl), 2.19 (s, 6H, 4,4'-Me of mesityl), 2.08 (s, 6H, 6,6'-Me of mesityl), 1.84 (s, 6H, 2,2'-Me of indenyl). $^{13}C\{^1H\}$ NMR (75 MHz, $CD_2Cl_2$): δ 143.0, 138.9, 138.1, 137.8, 136.1, 135.6, 132.4, 130.3, 129.9, 129.5, 129.0, 123.1, 112.7, 111.2, 104.5, 23.3, 22.4, 21.9, 18.4.

EXAMPLE 10g 4,4'-Sulfandiyl-bis[η$^5$-2-methyl-7-(5-methyl-thien-2-yl)indenyl]zirconium dichloride (10g)

Under a nitrogen atmosphere, in a 16 ml vial equipped with PTFE coated stir bar to 1.68 ml of 0.51 M (0.86 mmol) of 2-methylthiophene in THF, 1.71 ml of 0.5 M (0.86 mmol) $^n$BuLi in hexanes was added by a dosing pipette with vigorous stirring at −80° C. This mixture was stirred and slowly warmed (for ca. 1 hour) to 0° C. Then, 1.88 ml of 0.5 M (0.94 mmol) $ZnCl_2$ in THF was added at −80° C., and the obtained mixture was stirred and slowly warmed to ambient temperature and then evaporated to dryness. In a separate 16 ml vial equipped with PTFE coated stir bar containing a mixture of 200 mg (0.33 mmol) of 10, 0.66 ml of 0.02 M (0.013 mmol) Pd(P$^t$Bu$_3$)$_2$ in THF, and 4 ml of THF, the above described organozinc reagent was added. This mixture was stirred for 4 hours at room temperature, and then evaporated to dryness. To the residue, a solution of 1.0 ml of MeSiCl$_3$ in 10 ml of dry dichloromethane was added to eliminate an excess of the organozinc reagent. The resulting mixture was stirred at ambient temperature for 1 hour and then evaporated to dryness. In order to eliminate THF contamination, toluene (20 ml) was added and the mixture was vigorously stirred and brought to reflux; then the suspension was evaporated to dryness. This procedure was repeated a second time using 60 ml of toluene, and the resulting suspension was filtered through Celite 503. The resulting toluene filtrate was evaporated to dryness. The obtained solid was washed with 3×15 ml of hexanes and dried in vacuum. Yield, 181 mg (86%) of a yellow solid.

Anal. calc. for $C_{30}H_{24}Cl_2S_3Zr$: C, 56.05; H, 3.76. Found: C, 55.88; H, 3.85. $^1$H NMR (300 MHz, $CD_2Cl_2$): δ 7.63 (d, J=7.5 Hz, 2H, 5,5'-H of indenyl), 7.46 (d, J=3.6 Hz, 3,3'-H of thienyl), 7.35 (d, J=7.5 Hz, 2H, 6,6'-H of indenyl), 6.84 (d, J=2.4 Hz, 2H, 1,1'-H of indenyl), 6.80 (m, 2H, 4,4'-H of thienyl), 4.79 (d, J=2.4 Hz, 2H, 3,3'-H), 2.51 (s, 6H, 5,5'-Me of thienyl), 2.09 (s, 6H, 2,2'-Me of indenyl).

EXAMPLE 10h 4,4'-Sulfandiyl-bis[η$^5$-2-methyl-7-(5-methyl-furan-2-yl)indenyl]zirconium dichloride (10h)

Under a nitrogen atmosphere, following the procedure described for 10g, 1.41 ml of 0.61 M (0.85 mmol) of 2-methylfuran, 1.71 ml of 0.5 M $^n$BuLi (0.86 mmol), 1.88 ml of 0.5 M (0.94 mmol) $ZnCl_2$ in THF, 200 mg (0.33 mmol) of 10, and 0.66 ml of 0.02 M (0.013 mmol) Pd(P$^t$Bu$_3$)$_2$ in THF gave a yellow solid. Yield, 162 mg (81%).

Anal. calc. for $C_{30}H_{24}Cl_2O_2SZr$: C, 59.00; H, 3.96. Found: C, 58.78; H, 4.10. $^1$H NMR (300 MHz, $CD_2Cl_2$): δ 7.65 (d, J=7.6 Hz, 2H, 5,5'-H of indenyl), 7.52 (d, J=7.6 Hz, 2H, 6,6'-H of indenyl), 6.90 (d, J=3.3 Hz, 3,3'-H of furyl), 6.87 (d, J=2.4 Hz, 2H, 1,1'-H of indenyl), 6.15 (m, 2H, 4,4'-H of furyl), 4.73 (d, J=2.4 Hz, 2H, 3,3'-H), 2.39 (s, 6H, 5,5'-Me of furyl), 2.08 (s, 6H, 2,2'-Me of indenyl).

EXAMPLE 10i 4,4'-Sulfandiyl-bis[η$^5$-2-methyl-7-(2-benzothienyl)indenyl]zirconium dichloride (10i)

Under a nitrogen atmosphere, to a solution of 115 mg (0.855 mmol) of benzothiophene in 4 ml of THF, 1.71 ml of 0.5 M (0.855 mmol) of $^n$BuLi in hexanes was added at −80° C. The resulted mixture was stirred for 3 hours at room temperature, then cooled to −80° C., and 0.954 ml (0.954 mmol) of 1.0 M $ZnCl_2$ in THF was added. This mixture was slowly warmed to ambient temperature and additionally stirred for 1 hour at this temperature. The solution of organozinc reagent was added to a mixture of 200 mg (0.329 mmol) of 10. Then, 0.825 ml of 0.02 M (0.0165 mmol) Pd(P$^t$Bu$_3$)$_2$ in THF was added. The cross-coupling reaction was carried out by vigorous stirring for 2 hours at 65° C. Then, this mixture was evaporated to dryness, and 30 ml of toluene was added to the residue. This mixture was heated to 110° C., then evaporated to dryness. To the residue 30 ml of toluene was added, the mixture was heated to 110° C. and filtered through Celite 503. The Celite layer was additionally washed by 2×15 ml of hot toluene. The combined toluene extract was evaporated to dryness. The residue was washed by 2×10 ml of hexanes and dried in vacuum. Yield 175 mg (75%).

Anal. calc. for $C_{36}H_{24}Cl_2S_3Zr$: C, 60.48; H, 3.38. Found: C, 60.69; H, 3.47. $^1$H NMR (300 MHz, $CD_2Cl_2$): δ 7.84 (d, J=7.6 Hz, 2H, 5,5'-H of indenyl), 7.76 (d, J=7.6 Hz, 2H, 6,6'-H of indenyl), 7.63 (m, 2H, 4/7,4'/7'-H in benzothienyl), 7.55 (m, 2H, 7/4,7'/4'-H in benzothienyl), 7.41 (m, 2H, 3,3'-H in benzothienyl), 7.32 (m, 2H, 5/6, 5'/6'-H in benzothienyl), 7.24 (m, 2H, 6/5,6'/5'-H in benzothienyl), 7.05 (m, 2H, 1,1'-H of indenyl), 4.85 (m, 2H, 3,3'-H of indenyl), 2.11 (s, 6H, 2,2'-Me of indenyl).

EXAMPLE 10k 4,4'-Sulfandiyl-bis[η$^5$-2-methyl-7-(2-benzofuryl)indenyl]zirconium dichloride (10k)

Under a nitrogen atmosphere, to a solution of 101 mg (0.855 mmol) of benzofuran in 4 ml of THF, 1.71 ml of 0.5 M (0.855 mmol) of $^n$BuLi in hexanes was added at −80° C. The resulted mixture was stirred for 3 hours at room temperature, then cooled to −80° C., and 0.954 ml (0.954 mmol) of 1.0 M $ZnCl_2$ in THF was added. This mixture was slowly warmed to ambient temperature and additionally stirred for 1 hour at this temperature. The solution of organozinc reagent was added to a mixture of 200 mg (0.329 mmol) of 10. Then, 0.825 ml of 0.02 M (0.0165 mmol) Pd(P$^t$Bu$_3$)$_2$ in THF was added. The cross-coupling reaction was carried out by vigorous stirring for 2 hours at 65° C. Then, this mixture was evaporated to dryness, and 30 ml of toluene was added to the residue. This mixture was heated to 110° C., then evaporated to dryness. To the residue 30 ml of toluene was added, the mixture was heated to 110° C. and filtered through Celite 503. The Celite layer was additionally washed by 2×15 ml of hot toluene. The combined toluene extract was evaporated to dryness. The residue was washed by 2×10 ml of hexanes and dried in vacuum. Yield 162 mg (72%).

Anal. calc. for $C_{36}H_{24}Cl_2O_2SZr$: C, 63.33; H, 3.54. Found: C, 63.51; H, 3.66. $^1$H NMR (300 MHz, $CD_2Cl_2$): δ 7.84 (d, J=7.6 Hz, 2H, 5,5'-H of indenyl), 7.77 (d, J=7.6 Hz, 2H, 6,6'-H of indenyl), 7.63 (m, 2H, 4/7,4'/7'-H in benzofuryl), 7.55 (m, 2H, 7/4,7'/4'-H in benzofuryl), 7.42 (m, 2H, 3,3'-H in benzofuryl), 7.32 (m, 2H, 5/6, 5'/6'-H in benzofuryl), 7.24 (m, 2H, 6/5,6'/5'-H in benzofuryl), 7.05 (m, 2H, 1,1'-H of indenyl), 4.86 (m, 2H, 3,3'-H of indenyl), 2.12 (s, 6H, 2,2'-Me of indenyl).

EXAMPLE 10l 4,4'-Sulfandiyl-bis[$\eta^5$-2-methyl-7-(4-fluorophenyl)indenyl]zirconium dichloride (10l)

Under a nitrogen atmosphere, to a mixture of 0.954 ml (0.954 mmol) of 1.0 M ZnCl$_2$ in THF and 4 ml of THF 0.725 ml of 1.18 M (0.855 mmol), para-fluorophenylmagnesium bromide in THF was added. This mixture was stirred for 1 hour at room temperature. The resulted white suspension was added to 200 mg (0.329 mmol) of 10 in 3 ml of THF. Then, 0.825 ml of 0.02 M (0.0165 mmol) Pd(P$^t$Bu$_3$)$_2$ in THF was added. The cross-coupling reaction was carried out by vigorous stirring for 2 hours at 70° C. Then, this mixture was evaporated to dryness, and 30 ml of toluene was added to the residue. This mixture was heated to 110° C., then evaporated to dryness. To the residue 30 ml of toluene was added, the mixture was heated to 110° C. and filtered through Celite 503. The Celite layer was additionally washed by 2×15 ml of hot toluene. The combined toluene extract was evaporated to dryness. The residue was washed by 2×10 ml of hexanes and dried in vacuum. Yield 175 mg (83%).

Anal. calc. for C$_{32}$H$_{22}$Cl$_2$F$_2$SZr: C, 60.17; H, 3.47. Found: C, 60.35; H, 3.56. $^1$H NMR (300 MHz, CD$_2$Cl$_2$): δ 7.73 (d, J=7.3 Hz, 2H, 5,5'-H of indenyl), 7.64 (m, 4H, 2,2',6,6'-H of C$_6$H$_4$F), 7.20 (d, J=7.3 Hz, 2H, 6,6'-H of indenyl), 7.14 (m, 4H, 3,3',5,5'-H of C$_6$H$_4$), 6.55 (d, J=2.5 Hz, 2H, 1,1'-H of indenyl), 4.80 (d, J=2.5 Hz, 2H, 3,3'-H of indenyl), 2.09 (s, 6H, 2,2'-Me of indenyl).

EXAMPLE 10m 4,4'-Sulfandiyl-bis[$\eta^5$-2-methyl-7-(3-trifluoromethylphenyl)indenyl]zirconium dichloride (10m)

Under a nitrogen atmosphere, to a mixture of 0.954 ml (0.954 mmol) of 1.0 M ZnCl$_2$ in THF and 4 ml of THF 0.838 ml of 1.02 M (0.855 mmol), meta-trifluoromethylphenylmagnesium bromide in THF was added. This mixture was stirred for 1 hour at room temperature. The resulted white suspension was added to 200 mg (0.329 mmol) of 10 in 3 ml of THF. Then, 0.825 ml of 0.02 M (0.0165 mmol) Pd(P$^t$Bu$_3$)$_2$ in THF was added. The cross-coupling reaction was carried out by vigorous stirring for 2 hours at 70° C. Then, this mixture was evaporated to dryness, and 30 ml of toluene was added to the residue. This mixture was heated to 110° C., then evaporated to dryness. To the residue 30 ml of toluene was added, the mixture was heated to 110° C. and filtered through Celite 503. The Celite layer was additionally washed by 2×15 ml of hot toluene. The combined toluene extract was evaporated to dryness. The residue was washed by 2×10 ml of hexanes and dried in vacuum. Yield 160 mg (66%).

Anal. calc. for C$_{34}$H$_{22}$Cl$_2$F$_6$SZr: C, 55.28; H, 3.00. Found: C, 55.12; H, 3.09. $^1$H NMR (300 MHz, CD$_2$Cl$_2$): δ 7.85-7.94 (m, 4H, 2,2',4,4'-H in C$_6$H$_4$CF$_3$), 7.77 (d, J=7.3 Hz, 2H, 5,5'-H of indenyl), 7.55-7.67 (m, 4H, 5,5',6,6'-H in C$_6$H$_4$CF$_3$), 7.26 (d, J=7.3 Hz, 2H, 6,6'-H of indenyl), 6.53 (m, 2H, 1,1'-H of indenyl), 4.84 (m, 2H, 3,3'-H of indenyl), 2.10 (s, 6H, 2,2'-Me of indenyl).

EXAMPLE 10n 4,4'-Sulfandiyl-bis[$\eta^5$-2-methyl-7-(2,5-dimethylphenyl)indenyl]zirconium dichloride (10n)

Under a nitrogen atmosphere in a 16 ml vial equipped with PTFE coated stir bar and containing 8.80 ml of 0.25 M (2.20 mmol) ZnCl$_2$ in THF, 2.0 ml of 1.0 M (2.00 mmol) 2,5-dimethylphenylmagnesium bromide in THF was added at room temperature. This mixture was stirred for 1 hour. Then, in a separate 16 ml vial equipped with PTFE coated stir bar and containing a suspension of 150 mg (0.25 mmol) of 10 in 4.0 ml of THF, 3.40 ml of the solution of the above obtained organozinc reagent and 0.50 ml of 0.02 M (0.010 mmol) Pd(P$^t$Bu$_3$)$_2$ in THF were added by a dosing pipette. The reaction mixture was stirred for 3 hours at 70° C. and then evaporated to dryness. To the residue, a solution of 1.0 ml of MeSiCl$_3$ in 10 ml of dry dichloromethane was added to eliminate an excess of the organozinc reagent. The resulted mixture was stirred at ambient temperature for 1 hour and then evaporated to dryness. In order to eliminate THF contamination, the residue was treated with hot toluene (20 ml), then, the suspension was evaporated to dryness. The residue was additionally treated with 60 ml of hot toluene, and the resulted suspension filtered through Celite 503. The toluene extract was evaporated to dryness. The obtained solid was washed with 3×15 ml of hexanes and dried in vacuum. Yield 130 mg (80%) of yellowish solid.

Anal. calc. for C$_{36}$H$_{32}$Cl$_2$SZr: C, 65.63; H, 4.90. Found: C, 65.81; H, 5.00. $^1$H NMR (CD$_2$Cl$_2$): δ 7.72 (d, J=7.3 Hz, 2H, 5,5'-H in indenyl), 7.05-7.20 (m, 8H, 6,6'-H in indenyl and 3,3',4,4',6,6'-H in 2,5-Me$_2$C$_6$H$_3$), 6.25 (br.s, 2H, 1,1'-H in indenyl), 4.80 (d, J=2.4 Hz, 2H, 3,3'-H in indenyl), 2.31 (s, 6H, 5,5'-Me in 2,5-Me$_2$C$_6$H$_3$), 2.11 (s, 6H, 2,2'-Me in indenyl), 2.10 (br.s, 6H, 2,2'-Me in 2,5-Me$_2$C$_6$H$_3$).

EXAMPLE 10o 4,4'-Sulfandiyl-bis[$\eta^5$-2-methyl-7-(4-biphenyl)indenyl]zirconium dichloride (10o)

Under a nitrogen atmosphere in a 16 ml vial equipped with PTFE coated stir bar and containing 8.80 ml of 0.25 M (2.20 mmol) ZnCl$_2$ in THF, 2.0 ml of 1.0 M (2.00 mmol) 4-biphenylmagnesium bromide in THF was added at room temperature. This mixture was stirred for 1 hour. Then, in a separate 16 ml vial equipped with PTFE coated stir bar and containing a suspension of 150 mg (0.25 mmol) of 10 in 4.0 ml of THF, 3.40 ml of the solution of the above obtained organozinc reagent in THF and 0.50 ml of 0.02 M (0.010 mmol) Pd(P$^t$Bu$_3$)$_2$ in THF were added by a dosing pipette. The reaction mixture was stirred for 3 hours at 70° C. and then evaporated to dryness. To the residue, a solution of 1.0 ml of MeSiCl$_3$ in 10 ml of dry dichloromethane was added to eliminate an excess of the organozinc reagent. The resulted mixture was stirred at ambient temperature for 1 hour and then evaporated to dryness. In order to eliminate THF contamination, the residue was treated with hot toluene (20 ml), then, the suspension was evaporated to dryness. The residue was additionally treated with 60 ml of hot toluene, and the resulted suspension filtered through Celite 503. The toluene extract was evaporated to dryness. The obtained solid was washed with 3×15 ml of hexanes and dried in vacuum. Yield 140 mg (75%) of yellowish solid.

Anal. calc. for C$_{44}$H$_{32}$Cl$_2$SZr: C, 70.00; H, 4.27. Found: C, 70.29; H, 4.36. $^1$H NMR (CD$_2$Cl$_2$): δ 7.28-7.80 (m, 22H, 5,5',6,6'-H in indenyls and 4-biphenyls), 6.67 (d, J=2.4 Hz, 2H, 1,1'-H in indenyl), 4.85 (d, J=2.4 Hz, 2H, 3,3'-H in indenyl), 2.12 (s, 6H, 2,2'-Me in indenyl).

EXAMPLES 11a-11r

Negishi Coupling Applying dimethylsilyl($\eta^5$-2-methyl-4-bromoinden-1-yl)-($\eta^1$-tert-butylamido)zirconium dichloride (11)

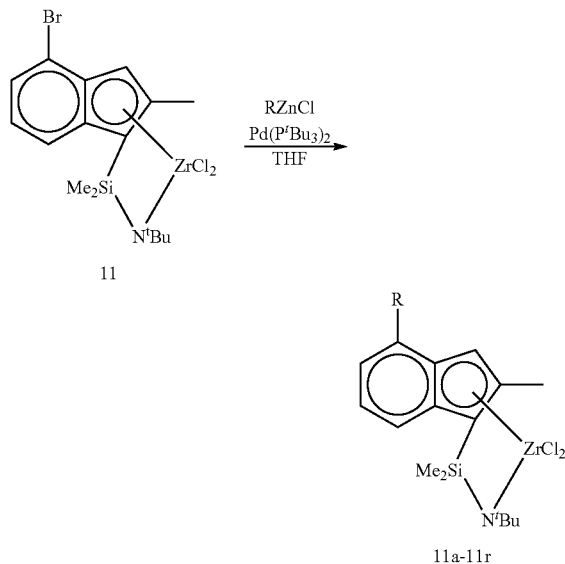

R=Me (11a), 4-MeC$_6$H$_4$ (11b), 3-MeC$_6$H$_4$ (11c), 2-MeC$_6$H$_4$ (11d), 2,4,6-Me$_3$C$_6$H$_2$ (11e), 2,5-Me$_2$C$_6$H$_3$ (11f), 4-FC$_6$H$_4$ (11g), 3-CF$_3$C$_6$H$_4$ (11h), 4-PhC$_6$H$_4$ (11i), 4-Me$_2$NC$_6$H$_4$ (11k), 2-MeOC$_6$H$_4$ (11l), 3-methoxy-2-methyl-2,3-dihydro-1H-inden-4-yl (11m), 5-methyl-2-furyl (11n), 5-methyl-2-thienyl (11o), 2-benzothienyl (11p), 2-benzofuryl (11r)

EXAMPLE 11a

Dimethylsilyl($\eta^5$-2,4-dimethylinden-1-yl)($\eta^1$-tert-butylamido)zirconium dichloride (11a)

In a nitrogen atmosphere Glove box, in a 16 ml vial equipped with a PTFE coated stir bar and containing a suspension of 200 mg (0.40 mmol) of 11 in 10.0 ml of THF, 0.265 ml of 2.0 M MeZnCl (0.52 mmol) in THF and 0.40 ml of 0.02 M (0.008 mmol) Pd(P$^t$Bu$_3$)$_2$ in THF were added by a dosing pipette. The reaction mixture was stirred for 20 hours at room temperature and then evaporated to dryness. The product was extracted with 3×30 ml of hot hexanes. The extract was filtered through Celite 503 and then evaporated to dryness. The residue was dried in vacuum. Yield 120 mg (69%) of yellowish solid.

Anal. calc. for C$_{17}$H$_{25}$Cl$_2$NSiZr: C, 47.09; H, 5.81. Found: C, 47.21; H, 5.76. $^1$H NMR (CD$_2$Cl$_2$): δ 7.56 (m, 1H, 5-H in indenyl), 7.10 (dd, J=8.5 Hz, J=6.9 Hz, 1H, 6-H in indenyl), 7.03 (m, 1H, 7-H in indenyl), 6.88 (m, 1H, 3-H in indenyl), 2.46 (s, 3H, 4-Me in indenyl), 2.39 (m, 3H, 2-Me in indenyl), 1.31 (s, 9H, $^t$Bu), 0.84 (s, 3H, SiMeMe'), 0.69 (s, 3H, SiMeMe'). $^{13}$C{$^1$H} NMR (CD$_2$Cl$_2$): δ 142.5, 135.4 (two resonances), 135.2, 132.1, 128.0, 126.3, 122.7, 112.3, 56.8, 33.2, 19.6, 18.6, 6.1, 5.8.

EXAMPLE 11b

Dimethylsilyl($\eta^5$-2-methyl-4-p-tolylinden-1-yl)($\eta^1$-tert-butylamido)zirconium dichloride (11b)

In a nitrogen atmosphere Glove box, in a 16 ml vial equipped with a PTFE coated stir bar, 0.39 ml of 1.0 M (0.39 mmol) p-tolylmagnesium bromide in THF was added by a dosing pipette to a mixture of 0.86 ml of 0.5 M (0.43 mmol) ZnCl$_2$ in THF and 3 ml of THF by vigorous stirring at ambient temperature. This organozinc reagent was additionally stirred for 1 hour and then added to a mixture of 150 mg (0.30 mmol) of 11, 0.30 ml of 0.02 M (0.006 mmol) Pd(P$^t$Bu$_3$)$_2$ in THF, and 3 ml of THF placed in a separate 16 ml vial equipped with a PTFE coated stir bar. The reaction mixture was stirred for 20 hours at room temperature and then evaporated to dryness. The product was extracted with 3×30 ml of hot hexanes. The extract was filtered through Celite 503 and then evaporated to dryness. The residue was dried in vacuum. Yield 139 mg (91%) of yellowish solid.

Anal. calc. for C$_{23}$H$_{29}$Cl$_2$NSiZr: C, 54.20; H, 5.73. Found: C, 54.38; H, 5.80. $^1$H NMR (CD$_2$Cl$_2$): δ 7.70 (m, 1H, 5-H in indenyl), 7.45 (m, 2H, 2,6-H in p-tolyl), 7.29 (m, 2H, 3,5-H in p-tolyl), 7.18-7.27 (m, 2H, 6,7-H in indenyl), 6.99 (m, 1H, 3-H in indenyl), 2.40 (s, 3H, 4-Me in p-tolyl), 2.36 (s, 3H, 2-Me in indenyl), 1.33 (s, 9H, $^t$Bu), 0.88 (s, 3H, SiMeMe'), 0.71 (s, 3H, SiMeMe'). $^{13}$C{$^1$H} NMR (CD$_2$Cl$_2$): δ 142.0, 139.7, 139.6, 138.1, 137.7, 136.6, 134.7, 131.1, 129.7, 129.2, 127.6, 125.3, 114.6, 58.1, 34.4, 22.6, 19.8, 7.9, 7.1.

EXAMPLE 11c

Dimethylsilyl($\eta^5$-2-methyl-4-m-tolylinden-1-yl)($\eta^1$-tert-butylamido)zirconium dichloride (11c)

Following the procedure described for 11b, 0.39 ml of 1.0 M (0.39 mmol) m-tolylmagnesium bromide in THF gave yellowish solid. Yield 143 mg (93%).

Anal. calc. for C$_{23}$H$_{29}$Cl$_2$NSiZr: C, 54.20; H, 5.73. Found: C, 54.39; H, 5.68. $^1$H NMR (CD$_2$Cl$_2$): δ 7.71 (m, 1H, 5-H in indenyl), 7.34-7.39 (m, 3H, 2,5,6-H in m-tolyl), 7.20-7.29 (m, 3H, 6,7-H in indenyl and 4-H in m-tolyl), 7.00 (br.s, 1H, 3-H in indenyl), 2.41 (s, 3H, 3-Me in m-tolyl), 2.37 (m, 3H, 2-Me in indenyl), 1.33 (s, 9H, $^t$Bu), 0.88 (s, 3H, SiMeMe'), 0.71 (s, 3H, SiMeMe').

EXAMPLE 11d

Dimethylsilyl($\eta^5$-2-methyl-4-o-tolylinden-1-yl)($\eta^1$-tert-butylamido)zirconium dichloride (11d)

Following the procedure described for 11b, 0.47 ml of 0.83 M (0.39 mmol) o-tolylmagnesium bromide in THF gave yellowish solid. Yield 143 mg (93%).

Anal. calc. for C$_{23}$H$_{29}$Cl$_2$NSiZr: C, 54.20; H, 5.73. Found: C, 54.41; H, 5.70. $^1$H NMR (CD$_2$Cl$_2$): δ 7.74 (d, J=8.5 Hz, 1H, 5-H in indenyl), 7.17-7.33 (m, 6H, 6,7-H in indenyl and 3,4,5,6-H in o-tolyl), 7.13 (m, 1H, 3-H in indenyl), 2.33 (s, 3H, 2-Me in indenyl), 2.11 (br.s, 3H, 2-Me in o-tolyl), 1.33 (s, 9H, $^t$Bu), 0.89 (s, 3H, SiMeMe'), 0.71 (s, 3H, SiMeMe').

EXAMPLE 11e

Dimethylsilyl(η$^5$-2-methyl-4-mesitylinden-1-yl)(η$^1$-tert-butylamido)zirconium dichloride (11e)

Following the procedure described for 11b, 0.44 ml of 0.88 M (0.39 mmol) mesitylmagnesium bromide in THF gave yellowish solid. Yield 159 mg (98%).

Anal. calc. for $C_{25}H_{33}Cl_2NSiZr$: C, 55.84; H, 6.19. Found: C, 55.95; H, 6.07. $^1$H NMR ($CD_2Cl_2$): δ 7.73 (d, J=8.7 Hz, 1H, 5-H in indenyl), 7.26 (dd, J=8.7 Hz, J=7.0 Hz, 1H, 6-H in indenyl), 7.07 (dd, J=7.0 Hz, J=0.7 Hz, 1H, 7-H in indenyl), 6.97 (m, 1H, 3-H in mesityl), 6.90 (m, 1H, 5-H in mesityl), 6.45 (br.s, 1H, 3-H in indenyl), 2.31 (s, 3H, 2-Me in mesityl), 2.30 (s, 3H, 6-Me in mesityl), 2.24 (s, 3H, 4-Me in mesityl), 1.70 (s, 3H, 2-Me in indenyl), 1.34 (s, 9H, $^t$Bu), 0.87 (s, 3H, SiMeMe'), 0.71 (s, 3H, SiMeMe'). $^{13}C\{^1H\}$ NMR ($CD_2Cl_2$): δ 145.5, 144.3, 139.3, 138.9, 138.13, 138.06, 136.9, 135.0, 134.3, 130.1, 129.8, 129.4, 128.6, 126.3, 115.5, 58.3, 34.3, 23.1, 22.3, 21.5, 19.7, 7.2, 7.0.

EXAMPLE 11f

Dimethylsilyl[η$^5$-2-methyl-4-(2,5-dimethylphenyl)inden-1-yl](η$^1$-tert-butylamido)zirconium dichloride (11f)

Following the procedure described for 11b, 0.45 ml of 0.87 M (0.39 mmol) 2,5-dimethylphenylmagnesium bromide in THF gave yellowish solid. Yield 142 mg (90%).

Anal. calc. for $C_{24}H_{31}Cl_2NSiZr$: C, 55.04; H, 5.97. Found: C, 55.28; H, 6.11. $^1$H NMR ($CD_2Cl_2$): δ 7.73 (d, J=8.7 Hz, 1H, 5-H in indenyl), 7.27 (dd, J=8.7 Hz, J=7.0 Hz, 1H, 6-H in indenyl), 7.20 (d, J=8.1 Hz, 1H, 4-H in $Me_2C_6H_3$), 7.09-7.15 (m, 3H, 3,6-H in $Me_2C_6H_3$ and 7-H in indenyl), 6.53 (br.s, 1H, 3-H in indenyl), 2.34 (s, 3H, 2-Me in indenyl), 2.33 (s, 3H, 5-Me in $Me_2C_6H_3$), 2.07 (br.s, 3H, 2-Me in $Me_2C_6H_3$), 1.35 (s, 9H, $^t$Bu), 0.89 (s, 3H, SiMeMe'), 0.72 (s, 3H, SiMeMe'). $^{13}C\{^1H\}$ NMR ($CD_2Cl_2$): δ 144.1, 140.2, 140.0, 139.2, 137.0 (br), 136.5, 135.8, 134.1, 131.5, 131.2, 130.3, 129.3, 128.6 (br), 125.5 (br), 115.0 (br), 58.2, 34.4, 20.6, 19.8 (br), 15.5, 7.8, 7.1.

EXAMPLE 11g

Dimethylsilyl[η$^5$-2-methyl-4-p-fluorophenyl)inden-1-yl](η$^1$-tert-butylamido)zirconium dichloride (11g)

Following the procedure described for 11b, 0.33 ml of 1.18 M (0.39 mmol) p-fluorophenylmagnesium bromide in THF gave yellowish solid. Yield 152 mg (98%).

Anal. calc. for $C_{22}H_{26}Cl_2FNSiZr$: C, 51.44; H, 5.10. Found: C, 51.60; H, 5.17. $^1$H NMR ($CD_2Cl_2$): δ 7.72 (dt, J=8.4 Hz, J=1.1 Hz, 1H, 5-H in indenyl), 7.54 (dd, J=8.8 Hz, J=5.4 Hz, 2H, 2,6-H in $FC_6H_4$), 7.26 (dd, J=8.4 Hz, J=7.0 Hz, 1H, 6-H in indenyl), 7.22 (dd, J=7.0 Hz, J=1.1 Hz, 1H, 7-H in indenyl), 7.18 (t, J=8.8 Hz, 2H, 3,5-H in $FC_6H_4$), 6.94 (br.s, 1H, 3-H in indenyl), 2.37 (d, J=0.5 Hz, 3H, 2-Me in indenyl), 1.33 (s, 9H, $^t$Bu), 0.88 (s, 3H, SiMeMe'), 0.71 (s, 3H, SiMeMe').

EXAMPLE 11h

Dimethylsilyl[η$^5$-2-methyl-4-(m-trifluoromethylphenyl)inden-1-yl](η$^1$-tert-butylamido)zirconium dichloride (11h)

Following the procedure described for 11b, 0.38 ml of 1.02 M (0.39 mmol) m-trifluoromethylphenylmagnesium bromide in THF gave yellowish solid. Yield 163 mg (96%).

Anal. calc. for $C_{23}H_{26}Cl_2F_3NSiZr$: C, 49.01; H, 4.65. Found: C, 48.89; H, 4.53. $^1$H NMR ($CD_2Cl_2$): δ 7.55-7.85 (m, 5H, 5-H in indenyl and $FC_6H_4$), 7.27-7.32 (m, 2H, 6,7-H in indenyl), 6.93 (br.s, 1H, 3-H in indenyl), 2.38 (d, J=0.7 Hz, 3H, 2-Me in indenyl), 1.34 (s, 9H, $^t$Bu), 0.89 (s, 3H, SiMeMe'), 0.72 (s, 3H, SiMeMe').

EXAMPLE 11i

Dimethylsilyl[η$^5$-2-methyl-4-(1,1'-biphen-4-yl)inden-1-yl](η$^1$-tert-butylamido)zirconium dichloride (11i)

Following the procedure described for 11b, 1.26 ml of 0.31 M (0.39 mmol) 1,1'-biphen-4-ylmagnesium bromide in THF gave yellowish solid. Yield 161 mg (94%).

Anal. calc. for $C_{28}H_{31}Cl_2NSiZr$: C, 58.82; H, 5.46. Found: C, 59.01; H, 5.40. $^1$H NMR ($CD_2Cl_2$): δ 7.27-7.76 (m, 12H, 5,6,7-H in indenyl and $PhC_6H_4$), 7.06 (m, 1H, 3-H in indenyl), 2.39 (d, J=0.6 Hz, 3H, 2-Me in indenyl), 1.34 (s, 9H, $^t$Bu), 0.89 (s, 3H, SiMeMe'), 0.72 (s, 3H, SiMeMe').

EXAMPLE 11k

Dimethylsilyl[η$^5$-2-methyl-4-(p-dimethylaminophenyl)inden-1-yl](η$^1$-tert-butylamido)zirconium dichloride (11k)

Following the procedure described for 11b, 0.83 ml of 0.47 M (0.39 mmol) p-dimethylaminophenylmagnesium bromide in THF gave yellowish solid. Yield 120 mg (74%).

Anal. calc. for $C_{24}H_{32}Cl_2N_2SiZr$: C, 53.51; H, 5.99. Found: C, 53.73; H, 6.12. $^1$H NMR ($CD_2Cl_2$): δ 7.63 (dt, J=8.3 Hz, J=1.2 Hz, 1H, 5-H in indenyl), 7.45 (m, 2H, 2,6-H in $Me_2NC_6H_4$), 7.23 (dd, J=8.3 Hz, J=7.1 Hz, 1H, 6-H in indenyl), 7.19 (dd, J=7.1 Hz, J=1.2 Hz, 1H, 7-H in indenyl), 7.04 (m, 1H, 3-H in indenyl), 6.81 (m, 2H, 3,5-H in $Me_2NC_6H_4$), 2.98 (s, 6H, $Me_2N$), 2.37 (d, J=0.5 Hz, 3H, 2-Me in indenyl), 1.32 (s, 9H, $^t$Bu), 0.87 (s, 3H, SiMeMe'), 0.70 (s, 3H, SiMeMe'). $^{13}C\{^1H\}$ NMR ($CD_2Cl_2$): δ 144.0, 140.8, 139.1, 138.4, 136.5, 133.1, 131.3, 130.5, 129.4, 126.7, 124.2, 115.0, 114.1, 58.0, 41.8, 34.4, 19.8, 7.4, 7.1.

EXAMPLE 11l

Dimethylsilyl(η$^5$-2-methyl-4-o-anisylinden-1-yl)(η$^1$-tert-butylamido)zirconium dichloride (11l)

Following the procedure described for 11b, 0.45 ml of 0.86 M (0.39 mmol) o-anisylmagnesium bromide in THF gave yellowish solid. Yield 138 mg (87%).

Anal. calc. for $C_{23}H_{29}Cl_2NOSiZr$: C, 52.55; H, 5.56. Found: C, 52.67; H, 5.45. $^1$H NMR ($CD_2Cl_2$): δ 7.75 (dt, J=8.6 Hz, J=0.9 Hz, 1H, 5-H in indenyl), 7.40 (ddd, J=8.4 Hz, J=7.4 Hz, J=1.7 Hz, 1H, 4-H in $MeOC_6H_4$), 7.28 (dd, J=7.4 Hz, J=1.7 Hz, 1H, 5-H in $MeOC_6H_4$), 7.26 (dd, J=8.6 Hz, J=6.8 Hz, 1H, 6-H in indenyl), 7.15 (dd, J=6.8 Hz, J=0.9 Hz, 1H, 7-H in indenyl), 7.06 (dd, J=8.4 Hz, J=0.9 Hz, 1H, 6-H in MeOC$_6$H$_4$), 7.04 (dt, J=7.4 Hz, J=0.9 Hz, 1H, 3-H in MeOC$_6$H$_4$), 6.56 (s, 1H, 3-H in indenyl), 3.81 (s, 3H, OMe), 2.34 (d, J=0.5 Hz, 3H, 2-Me in indenyl), 1.34 (s, 9H, $^t$Bu), 0.87 (s, 3H, SiMeMe'), 0.70 (s, 3H, SiMeMe'). $^{13}$C{$^1$H} NMR (CD$_2$Cl$_2$): δ 140.5, 135.9, 132.3, 131.2, 130.1, 129.3, 128.7, 128.1, 126.4, 126.0, 125.1, 122.6, 120.6, 115.6, 113.2, 58.1, 34.2, 33.2, 19.8, 7.9, 7.3.

EXAMPLE 11m

Dimethylsilyl[η$^5$-2-methyl-4-(3-methoxy-2-methyl-2,3-dihydro-1H-inden-4-yl)inden-1-yl](η$^1$-tert-butylamido)zirconium dichloride (11m)

Following the procedure described for 11b, 0.71 ml of 0.55 M (0.39 mmol of bromo(1-methoxy-2-methyl-2,3-dihydro-1H-inden-4-yl)magnesium in THF gave yellowish solid as a mixture of two diastereomers. Yield 160 mg (92%). On the evidence of NMR spectroscopy, each diastereomer consists of two conformers in CD$_2$Cl$_2$ solution at ambient temperature.

Anal. calc. for C$_{27}$H$_{35}$Cl$_2$NOSiZr: C, 55.93; H, 6.08. Found: C, 56.24; H, 6.20. $^1$H NMR (CD$_2$Cl$_2$): δ 7.73 (d, J=8.6 Hz, 1H, 5-H in indenyl), 7.18-7.43 (m, 5H, 6,7-H in indenyl and 5,6,7-H in indanyl), 6.74, 6.73, 6.72, 6.70 (four singlets, 1H, 3-H in indenyl), 4.58, 4.54, 4.44, and 4.40 (four dublets, J=5.6, 5.9, 4.6, and 4.2 Hz, respectively; 1H, CHOMe), 3.47, 3.46, 3.42, 3.41 (four singlets, 3H, OMe), 2.37-3.34 (m, 3H, CH$_2$ and CHMe), 2.35 (m, 3H, 2-Me in indenyl), 1.34 (s, 9H, $^t$Bu), 1.12, 1.08, 1.02, and 0.98 (four dublets, J=6.8 Hz, 3H, CHMe), 0.89 (s, 3H, SiMeMe'), 0.71 (s, 3H, SiMeMe').

EXAMPLE 11n

Dimethylsilyl[η$^5$-2-methyl-4-(5-methyl-2-furyl)inden-1-yl](η$^1$-tert-butylamido)zirconium dichloride (11n)

In 16 ml vial equipped with PTFE coated stir bar containing a mixture of 1.30 ml of 0.30 M (0.39 mmol) of 2-methylfuran in THF and 1.0 ml of THF, 0.78 ml of 0.5 M (0.39 mmol) $^n$BuLi in hexanes was added by a dosing pipette by vigorous stirring at –80° C. This mixture was stirred and slowly warmed (for ca. 1 hour) to 0° C. Then, 0.86 ml of 0.5 M (0.43 mmol) ZnCl$_2$ in THF was added at –80° C., and the obtained mixture was stirred and slowly warmed to ambient temperature and then evaporated to dryness. In a separate 16 ml vial equipped with PTFE coated stir bar to a mixture of 150 mg (0.30 mmol) of 11, 0.30 ml of 0.02 M (0.006 mmol) Pd(P$^t$Bu$_3$)$_2$ in THF, and 3 ml of THF the above described organozinc reagent was added. This mixture was stirred for 20 hours at room temperature and then evaporated to dryness. The product was extracted by 3×30 ml of hot hexanes. The resulted extract was filtered through Celite 503 and then evaporated to dryness. The residue was dried in vacuum. Yield 96 mg (64%) of yellowish solid.

Anal. calc. for C$_{21}$H$_{27}$Cl$_2$NOSiZr: C, 50.48; H, 5.45. Found: C, 50.65; H, 5.51. $^1$H NMR (CD$_2$Cl$_2$): δ 7.63 (dt, J=8.6 Hz, J=0.7 Hz, 1H, 5-H in indenyl), 7.55 (dd, J=7.3 Hz, J=0.7 Hz, 1H, 7-H in indenyl), 7.35 (br.s, 1H, 3-H in indenyl), 7.22 (dd, J=8.6 Hz, J=7.3 Hz, 1H, 6-H in indenyl), 6.76 (d, J=3.3 Hz, 1H, 3-H in furyl), 6.17 (dq, J=3.3 Hz, J=1.0 Hz, 1H, 4-H in furyl), 2.42 (d, J=0.5 Hz, 3H, 2-Me in indenyl), 2.41 (d, J=1.0 Hz, 3H, 5-Me in furyl), 1.33 (s, 9H, $^t$Bu), 0.86 (s, 3H, SiMeMe'), 0.71 (s, 3H, SiMeMe'). $^{13}$C{$^1$H} NMR (CD$_2$Cl$_2$): δ 154.8, 152.3, 139.0, 136.8, 130.9, 126.8, 125.7, 125.0, 123.4, 115.1, 111.1, 109.7, 96.0, 58.1, 34.3, 19.8, 15.2, 7.3, 7.1.

EXAMPLE 11o

Dimethylsilyl[η$^5$-2-methyl-4-(5-methyl-2-thienyl)inden-1-yl](η$^1$-tert-butylamido)zirconium dichloride (11o)

Following the procedure described for 11n, 1.30 ml of 0.30 M (0.39 mmol) of 2-methylthiophene in THF gave yellowish solid. Yield 108 mg (70%).

Anal. calc. for C$_{21}$H$_{27}$Cl$_2$NSSiZr: C, 48.91; H, 5.28. Found: C, 49.24; H, 5.39. $^1$H NMR (CD$_2$Cl$_2$): δ 7.66 (dt, J=8.6 Hz, J=0.9 Hz, 1H, 5-H in indenyl), 7.35 (dd, J=7.2 Hz, J=0.9 Hz, 1H, 7-H in indenyl), 7.27 (br.s, 1H, 3-H in indenyl), 7.21 (d, J=3.6 Hz, 1H, 3-H in thienyl), 7.20 (dd, J=8.6 Hz, J=7.2 Hz, 1H, 6-H in indenyl), 6.82 (dq, J=3.6 Hz, J=1.1 Hz, 1H, 4-H in thienyl), 2.53 (d, J=1.1 Hz, 3H, 5-Me in thienyl), 2.40 (d, J=0.5 Hz, 3H, 2-Me in indenyl), 1.34 (s, 9H, $^t$Bu), 0.87 (s, 3H, SiMeMe'), 0.72 (s, 3H, SiMeMe'). $^{13}$C{$^1$H} NMR (CD$_2$Cl$_2$): δ 144.3, 142.5, 140.6, 136.8, 133.4, 131.0, 129.3, 129.0, 127.8, 127.4, 126.8, 125.3, 114.8, 58.1, 34.3, 19.8, 16.8, 7.4, 7.0.

EXAMPLE 11p

Dimethylsilyl[η$^5$-2-methyl-4-(2-benzothienyl)inden-1-yl](η$^1$-tert-butylamido)zirconium dichloride (11p)

Following the procedure described for 11n, 1.30 ml of 0.30 M (0.39 mmol) of benzothiophene in THF gave yellowish solid. Yield 70 mg (42%).

Anal. calc. for C$_{24}$H$_{27}$Cl$_2$NSSiZr: C, 52.24; H, 4.93. Found: C, 52.48; H, 5.09. $^1$H NMR (CD$_2$Cl$_2$): δ 7.86 (m, 2H, 4,7-H in benzothienyl), 7.76 (dt, J=8.7 Hz, J=0.9 Hz, 1H, 5-H in indenyl), 7.64 (m, 1H, 3-H in indenyl), 7.52 (dd, J=7.1 Hz, J=0.9 Hz, 1H, 7-H in indenyl), 7.32-7.41 (m, 3H, 3,5,6-H in benzothienyl), 7.27 (dd, J=8.7 Hz, J=7.1 Hz, 1H, 6-H in indenyl), 2.43 (d, J=0.5 Hz, 3H, 2-Me in indenyl), 1.35 (s, 9H, $^t$Bu), 0.89 (s, 3H, SiMeMe'), 0.73 (s, 3H, SiMeMe'). $^{13}$C{$^1$H} NMR (CD$_2$Cl$_2$): δ 144.5, 143.0, 141.9, 141.2, 136.6, 132.9, 130.5, 128.8, 128.5, 126.6, 126.3, 126.2, 125.5, 125.4, 124.0, 123.7, 114.5, 58.2, 34.3, 19.8, 7.3, 7.0.

EXAMPLE 11r

Dimethylsilyl[η$^5$-2-methyl-4-(2-benzofuryl)inden-1-yl](η$^1$-tert-butylamido) zirconium dichloride (11r)

Following the procedure described for 11n, 1.30 ml of 0.30 M (0.39 mmol) of benzofuran in THF gave yellowish solid. Yield 59 mg (37%).

Anal. calc. for C$_{24}$H$_{27}$Cl$_2$NOSiZr: C, 53.81; H, 5.08. Found: C, 54.04; H, 5.15. $^1$H NMR (CD$_2$Cl$_2$): δ 7.64 (m, 1H, 4-H in benzofuryl), 7.58 (m, 1H, 7-H in benzothienyl), 7.77 (dt, J=8.7 Hz, J=0.9 Hz, 1H, 5-H in indenyl), 7.50 (br.s, 1H, 3-H in indenyl), 7.33 (dt, J=7.4 Hz, J=1.4 Hz, 1H, 5-H in benzofuryl), 7.30 (dd, J=8.6 Hz, J=7.3 Hz, 1H, 6-H in indenyl), 7.26 (dt, J=7.4 Hz, J=1.1 Hz, 1H, 6-H in benzofuryl), 7.22 (d, J=0.9 Hz, 1H, 3-H in benzofuryl), 2.47 (d, J=0.5 Hz, 3H, 2-Me in indenyl), 1.34 (s, 9H, $^t$Bu), 0.89 (s, 3H, SiMeMe'), 0.74 (s, 3H, SiMeMe'). $^{13}$C{$^1$H} NMR (CD$_2$Cl$_2$): δ 156.4, 155.8, 144.7, 144.6, 136.6, 130.5, 128.6, 128.3, 127.0, 126.6, 126.1, 124.8, 122.8, 122.0, 115.0, 112.8, 106.2, 58.2, 34.3, 19.8, 7.3, 7.0.

EXAMPLE 12a

Negishi reaction of metallocene 12 to produce dimethylsilyl($\eta^5$-tetramethylcyclopentadienyl)($\eta^1$-4-methyl-2,6-diisopropylphenyl)zirconium dichloride (12a)

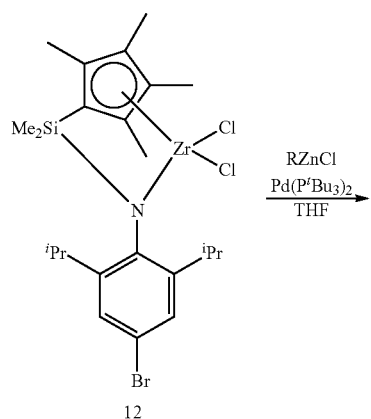

R = Me(12a)

Following the procedure described for 11a, 200 mg (0.34 mmol) of 12 in 4 ml of THF, 0.22 ml of 2.0 M (0.44 mmol) MeZnCl in THF, and 0.35 ml of 0.02 M (0.007 mmol) Pd(P$^t$Bu$_3$)$_2$ in THF gave yellowish solid. Yield 117 mg (66%).

Anal. calc. for C$_{24}$H$_{37}$Cl$_2$NSiZr: C, 54.41; H, 7.04. Found: C, 54.60; H, 7.17. $^1$H NMR (CD$_2$Cl$_2$): δ 6.91 (q, J=0.6 Hz, 2H, 3,5-H in C$_6$H$_2$), 3.30 (sept, J=6.7 Hz, 2H, CHMe$_2$), 2.34 (s, 6H, 3,4-Me in C$_5$Me$_4$), 2.28 (t, J=0.6 Hz, 3H, 4-Me in C$_6$H$_2$), 2.23 (s, 6H, 2,5-Me in C$_5$Me$_4$), 1.22 (d, J=6.7 Hz, 6H, CHMeMe'), 1.08 (d, J=6.7 Hz, 6H, CHMeMe'), 0.63 (s, 6H, SiMe$_2$).

EXAMPLE 13i2

Suzuki-Miyaura reaction of metallocene 13 to produce rac-dimethylsilyl-bis($\eta^5$-4-phenyl-6-isopropyl-2,5-dimethylinden-1-yl)zirconium dichloride (13i)

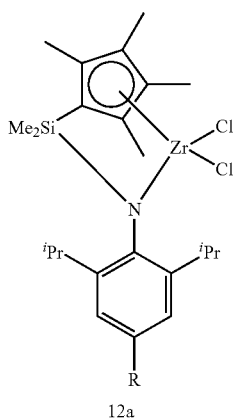

In a 16 ml vial equipped with PTFE coated stir bar, to a solution of 92 mg (0.14 mmol) of 13 in 10 ml of toluene, 105 mg (0.31 mmol) of NaBPh$_4$, and 0.28 ml (0.0056 mmol) of 0.02 M solution of Pd(P$^t$Bu$_3$)$_2$ in toluene were added. The reaction mixture was stirred for 20 h at 90° C. The reaction mixture was cooled to ambient temperature and filtered through a glass frit (G4). The filtrate was evaporated to dryness. The residue was washed with 2×15 ml of hot hexanes and dried in vacuum. Yield 66 mg (72%) of orange solid.

Anal. calc. for C$_{36}$H$_{34}$Cl$_2$SiZr: C, 65.83; H, 5.22. Found: C, 66.01; H, 5.28. $^1$H NMR (CD$_2$Cl$_2$): δ 7.55 (m, 2H, 6,6'-H in indenyls), 7.17-7.50 (m, 10H, Ph and Ph'), 6.99 (d, J=9.0 Hz, 2H, 7,7'-H in indenyls), 6.39 (s, 2H, 3,3'-H in indenyls), 2.27 (s, 6H, 2,2'-Me), 2.18 (s, 6H, 5,5'-Me), 1.30 (s, 6H, SiMe$_2$).

EXAMPLE 15a2

Suzuki-Miyaura reaction of metallocene 15 to produce rac-dimethylsilyl-bis($\eta^5$-4-phenyl-6-isopropyl-2-methylinden-1-yl)zirconium dichloride (15a)

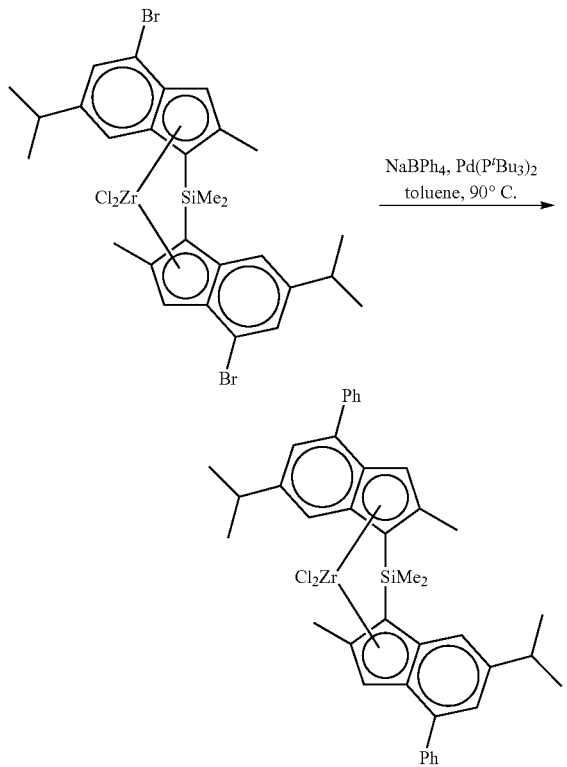

In a 16 ml vial equipped with PTFE coated stir bar, to a solution of 100 mg (0.14 mmol) of 15 in 10 ml of toluene, 105 mg (0.31 mmol) of NaBPh$_4$, and 0.28 ml (0.0056 mmol) of 0.02 M solution of Pd(P$^t$Bu$_3$)$_2$ in toluene were added. The reaction mixture was stirred for 20 h at 90° C. The reaction mixture was cooled to ambient temperature and filtered through a glass frit (G4). The filtrate was evaporated to dryness. The product was extracted from the residue with 4×25 ml of hexanes. The combined filtrate was evaporated to dryness, and the residue was dried in vacuum. Yield 73 mg (73%) of orange solid.

Anal. calc. for $C_{40}H_{42}Cl_2SiZr$: C, 67.38; H, 5.94. Found: C, 67.66; H, 6.10. $^1$H NMR (CD$_2$Cl$_2$): δ 7.29-7.71 (m, 14H, 5,5',7,7'-H in indenyls and Ph, Ph'), 6.87 (s, 2H, 3,3'-H in indenyls), 2.93 (m, 2H, CHMe$_2$ in both indenyls), 2.26 (s, 6H, 2,2'-Me in indenyls), 1.26 (m, 12H, CHMe$_2$ in both indenyls).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Experimental—Polymerizations

In the following experiments pressure is reported in atmospheres and pounds per square inch. The conversion factors to S. I. Units are; 1 psi equals 6.894757 kPa and 1 atm equals 101.325 kPa.

Transition metal compound (TMC) solutions were typically prepared using toluene (ExxonMobil Chemical—anhydrous, stored under N$_2$) (98%). Unless otherwise mentioned, TMC solutions are 0.2 mmol/L for C$_2$ and C$_2$/C$_8$ (co)polymerizations, and 0.6 mmol/L for C$_3$ and C$_3$/C$_2$ (co)polymerizations.

Solvents, polymerization grade toluene and hexanes were supplied by ExxonMobil Chemical Co. and thoroughly dried and degassed prior to use.

1-octene (98%) was purchased from Aldrich Chemical Company and dried by stirring over NaK overnight followed by filtration through basic alumina (Aldrich Chemical Company, Brockman Basic 1).

Polymerization grade ethylene was used and further purified by passing it through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves purchased from Aldrich Chemical Company.

Polymerization grade propylene was used without further purification.

MAO (methylalumoxane, 10 wt % in toluene) was purchased from Albemarle Corporation and was used as a 1 wt % or 2 wt % in toluene solution. Micromoles of MAO reported in the experimental section are based on the micromoles of aluminum in MAO. The formula weight of MAO is 58.0 grams/mole.

Reactor Description and Preparation: Polymerizations were conducted in an inert atmosphere (N2) drybox using autoclaves equipped with an external heater for temperature control, glass inserts (internal volume of reactor=23.5 mL for C2 and C2/C8 runs; 22.5 mL for C3 and C2/C3 runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours.

Ethylene Polymerization or Ethylene/1-octene Copolymerization. The reactor was prepared as described above, and then purged with ethylene. Toluene, 1-octene (100 µL when used), and activator (MAO) were added via syringe at room temperature and atmospheric pressure. The reactor was then brought to process temperature (80° C.) and charged with ethylene to process pressure (75 psig=618.5 kPa) while stirring at 800 RPM. The TMC (0.02 µmol, unless indicated otherwise) was added via syringe with the reactor at process conditions. Amounts of reagents not specified above are given in Tables a and c. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psid O$_2$/Ar (5 mole % O2) gas mixture to the autoclaves for approximately 30 seconds. The polymerizations were quenched after a predetermined cumulative amount of ethylene had been added or for a maximum of 20 minutes polymerization time. The final conversion (in psi) of ethylene added/consumed is reported in the Tables a and c, in addition to the quench time for each run. The reactors were cooled and vented. The polymer was isolated after the solvent was removed in-vacuo. Yields reported include total weight of polymer and residual catalyst.

Propylene Polymerization. The reactor was prepared as described above, then heated to 40° C. and then purged with propylene gas at atmospheric pressure. Hexanes, MAO, and liquid propylene (1.066 mL, unless indicated otherwise in Table e) were added via syringe. The reactor was then heated to process temperature (70° C.) while stirring at 800 RPM. The TMC was added via syringe with the reactor at process conditions. Amounts of reagents not specified above are given in Table e. Reactor temperature was monitored and typically maintained within +/−1° C. Polymerizations were halted by addition of approximately 50 psid $O_2$/Ar (5 mole % $O_2$) gas mixture to the autoclaves for approximately 30 seconds. The polymerizations were quenched based on a predetermined pressure loss of approximately 5 psid. The actual quench time is reported in Table e for each run. The reactors were cooled and vented. The polymer was isolated after the solvent was removed in-vacuo. Yields reported include total weight of polymer and residual catalyst. Catalyst activity is reported as grams of polymer per mmol transition metal compound per hour of reaction time (g/mmol·hr).

Ethylene/Propylene Copolymerization. The reactor was prepared as described above, and then purged with ethylene. Reactors were heated to 40° C. and ethylene was then added to the reactor to a target pressure of 10 psig (single addition), followed by the addition of hexanes, MAO, and then liquid propylene (1.066 mL). All additions were made via syringe. The reactor was then heated to process temperature (70° C.) while stirring at 800 RPM. The TMC was added via syringe with the reactor at process conditions. Amounts of reagents not specified above are given in Table g. Reactor temperature was monitored and typically maintained within +/−1° C. Polymerizations were halted by addition of approximately 50 psid $O_2$/Ar (5 mole % $O_2$) gas mixture to the autoclaves for approximately 30 seconds. The polymerizations were quenched based on a predetermined pressure loss of approximately 5 psid. The actual quench time is reported in Table g for each run. The reactors were cooled and vented. The polymer was isolated after the solvent was removed in-vacuo. Yields reported include total weight of polymer and residual catalyst.

Polymer characterization. Polymer characterization results for polyethylene samples are reported in Table b, for ethylene-1-octene copolymers are reported in Table d, for polypropylene samples are reported in Table f, and for ethylene-propylene copolymers are reported in Table h.

For analytical testing, polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 160° C. in a shaker oven for approximately 3 hours. The typical concentration of polymer in solution is between 0.4 to 0.9 mg/mL with a BHT concentration of 1.25 mg BHT/mL of TCB. Samples are cooled to 135° C. for testing.

Molecular weights (weight average molecular weight (Mw) and number average molecular weight (Mn)) and molecular weight distribution (MWD=Mw/Mn), which is also sometimes referred to as the polydispersity (PDI) of the polymer, were measured by Gel Permeation Chromatography using a Symyx Technology GPC equipped with evaporative light scattering detector and calibrated using polystyrene standards (Polymer Laboratories: Polystyrene Calibration Kit S-M-10: Mp (peak Mw) between 5000 and 3,390,000). Samples were run in TCB at (135° C. sample temperatures, 160° C. oven/columns) using three Polymer Laboratories: PLgel 10 μm Mixed-B 300×7.5 mm columns in series. No column spreading corrections were employed. Numerical analyses were performed using Epoch® software available from Symyx Technologies.

The sample preparation for SAMMS (Sensory Array Modular Measurement System) thermal analysis measurements involved depositing the stabilized polymer solution onto a silanized wafer (Part Number S10457, Symyx). The solvent was then evaporated off at ~145° C. By this method, approximately between 0.12 and 0.24 mg of polymer is deposited onto each corresponding wafer cell. Thermal analysis was measured on a Symyx Technologies SAMMS instrument that measures polymer melt temperatures via the 3ω technique. The analysis first employs a rapid-scan protocol that heats each cell from 27° C. to 200° C. in ~35 seconds and then rapidly cools the sample to room temperature. This complete procedure takes approximately 60 seconds per cell and is used to minimize each sample's thermal history. The second step involves running a high-resolution scan protocol to measure the second melt of the sample. The protocol heats each cell from 27° C. to 200° C. in ~3 minutes and then rapidly cools the sample to room temperature. The high-resolution scan takes approximately three times the amount of time to complete as the rapid-scan protocol. If multiple melting peaks are present, Epoch® Software reports the largest amplitude peak. SAMMS data is reported under the heading of Tm (° C.) in Tables b and d.

For propylene homopolymers, the thermal analysis was performed using a 1290 TA Instruments Differential Scanning Calorimeter (DSC) by first heating the sample from 25° C. to 220° C. at 10° C./min, holding the temperature at 220° C. for 5 minutes, then cooling at 10° C./min from 220° C. to 25° C., and finally again heating to 220° C. at 10° C./min. The second heat results have been reported under the heading of DSC (° C.) in Table f. A value of zero indicates that the polymer had no melting point. Multiple numbers indicate a polymer with more than one melting point. The heat of fusion, delta H, is also recorded in Table f.

Samples for infrared analysis were prepared by depositing the stabilized polymer solution onto a silanized wafer (Part number S10860, Symyx). By this method, approximately between 0.12 and 0.24 mg of polymer is deposited on the wafer cell. The samples were subsequently analyzed on a Brucker Equinox 55 FTIR spectrometer equipped with Pikes's MappIR specular reflectance sample accessory. Spectra, covering a spectral range of 5000 $cm^{-1}$ to 500 $cm^{-1}$, were collected at a 2 $cm^{-1}$ resolution with 32 scans.

For ethylene-1-octene copolymers, the wt. % copolymer is determined via measurement of the methyl deformation band at ~1375 $cm^{-1}$. The peak height of this band is normalized by the combination and overtone band at ~4321 $cm^{-1}$, which corrects for path length differences. The normalized peak height is correlated to individual calibration curves from $^1$H NMR data to predict the wt. % copolymer content within a concentration range of ~2 to 35 wt. % for octene. Typically, $R^2$ correlations of 0.98 or greater are achieved. These numbers are reported in Table d under the heading, Octene wt %).

For ethylene-propylene copolymers, the wt. % ethylene is determined via measurement of the methylene rocking band (~770 $cm^{-1}$ to 700 $cm^{-1}$). The peak area of this band is normalized by sum of the band areas of the combination and overtone bands in the 4500 $cm^{-1}$ to 4000 $cm^{-1}$ range. The normalized band area is then correlated to a calibration curved from $^{13}$C NMR data to predict the wt. % ethylene within a concentration range of ~5 to 40 wt. %. Typically, $R^2$ correlations of 0.98 or greater are achieved. These numbers are reported in Table h under the heading, Ethylene (wt %).

For propylene homo-polymers, an infrared spectroscopy-based partial least-squares (PLS) model was developed for predicting an IR tacticity index, reported as an estimated Tm, for isotactic polypropylene (iPP). The model was built using PLSplus/IQ add-on application to the Grams/AI (Version 7.00) software from ThermoGalactic. The model is based on a training set consisting of IR spectra of iPP samples with known Tm values spanning a range of ~100° C. to ~166° C. The iPPs were prepared in lab and commercial reactors using metallocene and Zieglar-Natta catalyst systems. Their average Mw ranged from 157 k to 436 k. Their IR spectra were collected from solution cast films supported on gold-coated silicon wafers via a Bruker Equinox 55 FTIR spectrometer with a Pike MappIR specular reflectance sample accessory. Each sample was prepared and cast in triplicate. Briefly, before model development, each spectra was baseline-corrected with a cubic function fit, mean-centered, and path length-corrected using the ~1165/1155 cm−1 band. Then the optimum number of PLS factors to include in the final model was determined using leave-one-out cross validation analysis and the selected spectral region of 1364 cm$^{-1}$ to 764 cm$^{-1}$. This resulted in a model with 7 factors and standard error of prediction of 3° C. These calculated Tm's are reported in Table f under the heading, FTIR Crystallinity Index (° C.). Values reported under 100° C., are outside the calibration range of the model.

TABLE a

Ethylene Polymerization - Part 1.

| Ex# | TMC | MAO* (μmol) | Total Toluene (mL) | Final Conversion (psi) | Actual Quench Time (sec) | Polymer Yield (g) |
|---|---|---|---|---|---|---|
| PE-1 | 1c | 10.000 | 5.00 | 20.1 | 160.2 | 0.0504 |
| PE-2 | 1c | 10.000 | 5.00 | 20.1 | 156.9 | 0.0554 |
| PE-3 | 1c | 10.000 | 5.00 | 20.1 | 136.0 | 0.0554 |
| PE-4 | 1c | 10.000 | 5.00 | 20.1 | 115.7 | 0.0326 |
| PE-5 | 1g | 10.000 | 5.00 | 20.1 | 164.5 | 0.0486 |
| PE-6 | 1g | 10.000 | 5.00 | 20.1 | 157.3 | 0.0503 |
| PE-7 | 1g | 10.000 | 5.00 | 20.5 | 206.9 | 0.0525 |
| PE-8 | 1g | 10.000 | 5.00 | 20.1 | 91.7 | 0.0362 |
| PE-9 | 1h | 10.000 | 5.00 | 20.1 | 87.2 | 0.0394 |
| PE-10 | 1h | 10.000 | 5.00 | 20.1 | 79.5 | 0.0404 |
| PE-11 | 1h | 10.000 | 5.00 | 20.1 | 146.5 | 0.0496 |
| PE-12 | 1h | 10.000 | 5.00 | 20.1 | 140.4 | 0.0491 |
| PE-13 | 1n | 9.984 | 3.80 | 25.0 | 404.7 | 0.0513 |
| PE-14 | 1n | 9.984 | 3.80 | 25.0 | 509.6 | 0.0646 |
| PE-15 | 1n | 9.984 | 3.80 | 25.0 | 526.3 | 0.0578 |
| PE-16 | 1n | 9.984 | 3.80 | 25.0 | 508.7 | 0.0623 |
| PE-17 | 1p | 9.984 | 3.80 | 25.0 | 578.6 | 0.0781 |
| PE-18 | 1p | 9.984 | 3.80 | 25.0 | 376.8 | 0.0768 |
| PE-19 | 1p | 9.984 | 3.80 | 25.0 | 396.4 | 0.0746 |
| PE-20 | 1p | 9.984 | 3.80 | 25.0 | 427.0 | 0.0724 |
| PE-21 | 6a | 10.000 | 5.00 | 20.1 | 186.5 | 0.0434 |
| PE-22 | 6a | 10.000 | 5.00 | 20.1 | 215.8 | 0.0459 |
| PE-23 | 6a | 10.000 | 5.00 | 20.1 | 178.0 | 0.0422 |
| PE-24 | 6a | 10.000 | 5.00 | 20.1 | 238.1 | 0.0461 |
| PE-25 | 6b | 9.984 | 3.80 | 25.0 | 370.8 | 0.0690 |
| PE-26 | 6b | 9.984 | 3.80 | 25.0 | 269.3 | 0.0770 |
| PE-27 | 6b | 9.984 | 3.80 | 25.0 | 298.9 | 0.0740 |
| PE-28 | 6b | 9.984 | 3.80 | 25.0 | 247.1 | 0.0770 |
| PE-29 | 6c | 9.984 | 3.80 | 25.0 | 443.2 | 0.0650 |
| PE-30 | 6c | 9.984 | 3.80 | 25.0 | 507.9 | 0.0660 |
| PE-31 | 6c | 9.984 | 3.80 | 25.0 | 431.8 | 0.0680 |
| PE-32 | 6c | 9.984 | 3.80 | 25.0 | 271.3 | 0.0720 |
| PE-33 | 6d | 10.000 | 5.00 | 20.1 | 165.7 | 0.0747 |
| PE-34 | 6d | 10.000 | 5.00 | 20.1 | 205.3 | 0.0756 |
| PE-35 | 6d | 10.000 | 5.00 | 20.3 | 196.5 | 0.0762 |
| PE-36 | 6d | 10.000 | 5.00 | 20.1 | 93.2 | 0.0669 |
| PE-37 | 7a | 10.000 | 5.00 | 20.5 | 255.8 | 0.0683 |
| PE-38 | 7a | 10.000 | 5.00 | 20.1 | 209.6 | 0.0663 |
| PE-39 | 7a | 10.000 | 5.00 | 20.1 | 282.0 | 0.0654 |
| PE-40 | 7a | 10.000 | 5.00 | 20.1 | 254.6 | 0.0657 |
| PE-41 | 7b | 10.000 | 5.00 | 20.1 | 173.8 | 0.0859 |
| PE-42 | 7b | 10.000 | 5.00 | 20.1 | 215.7 | 0.0795 |
| PE-43 | 7b | 10.000 | 5.00 | 20.1 | 196.0 | 0.0793 |
| PE-44 | 7b | 10.000 | 5.00 | 20.1 | 146.8 | 0.0841 |
| PE-45 | 7c | 10.000 | 5.00 | 20.1 | 169.8 | 0.0861 |
| PE-46 | 7c | 10.000 | 5.00 | 20.1 | 177.2 | 0.0840 |
| PE-47 | 7c | 10.000 | 5.00 | 20.1 | 186.9 | 0.0846 |
| PE-48 | 7c | 10.000 | 5.00 | 20.1 | 198.3 | 0.0842 |
| PE-49 | 7d | 10.000 | 5.00 | 20.3 | 185.0 | 0.0833 |
| PE-50 | 7d | 10.000 | 5.00 | 20.1 | 165.7 | 0.0847 |
| PE-51 | 7d | 10.000 | 5.00 | 20.1 | 157.7 | 0.0846 |
| PE-52 | 7d | 10.000 | 5.00 | 20.1 | 178.4 | 0.0833 |
| PE-53 | 7e | 10.000 | 5.00 | 20.1 | 253.1 | 0.0847 |
| PE-54 | 7e | 10.000 | 5.00 | 20.3 | 196.4 | 0.0891 |
| PE-55 | 7e | 10.000 | 5.00 | 20.3 | 255.6 | 0.0795 |
| PE-56 | 7e | 10.000 | 5.00 | 20.1 | 184.9 | 0.0805 |
| PE-57 | 10a | 10.000 | 5.00 | 20.1 | 280.9 | 0.0879 |
| PE-58 | 10a | 10.000 | 5.00 | 20.1 | 289.9 | 0.0889 |
| PE-59 | 10a | 10.000 | 5.00 | 20.1 | 273.1 | 0.0852 |
| PE-60 | 10a | 10.000 | 5.00 | 20.1 | 172.7 | 0.0824 |
| PE-61 | 10c | 10.000 | 5.00 | 20.1 | 164.1 | 0.0882 |
| PE-62 | 10c | 10.000 | 5.00 | 20.1 | 229.2 | 0.0931 |
| PE-63 | 10c | 10.000 | 5.00 | 20.1 | 228.0 | 0.0880 |
| PE-64 | 10c | 10.000 | 5.00 | 20.1 | 241.5 | 0.0880 |
| PE-65 | 10d | 10.000 | 5.00 | 20.1 | 347.4 | 0.0754 |
| PE-66 | 10d | 10.000 | 5.00 | 20.1 | 254.7 | 0.0770 |
| PE-67 | 10d | 10.000 | 5.00 | 20.1 | 245.7 | 0.0728 |
| PE-68 | 10d | 10.000 | 5.00 | 20.1 | 255.9 | 0.0657 |
| PE-69 | 10f | 10.000 | 4.90 | 20.15 | 297.55 | 0.0406 |
| PE-70 | 10f | 10.000 | 4.90 | 20.15 | 282.51 | 0.0396 |
| PE-71 | 10f | 10.000 | 4.90 | 20.15 | 302.83 | 0.0334 |
| PE-72 | 10f | 10.000 | 4.90 | 20.15 | 501.12 | 0.0442 |
| PE-73 | 10h | 10.000 | 4.90 | 20.30 | 206.99 | 0.0821 |
| PE-74 | 10h | 10.000 | 4.90 | 20.45 | 281.81 | 0.0811 |
| PE-75 | 10h | 10.000 | 4.90 | 20.15 | 344.33 | 0.0806 |
| PE-76 | 10h | 10.000 | 4.90 | 20.15 | 230.55 | 0.0840 |
| PE-77 | 10i | 10.000 | 4.90 | 20.15 | 226.26 | 0.0761 |
| PE-78 | 10i | 10.000 | 4.90 | 20.15 | 235.08 | 0.0740 |
| PE-79 | 10i | 10.000 | 4.90 | 20.15 | 212.94 | 0.0764 |
| PE-80 | 10i | 10.000 | 4.90 | 20.30 | 223.29 | 0.0778 |
| PE-81 | 10l | 10.000 | 4.90 | 20.15 | 348.37 | 0.0716 |
| PE-82 | 10l | 10.000 | 4.90 | 20.15 | 364.68 | 0.0634 |
| PE-83 | 10l | 10.000 | 4.90 | 20.15 | 298.88 | 0.0669 |
| PE-84 | 10l | 10.000 | 4.90 | 20.15 | 340.79 | 0.0590 |
| PE-85 | meso-8b | 9.984 | 3.80 | 20.1 | 178.1 | 0.0799 |
| PE-86 | meso-8b | 9.984 | 3.80 | 20.1 | 279.4 | 0.0794 |
| PE-87 | meso-8b | 9.984 | 3.80 | 20.1 | 184.0 | 0.0782 |
| PE-88 | meso-8b | 9.984 | 3.80 | 20.1 | 568.3 | 0.0831 |
| PE-89 | rac-9a | 10.000 | 5.00 | 20.1 | 224.6 | 0.0990 |
| PE-90 | rac-9a | 10.000 | 5.00 | 20.3 | 233.2 | 0.0975 |
| PE-91 | rac-9a | 10.000 | 5.00 | 20.1 | 211.3 | 0.0956 |
| PE-92 | rac-9a | 10.000 | 5.00 | 20.1 | 225.1 | 0.0976 |
| PE-93 | rac-8m | 10.000 | 5.00 | 20.1 | 35.4 | 0.0959 |
| PE-94 | rac-8m | 10.000 | 5.00 | 20.1 | 57.6 | 0.1006 |
| PE-95 | rac-8m | 10.000 | 5.00 | 20.1 | 48.7 | 0.0985 |
| PE-96 | rac-8m | 10.000 | 5.00 | 20.3 | 44.4 | 0.0910 |

*Micromoles of Al in MAO..

TABLE b

Ethylene Polymerization - Part 2.

| Ex# | TMC | Mw | Mn | PDI | Tm (° C.) |
|---|---|---|---|---|---|
| PE-1 | 1c | 761,038 | 419,941 | 1.8 | — |
| PE-2 | 1c | 739,920 | 403,504 | 1.8 | — |
| PE-3 | 1c | 807,478 | 437,895 | 1.8 | — |
| PE-4 | 1c | 794,370 | 499,375 | 1.6 | — |
| PE-5 | 1g | 795,305 | 423,951 | 1.9 | — |
| PE-6 | 1g | 813,443 | 433,785 | 1.9 | — |
| PE-7 | 1g | 865,928 | 450,265 | 1.9 | — |
| PE-8 | 1g | 824,290 | 458,065 | 1.8 | — |
| PE-9 | 1h | 715,657 | 402,526 | 1.8 | — |
| PE-10 | 1h | 735,052 | 416,961 | 1.8 | — |
| PE-11 | 1h | 708,790 | 379,926 | 1.9 | — |
| PE-12 | 1h | 729,651 | 394,773 | 1.8 | — |

TABLE b-continued

Ethylene Polymerization - Part 2.

| Ex# | TMC | Mw | Mn | PDI | Tm (° C.) |
|---|---|---|---|---|---|
| PE-13 | 1n | 801,849 | 381,220 | 2.1 | 139.5 |
| PE-14 | 1n | 714,747 | 404,717 | 1.8 | 138.3 |
| PE-15 | 1n | 615,091 | 224,912 | 2.7 | 137.4 |
| PE-16 | 1n | 667,810 | 209,028 | 3.2 | 139.1 |
| PE-17 | 1p | 673,899 | 204,803 | 3.3 | 138.7 |
| PE-18 | 1p | 625,019 | 372,068 | 1.7 | 139.0 |
| PE-19 | 1p | 693,515 | 380,190 | 1.8 | 138.3 |
| PE-20 | 1p | 686,130 | 260,705 | 2.6 | 140.1 |
| PE-21 | 6a | 1,331,940 | 552,878 | 2.4 | — |
| PE-22 | 6a | 1,371,953 | 554,232 | 2.5 | — |
| PE-23 | 6a | 1,244,742 | 517,793 | 2.4 | — |
| PE-24 | 6a | 1,251,372 | 508,574 | 2.5 | — |
| PE-25 | 6b | 812,904 | 466,607 | 1.7 | 140.8 |
| PE-26 | 6b | 895,805 | 520,697 | 1.7 | 140.7 |
| PE-27 | 6b | 856,346 | 480,664 | 1.8 | 139.8 |
| PE-28 | 6b | 896,918 | 522,692 | 1.7 | 139.9 |
| PE-29 | 6c | 1,022,453 | 463,627 | 2.2 | 139.9 |
| PE-30 | 6c | 820,536 | 398,884 | 2.1 | 137.0 |
| PE-31 | 6c | 765,021 | 347,648 | 2.2 | 139.5 |
| PE-32 | 6c | 790,751 | 327,648 | 2.4 | 140.8 |
| PE-33 | 6d | 802,973 | 382,833 | 2.1 | — |
| PE-34 | 6d | 861,904 | 431,596 | 2.0 | — |
| PE-35 | 6d | 838,496 | 404,226 | 2.1 | — |
| PE-36 | 6d | 859,982 | 448,655 | 1.9 | — |
| PE-37 | 7a | 1,181,813 | 461,259 | 2.6 | — |
| PE-38 | 7a | 1,218,703 | 480,818 | 2.5 | — |
| PE-39 | 7a | 1,185,764 | 481,988 | 2.5 | — |
| PE-40 | 7a | 1,267,647 | 537,087 | 2.4 | — |
| PE-41 | 7b | 993,541 | 348,587 | 2.9 | — |
| PE-42 | 7b | 1,000,756 | 333,856 | 3.0 | — |
| PE-43 | 7b | 958,031 | 301,876 | 3.2 | — |
| PE-44 | 7b | 1,080,409 | 359,149 | 3.0 | — |
| PE-45 | 7c | 888,219 | 280,605 | 3.2 | — |
| PE-46 | 7c | 892,119 | 285,898 | 3.1 | — |
| PE-47 | 7c | 858,009 | 265,665 | 3.2 | — |
| PE-48 | 7c | 947,015 | 298,691 | 3.2 | — |
| PE-49 | 7d | 868,000 | 305,301 | 2.8 | — |
| PE-50 | 7d | 860,324 | 299,295 | 2.9 | — |
| PE-51 | 7d | 843,443 | 292,053 | 2.9 | — |
| PE-52 | 7d | 899,146 | 322,769 | 2.8 | — |
| PE-53 | 7e | 1,038,178 | 518,781 | 2.0 | — |
| PE-54 | 7e | 1,188,633 | 340,653 | 3.5 | — |
| PE-55 | 7e | 1,004,573 | 412,394 | 2.4 | — |
| PE-56 | 7e | 1,170,840 | 546,434 | 2.1 | — |
| PE-57 | 10a | 1,597,972 | 809,117 | 2.0 | — |
| PE-58 | 10a | 1,476,887 | 733,458 | 2.0 | — |
| PE-59 | 10a | 1,503,445 | 745,634 | 2.0 | — |
| PE-60 | 10a | — | — | — | — |
| PE-61 | 10c | 868,039 | 421,203 | 2.1 | — |
| PE-62 | 10c | 885,542 | 413,962 | 2.1 | — |
| PE-63 | 10c | 897,886 | 435,584 | 2.1 | — |
| PE-64 | 10c | 883,041 | 439,963 | 2.0 | — |
| PE-65 | 10d | 987,849 | 507,307 | 1.9 | — |
| PE-66 | 10d | 1,109,300 | 569,078 | 1.9 | — |
| PE-67 | 10d | 1,121,787 | 571,158 | 2.0 | — |
| PE-68 | 10d | 1,035,416 | 544,016 | 1.9 | — |
| PE-69 | 10f | 369,189 | 220,852 | 1.7 | — |
| PE-70 | 10f | 338,273 | 209,756 | 1.6 | — |
| PE-71 | 10f | 364,019 | 226,037 | 1.6 | — |
| PE-72 | 10f | 360,570 | 216,986 | 1.7 | — |
| PE-73 | 10h | 1,747,022 | 966,770 | 1.8 | — |
| PE-74 | 10h | 1,686,875 | 947,112 | 1.8 | — |
| PE-75 | 10h | 1,570,490 | 839,810 | 1.9 | — |
| PE-76 | 10h | 1,743,700 | 963,941 | 1.8 | — |
| PE-77 | 10i | 1,270,137 | 742,247 | 1.7 | — |
| PE-78 | 10i | 1,244,880 | 712,931 | 1.7 | — |
| PE-79 | 10i | 1,254,487 | 717,342 | 1.7 | — |
| PE-80 | 10i | 1,266,887 | 731,985 | 1.7 | — |
| PE-81 | 10l | 1,053,566 | 641,260 | 1.6 | — |
| PE-82 | 10l | 1,064,339 | 645,602 | 1.6 | — |
| PE-83 | 10l | 1,183,817 | 700,852 | 1.7 | — |
| PE-84 | 10l | 1,112,845 | 678,478 | 1.6 | — |
| PE-85 | meso-8b | 375,268 | 162,947 | 2.3 | 136.0 |
| PE-86 | meso-8b | 403,094 | 226,281 | 1.8 | 131.8 |
| PE-87 | meso-8b | 419,297 | 191,468 | 2.2 | 133.3 |
| PE-88 | meso-8b | 515,680 | 278,877 | 1.8 | 133.9 |
| PE-89 | rac-9a | 1,027,584 | 536,628 | 1.9 | — |
| PE-90 | rac-9a | 998,436 | 533,825 | 1.9 | — |
| PE-91 | rac-9a | — | — | — | — |
| PE-92 | rac-9a | 1,045,090 | 543,746 | 1.9 | — |
| PE-93 | rac-8m | 758,014 | 414,334 | 1.8 | — |
| PE-94 | rac-8m | 961,932 | 554,534 | 1.7 | — |
| PE-95 | rac-8m | 1,013,874 | 595,928 | 1.7 | — |
| PE-96 | rac-8m | 1,119,259 | 695,853 | 1.6 | — |

TABLE c

Ethylene-1-Octene Polymerization Runs - Part 1.

| Ex# | TMC | MAO* (µmol) | 1-Octene (µmol) | Total Toluene (mL) | Final Conversion (psi) | Quench Time (sec) | Polymer Yield (g) |
|---|---|---|---|---|---|---|---|
| EO-1 | 1c | 10.000 | 637.1 | 4.90 | 20.1 | 146.3 | 0.0401 |
| EO-2 | 1c | 10.000 | 637.1 | 4.90 | 20.1 | 143.4 | 0.0344 |
| EO-3 | 1c | 10.000 | 637.1 | 4.90 | 20.1 | 132.9 | 0.0349 |
| EO-4 | 1c | 10.000 | 637.1 | 4.90 | 20.1 | 214.2 | 0.0321 |
| EO-5 | 1g | 10.000 | 637.1 | 4.90 | 20.5 | 94.8 | 0.0421 |
| EO-6 | 1g | 10.000 | 637.1 | 4.90 | 20.1 | 96.0 | 0.0404 |
| EO-7 | 1g | 10.000 | 637.1 | 4.90 | 20.3 | 97.6 | 0.0410 |
| EO-8 | 1g | 10.000 | 637.1 | 4.90 | 20.1 | 110.6 | 0.0396 |
| EO-9 | 1h | 10.000 | 637.1 | 4.90 | 20.1 | 99.0 | 0.0369 |
| EO-10 | 1h | 10.000 | 637.1 | 4.90 | 20.1 | 93.1 | 0.0405 |
| EO-11 | 1h | 10.000 | 637.1 | 4.90 | 20.1 | 76.9 | 0.0388 |
| EO-12 | 1h | 10.000 | 637.1 | 4.90 | 20.1 | 87.1 | 0.0420 |
| EO-13 | 1n | 9.984 | 638.1 | 3.80 | 25.0 | 172.7 | 0.0530 |
| EO-14 | 1n | 9.984 | 638.1 | 3.80 | 25.0 | 197.6 | 0.0606 |
| EO-15 | 1n | 9.984 | 638.1 | 3.80 | 25.5 | 213.0 | 0.0573 |
| EO-16 | 1n | 9.984 | 638.1 | 3.80 | 25.2 | 317.1 | 0.0623 |
| EO-17 | 1p | 9.984 | 638.1 | 3.80 | 25.0 | 178.1 | 0.0711 |
| EO-18 | 1p | 9.984 | 638.1 | 3.80 | 32.4 | 4.1 | — |
| EO-19 | 1p | 9.984 | 638.1 | 3.80 | 25.0 | 202.8 | 0.0744 |

TABLE c-continued

Ethylene-1-Octene Polymerization Runs - Part 1.

| Ex# | TMC | MAO* (μmol) | 1-Octene (μmol) | Total Toluene (mL) | Final Conversion (psi) | Quench Time (sec) | Polymer Yield (g) |
|---|---|---|---|---|---|---|---|
| EO-20 | 1p | 9.984 | 638.1 | 3.80 | 25.0 | 190.7 | 0.0761 |
| EO-21 | 6a | 10.000 | 637.1 | 4.90 | 20.1 | 153.6 | 0.0302 |
| EO-22 | 6a | 10.000 | 637.1 | 4.90 | 20.1 | 124.1 | 0.0320 |
| EO-23 | 6a | 10.000 | 637.1 | 4.90 | 20.1 | 123.1 | 0.0355 |
| EO-24 | 6a | 10.000 | 637.1 | 4.90 | 20.1 | 127.4 | 0.0352 |
| EO-25 | 6b | 9.984 | 638.1 | 3.80 | 25.0 | 132.0 | 0.0600 |
| EO-26 | 6b | 9.984 | 638.1 | 3.80 | 25.2 | 129.5 | 0.0600 |
| EO-27 | 6b | 9.984 | 638.1 | 3.80 | 25.2 | 127.8 | 0.0650 |
| EO-28 | 6b | 9.984 | 638.1 | 3.80 | 25.0 | 147.9 | 0.0610 |
| EO-29 | 6c | 9.984 | 638.1 | 3.80 | 25.0 | 123.6 | 0.0680 |
| EO-30 | 6c | 9.984 | 638.1 | 3.80 | 25.2 | 134.8 | 0.0680 |
| EO-31 | 6c | 9.984 | 638.1 | 3.80 | 25.0 | 127.1 | 0.0710 |
| EO-32 | 6c | 9.984 | 638.1 | 3.80 | 25.0 | 158.8 | 0.0740 |
| EO-33 | 6d | 10.000 | 637.1 | 4.90 | 20.5 | 53.0 | 0.0687 |
| EO-34 | 6d | 10.000 | 637.1 | 4.90 | 20.1 | 50.3 | 0.0667 |
| EO-35 | 6d | 10.000 | 637.1 | 4.90 | 20.5 | 50.1 | 0.0678 |
| EO-36 | 6d | 10.000 | 637.1 | 4.90 | 20.6 | 50.4 | 0.0689 |
| EO-37 | 7a | 10.000 | 637.1 | 4.90 | 20.1 | 57.8 | 0.0524 |
| EO-38 | 7a | 10.000 | 637.1 | 4.90 | 20.6 | 53.2 | 0.0588 |
| EO-39 | 7a | 10.000 | 637.1 | 4.90 | 20.5 | 60.6 | 0.0593 |
| EO-40 | 7a | 10.000 | 637.1 | 4.90 | 20.3 | 63.5 | 0.0601 |
| EO-41 | 7b | 10.000 | 637.1 | 4.90 | 20.5 | 48.4 | 0.0664 |
| EO-42 | 7b | 10.000 | 637.1 | 4.90 | 20.5 | 52.9 | 0.0613 |
| EO-43 | 7b | 10.000 | 637.1 | 4.90 | 20.3 | 48.7 | 0.0683 |
| EO-44 | 7b | 10.000 | 637.1 | 4.90 | 20.6 | 50.3 | 0.0666 |
| EO-45 | 7c | 10.000 | 637.1 | 4.90 | 20.1 | 42.6 | 0.0692 |
| EO-46 | 7c | 10.000 | 637.1 | 4.90 | 20.3 | 42.8 | 0.0736 |
| EO-47 | 7c | 10.000 | 637.1 | 4.90 | 20.1 | 44.2 | 0.0725 |
| EO-48 | 7c | 10.000 | 637.1 | 4.90 | 20.1 | 44.2 | 0.0742 |
| EO-49 | 7d | 10.000 | 637.1 | 4.90 | 20.3 | 51.5 | 0.0650 |
| EO-50 | 7d | 10.000 | 637.1 | 4.90 | 20.1 | 48.7 | 0.0679 |
| EO-51 | 7d | 10.000 | 637.1 | 4.90 | 20.5 | 51.5 | 0.0677 |
| EO-52 | 7d | 10.000 | 637.1 | 4.90 | 20.3 | 51.4 | 0.0672 |
| EO-53 | 7e | 10.000 | 637.1 | 4.90 | 20.1 | 97.8 | 0.0509 |
| EO-54 | 7e | 10.000 | 637.1 | 4.90 | 20.3 | 90.0 | 0.0501 |
| EO-55 | 7e | 10.000 | 637.1 | 4.90 | 20.3 | 91.6 | 0.0522 |
| EO-56 | 7e | 10.000 | 637.1 | 4.90 | 20.3 | 94.6 | 0.0533 |
| EO-57 | 10a | 10.000 | 637.1 | 4.90 | 20.3 | 613.9 | 0.0977 |
| EO-58 | 10a | 10.000 | 637.1 | 4.90 | 20.1 | 565.4 | 0.0964 |
| EO-59 | 10a | 10.000 | 637.1 | 4.90 | 20.1 | 542.3 | 0.0932 |
| EO-60 | 10a | 10.000 | 637.1 | 4.90 | 20.1 | 401.8 | 0.0885 |
| EO-61 | 10c | 10.000 | 637.1 | 4.90 | 20.1 | 131.4 | 0.0558 |
| EO-62 | 10c | 10.000 | 637.1 | 4.90 | 20.1 | 130.0 | 0.0607 |
| EO-63 | 10c | 10.000 | 637.1 | 4.90 | 20.3 | 142.0 | 0.0583 |
| EO-64 | 10c | 10.000 | 637.1 | 4.90 | 20.1 | 142.0 | 0.0621 |
| EO-65 | 10d | 10.000 | 637.1 | 4.90 | 20.1 | 468.6 | 0.0635 |
| EO-66 | 10d | 10.000 | 637.1 | 4.90 | 20.1 | 523.3 | 0.0624 |
| EO-67 | 10d | 10.000 | 637.1 | 4.90 | 20.3 | 609.3 | 0.0723 |
| EO-68 | 10d | 10.000 | 637.1 | 4.90 | 20.1 | 542.4 | 0.0608 |
| EO-69 | 10f | 10.000 | 637.1 | 4.90 | 20.15 | 1001.4 | 0.0373 |
| EO-70 | 10f | 10.000 | 637.1 | 4.90 | 20.15 | 1035.8 | 0.0393 |
| EO-71 | 10f | 10.000 | 637.1 | 4.90 | 20.15 | 950.3 | 0.0338 |
| EO-72 | 10f | 10.000 | 637.1 | 4.90 | 20.15 | 1040.2 | 0.0333 |
| EO-73 | 10h | 10.000 | 637.1 | 4.90 | 20.15 | 237.0 | 0.0750 |
| EO-74 | 10h | 10.000 | 637.1 | 4.90 | 20.15 | 180.5 | 0.0700 |
| EO-75 | 10h | 10.000 | 637.1 | 4.90 | 20.15 | 335.4 | 0.0872 |
| EO-76 | 10h | 10.000 | 637.1 | 4.90 | 20.15 | 207.2 | 0.0748 |
| EO-77 | 10i | 10.000 | 637.1 | 4.90 | 20.30 | 205.2 | 0.0448 |
| EO-78 | 10i | 10.000 | 637.1 | 4.90 | 20.15 | 199.8 | 0.0394 |
| EO-79 | 10i | 10.000 | 637.1 | 4.90 | 20.15 | 198.2 | 0.0421 |
| EO-80 | 10i | 10.000 | 637.1 | 4.90 | 20.15 | 233.4 | 0.0462 |
| EO-81 | 10l | 10.000 | 637.1 | 4.90 | 20.15 | 251.1 | 0.0368 |
| EO-82 | 10l | 10.000 | 637.1 | 4.90 | 20.15 | 276.8 | 0.0399 |
| EO-83 | 10l | 10.000 | 637.1 | 4.90 | 20.15 | 279.0 | 0.0414 |
| EO-84 | 10l | 10.000 | 637.1 | 4.90 | 20.15 | 306.3 | 0.0400 |
| EO-85 | Meso-8b | 9.984 | 638.1 | 3.80 | 20.5 | 100.8 | 0.0811 |
| EO-86 | meso-8b | 9.984 | 638.1 | 3.80 | 20.1 | 128.4 | 0.0832 |
| EO-87 | meso-8b | 9.984 | 638.1 | 3.80 | 20.1 | 128.4 | 0.0773 |
| EO-88 | meso-8b | 9.984 | 638.1 | 3.80 | 20.5 | 153.3 | 0.0878 |
| EO-89 | rac-9a | 10.000 | 637.1 | 4.90 | 20.1 | 185.9 | 0.1126 |
| EO-90 | rac-9a | 10.000 | 637.1 | 4.90 | 20.1 | 221.5 | 0.1180 |
| EO-91 | rac-9a | 10.000 | 637.1 | 4.90 | 20.1 | 195.0 | 0.1158 |

TABLE c-continued

Ethylene-1-Octene Polymerization Runs - Part 1.

| Ex# | TMC | MAO* (µmol) | 1-Octene (µmol) | Total Toluene (mL) | Final Conversion (psi) | Quench Time (sec) | Polymer Yield (g) |
|---|---|---|---|---|---|---|---|
| EO-92 | rac-9a | 10.000 | 637.1 | 4.90 | 20.3 | 199.3 | 0.1126 |
| EO-93 | rac-8m | 10.000 | 637.1 | 4.90 | 20.1 | 33.9 | 0.1217 |
| EO-94 | rac-8m | 10.000 | 637.1 | 4.90 | 20.3 | 33.7 | 0.1208 |
| EO-95 | rac-8m | 10.000 | 637.1 | 4.90 | 20.6 | 34.0 | 0.1235 |
| EO-96 | rac-8m | 10.000 | 637.1 | 4.90 | 20.8 | 32.2 | 0.1240 |

*Micromoles of Al in MAO.

TABLE d

Ethylene-1-Octene Polymerization Runs - Part 2.

| Ex# | TMC | Mw | Mn | PDI | Octene (wt %) | Tm (° C.) |
|---|---|---|---|---|---|---|
| EO-1 | 1c | 756,860 | 351,521 | 2.2 | 4.4 | — |
| EO-2 | 1c | 665,528 | 317,970 | 2.1 | 4.1 | — |
| EO-3 | 1c | 650,617 | 325,844 | 2.0 | 4.2 | — |
| EO-4 | 1c | 580,008 | 323,366 | 1.8 | 3.7 | — |
| EO-5 | 1g | 606,129 | 292,145 | 2.1 | 3.8 | — |
| EO-6 | 1g | 620,771 | 312,597 | 2.0 | 3.6 | — |
| EO-7 | 1g | 610,585 | 319,604 | 1.9 | 3.5 | — |
| EO-8 | 1g | 602,604 | 321,491 | 1.9 | 3.6 | — |
| EO-9 | 1h | 460,292 | 250,965 | 1.8 | 3.8 | — |
| EO-10 | 1h | 498,563 | 272,078 | 1.8 | 3.8 | — |
| EO-11 | 1h | 506,522 | 270,390 | 1.9 | 4.0 | — |
| EO-12 | 1h | 535,741 | 287,816 | 1.9 | 4.3 | — |
| EO-13 | 1n | 496,527 | 273,642 | 1.8 | 3.3 | 126.0 |
| EO-14 | 1n | 415,759 | 206,182 | 2.0 | 3.1 | 126.4 |
| EO-15 | 1n | 469,526 | 167,808 | 2.8 | 3.9 | 126.8 |
| EO-16 | 1n | 540,763 | 316,243 | 1.7 | 3.1 | 127.3 |
| EO-17 | 1p | 464,393 | 259,260 | 1.8 | 3.9 | 126.6 |
| EO-18 | 1p | — | — | — | — | 112.6 |
| EO-19 | 1p | 504,991 | 258,077 | 2.0 | 3.2 | — |
| EO-20 | 1p | 477,196 | 251,338 | 1.9 | 3.4 | 126.5 |
| EO-21 | 6a | 913,823 | 533,604 | 1.7 | 3.9 | — |
| EO-22 | 6a | 996,653 | 555,659 | 1.8 | 3.9 | — |
| EO-23 | 6a | 902,722 | 368,170 | 2.5 | 3.7 | — |
| EO-24 | 6a | 950,674 | 522,379 | 1.8 | 3.5 | — |
| EO-25 | 6b | 349,466 | 182,800 | 1.9 | 5.3 | 119.8 |
| EO-26 | 6b | 357,882 | 187,018 | 1.9 | 5.4 | 117.7 |
| EO-27 | 6b | 373,097 | 188,457 | 2.0 | 5.3 | 119.8 |
| EO-28 | 6b | 366,198 | 185,034 | 2.0 | 5.8 | 118.0 |
| EO-29 | 6c | 408,429 | 173,886 | 2.3 | 4.5 | 118.3 |
| EO-30 | 6c | 360,560 | 157,593 | 2.3 | 6.0 | 119.5 |
| EO-31 | 6c | 374,542 | 136,881 | 2.7 | 4.4 | 121.3 |
| EO-32 | 6c | 387,681 | 116,539 | 3.3 | 5.1 | 122.9 |
| EO-33 | 6d | 383,751 | 184,254 | 2.1 | 6.6 | — |
| EO-34 | 6d | 386,954 | 194,510 | 2.0 | 6.9 | — |
| EO-35 | 6d | 389,655 | 189,652 | 2.1 | 6.7 | — |
| EO-36 | 6d | 425,697 | 214,065 | 2.0 | 6.2 | — |
| EO-37 | 7a | 444,465 | 220,516 | 2.0 | 4.1 | — |
| EO-38 | 7a | 462,135 | 231,513 | 2.0 | 3.8 | — |
| EO-39 | 7a | 454,252 | 222,916 | 2.0 | 4.3 | — |
| EO-40 | 7a | 463,153 | 216,258 | 2.1 | 4.1 | — |
| EO-41 | 7b | 211,515 | 105,710 | 2.0 | 7.4 | — |
| EO-42 | 7b | 203,365 | 105,495 | 1.9 | 7.9 | — |
| EO-43 | 7b | 236,353 | 113,707 | 2.1 | 6.6 | — |
| EO-44 | 7b | 222,496 | 110,848 | 2.0 | 6.8 | — |
| EO-45 | 7c | 165,064 | 81,476 | 2.0 | 7.3 | — |
| EO-46 | 7c | 178,922 | 86,772 | 2.1 | 7.1 | — |
| EO-47 | 7c | 174,597 | 84,269 | 2.1 | 7.1 | — |
| EO-48 | 7c | 189,282 | 90,598 | 2.1 | 7.6 | — |
| EO-49 | 7d | 170,514 | 90,428 | 1.9 | 7.8 | — |
| EO-50 | 7d | 186,654 | 96,385 | 1.9 | 7.1 | — |
| EO-51 | 7d | 193,123 | 102,134 | 1.9 | 7.7 | — |
| EO-52 | 7d | 185,348 | 98,294 | 1.9 | 8.1 | — |
| EO-53 | 7e | 287,601 | 180,502 | 1.6 | 5.9 | — |
| EO-54 | 7e | 303,210 | 193,077 | 1.6 | 5.5 | — |
| EO-55 | 7e | 282,060 | 173,377 | 1.6 | 6.3 | — |
| EO-56 | 7e | 287,156 | 175,759 | 1.6 | 6.2 | — |
| EO-57 | 10a | 1,218,474 | 557,821 | 2.2 | 7.4 | — |
| EO-58 | 10a | 1,251,099 | 586,370 | 2.1 | 7.3 | — |
| EO-59 | 10a | 1,262,217 | 611,220 | 2.1 | 7.7 | — |
| EO-60 | 10a | 1,277,225 | 645,928 | 2.0 | 7.0 | — |
| EO-61 | 10c | 868,385 | 498,841 | 1.7 | 11.2 | — |
| EO-62 | 10c | 814,718 | 470,094 | 1.7 | 10.8 | — |
| EO-63 | 10c | 865,442 | 501,104 | 1.7 | 11.5 | — |
| EO-64 | 10c | 872,038 | 501,300 | 1.7 | 12.0 | — |
| EO-65 | 10d | 908,742 | 499,591 | 1.8 | 11.1 | — |
| EO-66 | 10d | 939,313 | 512,396 | 1.8 | 11.9 | — |
| EO-67 | 10d | 980,527 | 537,104 | 1.8 | 11.7 | — |
| EO-68 | 10d | 928,925 | 533,605 | 1.7 | 12.9 | — |
| EO-69 | 10f | 283,023 | 169,829 | 1.7 | 19.2 | — |
| EO-70 | 10f | 285,259 | 175,716 | 1.6 | 19.7 | — |
| EO-71 | 10f | 346,064 | 188,594 | 1.8 | 15.9 | — |
| EO-72 | 10f | 300,375 | 178,109 | 1.7 | 19.8 | — |
| EO-73 | 10h | 1,351,068 | 874,463 | 1.5 | 9.7 | — |
| EO-74 | 10h | 1,311,510 | 823,148 | 1.6 | 9.6 | — |
| EO-75 | 10h | 1,142,379 | 702,456 | 1.6 | 12.0 | — |
| EO-76 | 10h | 1,297,679 | 839,149 | 1.5 | 10.7 | — |
| EO-77 | 10i | 1,125,916 | 750,609 | 1.5 | 11.4 | — |
| EO-78 | 10i | 1,160,571 | 802,503 | 1.4 | 11.8 | — |
| EO-79 | 10i | 1,164,150 | 796,644 | 1.5 | 11.6 | — |
| EO-80 | 10i | 1,154,685 | 819,920 | 1.4 | 11.1 | — |
| EO-81 | 10l | 1,192,177 | 788,044 | 1.5 | 19.5 | — |
| EO-82 | 10l | 1,119,818 | 781,029 | 1.4 | 17.5 | — |
| EO-83 | 10l | 1,200,596 | 829,844 | 1.4 | 26.5 | — |
| EO-84 | 10l | 1,113,991 | 760,611 | 1.5 | 12.1 | — |
| EO-85 | meso-8b | 219,758 | 126,642 | 1.7 | 17.6 | 90.3 |
| EO-86 | meso-8b | 220,284 | 128,036 | 1.7 | 17.4 | 92.9 |
| EO-87 | meso-8b | 194,817 | 113,225 | 1.7 | 19.5 | 89.4 |
| EO-88 | meso-8b | 219,346 | 133,778 | 1.6 | 18.3 | 94.8 |
| EO-89 | rac-9a | 712,854 | 197,712 | 3.6 | 19.5 | — |
| EO-90 | rac-9a | 756,737 | 335,347 | 2.3 | 15.7 | — |
| EO-91 | rac-9a | 741,746 | 209,961 | 3.5 | 15.9 | — |
| EO-92 | rac-9a | 696,755 | 205,042 | 3.4 | 15.2 | — |
| EO-93 | rac-8m | 239,188 | 153,331 | 1.6 | 24.9 | — |
| EO-94 | rac-8m | 248,879 | 160,867 | 1.5 | 23.6 | — |
| EO-95 | rac-8m | 246,961 | 158,777 | 1.6 | 23.8 | — |
| EO-96 | rac-8m | 245,804 | 160,014 | 1.5 | 23.0 | — |

| | | | | Part e: Propylene Polymerization Runs - Part 1. | | | | |
|---|---|---|---|---|---|---|---|---|
| Ex# | TMC | TMC (μmol) | MAO* (μmol) | Total Hexane (μL) | Total Toluene (μL) | Quench Time (sec) | Polymer Yield (g) | Activity (g/mmol · hr) |
| PP-1 | 10a | 0.10 | 50 | 3700 | 331 | 729.4 | 0.0496 | 2,448 |
| PP-2 | 10a | 0.10 | 50 | 3700 | 331 | 731.4 | 0.0497 | 2,446 |
| PP-3 | 10a | 0.08 | 40 | 3767 | 265 | 760.4 | 0.0383 | 2,267 |
| PP-4 | 10a | 0.08 | 40 | 3767 | 265 | 824.2 | 0.0426 | 2,326 |
| PP-5 | 10b | 0.08 | 40 | 3767 | 265 | 386.9 | 0.0575 | 6,688 |
| PP-6 | 10b | 0.08 | 40 | 3767 | 265 | 444.2 | 0.0508 | 5,147 |
| PP-7 | 10b | 0.10 | 50 | 3700 | 331 | 305.3 | 0.058 | 6,839 |
| PP-8 | 10b | 0.10 | 50 | 3700 | 331 | 324.1 | 0.0624 | 6,932 |
| PP-9 | 10e | 0.08 | 40 | 3767 | 265 | 415.3 | 0.0572 | 6,197 |
| PP-10 | 10e | 0.08 | 40 | 3767 | 265 | 404.3 | 0.0538 | 5,988 |
| PP-11 | 10e | 0.10 | 50 | 3700 | 331 | 314.3 | 0.0559 | 6,402 |
| PP-12 | 10e | 0.10 | 50 | 3700 | 331 | 323.9 | 0.0549 | 6,102 |
| PP-13 | 10f | 0.10 | 50 | 3633 | 499 | 901.8 | 0.0067 | 267 |
| PP-14 | 10f | 0.10 | 50 | 3633 | 499 | 900.0 | 0.0069 | 276 |
| PP-15 | 10f | 0.08 | 40 | 3733 | 399 | 900.0 | 0.0051 | 255 |
| PP-16 | 10f | 0.08 | 40 | 3733 | 399 | 900.8 | 0.0053 | 265 |
| PP-17 | 10g | 0.10 | 50 | 3700 | 331 | 587.1 | 0.0487 | 2,986 |
| PP-18 | 10g | 0.10 | 50 | 3700 | 331 | 563.7 | 0.0429 | 2,740 |
| PP-19 | 10g | 0.08 | 40 | 3767 | 265 | 900.7 | 0.0392 | 1,958 |
| PP-20 | 10g | 0.08 | 40 | 3767 | 265 | 900.2 | 0.042 | 2,099 |
| PP-21 | 10h | 0.10 | 50 | 3700 | 331 | 485.9 | 0.0581 | 4,305 |
| PP-22 | 10h | 0.10 | 50 | 3700 | 331 | 479.7 | 0.0545 | 4,090 |
| PP-23 | 10h | 0.08 | 40 | 3767 | 265 | 546.6 | 0.0497 | 4,092 |
| PP-24 | 10h | 0.08 | 40 | 3767 | 265 | 558.3 | 0.0491 | 3,957 |
| PP-25 | 10i | 0.10 | 50 | 3633 | 499 | 564.8 | 0.053 | 3,378 |
| PP-26 | 10i | 0.10 | 50 | 3633 | 499 | 519.2 | 0.0516 | 3,578 |
| PP-27 | 10i | 0.08 | 40 | 3733 | 399 | 631.5 | 0.0451 | 3,214 |
| PP-28 | 10i | 0.08 | 40 | 3733 | 399 | 900.5 | 0.0335 | 1,674 |
| PP-29 | 10k | 0.10 | 50 | 3633 | 499 | 571.3 | 0.0557 | 3,510 |
| PP-30 | 10k | 0.10 | 50 | 3633 | 499 | 553.7 | 0.0532 | 3,459 |
| PP-31 | 10k | 0.08 | 40 | 3733 | 399 | 663.7 | 0.0463 | 3,139 |
| PP-32 | 10k | 0.08 | 40 | 3733 | 399 | 637.4 | 0.0489 | 3,452 |
| PP-33 | 10l | 0.08 | 40 | 3733 | 399 | 900.6 | 0.0298 | 1,489 |
| PP-34 | 10l | 0.08 | 40 | 3733 | 399 | 669.4 | 0.0511 | 3,435 |
| PP-35 | 10l | 0.10 | 50 | 3633 | 499 | 409.4 | 0.057 | 5,012 |
| PP-36 | 10l | 0.10 | 50 | 3633 | 499 | 467.6 | 0.0537 | 4,135 |
| PP-37 | 10m | 0.08 | 40 | 3733 | 399 | 630.6 | 0.0448 | 3,197 |
| PP-38 | 10m | 0.08 | 40 | 3733 | 399 | 672.1 | 0.0417 | 2,792 |
| PP-39 | 10m | 0.10 | 50 | 3633 | 499 | 547.0 | 0.0501 | 3,297 |
| PP-40 | 10m | 0.10 | 50 | 3633 | 499 | 554.6 | 0.0479 | 3,110 |
| PP-41 | rac-8a | 0.08 | 40 | 3767 | 265 | 301.2 | 0.0521 | 7,783 |
| PP-42 | rac-8a | 0.08 | 40 | 3767 | 265 | 324.2 | 0.0527 | 7,315 |
| PP-43 | rac-8a | 0.10 | 50 | 3700 | 331 | 240.2 | 0.0624 | 9,353 |
| PP-44 | rac-8a | 0.10 | 50 | 3700 | 331 | 222.5 | 0.056 | 9,062 |
| PP-45 | rac-8c | 0.10 | 50 | 3700 | 331 | 83.0 | 0.1894 | 82,189 |
| PP-46 | rac-8c | 0.10 | 50 | 3700 | 331 | 83.0 | 0.193 | 83,671 |
| PP-47 | rac-8c | 0.08 | 40 | 3767 | 265 | 111.3 | 0.1064 | 43,011 |
| PP-48 | rac-8c | 0.08 | 40 | 3767 | 265 | 90.9 | 0.1412 | 69,916 |
| PP-49 | rac-8d | 0.08 | 40 | 3767 | 265 | 38.5 | 0.2552 | 298,053 |
| PP-50 | rac-8d | 0.08 | 40 | 3767 | 265 | 44.7 | 0.2823 | 284,385 |
| PP-51 | rac-8d | 0.10 | 50 | 3700 | 331 | 34.9 | 0.2914 | 300,240 |
| PP-52 | rac-8d | 0.10 | 50 | 3700 | 331 | 38.5 | 0.2757 | 257,797 |
| PP-53 | rac-8e | 0.10 | 50 | 3700 | 331 | 90.1 | 0.195 | 77,896 |
| PP-54 | rac-8e | 0.10 | 50 | 3700 | 331 | 66.3 | 0.223 | 121,086 |
| PP-55 | rac-8e | 0.08 | 40 | 3767 | 265 | 69.9 | 0.1826 | 117,621 |
| PP-56 | rac-8e | 0.08 | 40 | 3767 | 265 | 351.0 | 0.0466 | 5,975 |
| PP-57 | rac-8f | 0.08 | 40 | 3767 | 265 | 49.1 | 0.2214 | 202,789 |
| PP-58 | rac-8f | 0.08 | 40 | 3767 | 265 | 50.5 | 0.2 | 178,183 |
| PP-59 | rac-8f | 0.10 | 50 | 3700 | 331 | 43.0 | 0.2474 | 207,077 |
| PP-60 | rac-8f | 0.10 | 50 | 3700 | 331 | 44.6 | 0.2318 | 186,977 |
| PP-61 | rac-8g | 0.08 | 40 | 3767 | 265 | 44.5 | 0.2943 | 297,874 |
| PP-62 | rac-8g | 0.08 | 40 | 3767 | 265 | 40.1 | 0.3043 | 341,739 |
| PP-63 | rac-8g | 0.10 | 50 | 3700 | 331 | 29.9 | 0.3288 | 396,145 |
| PP-64 | rac-8g | 0.10 | 50 | 3700 | 331 | 31.0 | 0.3131 | 363,600 |
| PP-65 | rac-8h | 0.08 | 40 | 3767 | 265 | 493.8 | 0.0493 | 4,493 |
| PP-66 | rac-8h | 0.10 | 50 | 3700 | 331 | 180.9 | 0.0806 | 16,039 |
| PP-67 | rac-8h | 0.10 | 50 | 3700 | 331 | 188.7 | 0.0778 | 14,843 |
| PP-68 | rac-9b | 0.08 | 40 | 3767 | 265 | 31.1 | 0.2461 | 356,208 |
| PP-73 | rac-9b | 0.08 | 40 | 3767 | 265 | 31.0 | 0.2463 | 357,417 |
| PP-74 | rac-9c | 0.08 | 40 | 3767 | 265 | 23.8 | 0.2503 | 473,654 |
| PP-75 | rac-9c | 0.08 | 40 | 3767 | 265 | 26.8 | 0.2552 | 428,988 |
| PP-76 | rac-9d | 0.08 | 40 | 3767 | 265 | 31.2 | 0.2772 | 399,936 |
| PP-77 | rac-9d | 0.08 | 40 | 3767 | 265 | 26.9 | 0.2332 | 389,677 |

Part e: Propylene Polymerization Runs - Part 1.

| Ex# | TMC | TMC (μmol) | MAO* (μmol) | Total Hexane (μL) | Total Toluene (μL) | Quench Time (sec) | Polymer Yield (g) | Activity (g/mmol · hr) |
|---|---|---|---|---|---|---|---|---|
| PP-78 | rac-9e | 0.08 | 40 | 3767 | 265 | 30.5 | 0.2579 | 380,010 |
| PP-79 | rac-9e | 0.08 | 40 | 3767 | 265 | 32.5 | 0.2462 | 341,102 |

*Micromoles of Al in MAO.

Part f: Propylene Polymerization Runs - Part 2.

| Ex# | TMC | Mw | Mn | PDI | FTIR Crystallinity Index (° C.) | DSC (° C.) | dH (J/g) |
|---|---|---|---|---|---|---|---|
| PP-1 | 10a | 15,574 | 9,303 | 1.67 | 79.3* | 0 | — |
| PP-2 | 10a | 14,530 | 8,780 | 1.65 | 81.6* | — | — |
| PP-3 | 10a | 15,124 | 9,033 | 1.67 | 76.6* | — | — |
| PP-4 | 10a | 15,223 | 9,202 | 1.65 | 77.0* | — | — |
| PP-5 | 10b | 151,074 | 97,313 | 1.55 | 106.4 | — | — |
| PP-6 | 10b | 128,894 | 83,361 | 1.55 | 104.9 | — | — |
| PP-7 | 10b | 145,401 | 93,723 | 1.55 | 105.7 | — | — |
| PP-8 | 10b | 145,076 | 92,497 | 1.57 | 104.2 | 96.0 | 15 |
| PP-9 | 10e | 157,340 | 90,116 | 1.75 | 114.3 | 111 | 33.1 |
| PP-10 | 10e | 156,374 | 92,740 | 1.69 | 115.1 | — | — |
| PP-11 | 10e | 154,659 | 85,721 | 1.80 | 114.0 | — | — |
| PP-12 | 10e | 158,271 | 89,187 | 1.77 | 112.7 | — | — |
| PP-13 | 10f | — | — | — | — | — | — |
| PP-14 | 10f | — | — | — | — | — | — |
| PP-15 | 10f | — | — | — | — | — | — |
| PP-16 | 10f | — | — | — | — | — | — |
| PP-17 | 10g | 45,219 | 24,853 | 1.82 | 92.5* | 68 | — |
| PP-18 | 10g | 42,389 | 23,044 | 1.84 | 91.2* | — | — |
| PP-19 | 10g | 41,901 | 23,230 | 1.80 | 91.7* | — | — |
| PP-20 | 10g | 42,547 | 23,813 | 1.79 | 97.2* | — | — |
| PP-21 | 10h | 41,779 | 24,095 | 1.73 | 97.3* | 0 | — |
| PP-22 | 10h | 41,586 | 24,259 | 1.71 | 95.2* | — | — |
| PP-23 | 10h | 41,705 | 24,000 | 1.74 | 89.9* | — | — |
| PP-24 | 10h | 42,175 | 24,716 | 1.71 | 89.9* | — | — |
| PP-25 | 10i | 56,906 | 33,608 | 1.69 | 86.1* | 0 | — |
| PP-26 | 10i | 60,267 | 35,759 | 1.69 | 84.8* | — | — |
| PP-27 | 10i | 56,731 | 33,300 | 1.70 | — | 0 | — |
| PP-28 | 10i | 66,921 | 38,883 | 1.72 | 31.2* | — | — |
| PP-29 | 10k | 62,268 | 37,935 | 1.64 | 92.9* | 0 | — |
| PP-30 | 10k | 61,485 | 37,558 | 1.64 | 86.5* | — | — |
| PP-31 | 10k | 57,212 | 36,399 | 1.57 | 95.4* | — | — |
| PP-32 | 10k | 57,643 | 38,672 | 1.49 | 82.6* | 0 | — |
| PP-33 | 10l | 168,001 | 100,790 | 1.67 | 105.2 | — | — |
| PP-34 | 10l | 185,262 | 109,720 | 1.69 | 103.7 | 80 | — |
| PP-35 | 10l | 171,939 | 103,773 | 1.66 | 102.5 | 79 | — |
| PP-36 | 10l | 172,948 | 103,924 | 1.66 | 102.2 | — | — |
| PP-37 | 10m | 174,133 | 106,451 | 1.64 | 69.3* | 0 | — |
| PP-38 | 10m | 175,092 | 106,871 | 1.64 | 96.7* | — | — |
| PP-39 | 10m | 179,738 | 107,811 | 1.67 | 102.1 | 89 | — |
| PP-40 | 10m | 118,275 | 58,217 | 2.03 | 102.6 | — | — |
| PP-41 | rac-8a | 110,301 | 66,393 | 1.66 | 138.5 | — | — |
| PP-42 | rac-8a | 106,092 | 63,094 | 1.68 | 138.6 | — | — |
| PP-43 | rac-8a | 112,805 | 64,138 | 1.76 | 134.9 | 146, 137 | — |
| PP-44 | rac-8a | 105,815 | 63,788 | 1.66 | 133.3 | — | — |
| PP-45 | rac-8c | 353,539 | 188,765 | 1.87 | 146.4 | 154 | — |
| PP-46 | rac-8c | 317,909 | 162,374 | 1.96 | 146.5 | — | — |
| PP-47 | rac-8c | 480,648 | 274,047 | 1.75 | 157.1 | — | — |
| PP-48 | rac-8c | 415,191 | 234,678 | 1.77 | 152.1 | — | — |
| PP-49 | rac-8d | 216,220 | 98,296 | 2.20 | 150.1 | — | — |
| PP-50 | rac-8d | 225,742 | 101,937 | 2.21 | 143.9 | — | — |
| PP-51 | rac-8d | 212,060 | 94,716 | 2.24 | 154.0 | 153.0 | 95 |
| PP-52 | rac-8d | 202,773 | 88,992 | 2.28 | 151.5 | — | — |
| PP-53 | rac-8e | 302,223 | 155,932 | 1.94 | 153.7 | 147, 153 | — |
| PP-54 | rac-8e | 254,795 | 121,686 | 2.09 | 159.1 | — | — |
| PP-55 | rac-8e | 291,081 | 152,525 | 1.91 | 154.2 | — | — |
| PP-56 | rac-8e | 569,635 | 338,306 | 1.68 | 152.7 | — | — |
| PP-57 | rac-8f | 226,979 | 120,489 | 1.88 | 148.7 | 152, 146 | 89.2 |
| PP-58 | rac-8f | 237,642 | 129,934 | 1.83 | 150.1 | — | — |

-continued

Part f: Propylene Polymerization Runs - Part 2.

| Ex# | TMC | Mw | Mn | PDI | FTIR Crystallinity Index (° C.) | DSC (° C.) | dH (J/g) |
|---|---|---|---|---|---|---|---|
| PP-59 | rac-8f | 187,790 | 89,439 | 2.10 | 151.9 | — | — |
| PP-60 | rac-8f | 208,353 | 108,165 | 1.93 | 151.8 | — | — |
| PP-61 | rac-8g | 245,298 | 95,055 | 2.58 | 152.5 | 150, 143 | 87.8 |
| PP-62 | rac-8g | 241,034 | 90,209 | 2.67 | 152.8 | — | — |
| PP-63 | rac-8g | 196,257 | 66,070 | 2.97 | 151.4 | — | — |
| PP-64 | rac-8g | 205,024 | 69,820 | 2.94 | 150.2 | — | — |
| PP-65 | rac-8h | 257,566 | 153,011 | 1.68 | 160.8 | — | — |
| PP-66 | rac-8h | 236,995 | 146,284 | 1.62 | 152.5 | 156 | — |
| PP-67 | rac-8h | 224,672 | 138,178 | 1.63 | 157.8 | — | — |
| PP-68 | rac-9b | 68,800 | 36,302 | 1.90 | 152.5 | 145 | 75.2 |
| PP-73 | rac-9b | 67,952 | 35,766 | 1.90 | 151.8 | — | — |
| PP-74 | rac-9c | 49,621 | 25,100 | 1.98 | 150.7 | 145 | 78.8 |
| PP-75 | rac-9c | 53,945 | 27,042 | 1.99 | 147.3 | — | — |
| PP-76 | rac-9d | 61,356 | 31,043 | 1.98 | 147.7 | 145 | 92.5 |
| PP-77 | rac-9d | 65,818 | 35,729 | 1.84 | 148.9 | — | — |
| PP-78 | rac-9e | 57,320 | 31,370 | 1.83 | 149.4 | 145 | 73.9 |
| PP-79 | rac-9e | 57,022 | 30,842 | 1.85 | 149.0 | — | — |

*Outside of the calibration range of the model.

Part g: Ethylene-Propylene Polymerization Runs - Part 1.

| Ex# | TMC | TMC (µmol) | MAO* (µmol) | Total Hexane (mL) | Total Toluene (mL) | Quench Time (sec) | Polymer Yield (g) |
|---|---|---|---|---|---|---|---|
| EP-1 | 10a | 0.10 | 50 | 3.657 | 0.331 | 134.2 | 0.0417 |
| EP-2 | 10a | 0.10 | 50 | 3.657 | 0.331 | 249.7 | 0.0582 |
| EP-3 | 10a | 0.08 | 40 | 3.724 | 0.265 | 314.5 | 0.0355 |
| EP-4 | 10a | 0.08 | 40 | 3.724 | 0.265 | 177.4 | 0.0392 |
| EP-5 | 10b | 0.08 | 40 | 3.724 | 0.265 | 134.3 | 0.0604 |
| EP-6 | 10b | 0.08 | 40 | 3.724 | 0.265 | 156.5 | 0.0543 |
| EP-7 | 10b | 0.10 | 50 | 3.657 | 0.331 | 127.7 | 0.0616 |
| EP-8 | 10b | 0.10 | 50 | 3.657 | 0.331 | 206.0 | 0.0981 |
| EP-9 | 10c | 0.10 | 50 | 3.657 | 0.331 | 105.9 | 0.0751 |
| EP-10 | 10c | 0.10 | 50 | 3.657 | 0.331 | 182.1 | 0.1050 |
| EP-11 | 10c | 0.08 | 40 | 3.724 | 0.265 | 98.1 | 0.0676 |
| EP-12 | 10c | 0.08 | 40 | 3.724 | 0.265 | 107.1 | 0.0649 |
| EP-13 | 10d | 0.08 | 40 | 3.724 | 0.265 | 900.7 | 0.0275 |
| EP-14 | 10d | 0.08 | 40 | 3.724 | 0.265 | 729.8 | 0.0308 |
| EP-15 | 10d | 0.10 | 50 | 3.657 | 0.331 | 402.8 | 0.0440 |
| EP-16 | 10d | 0.10 | 50 | 3.657 | 0.331 | 900.5 | 0.0284 |
| EP-17 | 10e | 0.08 | 40 | 3.724 | 0.265 | 145.3 | 0.0594 |
| EP-18 | 10e | 0.08 | 40 | 3.724 | 0.265 | 179.7 | 0.0501 |
| EP-19 | 10e | 0.10 | 50 | 3.657 | 0.331 | 122.3 | 0.0613 |
| EP-20 | 10e | 0.10 | 50 | 3.657 | 0.331 | 126.7 | 0.0622 |
| EP-21 | 10f | 0.10 | 50 | 3.700 | 0.331 | 900.7 | 0.0295 |
| EP-22 | 10f | 0.10 | 50 | 3.700 | 0.331 | 865.2 | 0.0315 |
| EP-23 | 10f | 0.08 | 40 | 3.767 | 0.265 | 900.1 | 0.0200 |
| EP-24 | 10f | 0.08 | 40 | 3.767 | 0.265 | 900.4 | 0.0275 |
| EP-25 | 10h | 0.10 | 50 | 3.657 | 0.331 | 97.1 | 0.0620 |
| EP-26 | 10h | 0.10 | 50 | 3.657 | 0.331 | 89.4 | 0.0683 |
| EP-27 | 10h | 0.08 | 40 | 3.724 | 0.265 | 110.2 | 0.0845 |
| EP-28 | 10h | 0.08 | 40 | 3.724 | 0.265 | 112.6 | 0.0534 |
| EP-29 | 10l | 0.08 | 40 | 3.767 | 0.265 | 251.0 | 0.0429 |
| EP-30 | 10l | 0.08 | 40 | 3.767 | 0.265 | 246.8 | 0.0416 |
| EP-31 | 10l | 0.10 | 50 | 3.700 | 0.331 | 181.4 | 0.0607 |
| EP-32 | 10l | 0.10 | 50 | 3.700 | 0.331 | 184.6 | 0.0578 |
| EP-33 | 10m | 0.08 | 40 | 3.767 | 0.265 | 170.2 | 0.0368 |
| EP-34 | 10m | 0.08 | 40 | 3.767 | 0.265 | 190.6 | 0.0339 |
| EP-35 | 10m | 0.10 | 50 | 3.700 | 0.331 | 150.5 | 0.0403 |
| EP-36 | 10m | 0.10 | 50 | 3.700 | 0.331 | 144.0 | 0.0418 |
| EP-37 | rac-8b | 0.08 | 40 | 3.724 | 0.265 | 14.7 | 0.2999 |
| EP-38 | rac-8b | 0.08 | 40 | 3.724 | 0.265 | 20.8 | 0.2799 |
| EP-39 | rac-8d | 0.08 | 40 | 3.724 | 0.265 | 22.1 | 0.3489 |
| EP-40 | rac-8d | 0.08 | 40 | 3.724 | 0.265 | 27.7 | 0.3326 |
| EP-41 | rac-8d | 0.10 | 50 | 3.657 | 0.331 | 23.7 | 0.3361 |
| EP-42 | rac-8d | 0.10 | 50 | 3.657 | 0.331 | 23.7 | 0.2914 |
| EP-43 | rac-8f | 0.08 | 40 | 3.724 | 0.265 | 40.4 | 0.2305 |

-continued

Part g: Ethylene-Propylene Polymerization Runs - Part 1.

| Ex# | TMC | TMC (μmol) | MAO* (μmol) | Total Hexane (mL) | Total Toluene (mL) | Quench Time (sec) | Polymer Yield (g) |
|---|---|---|---|---|---|---|---|
| EP-44 | rac-8f | 0.08 | 40 | 3.724 | 0.265 | 41.7 | 0.1781 |
| EP-45 | rac-8f | 0.10 | 50 | 3.657 | 0.331 | 29.8 | 0.2488 |
| EP-46 | rac-8f | 0.10 | 50 | 3.657 | 0.331 | 29.6 | 0.2537 |
| EP-47 | rac-8g | 0.08 | 40 | 3.724 | 0.265 | 21.1 | 0.3431 |
| EP-48 | rac-8g | 0.08 | 40 | 3.724 | 0.265 | 24.1 | 0.3388 |
| EP-49 | rac-9b | 0.04 | 20 | 3.857 | 0.132 | 40.3 | 0.1993 |
| EP-50 | rac-9b | 0.04 | 20 | 3.857 | 0.132 | 43.6 | 0.1640 |
| EP-51 | rac-9b | 0.06 | 30 | 3.791 | 0.199 | 29.7 | 0.2436 |
| EP-52 | rac-9b | 0.06 | 30 | 3.791 | 0.199 | 31.3 | 0.2424 |
| EP-53 | rac-9c | 0.04 | 20 | 3.857 | 0.132 | 23.7 | 0.3914 |
| EP-54 | rac-9c | 0.04 | 20 | 3.857 | 0.132 | 28.3 | 0.2309 |
| EP-55 | rac-9d | 0.04 | 20 | 3.857 | 0.132 | 26.9 | 0.3685 |
| EP-56 | rac-9d | 0.04 | 20 | 3.857 | 0.132 | 26.6 | 0.2056 |
| EP-57 | rac-9e | 0.04 | 20 | 3.857 | 0.132 | 29.7 | 0.3771 |
| EP-58 | rac-9e | 0.04 | 20 | 3.857 | 0.132 | 37.0 | 0.2170 |

*Micromoles of Al in MAO.

Part h: Ethylene-Propylene Polymerization Runs - Part 2.

| Ex# | TMC | Mw | Mn | PDI | Ethylene (wt. %) |
|---|---|---|---|---|---|
| EP-1 | 10a | 92,503 | 55,432 | 1.7 | 35.9 |
| EP-2 | 10a | 71,232 | 35,791 | 2.0 | 30.5 |
| EP-3 | 10a | 41,728 | 22,993 | 1.8 | 25.0 |
| EP-4 | 10a | 96,435 | 52,601 | 1.8 | 30.5 |
| EP-5 | 10b | 167,275 | 99,785 | 1.7 | 23.4 |
| EP-6 | 10b | 161,430 | 96,226 | 1.7 | 21.0 |
| EP-7 | 10b | 152,791 | 86,618 | 1.8 | 18.7 |
| EP-8 | 10b | 135,789 | 79,606 | 1.7 | 21.5 |
| EP-9 | 10c | 150,338 | 87,012 | 1.7 | 20.4 |
| EP-10 | 10c | 128,583 | 71,785 | 1.8 | 19.3 |
| EP-11 | 10c | 160,233 | 96,920 | 1.7 | 24.4 |
| EP-12 | 10c | 166,938 | 96,667 | 1.7 | 21.7 |
| EP-13 | 10d | 245,783 | 129,894 | 1.9 | 27.4 |
| EP-14 | 10d | 265,550 | 145,750 | 1.8 | 15.3 |
| EP-15 | 10d | 248,086 | 137,237 | 1.8 | 13.4 |
| EP-16 | 10d | 233,468 | 116,849 | 2.0 | 24.1 |
| EP-17 | 10e | 167,171 | 102,897 | 1.6 | 30.4 |
| EP-18 | 10e | 146,180 | 89,061 | 1.6 | 28.3 |
| EP-19 | 10e | 166,462 | 101,838 | 1.6 | 28.3 |
| EP-20 | 10e | 166,421 | 101,623 | 1.6 | 29.6 |
| EP-21 | 10f | 38,351 | 18,365 | 2.1 | 29.5 |
| EP-22 | 10f | 34,493 | 16,812 | 2.1 | 29.8 |
| EP-23 | 10f | 102,647 | 28,681 | 3.6 | 32.9 |
| EP-24 | 10f | 155,577 | 38,961 | 4.0 | 32.0 |
| EP-25 | 10h | 121,471 | 74,298 | 1.6 | 36.4 |
| EP-26 | 10h | 116,565 | 71,451 | 1.6 | 30.3 |
| EP-27 | 10h | 104,377 | 40,264 | 2.6 | — |
| EP-28 | 10h | 144,029 | 88,986 | 1.6 | 36.3 |
| EP-29 | 10l | 209,496 | 128,180 | 1.6 | 29.7 |
| EP-30 | 10l | 220,137 | 127,869 | 1.7 | 29.3 |
| EP-31 | 10l | 152,017 | 70,633 | 2.2 | 34.2 |
| EP-32 | 10l | 147,835 | 65,455 | 2.3 | 34.5 |
| EP-33 | 10m | 178,450 | 103,865 | 1.7 | 31.1 |
| EP-34 | 10m | 173,346 | 102,022 | 1.7 | 29.6 |
| EP-35 | 10m | 171,117 | 98,578 | 1.7 | 31.0 |
| EP-36 | 10m | 176,799 | 104,293 | 1.7 | 33.7 |
| EP-37 | rac-8b | 97,757 | 32,041 | 3.1 | 1.5* |
| EP-38 | rac-8b | 119,090 | 49,673 | 2.4 | 5.1 |
| EP-39 | rac-8d | 150,272 | 29,411 | 5.1 | 0.8* |
| EP-40 | rac-8d | 171,902 | 40,665 | 4.2 | 3.5* |
| EP-41 | rac-8d | 155,528 | 33,494 | 4.6 | 2.6* |
| EP-42 | rac-8d | 161,742 | 43,723 | 3.7 | 2.6* |
| EP-43 | rac-8f | 151,417 | 87,225 | 1.7 | — |
| EP-44 | rac-8f | 172,095 | 100,623 | 1.7 | 12.5 |
| EP-45 | rac-8f | 136,096 | 72,505 | 1.9 | 2.7* |
| EP-46 | rac-8f | 133,308 | 67,200 | 2.0 | 2.9* |
| EP-47 | rac-8g | 123,392 | 36,415 | 3.4 | 9.2 |
| EP-48 | rac-8g | 136,284 | 45,206 | 3.0 | 13.1 |
| EP-49 | rac-9b | 71,060 | 42,965 | 1.7 | 13.1 |
| EP-50 | rac-9b | 78,476 | 49,506 | 1.6 | 15.9 |
| EP-51 | rac-9b | 57,338 | 32,830 | 1.7 | 14.5 |
| EP-52 | rac-9b | 58,897 | 33,275 | 1.8 | 11.3 |
| EP-53 | rac-9c | 59,262 | 30,994 | 1.9 | 6.3 |
| EP-54 | rac-9c | 58,433 | 33,550 | 1.7 | 8.9 |
| EP-55 | rac-9d | 70,356 | 38,566 | 1.8 | 17.7 |
| EP-56 | rac-9d | 76,257 | 46,721 | 1.6 | 24.1 |
| EP-57 | rac-9e | 63,322 | 33,469 | 1.9 | 10.2 |
| EP-58 | rac-9e | 67,161 | 40,098 | 1.7 | 6.8 |

**Outside FTIR calibration range of 5.14 to 38.79 wt % ethylene.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. All documents described herein are incorporated by reference herein, including any priority documents and/or testing procedures to the extent they are not inconsistent with this text. Likewise, the term "comprising" is considered synonymous with the term "including" for purposes of Australian law.

What we claim is:

1. A process for producing a substituted metallocene compound, the process comprising:
(a) providing a first compound represented by the formula (1):

$$AMX_{n-1}$$

wherein:
M is a transition metal atom having a coordination number of n selected from Group 3, 4, 5 or 6 of the Periodic Table of Elements, or a lanthanide metal atom, or actinide metal atom;
n is 2, 3, 4, 5 or 6;

A is a monocyclic or polycyclic ligand that is pi-bonded to M and is substituted with at least one halogen or sulfonate substituent directly bonded to any sp² carbon atom at a bondable ring position of the ligand; and each X is, independently, a univalent anionic ligand, or two X are joined and bound to the metal atom to form a metallocycle ring, or two X are joined to form a chelating ligand, a diene ligand, or an alkylidene ligand; and (b) reacting said first compound with a transfer-agent which comprises a hydrocarbyl, substituted hydrocarbyl, halocarbyl, substituted halocarbyl, silylcarbyl, or germylcarbyl radical capable of replacing the halogen or sulfonate substituent of ligand A under reaction conditions in the presence of a coupling catalyst.

2. The process of claim 1 wherein A comprises a substituted monocyclic arenyl ligand or substituted polycyclic arenyl ligand.

3. The process of claim 1 wherein A comprises a halogenated cylopentadienyl, halogenated indenyl, or halogenated fluorenyl group, and the halogen substituent of ligand A is a bromo substituent.

4. The process of claim 1 wherein said A is a substituted cyclopentadienyl, substituted heterocyclopentadienyl, substituted indenyl, substituted heteroindenyl, substitutedfluorenyl, substituted heterofluorenyl, substituted cyclopentanaphthyl, substitutedheterocyclopentanaphthyl, substituted heterophenyl, substituted heterocyclopentapentalenyl, substituted heterocyclopentaindenyl, or substituted heterobenzocyclopentaindenyl ligand.

5. The process of claim 1 wherein the halogen or sulfonate substituent of ligand A is a chloro, bromo, iodo, tosylate or triflate substituent.

6. The process of claim 1 wherein ligand A is a halogenated cylopentadienyl, halogenated indenyl, or halogenated fluorenyl group, and the halogen substituent of ligand A is a chloro or bromo substituent.

7. The process of claim 1 wherein M is titanium, zirconium or hafnium.

8. The process of claim 1 wherein the transfer-agent is an organometallic compound.

9. The process of claim 8 wherein the metal of the organometallic compound is selected from boron, tin, copper, magnesium, zinc, aluminum, lithium and zirconium.

10. A process for producing a substituted metallocene compound, the process comprising:

(a) providing a first compound represented by the formula (2):

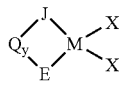

wherein

M is a group 3, 4, 5 or 6 transition metal atom, or a lanthanide metal atom, or actinide metal atom;

each of J and E is independently a substituted or unsubstituted, monocyclic or polycyclic ligand pi-bonded to M, wherein at least one of J and E includes at least one halogen or sulfonate substituent directly bonded to an sp² carbon atom at a bondable ring position of the ligand;

Q is an optional bridging group that is bonded to E and J, and is present when y is one and absent when y is zero;

y is zero or one; and each X is, independently, a univalent anionic ligand, or two X are joined and bound to the metal atom to form a metallocycle ring, or two X are joined to form a chelating ligand, a diene ligand, or an alkylidene ligand; and (b) reacting said first compound with a transfer-agent which comprises a hydrocarbyl, substituted hydrocarbyl, halocarbyl, substituted halocarbyl, silylcarbyl, germylcarbyl radical capable of replacing said at least one halogen or sulfonate substituent of said first compound under reaction conditions in the presence of a coupling catalyst.

11. The process of claim 10 wherein at least one of J and E comprises a substituted or unsubstituted monocyclic arenyl ligand or substituted or unsubstituted polycyclic arenyl ligand.

12. The process of claim 10 wherein at both J and E comprise a substituted monocyclic arenyl ligand or polycyclicarenyl ligand.

13. The process of claim 10 wherein each of J and E is independently a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, a substituted or unsubstituted cyclopentanaphthyl ligand, a substituted or unsubstituted heterocyclopentanaphthyl ligand, a substituted or unsubstituted heterophenyl ligand, a substituted or unsubstituted heterocyclopentapentalenyl ligand, a substituted or unsubstituted heterocyclopentaindenyl ligand, or a substituted or unsubstituted heterobenzocyclopentaindenyl ligand.

14. The process of claim 10 wherein the halogen or sulfonate substituent is a chloro, bromo or iodo substituent.

15. The process of claim 10 wherein the halogen substituent or sulfonate is a chloro or bromo substituent.

16. The process of claim 10 wherein y is 1, and Q is a bridging group containing at least one Group 13, 14, 15, or 16 element.

17. The process of claim 10 wherein y is 1, and Q is a bridging group containing boron or a Group 14, 15 or 16 element.

18. The process of claim 10 wherein y is 1 and Q is selected from:

P(=S)R', P(=Se)R', P(=O)R', R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', R'$_2$C—PR'—CR'$_2$, O, S, Se, Te, NR', PR', AsR', SbR', O—O, S—S, R'N—NR', R'P—PR', O—S, O—NR', O—PR', S—NR', S—PR', and R'N—PR' where R' is hydrogen, a C$_1$-C$_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic polycyclic substituent, or a substituted or unsubstituted, saturated partially unsaturated or aromatic cyclic substituent.

19. The process of claim 10 wherein y is 1 and Q is selected from the group consisting of CH$_2$, CH$_2$CH$_2$, SiMe$_2$, SiPh$_2$, SiMePh, Si(CH$_2$)$_3$, Si(CH$_2$)$_4$, O, S, NPh, PPh, NMe, PMe, NEt, NPr, NBu, PEt, PPr, and PBu, where Me is methyl, Ph is phenyl, Et is ethyl, Pr is propyl, and Bu is butyl.

20. The process of claim 10 wherein the transfer-agent is an organometallic compound.

21. The process of claim 20 wherein the metal of the organometallic compound is selected from boron, tin, copper, magnesium, zinc, aluminum, lithium and zirconium.

22. A process for producing a substituted metallocene compound, the process comprising:
(a) providing a first compound represented by the formula (3):

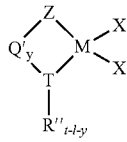

wherein
M is a Group 3, 4, 5 or 6 transition metal atom, or a lanthanide metal atom, or actinide metal atom;
Z is a substituted or unsubstituted, monocyclic or polycyclic ligand that is pi-bonded to M;
Q' is an optional bridging group that is bonded to Z and T, and is present when y is one and absent when y is zero;
y is zero or one;
T is a heteroatom with a coordination number of three from Group 15 or with a coordination number of two from Group 16 of the Periodic Table of Elements;
R" is selected from a $C_3$-$C_{100}$ substituted or unsubstituted monocyclic or polycyclic ring structure substituent that is partially unsaturated, unsaturated or aromatic; a $C_2$-$C_{100}$ substituted or unsubstituted, unsaturated or partially unsaturated, alicyclic hydrocarbyl substituent; or a $C_1$-$C_{100}$ substituted or unsubstituted saturated hydrocarbyl radical;
t is the coordination number of the heteroatom T (2 or 3) where "t-1-y" indicates the number of R" substituents bonded to T;
each X is, independently, a univalent anionic ligand, or two X are joined and bound to the metal atom to form a metallocycle ring, or two X are joined to form a chelating ligand, a diene ligand, or an alkylidene ligand; and
provided that Z is substituted with at least one halogen or sulfonate substituent directly bonded to any $sp^2$ carbon atom at a bondable ring position of the ligand Z, or that R" is substituted with at least one halogen or sulfonate substituent bonded to an $sp^2$ carbon atom, or both; and
(b) reacting said first compound with a transfer-agent which comprises a hydrocarbyl, substituted hydrocarbyl, halocarbyl, substituted halocarbyl, silylcarbyl, germylcarbyl radical capable of replacing said at least one halogen or sulfonate substituent of said first compound under reaction conditions in the presence of a coupling catalyst.

23. The process of claim 22 wherein Z comprises a substituted or unsubstituted monocyclic arenyl ligand or a substituted or unsubstituted polycyclic arenyl ligand.

24. The process of claim 22 wherein Z includes one or more ring heteroatoms selected from boron, a Group 14 atom that is not carbon, a Group 15 atom, and a Group 16 atom.

25. The process of claim 22 wherein Z is independently a substituted or unsubstituted cyclopentadienyl ligand, a substituted or unsubstituted heterocyclopentadienyl ligand, a substituted or unsubstituted indenyl ligand, a substituted or unsubstituted heteroindenyl ligand, a substituted or unsubstituted fluorenyl ligand, a substituted or unsubstituted heterofluorenyl ligand, a substituted or unsubstituted cyclopentanaphthyl, a substituted or unsubstituted heterocyclopentanaphthyl ligand, a substituted or unsubstituted heterophenyl ligand, a substituted or unsubstituted heterocyclopentapentalenyl ligand, a substituted or unsubstituted heterocyclopentaindenyl ligand, or a substituted or unsubstituted heterobenzocyclopentaindenyl ligand.

26. The process of claim 22 wherein the halogen or sulfonate substituent is a chloro, bromo or iodo substituent.

27. The process of claim 22 wherein the halogen substituent is a chloro or bromo substituent.

28. The process of claim 22 wherein t-1-y is equal to 1.

29. The process of claim 22 wherein T is nitrogen.

30. The process of claim 22 wherein R" is selected from the group consisting of methyl, ethyl, all propyl isomers, all butyl isomers, phenyl, benzyl, phenethyl, 1-adamantyl, cyclododecyl, cyclohexyl and norbornyl.

31. The process of claim 22 wherein when the halogen or sulfonate substituent is on R", then R" is selected from the group consisting of 2-bromophenyl, 3-bromophenyl, 4-bromophenyl, 2,6-diisopropyl-4-bromophenyl, 2,6-dimethyl-4-bromophenyl, 2,4,6-trimethyl-3-bromophenyl, 2-bromo-4,6-dimethylphenyl, 2-bromo-4-methylphenyl, 2-bromo-3,4,6-trimethylphenyl, 2-bromo-4-fluorophenyl, 2-bromo-4,6-difluorophenyl, 2,6-dibromophenyl, 2,6-dibromo-4-methylphenyl, 2,6-dibromo-4-fluorophenyl, 2,5-dibromophenyl, and 2,4-dibromophenyl.

32. The process of claim 22 wherein y is 1 and Q' is a bridging group containing boron or a Group 14, 15 or 16 element.

33. The process of claim 22 wherein y is 1 and Q' is selected from the group consisting of: P(=S)R', P(=Se)R', P(=O)R', $R'_2C$, $R'_2Si$, $R'_2Ge$, $R'_2CCR'_2$, $R'_2CCR'_2CR'_2$, $R'_2CCR'_2CR'_2CR'_2$, R'C=CR', R'C=CR'CR'_2, $R'_2CCR'=CR'CR'_2$, R'C=CR'CR'=CR', R'C=CR'CR'_2CR'_2, $R'_2CSiR'_2$, $R'_2SiSiR'_2$, $R'_2CSiR'_2CR'_2$, $R'_2SiCR'_2SiR'_2$, R'C=CR'SiR'_2, $R'_2CGeR'_2$, $R'_2GeGeR'_2$, $R'_2CGeR'_2CR'_2$, $R'_2GeCR'_2GeR'_2$, $R'_2SiGeR'_2$, R'C=CR'GeR'_2, R'B, $R'_2C$—BR', $R'_2C$—BR'—CR'_2, $R'_2C$—O—CR'_2, $R'_2CR'_2C$—O—CR'_2CR'_2, $R'_2C$—O—CR'_2CR'_2, R'_2C—O—CR'_2CR'_2, R'_2C—O—CR'=CR', R'_2C—S—CR'_2, $R'_2CR'_2C$—S—CR'_2CR'_2, $R'_2C$—S—CR'_2CR'_2, R'_2C—S—CR'=CR', $R'_2C$—Se—CR'_2, $R'_2CR'_2C$—Se—CR'_2CR'_2, $R'_2C$—Se—CR'_2CR'_2, R'_2C—Se—CR'=CR', $R'_2C$—N=CR', R'_2C—NR'—CR'_2, R'_2C—NR'—CR'_2CR'_2, $R'_2C$—NR'—CR'=CR', $R'_2CR'_2C$—NR'—CR'_2CR'_2, $R'_2C$—P=CR', and $R'_2C$—PR'—CR'_2 where R' is hydrogen, a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent.

34. The process of claim 22 wherein y is 1 and Q' is selected from the group consisting of $CH_2$, $CH_2CH_2$, $SiMe_2$, $SiPh_2$, SiMePh, $Si(CH_2)_3$, and $Si(CH_2)_4$, where Me is methyl, and Ph is phenyl.

35. The process of claim 22 wherein said transfer-agent is an organometallic compound.

36. The process of claim 35 wherein the metal of the organometallic compound is selected from boron, tin, copper, magnesium, zinc, aluminum, lithium and zirconium.

* * * * *